United States Patent
Zhang et al.

(10) Patent No.: US 12,162,880 B2
(45) Date of Patent: Dec. 10, 2024

(54) PYRIMIDOHETEROCYCLIC COMPOUNDS AND APPLICATION THEREOF

(71) Applicant: D3 BIO (WUXI) CO., LTD., Wuxi Jiangsu (CN)

(72) Inventors: Yang Zhang, Shanghai (CN); Wentao Wu, Shanghai (CN); Jing Zhang, Shanghai (CN); Jikui Sun, Shanghai (CN); Yangyang Xu, Shanghai (CN); Zhijian Chen, Shanghai (CN); John Fenyu Jin, Shanghai (CN); Shuhui Chen, Shanghai (CN)

(73) Assignee: D3 BIO (WUXI) CO., LTD. (CN)

( * ) Notice: Subject to any disclaimer, the term of this patent is extended or adjusted under 35 U.S.C. 154(b) by 131 days.

(21) Appl. No.: 17/905,973

(22) PCT Filed: Mar. 11, 2021

(86) PCT No.: PCT/CN2021/080278
§ 371 (c)(1),
(2) Date: Sep. 9, 2022

(87) PCT Pub. No.: WO2021/180181
PCT Pub. Date: Sep. 16, 2021

(65) Prior Publication Data
US 2023/0151004 A1    May 18, 2023

(30) Foreign Application Priority Data

| Mar. 12, 2020 | (CN) | ......................... 202010172140.2 |
| Apr. 22, 2020 | (CN) | ......................... 202010323035.4 |
| Sep. 11, 2020 | (CN) | ......................... 202010953203.8 |
| Dec. 29, 2020 | (CN) | ......................... 202011593642.9 |

(51) Int. Cl.
*C07D 471/04* (2006.01)
*C07D 491/052* (2006.01)
*C07D 519/00* (2006.01)

(52) U.S. Cl.
CPC ....... *C07D 471/04* (2013.01); *C07D 491/052* (2013.01); *C07D 519/00* (2013.01)

(58) Field of Classification Search
None
See application file for complete search history.

(56) References Cited

U.S. PATENT DOCUMENTS

| 12,012,404 B2 | 6/2024 | Zhang et al. |
| 2024/0116934 A1 | 4/2024 | Zhang et al. |

FOREIGN PATENT DOCUMENTS

| CN | 112390788 A | 2/2021 |
| JP | 2019516718 A | 6/2019 |
| JP | 2023504178 A | 2/2023 |
| WO | WO-2017201161 A1 | 11/2017 |
| WO | WO-2019155399 A1 | 8/2019 |
| WO | WO 2020/035031 A1 | 2/2020 |
| WO | WO 2020/239123 A1 | 12/2020 |
| WO | WO-2021037018 A1 | 3/2021 |
| WO | WO-2021109737 A1 | 6/2021 |
| WO | WO-2021180181 A1 | 9/2021 |
| WO | WO-2021248090 A1 | 12/2021 |
| WO | WO-2022081655 A1 | 4/2022 |

OTHER PUBLICATIONS

Patani et al., Bioisosterism: A Rational Approach in Drug Design. Chem Rev. Jul. 25, 1996;96(8):3147-76.
Co-pending U.S. Appl. No. 18/473,147, inventors Zhang; Yang et al., filed Sep. 22, 2023.

*Primary Examiner* — Samantha L Shterengarts
(74) *Attorney, Agent, or Firm* — COOLEY LLP; Chen Chen

(57) ABSTRACT

A class of pyrimidoheterocyclic compounds, and specifically disclosed is a compound represented by formula (III) or a pharmaceutically acceptable salt thereof.

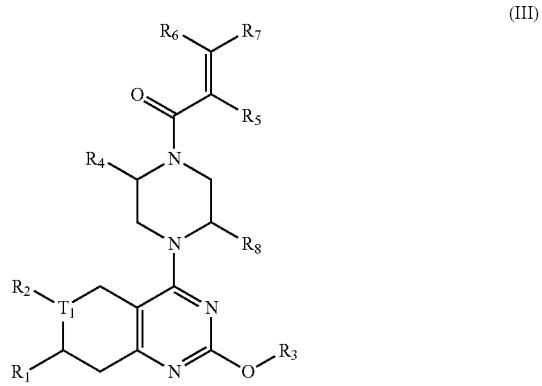

20 Claims, 1 Drawing Sheet

PYRIMIDOHETEROCYCLIC COMPOUNDS AND APPLICATION THEREOF

The present application is a United States National Phase under 35 U.S.C. § 371 of International Application No. PCT/CN2021/080278, filed Mar. 11, 2021, which claims the priority of: CN202010172140.2, filed on Mar. 12, 2020; CN202010323035.4, filed on Apr. 22, 2020; CN202010953203.8, filed on Sep. 11, 2020; and CN202011593642.9, filed on Dec. 29, 2020.

FIELD OF THE INVENTION

The present disclosure relates to a class of pyrimidoheterocyclic compounds, specifically to a compound represented by formula (III) or a pharmaceutically acceptable salt thereof.

BACKGROUND OF THE INVENTION

RAS oncogene mutations are the most common activating mutations in human cancers, occurring in 30% of human tumors. The RAS gene family includes three subtypes (KRAS, HRAS and NRAS), of which 85% of RAS-driven cancers are caused by mutations in the KRAS subtype. KRAS mutations are commonly found in solid tumors, such as lung adenocarcinoma, pancreatic ductal carcinoma and colorectal cancer, etc. In KRAS mutated tumors, 80% of oncogenic mutations occur at codon 12, and the most common mutations include: p.G12D (41%), p.G12V (28%) and p.G12C (14%).

The full name of KRAS gene is Kirsten rat sarcoma viraloncogene homolog. KRAS plays a pivotal role in the signaling regulation of cell growth. The upstream cell surface receptors such as EGFR (ErbB1), HER2 (ErbB2), ErbB3, and ErbB4, after receiving external signals, will transmit the signal to downstream through the RAS protein. When the KRAS protein is not activated, it binds tightly to GDP (guanosine diphosphate). After being activated by guanosine exchange factor such as SOS1, the KRAS protein binds to GTP (guanosine triphosphate) and becomes a kinase active state. After mutation, KRAS gene can independently transmit signals for growth and proliferation to downstream pathways independent of upstream growth factor receptor signals, causing uncontrolled cell growth and tumor progression. Meanwhile, whether KRAS gene has mutations or not is also an important indicator of tumor prognosis.

Although KRAS is the first oncogene to be discovered, it has long been considered an undruggable target. Until 2019, Amgen and Mirati Therapeutics successively published the clinical research results of their small molecule KRAS inhibitors AMG510 and MRTX849, which confirmed the clinical effectiveness of KRAS inhibitors in the clinical treatment of tumors for the first time. Both AMG 510 and MRTX849 are irreversible small molecule inhibitors that inhibit KRAS activity by forming irreversible covalent bonds with cysteine residues of KRAS G12C mutant protein.

Statistical results show that 12-36% of lung adenocarcinoma is driven by KRAS mutations; 27-56% of colon cancer is driven by KRAS; and 90% of pancreatic cancer, 21% of endometrial cancer, and 12-36% of lung adenocarcinoma are driven by KRAS, which indicate that the patient population is huge. In KRAS gene mutations, 97% of the mutations occur in amino acid residues at position 12 or 13, wherein G12D, G12V and G13D mutations have poor druggability, and KRAS (G12C) mutation in which glycine at position 12 is replaced by cysteine provides a good direction for the development of covalent inhibitors.

SUMMARY OF THE INVENTION

The present disclosure provides a compound represented by formula (III) or a pharmaceutically acceptable salt thereof,

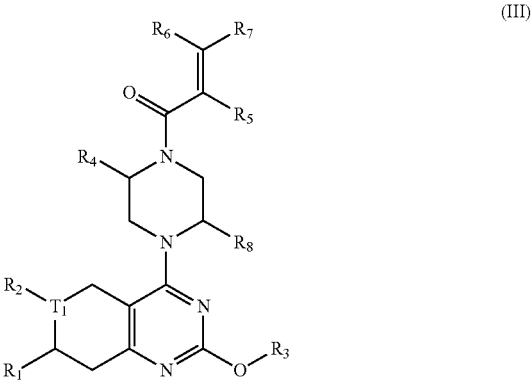

(III)

wherein $T_1$ is selected from O and N;

$R_1$ is selected from $C_{6-10}$ aryl and 5- to 10-membered heteroaryl, wherein the $C_{6-10}$ aryl and 5- to 10-membered heteroaryl are optionally substituted with 1, 2, 3, 4 or 5 $R_a$;

when $T_1$ is O, $R_2$ is not present;

when $T_1$ is N, $R_2$ is selected from H, $C_{1-3}$ alkyl, —C(=O)—$C_{1-3}$ alkyl and —S(=O)$_2$—$C_{1-3}$ alkyl, wherein the $C_{1-3}$ alkyl, —C(=O)—$C_{1-3}$ alkyl and —S(=O)$_2$—$C_{1-3}$ alkyl are optionally substituted with 1, 2 or 3 $R_b$;

$R_3$ is $C_{1-3}$ alkyl, wherein the $C_{1-3}$ alkyl is optionally substituted with 1, 2 or 3 $R_c$;

$R_4$ is selected from H and $C_{1-3}$ alkyl, wherein the $C_{1-3}$ alkyl is optionally substituted with 1, 2 or 3 $R_d$;

$R_5$, $R_6$ and $R_7$ are each independently selected from H, F, Cl, Br, I, and $C_{1-3}$ alkyl, wherein the $C_{1-3}$ alkyl is optionally substituted with 1, 2 or 3 F;

$R_8$ is selected from H and $CH_3$;

$R_a$ is each independently selected from F, Cl, Br, I, OH, $NH_2$, CN, $C_{1-3}$ alkyl, $C_{1-3}$ alkoxy, $C_{2-3}$ alkynyl and $C_{2-3}$ alkenyl, wherein the $C_{1-3}$ alkyl, $C_{1-3}$ alkoxy, $C_{2-3}$ alkynyl and $C_{2-3}$ alkenyl are optionally substituted with 1, 2 or 3 F;

$R_b$ is each independently selected from F, Cl, Br, I, OH and $NH_2$;

$R_c$ is each independently selected from 4- to 8-membered heterocycloalkyl, wherein the 4- to 8-membered heterocycloalkyl is optionally substituted with 1, 2 or 3 R;

$R_d$ is each independently selected from F, Cl, Br, I, OH, $NH_2$ and CN;

R is each independently selected from H, F, Cl, Br, OH, CN, $C_{1-3}$ alkyl, $C_{1-3}$ alkoxy and —$C_{1-3}$ alkyl-O—CO—$C_{1-3}$ alkylamino;

provided that when $R_1$ is naphthyl, the naphthyl is optionally substituted with F, Cl, Br, OH, $NH_2$, $CF_3$, $CH_2CH_3$ and —C≡CH, and $R_5$, $R_6$ and $R_7$ are each independently H.

In some embodiments of the present disclosure, the above $R_a$ is each independently selected from F, Cl, Br, I, OH, $NH_2$, CN, $CH_3$, $CH_2CH_3$, $OCH_3$, $OCH_2CH_3$, —CH=$CH_2$, —$CH_2$—CH=$CH_2$ and —C≡CH, wherein the $CH_3$, $CH_2CH_3$, $OCH_3$, $OCH_2CH_3$, —CH=$CH_2$, —$CH_2$—

CH=CH$_2$ and —C≡CH are optionally substituted with 1, 2 or 3 F, and other variables are as defined in this disclosure.

In some embodiments of the present disclosure, the above R$_a$ is each independently selected from F, OH, NH$_2$, CH$_3$, CF$_3$, CH$_2$CH$_3$ and —C≡CH, and other variables are as defined in this disclosure.

In some embodiments of the present disclosure, the above R$_1$ is selected from phenyl, naphthyl, indolyl and indazolyl, wherein the phenyl, naphthyl, indolyl and indazolyl are optionally substituted with 1, 2 or 3 R$_a$, and other variables are as defined in this disclosure.

In some embodiments of the present disclosure, the above R$_1$ is selected from

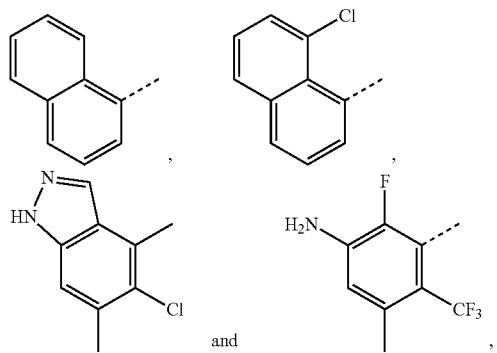

and other variables are as defined in this disclosure.

In some embodiments of the present disclosure, the above R$_2$ is selected from H, CH$_3$, CH$_2$CH$_3$ and CH(CH$_3$)$_2$, wherein the CH$_3$, CH$_2$CH$_3$ and CH(CH$_3$)$_2$ are optionally substituted with 1, 2 or 3 R$_b$, and other variables are as defined in this disclosure.

In some embodiments of the present disclosure, the above R$_2$ is selected from H and CH$_3$, and other variables are as defined in this disclosure.

In some embodiments of the present disclosure, the above R is each independently selected from H, F, Cl, Br, OH, CN, CH$_3$, CH$_2$CH$_3$, CH$_2$CF$_3$, OCH$_3$, OCF$_3$ and

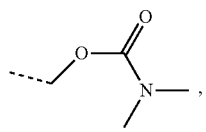

and other variables are as defined in this disclosure.

In some embodiments of the present disclosure, the above R$_c$ is selected from tetrahydropyrrolyl and hexahydro-1H-pyrrolizinyl, wherein the tetrahydropyrrolyl and hexahydro-1H-pyrrolizinyl are optionally substituted with 1, 2 or 3 R, and other variables are as defined in this disclosure.

In some embodiments of the present disclosure, the above R$_c$ is selected from

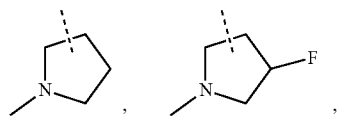

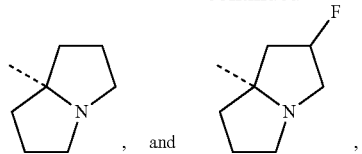

and other variables are as defined in this disclosure.

In some embodiments of the present disclosure, the above R$_c$ is selected from

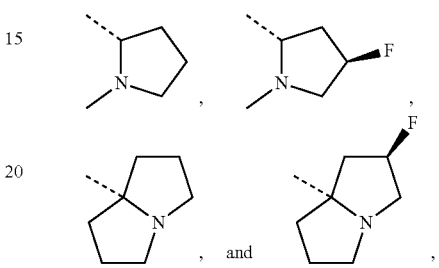

and other variables are as defined in this disclosure.

In some embodiments of the present disclosure, the above R$_3$ is CH$_3$, wherein the CH$_3$ is optionally substituted with 1, 2 or 3 R$_c$, and other variables are as defined in this disclosure.

In some embodiments of the present disclosure, the above R$_3$ is selected from

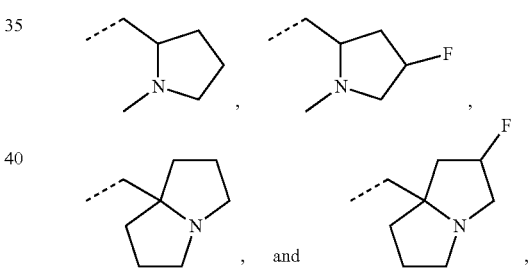

and other variables are as defined in this disclosure.

In some embodiments of the present disclosure, the above R$_3$ is selected from

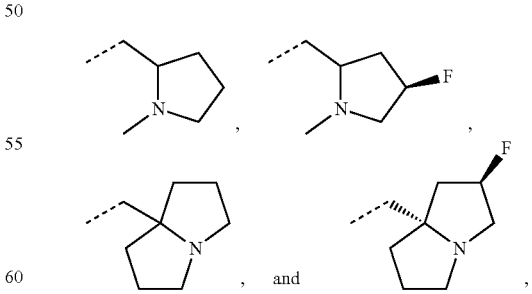

and other variables are as defined in this disclosure.

In some embodiments of the present disclosure, the above R$_4$ is selected from H and CH$_3$, wherein the CH$_3$ is optionally substituted with 1, 2 or 3 R$_d$, and other variables are as defined in this disclosure.

In some embodiments of the present disclosure, the above $R_4$ is selected from H, $CH_3$ and $CH_2CN$, and other variables are as defined in this disclosure.

The present disclosure provides a compound represented by formula (III) or a pharmaceutically acceptable salt thereof,

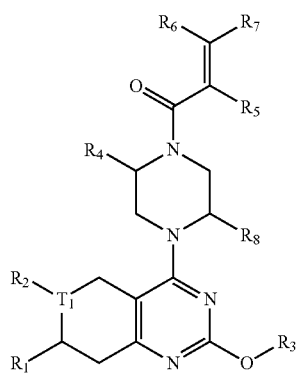

(III)

wherein $T_1$ is selected from O and N;

$R_1$ is selected from phenyl, naphthyl and indazolyl, wherein the phenyl, naphthyl and indazolyl are optionally substituted with 1, 2, 3, 4 or 5 $R_a$;

when $T_1$ is O, $R_2$ is not present;

when $T_1$ is N, $R_2$ is selected from H, $C_{1-3}$ alkyl, —C(=O)—$C_{1-3}$ alkyl and —S(=O)$_2$—$C_{1-3}$ alkyl, wherein the $C_{1-3}$ alkyl, —C(=O)—$C_{1-3}$ alkyl and —S(=O)$_2$—$C_{1-3}$ alkyl are optionally substituted with 1, 2 or 3 $R_b$;

$R_3$ is $C_{1-3}$ alkyl, wherein the $C_{1-3}$ alkyl is optionally substituted with 1, 2 or 3 $R_c$;

$R_4$ is selected from H and $C_{1-3}$ alkyl, wherein the $C_{1-3}$ alkyl is optionally substituted with 1, 2 or 3 $R_d$;

$R_5$, $R_6$ and $R_7$ are each independently selected from H, F, Cl, Br, I, OH and $NH_2$;

$R_8$ is selected from H and $CH_3$;

$R_a$ is each independently selected from F, Cl, Br, I, OH, $NH_2$, CN, $CH_3$, $CF_3$ and $OCH_3$;

$R_b$ is each independently selected from F, Cl, Br, I, OH and $NH_2$;

$R_c$ is each independently selected from tetrahydropyrrolyl and hexahydro-1H-pyrrolizinyl, wherein the tetrahydropyrrolyl and hexahydro-1H-pyrrolizinyl are substituted with 1, 2 or 3 R;

$R_d$ is each independently selected from F, Cl, Br, I, OH, $NH_2$ and CN;

R is each independently selected from H, F, Cl, Br and $CH_3$.

In some embodiments of the present disclosure, disclosed is the above compound or a pharmaceutically acceptable salt thereof, wherein the compound is selected from,

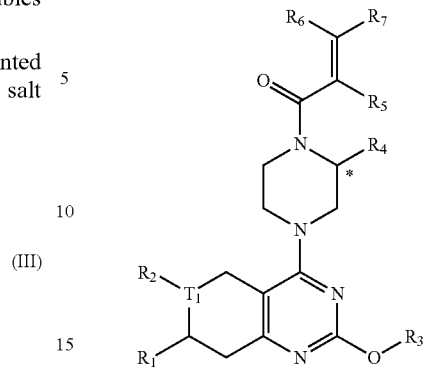

(II)

wherein $R_4$ is $C_{1-3}$ alkyl, wherein the $C_{1-3}$ alkyl is optionally substituted with 1, 2 or 3 $R_d$;

$T_1$, $R_1$, $R_2$, $R_3$, $R_5$, $R_6$, $R_7$ and $R_d$ are as defined in this disclosure;

the carbon atom with "*" is a chiral carbon atom, which exists in the form of (R) or (S) single enantiomer or is enriched in one enantiomer.

In some embodiments of the present disclosure, the above $R_1$ is selected from phenyl, naphthyl and

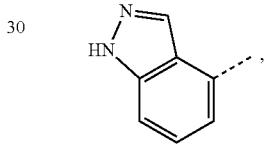

wherein the phenyl, naphthyl and

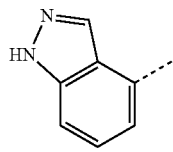

are optionally substituted with 1, 2 or 3 $R_a$, and other variables are as defined in this disclosure.

In some embodiments of the present disclosure, the above $R_1$ is selected from

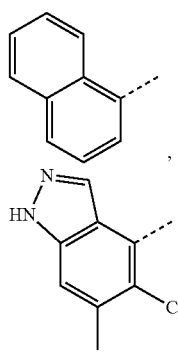

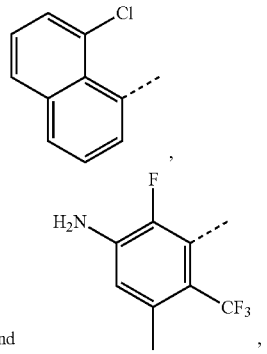

and and other variables are as defined in this disclosure.

In some embodiments of the present disclosure, the above R$_2$ is selected from H, CH$_3$, CH$_2$CH$_3$ and CH(CH$_3$)$_2$, wherein the CH$_3$, CH$_2$CH$_3$ and CH(CH$_3$)$_2$ are optionally substituted with 1, 2 or 3 R$_b$, and other variables are as defined in this disclosure.

In some embodiments of the present disclosure, the above R$_2$ is selected from H and CH$_3$, and other variables are as defined in this disclosure.

In some embodiments of the present disclosure, the above R$_c$ is selected from

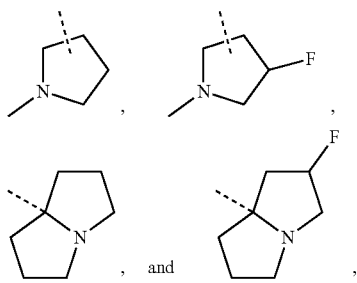

and other variables are as defined in this disclosure.

In some embodiments of the present disclosure, the above R$_c$ is selected from

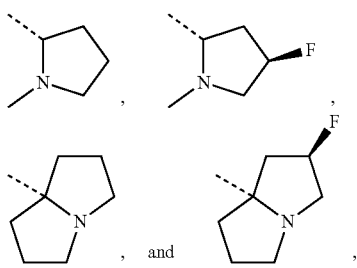

and other variables are as defined in this disclosure.

In some embodiments of the present disclosure, the above R$_3$ is CH$_3$, wherein the CH$_3$ is optionally substituted with 1, 2 or 3 R$_c$, and other variables are as defined in this disclosure.

In some embodiments of the present disclosure, the above R$_3$ is selected from

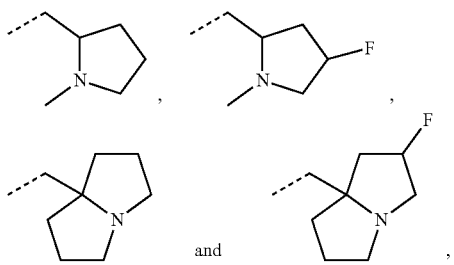

and other variables are as defined in this disclosure.

In some embodiments of the present disclosure, the above R$_3$ is selected from

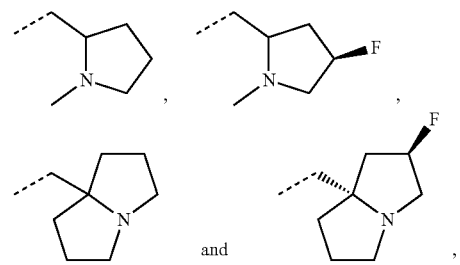

and other variables are as defined in this disclosure.

In some embodiments of the present disclosure, the above R$_4$ is selected from H and CH$_3$, wherein the CH$_3$ is optionally substituted with 1, 2 or 3 R$_d$, and other variables are as defined in this disclosure.

In some embodiments of the present disclosure, the above R$_4$ is selected from H, CH$_3$ and CH$_2$CN, and other variables are as defined in this disclosure.

The present disclosure provides a compound represented by formula (III) or a pharmaceutically acceptable salt thereof,

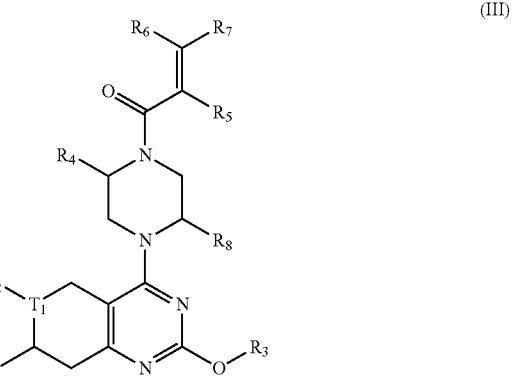

(III)

wherein

T$_1$ is selected from O and N;

R$_1$ is selected from phenyl, naphthyl and indazolyl, wherein the phenyl, naphthyl and indazolyl are optionally substituted with 1, 2, 3, 4 or 5 R$_a$;

when T$_1$ is O, R$_2$ is not present;

when T$_1$ is N, R$_2$ is selected from H, C$_{1-3}$ alkyl, —C(=O)—C$_{1-3}$ alkyl and —S(=O)$_2$—C$_{1-3}$ alkyl, wherein the C$_{1-3}$ alkyl, —C(=O)—C$_{1-3}$ alkyl and —S(=O)$_2$—C$_{1-3}$ alkyl are optionally substituted with 1, 2 or 3 R$_b$;

R$_3$ is C$_{1-3}$ alkyl, wherein the C$_{1-3}$ alkyl is optionally substituted with 1, 2 or 3 R$_c$;

R$_4$ is selected from H and C$_{1-3}$ alkyl, wherein the C$_{1-3}$ alkyl is optionally substituted with 1, 2 or 3 R$_d$;

R$_5$, R$_6$ and R$_7$ are each independently selected from H, F, Cl, Br, I, OH and NH$_2$;

R$_8$ is selected from H and CH$_3$;

R$_a$ is each independently selected from F, Cl, Br, I, OH, NH$_2$, CN, CH$_3$, CF$_3$ and OCH$_3$;

R$_b$ is each independently selected from F, Cl, Br, I, OH, NH$_2$ and CH$_3$;

R$_c$ is each independently tetrahydropyrrolyl, wherein the tetrahydropyrrolyl is substituted with 1, 2 or 3 R;

$R_d$ is each independently selected from F, Cl, Br, I, OH, $NH_2$ and CN;

R is each independently selected from F, Cl, Br and $CH_3$.

In some embodiments of the present disclosure, disclosed is the above compound or a pharmaceutically acceptable salt thereof, wherein the compound is selected from,

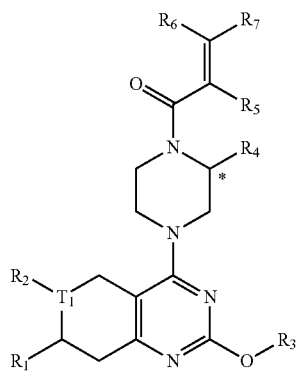
(II)

wherein $T_1$, $R_1$, $R_2$, $R_3$, $R_4$, $R_5$, $R_6$ and $R_7$ are as defined in this disclosure;

the carbon atom with "*" is a chiral carbon atom, which exists in the form of (R) or (S) single enantiomer or is enriched in one enantiomer.

In some embodiments of the present disclosure, the above $R_1$ is selected from phenyl, naphthyl and

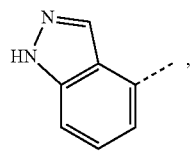, wherein the phenyl, naphthyl and

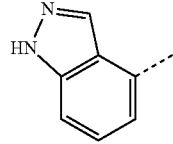

are optionally substituted with 1, 2 or 3 $R_a$, and other variables are as defined in this disclosure.

In some embodiments of the present disclosure, the above $R_1$ is selected from

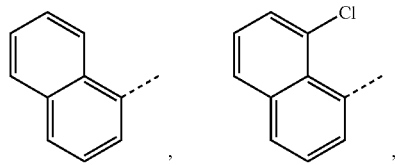

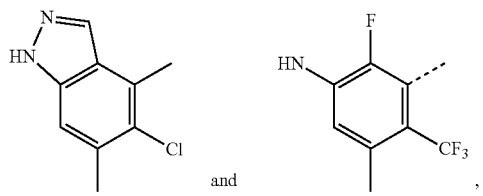

and other variables are as defined in this disclosure.

In some embodiments of the present disclosure, the above $R_2$ is selected from H, $CH_3$, $CH_2CH_3$ and $CH(CH_3)_2$, wherein the $CH_3$, $CH_2CH_3$ and $CH(CH_3)_2$ are optionally substituted with 1, 2 or 3 $R_b$, and other variables are as defined in this disclosure.

In some embodiments of the present disclosure, the above $R_2$ is selected from H and $CH_3$, and other variables are as defined in this disclosure.

In some embodiments of the present disclosure, the above $R_c$ is

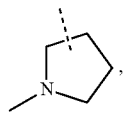, and other variables are as defined in this disclosure.

In some embodiments of the present disclosure, the above $R_3$ is $CH_3$, wherein the $CH_3$ is optionally substituted with 1, 2 or 3 $R_c$, and other variables are as defined in this disclosure.

In some embodiments of the present disclosure, the above $R_3$ is

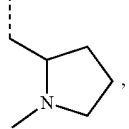, and other variables are as defined in this disclosure.

In some embodiments of the present disclosure, the above $R_4$ is $CH_3$, wherein the $CH_3$ is optionally substituted with 1, 2 or 3 $R_d$, and other variables are as defined in this disclosure.

In some embodiments of the present disclosure, the above $R_4$ is $CH_2CN$, and other variables are as defined in this disclosure.

The present disclosure provides a compound represented by formula (II) or a pharmaceutically acceptable salt thereof,

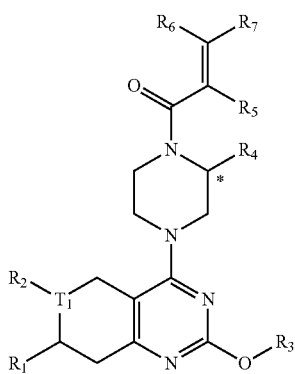

wherein $T_1$ is selected from O and N;

$R_1$ is selected from phenyl and naphthyl, wherein the phenyl and naphthyl are optionally substituted with 1, 2 or 3 $R_a$;

when $T_1$ is O, $R_2$ is not present;

when $T_1$ is N, $R_2$ is selected from $C_{1-3}$ alkyl, —C(=O)—$C_{1-3}$ alkyl and —S(=O)$_2$—$C_{1-3}$ alkyl, wherein the $C_{1-3}$ alkyl, —C(=O)—$C_{1-3}$ alkyl and —S(=O)$_2$—$C_{1-3}$ alkyl are optionally substituted with 1, 2 or 3 $R_b$;

$R_3$ is $C_{1-3}$ alkyl, wherein the $C_{1-3}$ alkyl is optionally substituted with 1, 2 or 3 $R_c$;

$R_4$ is $C_{1-3}$ alkyl, wherein the $C_{1-3}$ alkyl is optionally substituted with 1, 2 or 3 $R_d$;

$R_5$, $R_6$ and $R_7$ are each independently selected from H, F, Cl, Br, I, OH and $NH_2$;

$R_a$ is each independently selected from F, Cl, Br, I, OH, $NH_2$, CN, $CH_3$ and $OCH_3$;

$R_b$ is each independently selected from F, Cl, Br, I, OH, $NH_2$ and $CH_3$;

$R_c$ is each independently tetrahydropyrrolyl, wherein the tetrahydropyrrolyl is substituted with 1, 2 or 3 R;

$R_d$ is each independently selected from F, Cl, Br, I, OH, $NH_2$ and CN;

R is each independently selected from F, Cl, Br and $CH_3$;

the carbon atom with "*" is a chiral carbon atom, which exists in the form of (R) or (S) single enantiomer or is enriched in one enantiomer.

In some embodiments of the present disclosure, the above $R_1$ is naphthyl, wherein the naphthyl is optionally substituted with 1, 2 or 3 $R_a$, and other variables are as defined in this disclosure.

In some embodiments of the present disclosure, the above $R_1$ is selected from

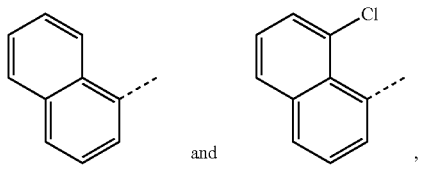

and other variables are as defined in this disclosure.

In some embodiments of the present disclosure, the above $R_2$ is selected from $CH_3$, $CH_2CH_3$ and $CH(CH_3)_2$, wherein the $CH_3$, $CH_2CH_3$ and $CH(CH_3)_2$ are optionally substituted with 1, 2 or 3 $R_b$, and other variables are as defined in this disclosure.

In some embodiments of the present disclosure, the above $R_2$ is $CH_3$, and other variables are as defined in this disclosure.

In some embodiments of the present disclosure, the above $R_c$ is

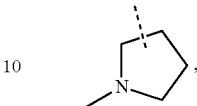

and other variables are as defined in this disclosure.

In some embodiments of the present disclosure, the above $R_3$ is $CH_3$, wherein the $CH_3$ is optionally substituted with 1, 2 or 3 $R_c$, and other variables are as defined in this disclosure.

In some embodiments of the present disclosure, the above $R_3$ is

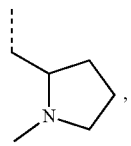

and other variables are as defined in this disclosure.

In some embodiments of the present disclosure, the above $R_4$ is $CH_3$, wherein the $CH_3$ is optionally substituted with 1, 2 or 3 $R_d$, and other variables are as defined in this disclosure.

In some embodiments of the present disclosure, the above $R_4$ is $CH_2CN$, and other variables are as defined in this disclosure.

The present disclosure provides a compound represented by formula (I) or a pharmaceutically acceptable salt thereof,

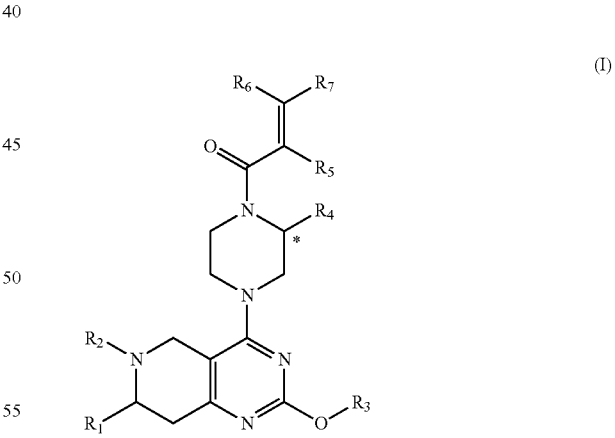

wherein $R_1$ is selected from phenyl and naphthyl, wherein the phenyl and naphthyl are optionally substituted with 1, 2 or 3 $R_a$;

$R_2$ is selected from $C_{1-3}$ alkyl, —C(=O)—$C_{1-3}$ alkyl and —S(=O)$_2$—$C_{1-3}$ alkyl, wherein the $C_{1-3}$ alkyl, —C(=O)—$C_{1-3}$ alkyl and —S(=O)$_2$—$C_{1-3}$ alkyl are optionally substituted with 1, 2 or 3 $R_b$;

$R_3$ is $C_{1-3}$ alkyl, wherein the $C_{1-3}$ alkyl is optionally substituted with 1, 2 or 3 $R_c$;

R$_4$ is C$_{1-3}$ alkyl, wherein the C$_{1-3}$ alkyl is optionally substituted with 1, 2 or 3 R$_d$;

R$_5$, R$_6$ and R$_7$ are each independently selected from H, F, Cl, Br, I, OH and NH$_2$;

R$_a$ and R$_b$ are each independently selected from F, Cl, Br, I, OH, NH$_2$ and CH$_3$;

R$_c$ is each independently tetrahydropyrrolyl, wherein the tetrahydropyrrolyl is substituted with 1, 2 or 3 R;

R$_d$ is each independently selected from F, Cl, Br, I, OH, NH$_2$ and CN;

R is each independently selected from F, Cl, Br and CH$_3$;

the carbon atom with "*" is a chiral carbon atom, which exists in the form of (R) or (S) single enantiomer or is enriched in one enantiomer.

In some embodiments of the present disclosure, the above R$_1$ is naphthyl, and other variables are as defined in this disclosure.

In some embodiments of the present disclosure, the above R$_1$ is

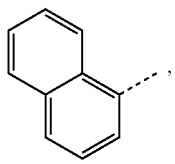

and other variables are as defined in this disclosure.

In some embodiments of the present disclosure, the above R$_2$ is selected from CH$_3$, CH$_2$CH$_3$ and CH(CH$_3$)$_2$, wherein the CH$_3$, CH$_2$CH$_3$ and CH(CH$_3$)$_2$ are optionally substituted with 1, 2 or 3 R$_b$, and other variables are as defined in this disclosure.

In some embodiments of the present disclosure, the above R$_2$ is CH$_3$, and other variables are as defined in this disclosure.

In some embodiments of the present disclosure, the above R$_c$ is

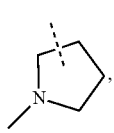

and other variables are as defined in this disclosure.

In some embodiments of the present disclosure, the above R$_3$ is CH$_3$, wherein the CH$_3$ is optionally substituted with 1, 2 or 3 R$_c$, and other variables are as defined in this disclosure.

In some embodiments of the present disclosure, the above R$_3$ is

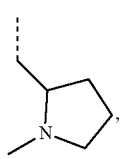

and other variables are as defined in this disclosure.

In some embodiments of the present disclosure, the above R$_4$ is CH$_3$, wherein the CH$_3$ is optionally substituted with 1, 2 or 3 R$_d$, and other variables are as defined in this disclosure.

In some embodiments of the present disclosure, the above R$_4$ is CH$_2$CN, and other variables are as defined in this disclosure.

In some embodiments of the present disclosure, disclosed is the above compound or a pharmaceutically acceptable salt thereof, wherein the compound is selected from,

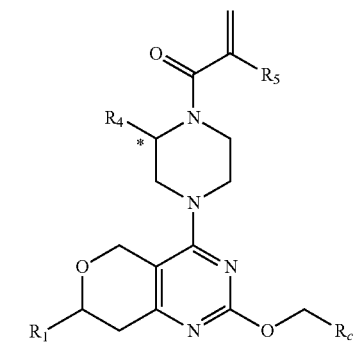

(P-1)

wherein R$_1$, R$_5$, and R$_c$ are as defined in this disclosure;

R$_4$ is C$_{1-3}$ alkyl, wherein the C$_{1-3}$ alkyl is optionally substituted with 1, 2 or 3 R$_d$;

R$_d$ is each independently selected from F, Cl, Br, I, OH, NH$_2$ and CN;

the carbon atom with "*" is a chiral carbon atom, which exists in the form of (R) or (S) single enantiomer or is enriched in one enantiomer.

In some embodiments of the present disclosure, disclosed is the above compound or a pharmaceutically acceptable salt thereof, wherein the compound is selected from:

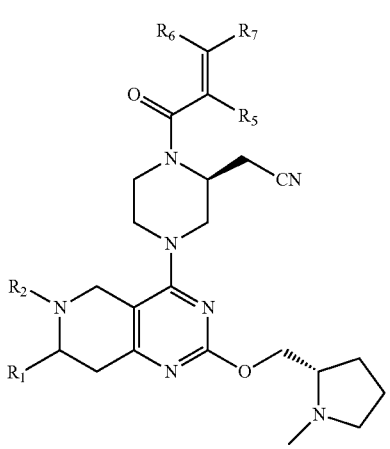

(I-1)

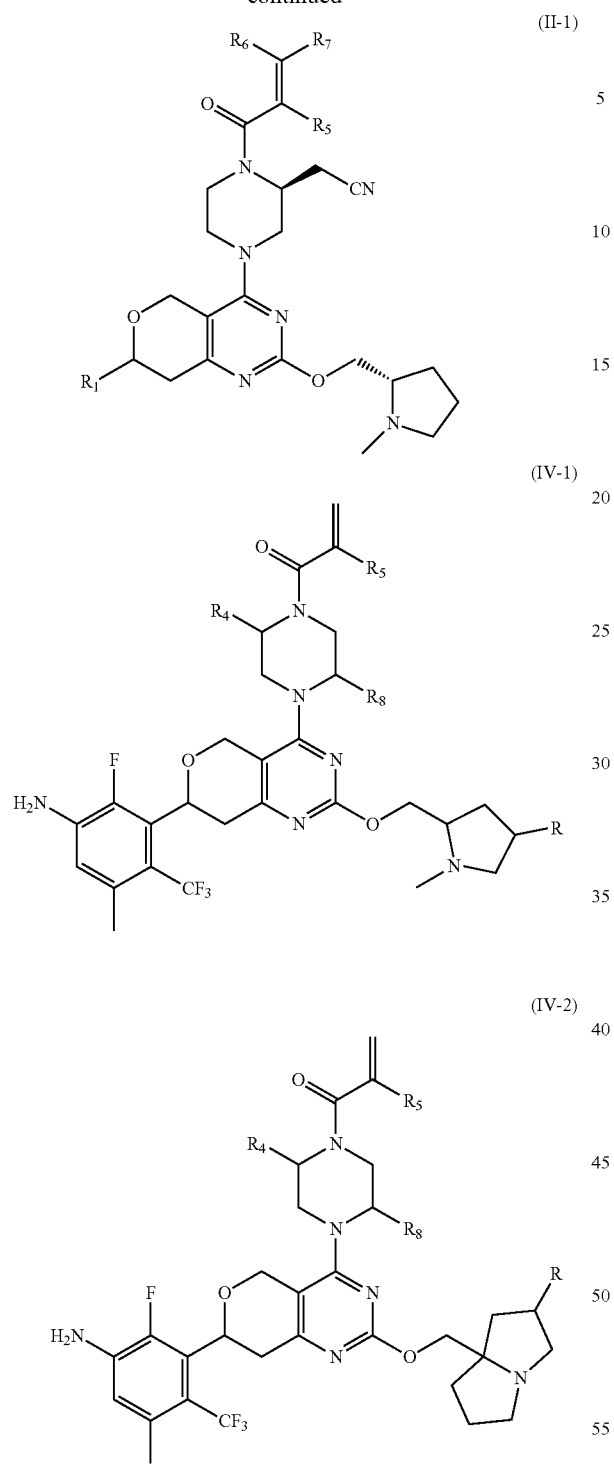
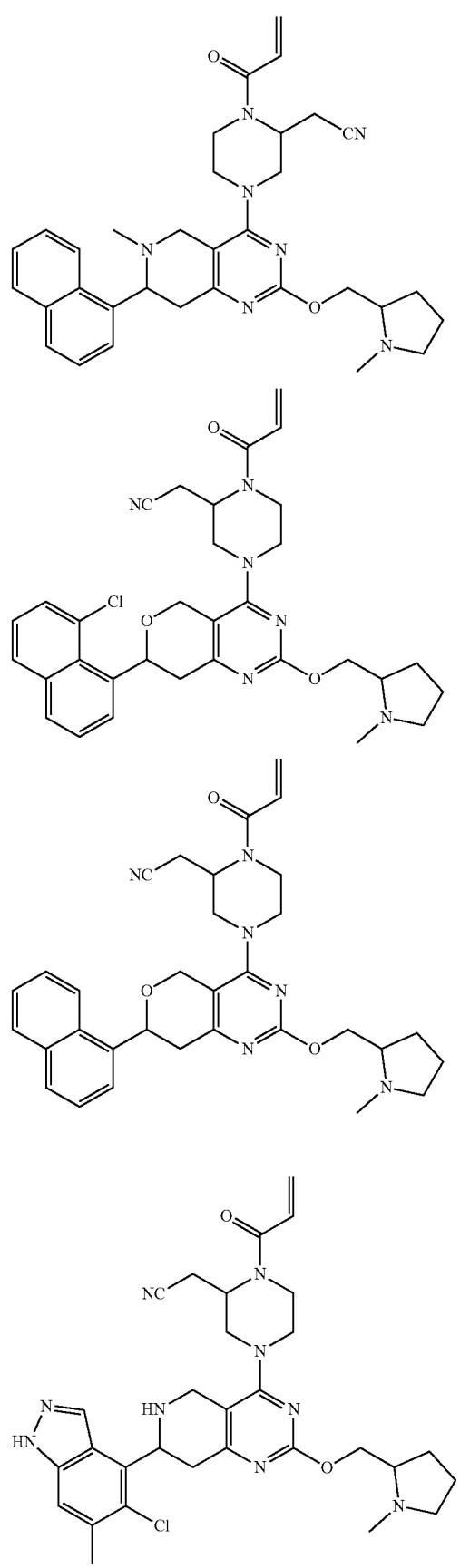
wherein
$R_1$, $R_2$, $R_4$, $R_5$, $R_6$, $R_7$, $R_8$ and R are as defined in this disclosure.
The present disclosure also includes some embodiments obtained by any combination of the above variables.
The present disclosure provides a compound of the following formula or a pharmaceutically acceptable salt thereof, 17
-continued
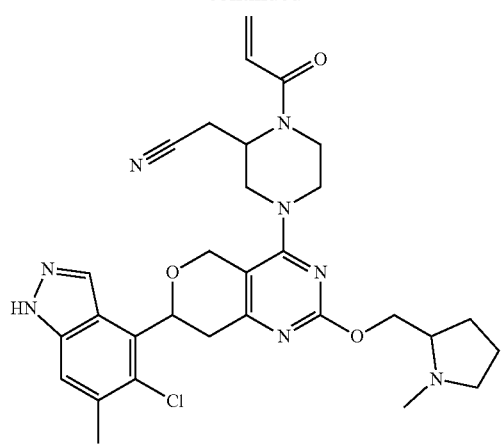
18
-continued
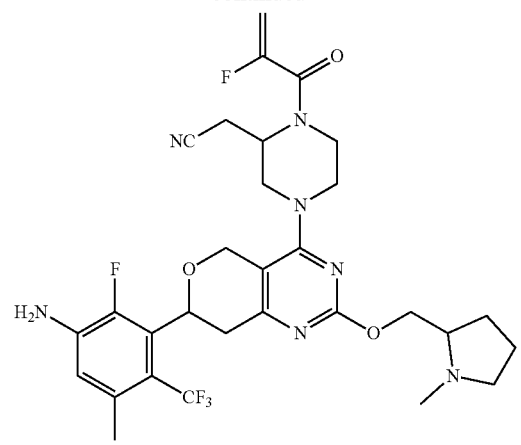
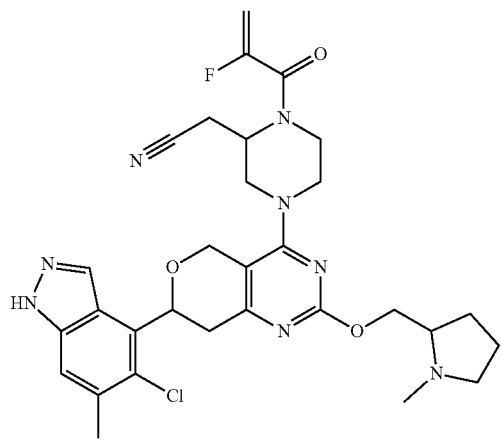
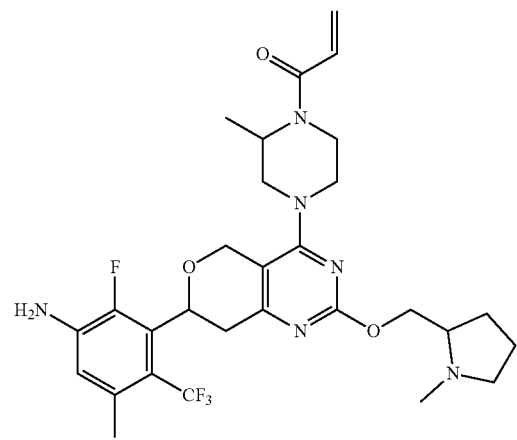

-continued
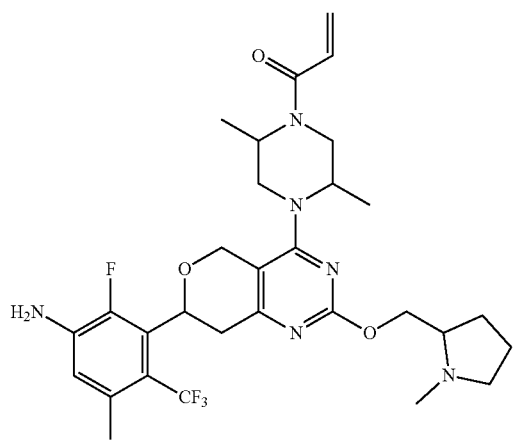
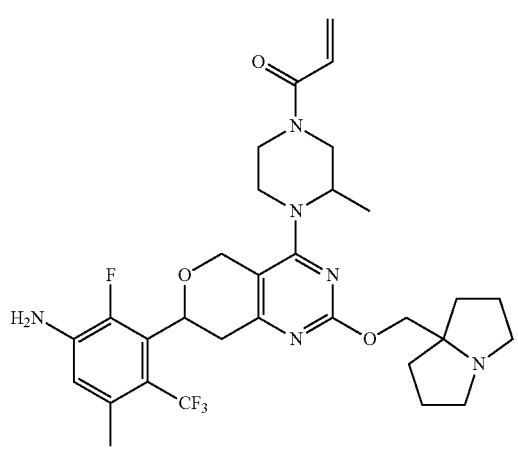
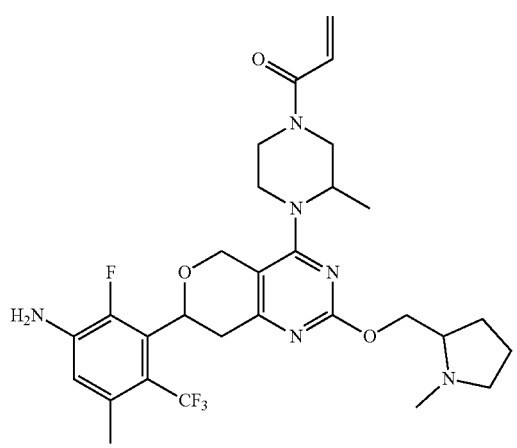
-continued
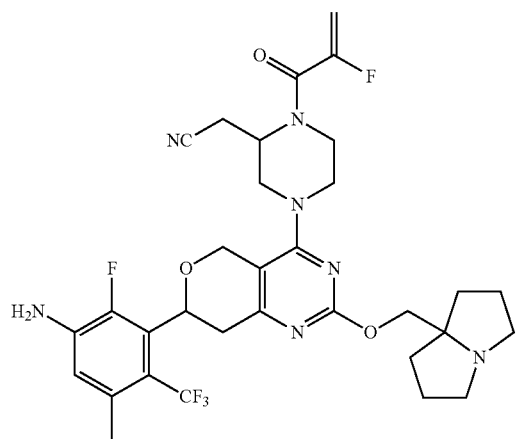
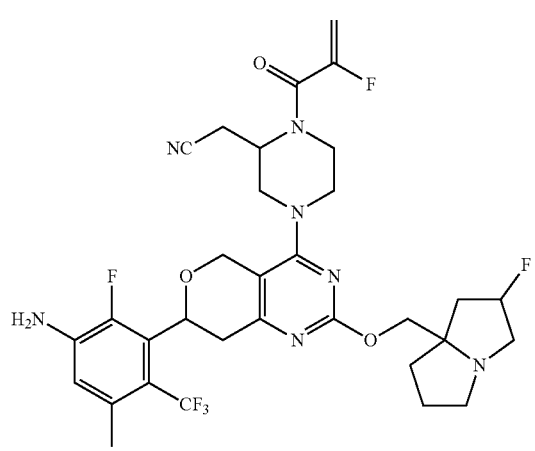
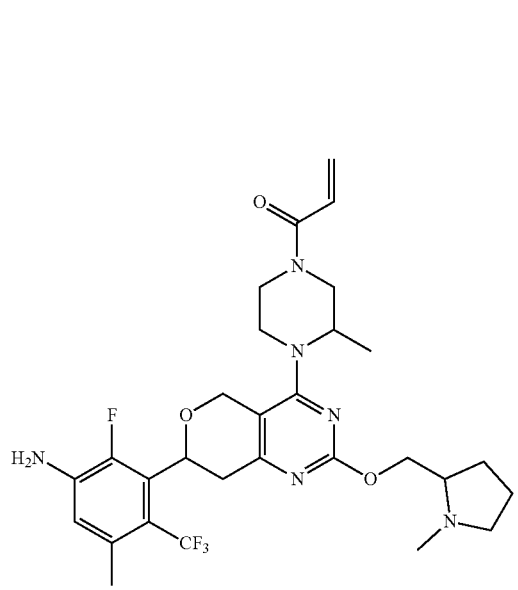

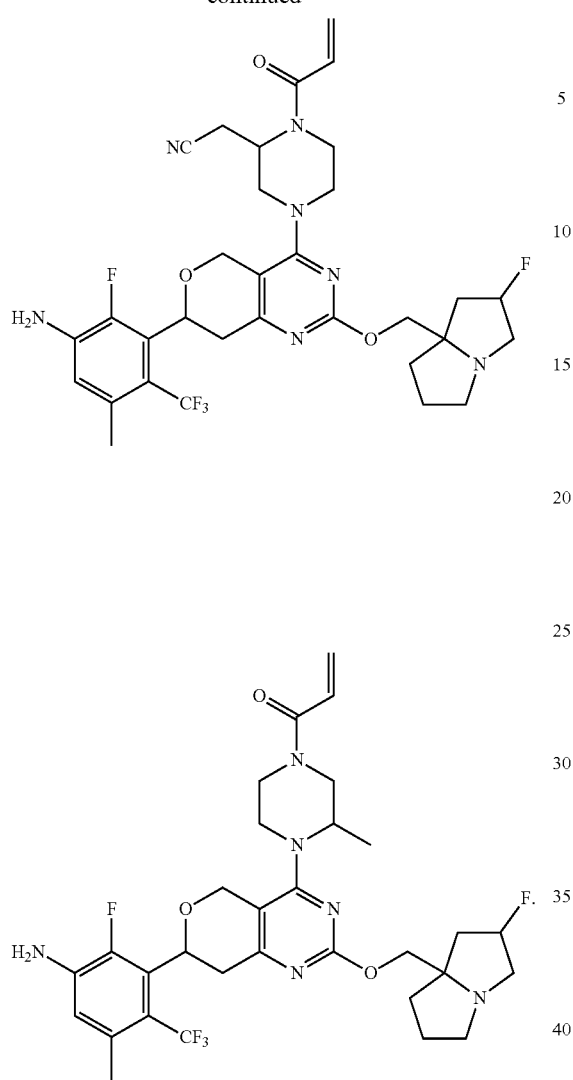
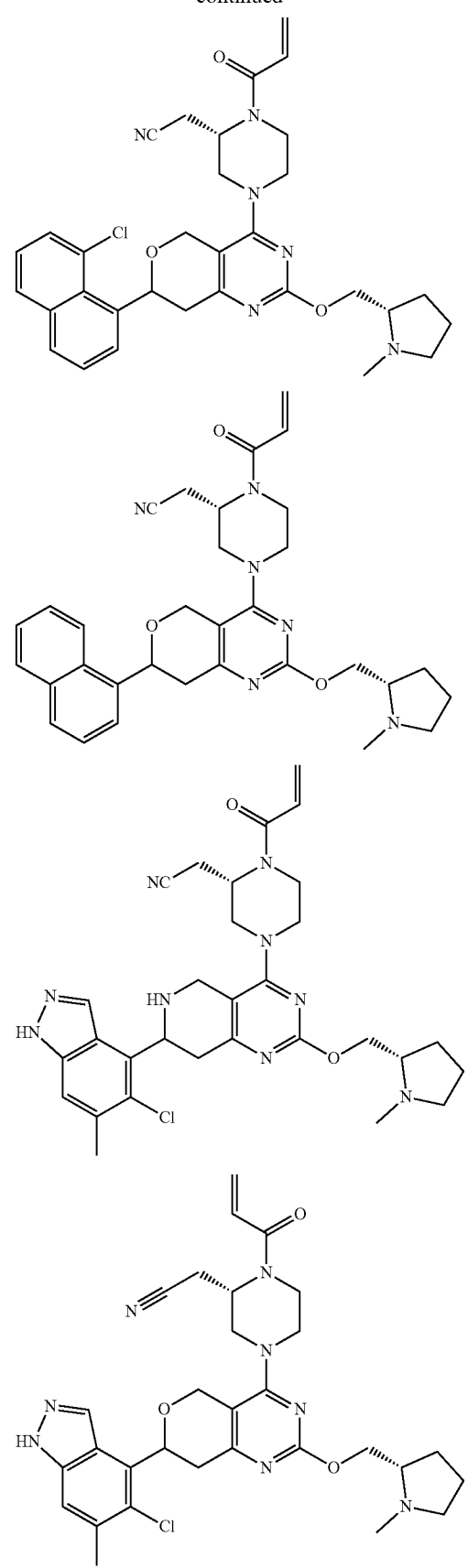
In some embodiments of the present disclosure, disclosed is the above compound or a pharmaceutically acceptable salt thereof, wherein the compound is selected from,
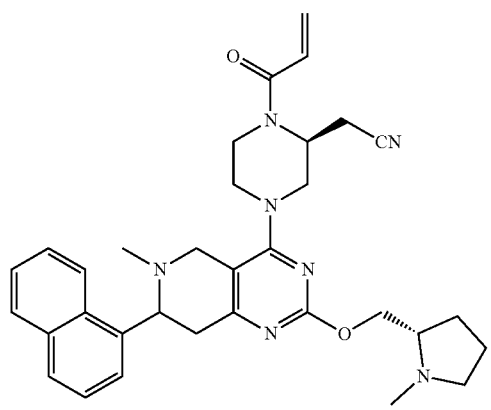

23
-continued
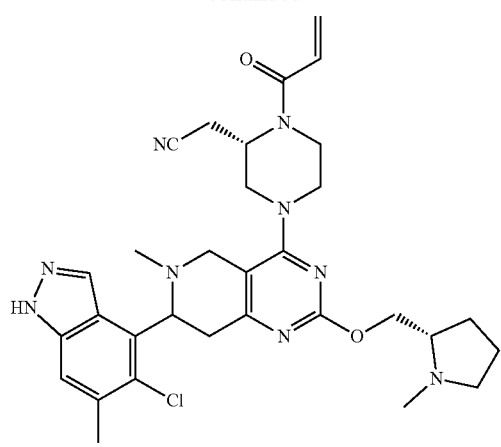
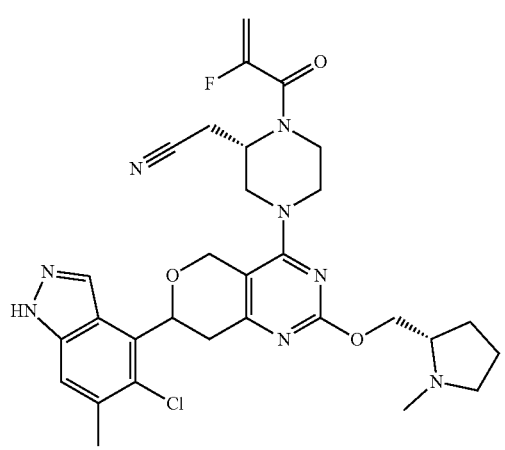
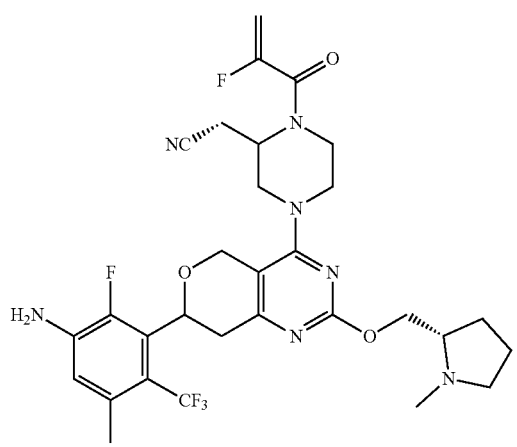
24
-continued
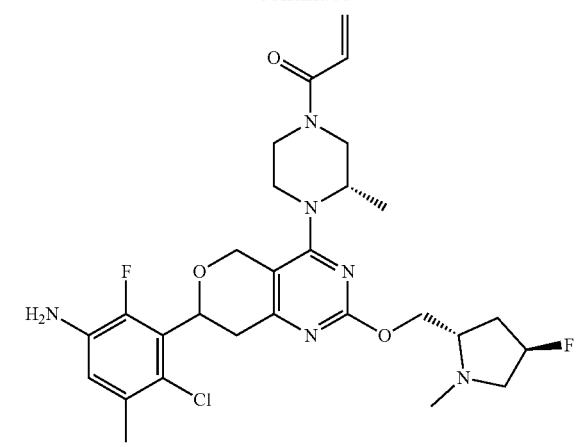
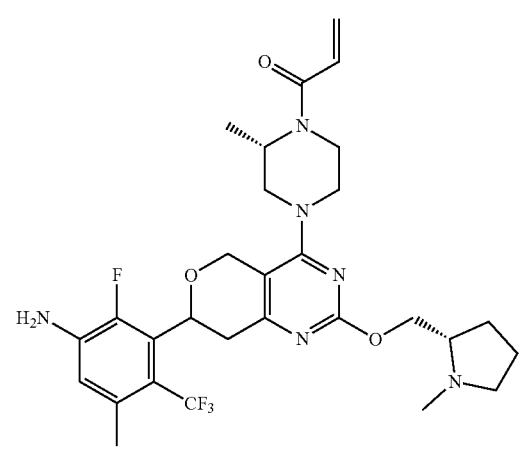

25
-continued
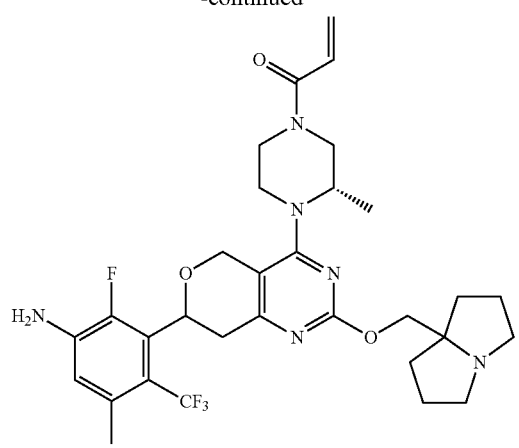
26
-continued
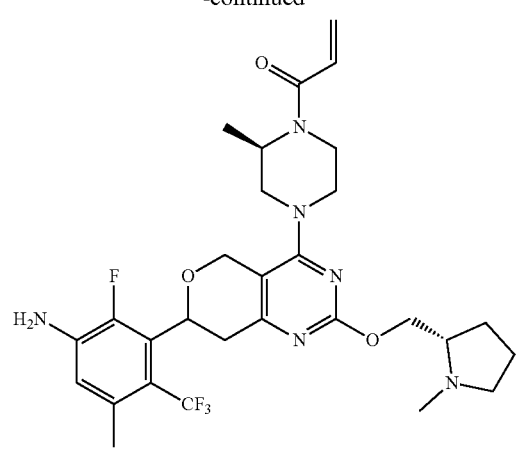
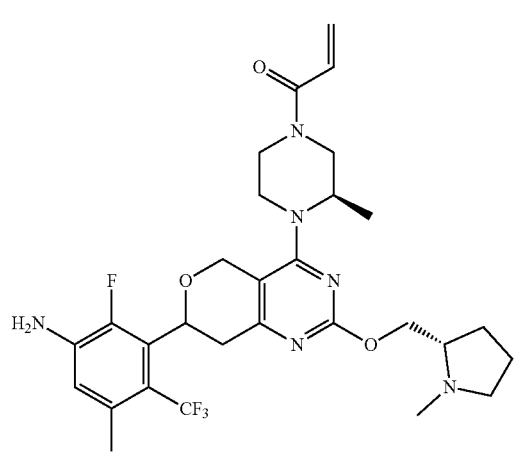
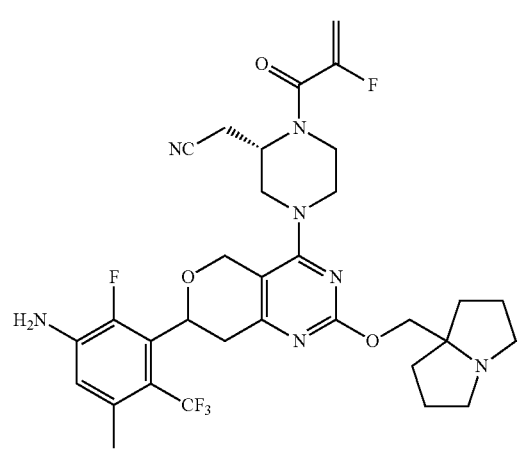
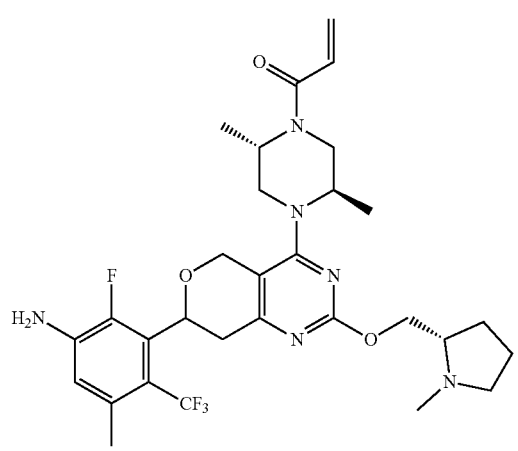
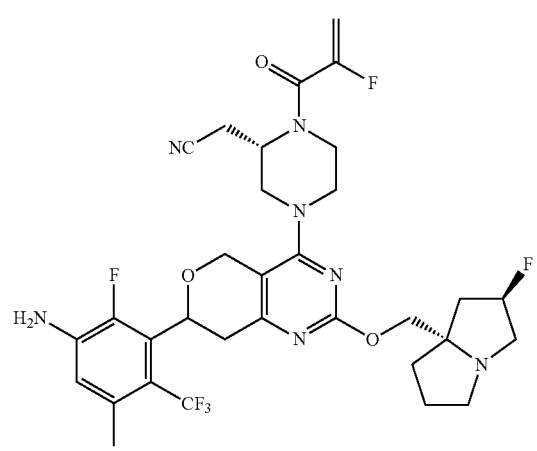

-continued
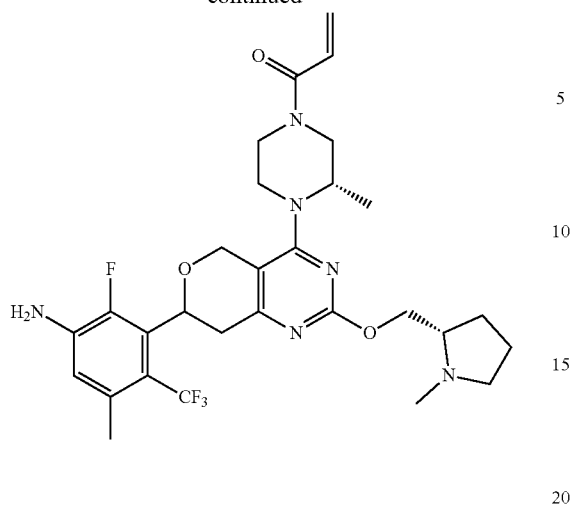
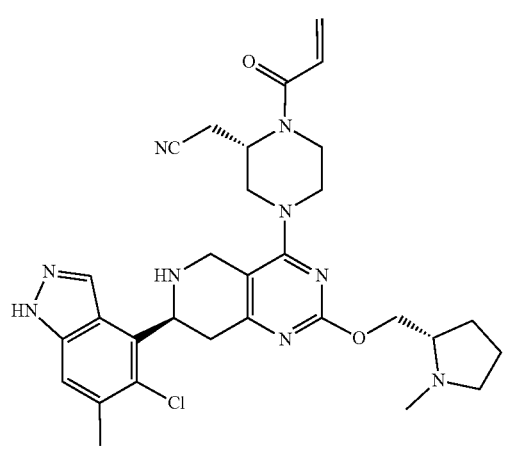
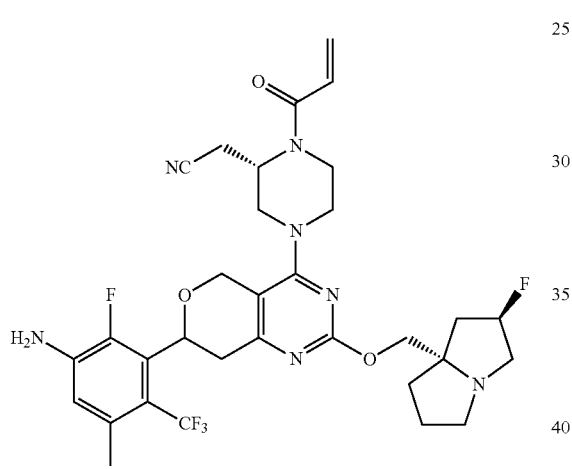
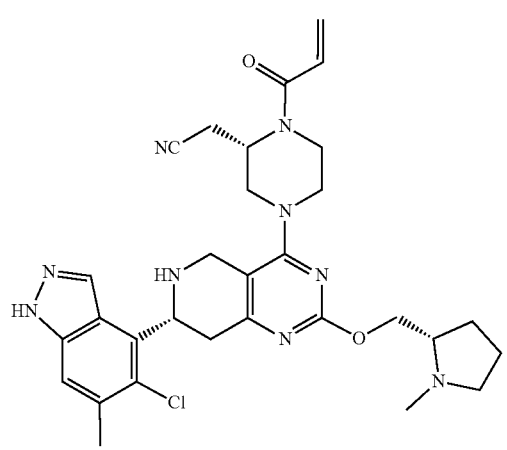
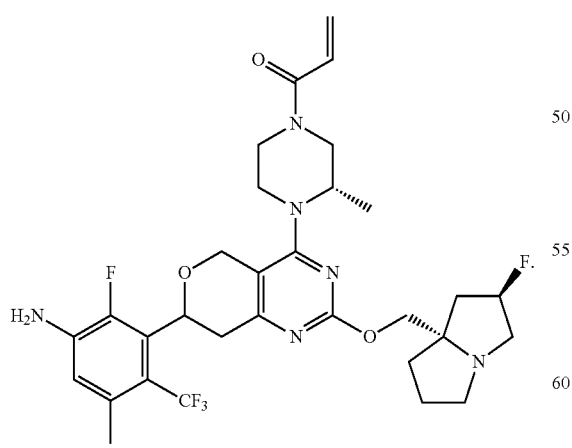
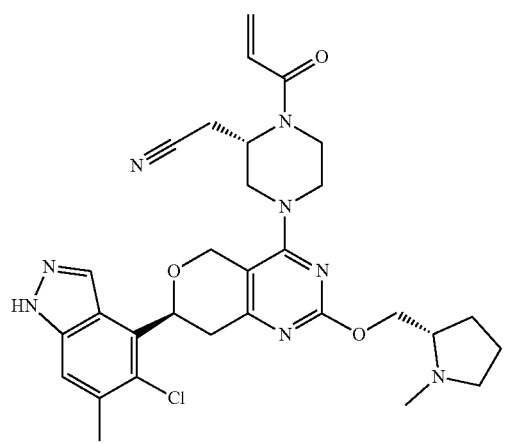
In some embodiments of the present disclosure, disclosed is the above compound or a pharmaceutically acceptable salt thereof, wherein the compound is selected from, 29
-continued
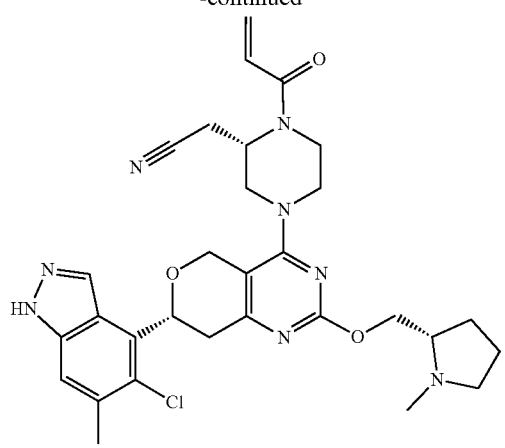
30
-continued
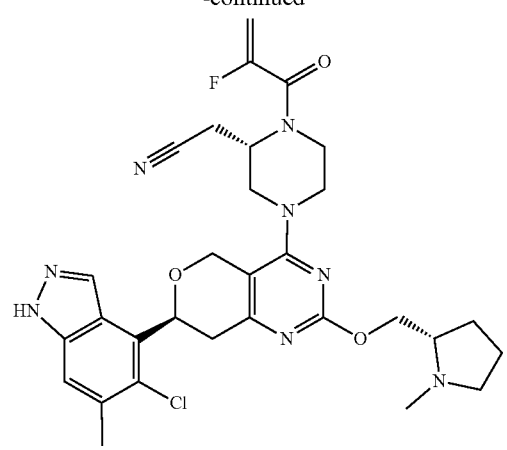
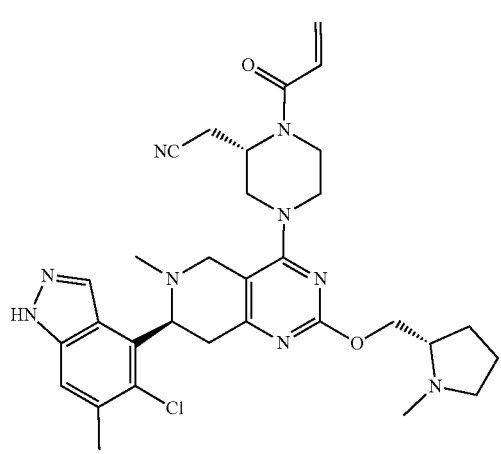
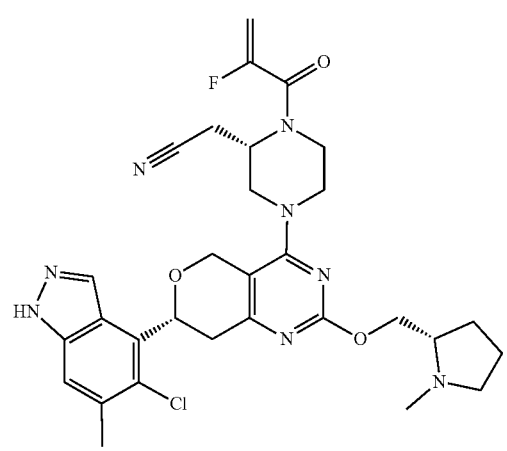
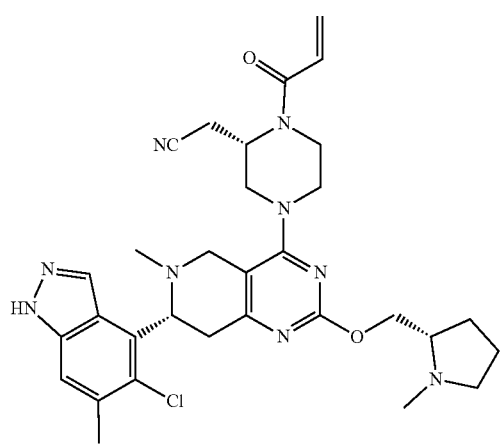
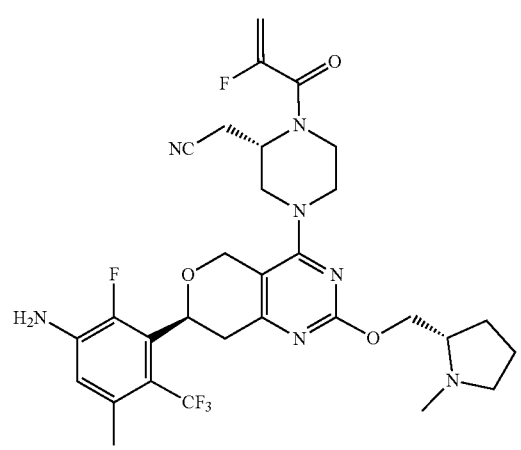

31
-continued
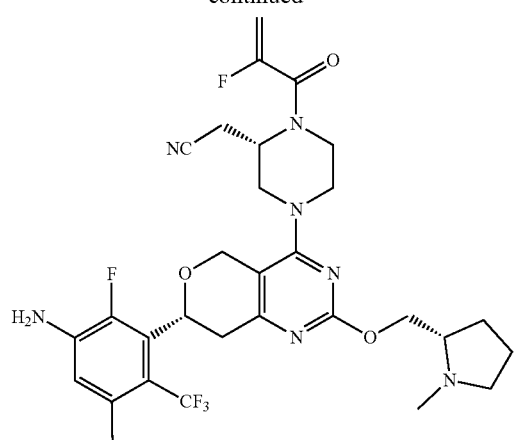
32
-continued
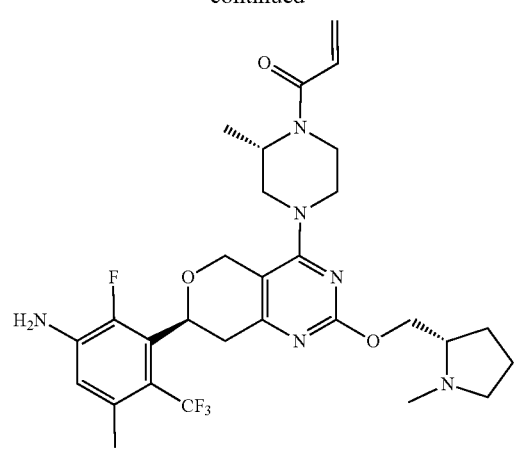
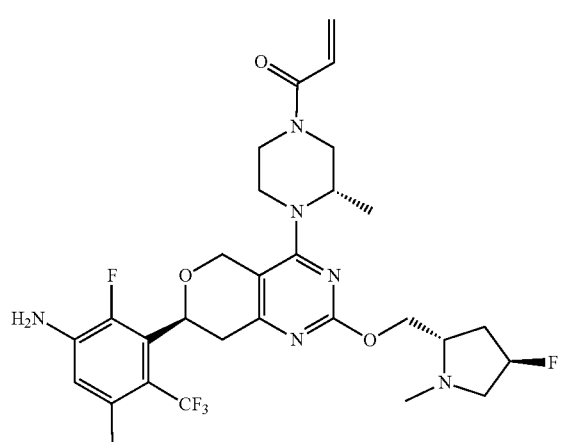
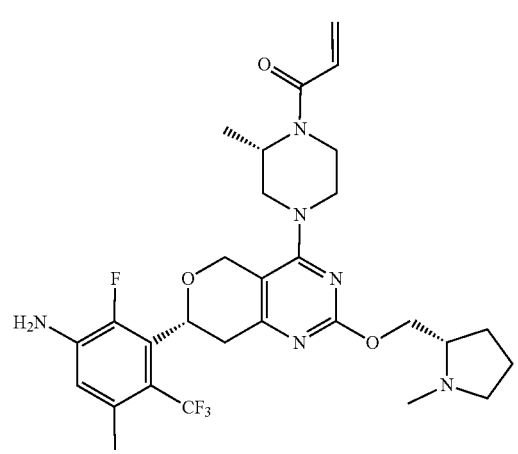
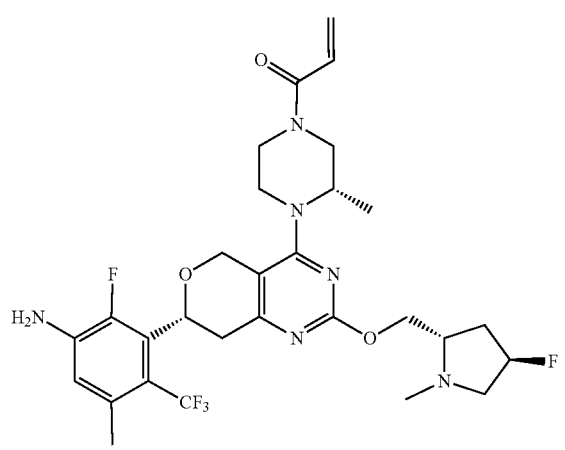
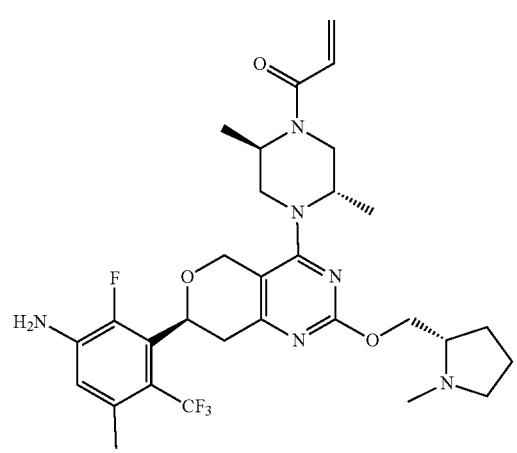

-continued
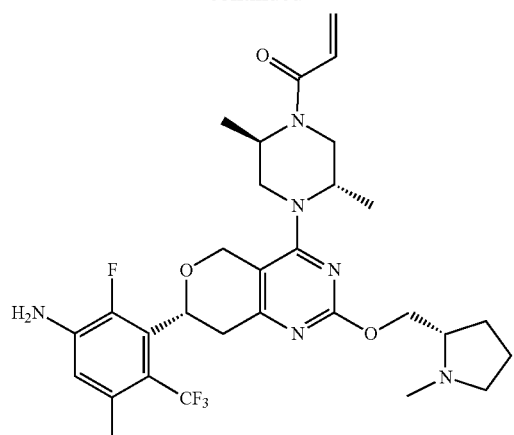
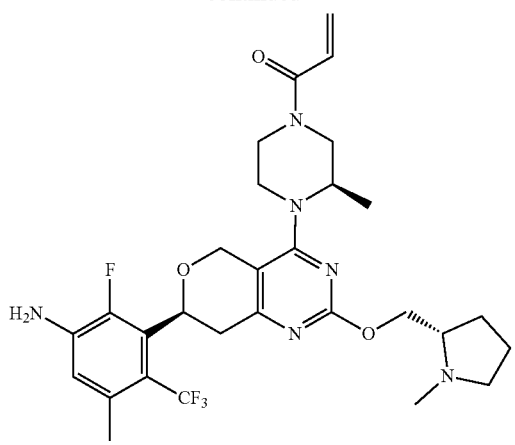
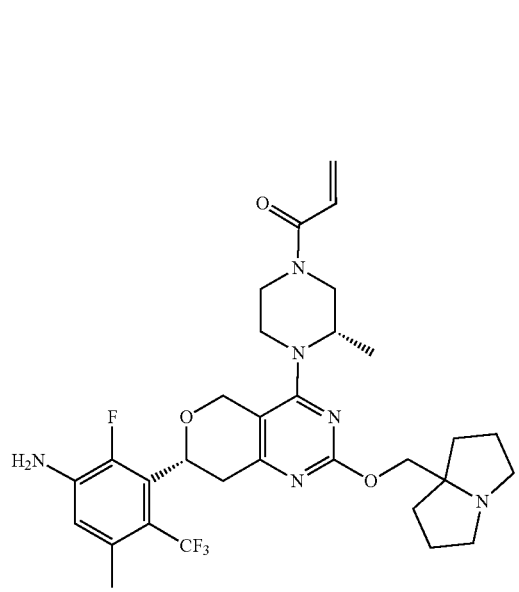
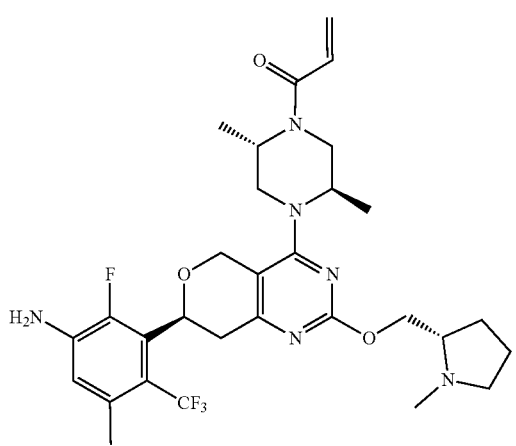

35
-continued
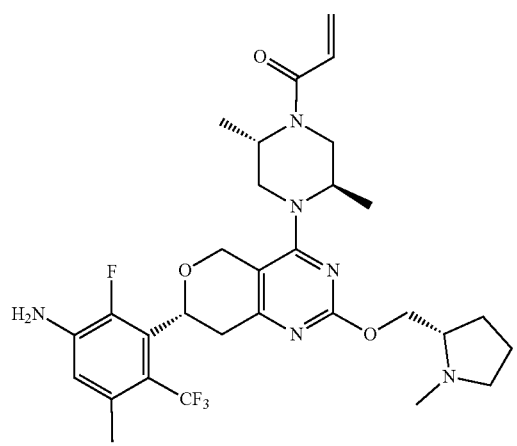
36
-continued
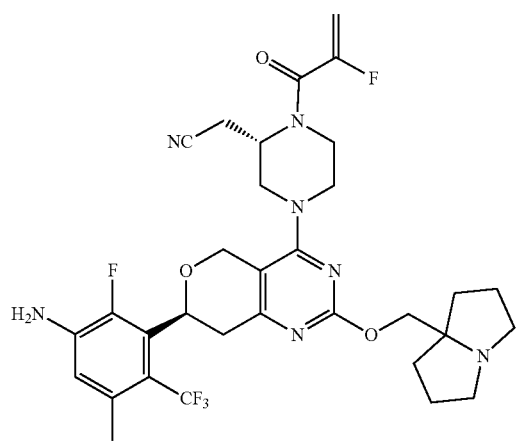
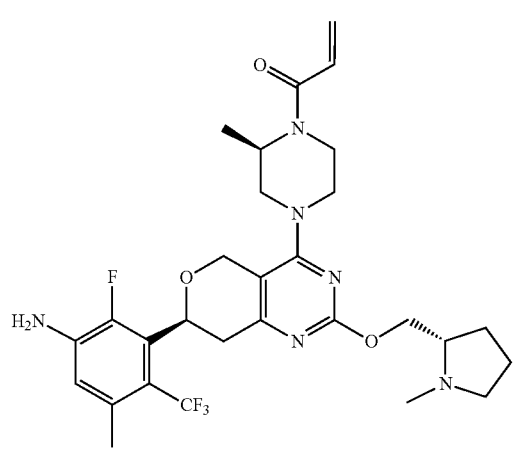
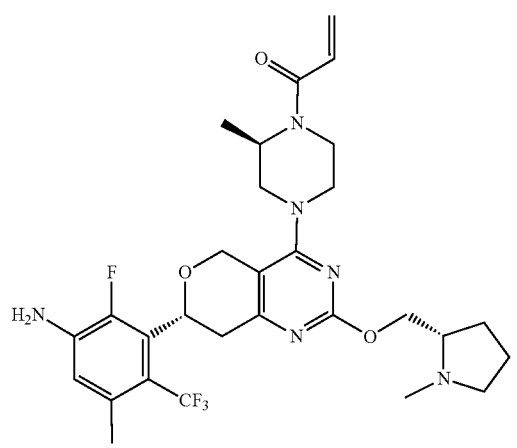

37
-continued
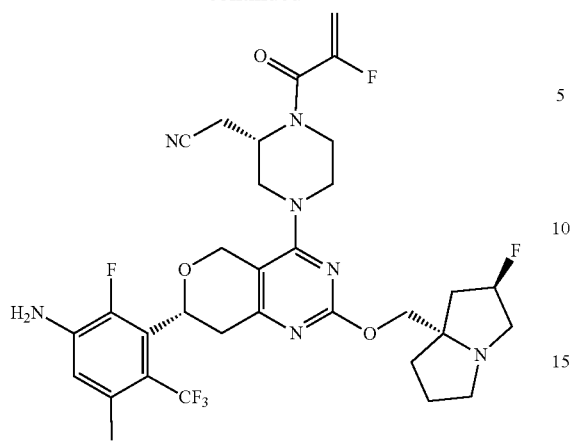
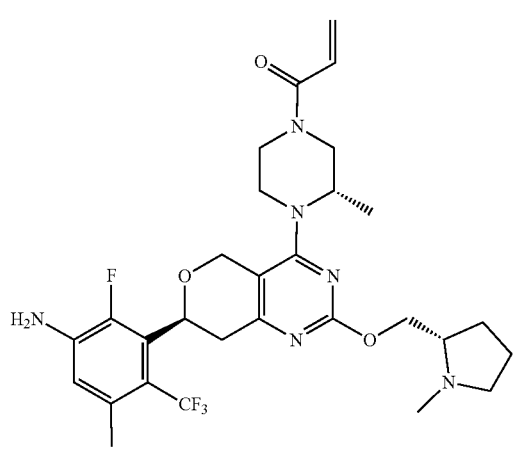
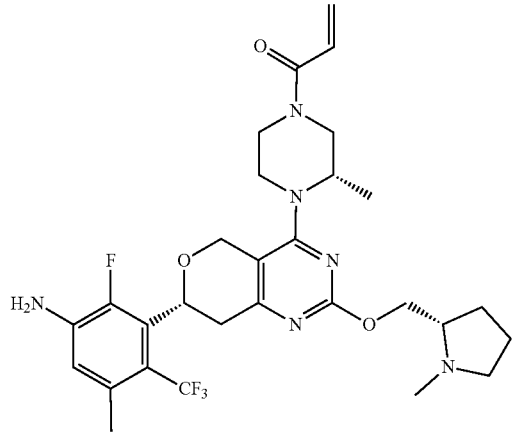
38
-continued
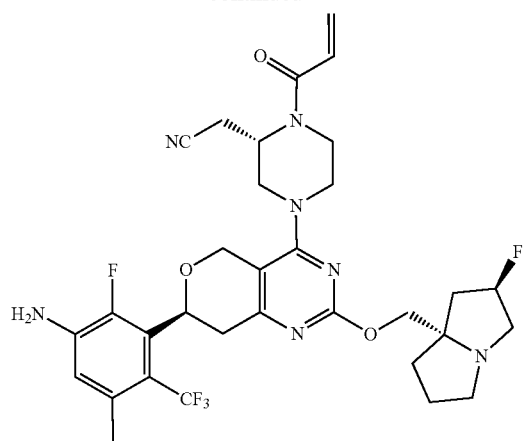
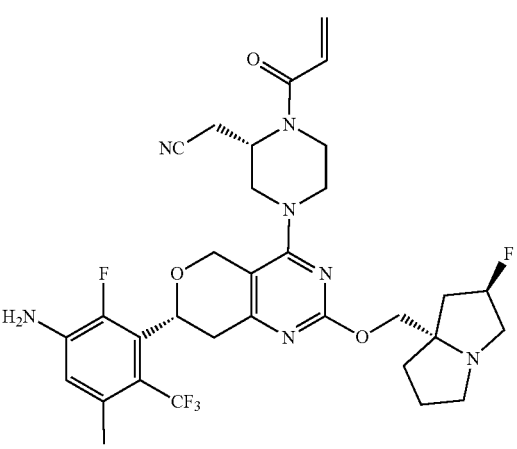
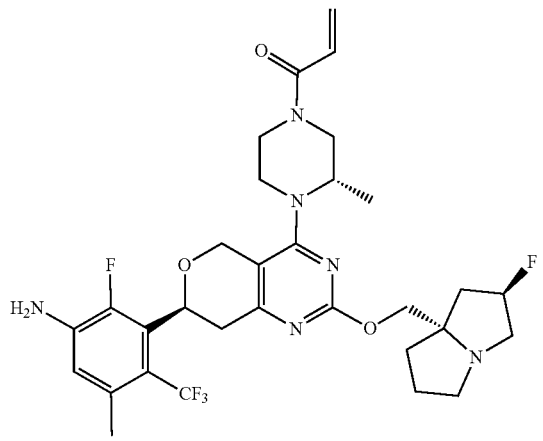

-continued

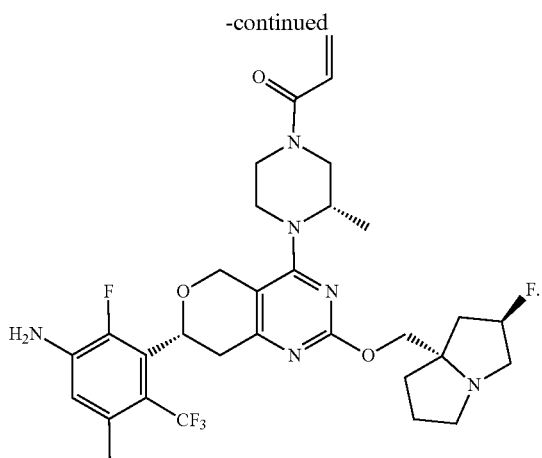

The present disclosure also provides use of the above compound or a pharmaceutically acceptable salt thereof in the manufacture of a medicament for treating diseases related to KRASG12C mutant protein.

Technical Effect

The compounds of the present disclosure have good cell proliferation inhibitory activity on KRASG12C-mutated MIA-PA-CA-2 cell line and NCI-H358 cells. The compounds of the present disclosure have good stability in liver microsomes, hepatocytes, plasma and whole blood, as well as good PK properties and significant anti-tumor effect.

Related Definitions

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Compounds disclosed herein may contain an unnatural proportion of atomic isotopes at one or more of the atoms that make up the compounds. For example, a compound may be labeled with a radioisotope such as tritium ($^{3}H$), iodine-125 ($^{125}I$) or C-14 ($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means that one or more than one hydrogen atoms on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of variables is a single bond, it means that the two groups linked by the single bond are connected directly. For example, when L in A-L-Z represents a single bond, the structure of A-L-Z is actually A-Z.

When an enumerated linking group does not indicate its linking direction, its linking direction is arbitrary. For example, when the linking group L in

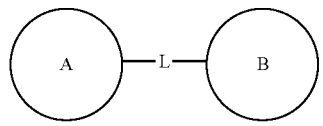

is -M-W—, the -M-W— can be linked to the ring A and the ring B in the same direction as the reading order from left to right to constitute

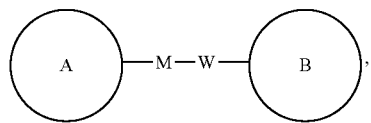

or can be linked to the ring A and the ring B in the reverse direction as the reading order from left to right to constitute

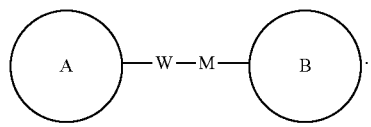

A combination of the linking groups, substituents and/or variants thereof is allowed only when such combination can result in a stable compound.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atom(s) is connected to the chemical bond, the number of H atom(s) at this site will correspondingly decrease as the number of the connected chemical bond increases, and the group will become a group of corresponding valence. The chemical bond between the site and other groups can be represented by a straight solid bond ( ), a straight dashed bond ( ), or a wavy line (  ). For example, the straight solid bond in —OCH$_3$ indicates that the group is connected to other groups through the oxygen atom in the group; the straight dashed bond in indicates that the group is connected to other groups through two ends of the nitrogen atom in the group; the wavy line in

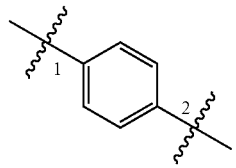 [SMILES: *c1ccc(*)cc1]

indicates that the group is connected to other groups through the 1- and 2-carbon atoms in the phenyl group;

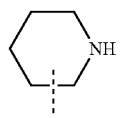

indicates that any connectable site on the piperidinyl group can be connected to other groups through one chemical bond, including at least four connection ways,

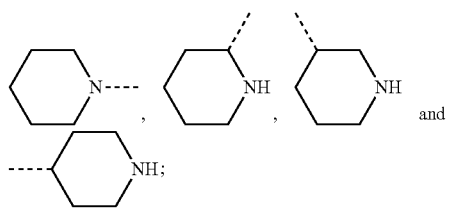

even if a H atom is drawn on —N—,

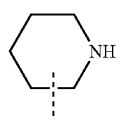

still includes the connection way of

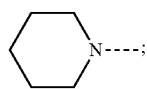

it's just that when one chemical bond is connected, the H at this site will be reduced by one, and the group will become the corresponding monovalent piperidinyl group.

Unless otherwise specified, a wedged solid bond ( ) and a wedged dashed bond ( ) indicate the absolute configuration of a stereocenter; a straight solid bond ( ) and a straight dashed bond ( ) indicate the relative configuration of a stereocenter; a wavy line ( ) indicates a wedged solid bond ( ) or a wedged dashed bond ( ); or a wavy line ( ) indicates a straight solid bond ( ) and a straight dashed bond ( ). For example,

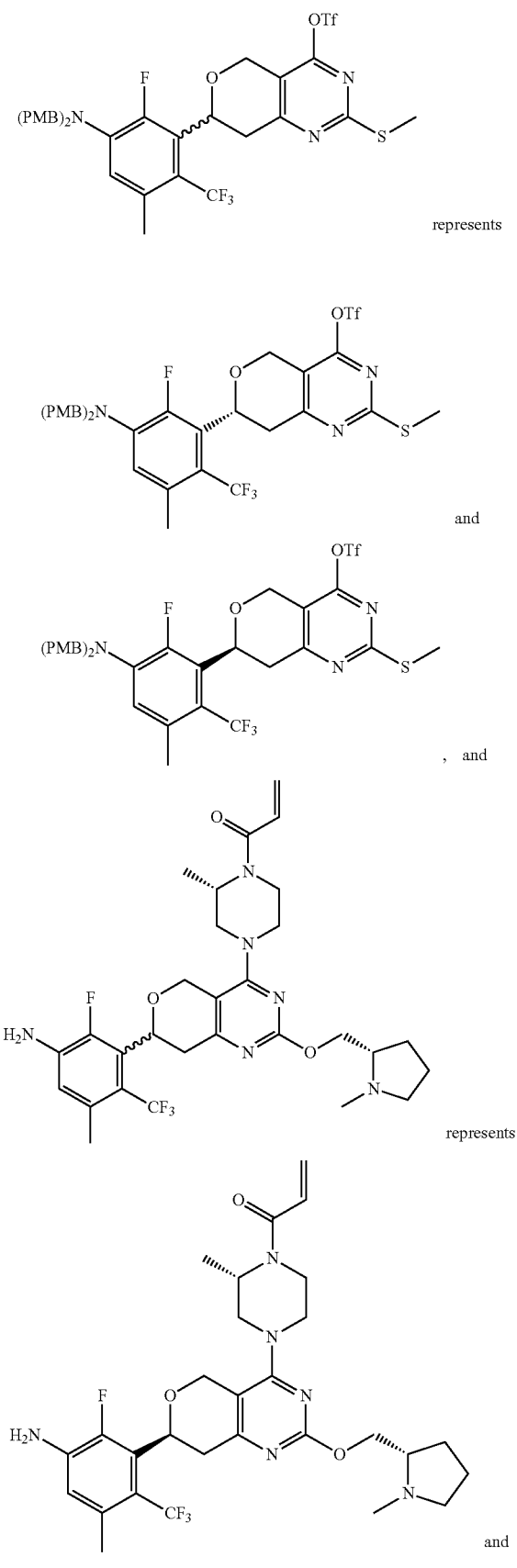

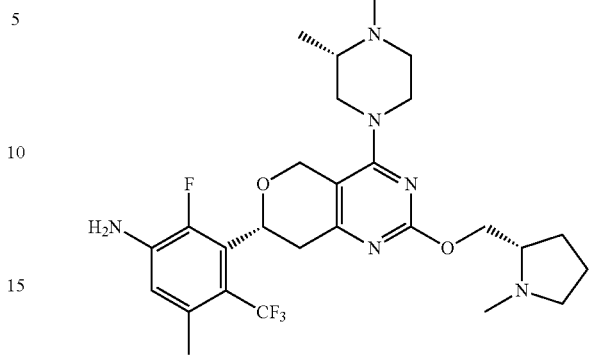

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to afford the pure enantiomer. In addition, the enantiomer and the diastereoisomer are generally isolated through chromatography which uses a chiral stationary phase and optionally combines with a chemical derivative method (for example, carbamate generated from amine).

Unless otherwise specified, the term "$C_{1-6}$ alkyl" is used to represent a linear or branched saturated hydrocarbon group composed of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc. It may be monovalent (such as methyl), divalent (such as methylene) or multivalent (such as methenyl). Examples of the $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "$C_{1-3}$ alkyl" is used to represent a linear or branched saturated hydrocarbon group composed of 1 to 3 carbon atoms. The $C_{1-3}$ alkyl includes $C_{1-2}$ alkyl, $C_{2-3}$ alkyl, etc. It may be monovalent (such as methyl), divalent (such as methylene) or multivalent (such as methenyl). Examples of the $C_{1-3}$ alkyl include, but are not limited to, methyl (Me), ethyl (Et), propyl (including n-propyl and isopropyl), and the like.

Unless otherwise specified, the term "$C_{1-3}$ alkoxy" means alkyl groups containing 1 to 3 carbon atoms and attached to the remainder of a molecule by an oxygen atom. The $C_{1-3}$ alkoxy group includes $C_{1-2}$, $C_{2-3}$, $C_3$, and $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, the term "$C_{1-3}$ alkylamino" means alkyl groups containing 1 to 3 carbon atoms and attached to the remainder of a molecule by an amino group. The $C_{1-3}$ alkylamino group includes $C_{1-2}$, $C_3$ and $C_2$ alkylamino groups and the like. Examples of $C_{1-3}$ alkylamino groups include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, and the like.

Unless otherwise specified, "$C_{2-3}$ alkenyl" is used to represent a linear or branched hydrocarbon group composed of 2 to 3 carbon atoms containing at least one carbon-carbon double bond, wherein the carbon-carbon double bond can be located at any position of the group. The $C_{2-3}$ alkenyl includes $C_3$ and $C_2$ alkenyl. The $C_{2-3}$ alkenyl may be monovalent, divalent or multivalent. Examples of the $C_{2-3}$ alkenyl include, but are not limited to, vinyl, propenyl, and the like.

Unless otherwise specified, "$C_{2-3}$ alkynyl" is used to represent a linear or branched hydrocarbon group composed of 2 to 3 carbon atoms containing at least one carbon-carbon triple bond, wherein the carbon-carbon triple bond can be located at any position of the group. The $C_{2-3}$ alkynyl includes $C_3$ and $C_2$ alkynyl. Examples of the $C_{2-3}$ alkynyl include, but are not limited to, ethynyl, propynyl, and the like.

Unless otherwise specified, the terms "$C_{6-10}$ aromatic ring" and "$C_{6-10}$ aryl" may be used interchangeably in this disclosure. The term "$C_{6-10}$ aromatic ring" or "$C_{6-10}$ aryl" means a cyclic hydrocarbon group having a conjugated pi electron system and composed of 6 to 10 carbon atoms. It may be a monocyclic, fused bicyclic or fused tricyclic ring system, wherein each ring is aromatic. It may be monovalent, divalent or multivalent. The $C_{6-10}$ aryl includes $C_{6-9}$, $C_9$, $C_{10}$ and $C_6$ aryl, etc. Examples of $C_{6-10}$ aryl include, but are not limited to, phenyl, naphthyl (including 1-naphthyl and 2-naphthyl, etc.).

Unless otherwise specified, the terms "5- to 10-membered heteroaromatic ring" and "5- to 10-membered heteroaryl" may be used interchangeably. The term "5- to 10-membered heteroaryl" means a cyclic group having a conjugated pi electron system and composed of 5 to 10 ring atoms, in which 1, 2, 3 or 4 ring atoms are heteroatoms independently selected from O, S and N, and the remainder is carbon atoms. It may be a monocyclic, fused bicyclic or fused tricyclic ring system, wherein each ring is aromatic, and wherein the nitrogen atom is optionally quaternized and the nitrogen and sulfur heteroatoms are optionally oxidized (i.e., NO and S(O)$_p$, p is 1 or 2). A 5- to 10-membered heteroaryl can be attached to the remainder of the molecule through a heteroatom or a carbon atom. The 5- to 10-membered heteroaryl group includes 5- to 8-membered, 5- to 7-membered, 5- to 6-membered, 5-membered and 6-membered heteroaryl groups. Examples of the 5-10 membered heteroaryl include, but are not limited to, pyrrolyl (including N-pyrrolyl, 2-pyrrolyl, 3-pyrrolyl, and the like), pyrazolyl (including 2-pyrazolyl and 3-pyrazolyl, and the like), imidazolyl (including N-imidazolyl, 2-imidazolyl, 4-imidazolyl, and 5-imidazolyl, and the like), oxazolyl (including 2-oxazolyl, 4-oxazolyl, and 5-oxazolyl, and the like), triazolyl (1H-1,2,3-triazolyl, 2H-1,2,3-triazolyl, 1H-1,2,4-triazolyl and 4H-1,2,4-triazolyl, and the like), tetrazolyl, isoxazolyl (3-isoxazolyl, 4-isoxazolyl and 5-isoxazolyl, and the like), thiazolyl (including 2-thiazolyl, 4-thiazolyl and 5-thiazolyl, and the like), furyl (including 2-furyl and 3-furyl, and the like), thienyl (including 2-thienyl and 3-thienyl, and the like), pyridyl (including 2-pyridyl, 3-pyridyl and 4-pyridyl, and the like), pyrazinyl or pyrimidinyl (including 2-pyrimidinyl and 4-pyrimidinyl, and the like), benzothiazolyl (including 5-benzothiazolyl, and the like), purinyl, benzimidazolyl (including 2-benzimidazolyl, and the like), benzoxazolyl, indolyl (including 5-indolyl, and the like), isoquinolyl (including 1-isoquinolyl, 5-isoquinolyl, and the like), quinoxalinyl (including 2-quinoxalinyl, 5-quinoxalinyl, and the like) or quinolyl (including 3-quinolyl, 6-quinolyl, and the like).

Unless otherwise specified, the term "4- to 8-membered heterocycloalkyl" alone or in combination with other terms respectively represents a saturated cyclic group composed of 4 to 8 ring atoms, in which 1, 2, 3 or 4 ring atoms are heteroatoms independently selected from O, S and N, and the remainder is carbon atoms, wherein the nitrogen atom is optionally quaternized, and the nitrogen and sulfur heteroatoms are optionally oxidized (i.e., NO and S(O)$_p$, p is 1 or 2). The ring comprises monocyclic and bicyclic ring systems, wherein the bicyclic ring systems comprise spiro, fused, and bridged cyclic rings. In addition, with respect to the "4- to 8-membered heterocycloalkyl", the heteroatom may be present on the position of attachment of the heterocycloalkyl group to the remainder of a molecule. The 4- to 8-membered heterocycloalkyl includes 4-6 membered, 5-6 membered, 4 membered, 5 membered, and 6 membered heterocycloalkyl, etc. Examples of the 4- to 8-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxanyl, dithianyl, isoxazolidinyl, isothiazolidinyl, 1,2-oxazinyl, 1,2-thiazinyl, hexahydropyridazinyl, homopiperazinyl, homopiperidinyl or dioxepanyl, and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc.; similarly, n membered to n+m membered indicates that the number of atoms on a ring is n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, also includes any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring, and the like.

The term "leaving group" refers to a functional group or atom which can be replaced by another functional group or atom through a substitution reaction (such as nucleophilic substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Solvents used in the present disclosure are commercially available.

Compounds are named according to general naming principles in the art or by ChemDraw® software, and commercially available compounds are named with their vendor directory names.

DETAILED DESCRIPTION OF THE INVENTION

Figure 1:
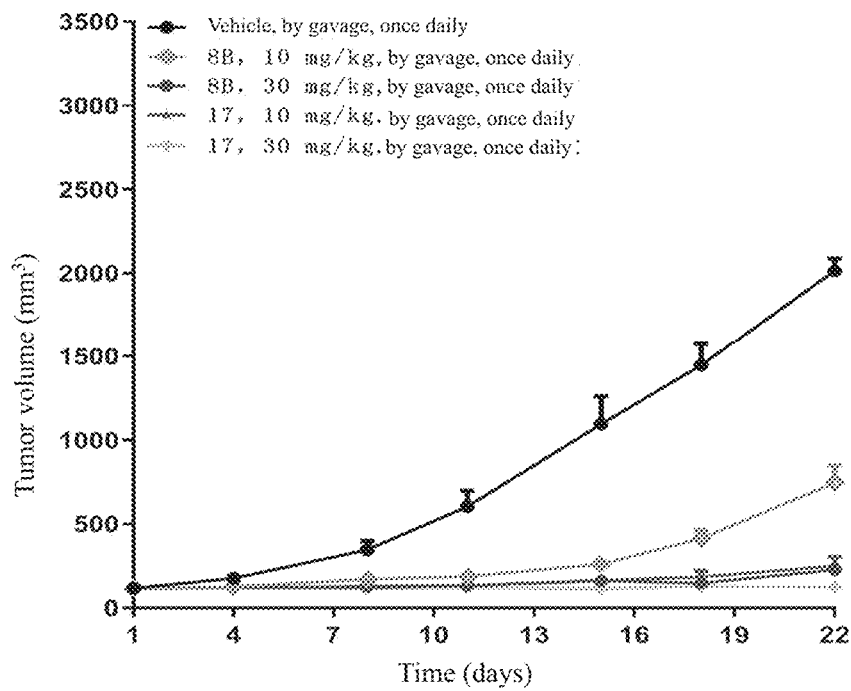
FIG. 1 shows changes in tumor volume over time at different doses.

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Example 1

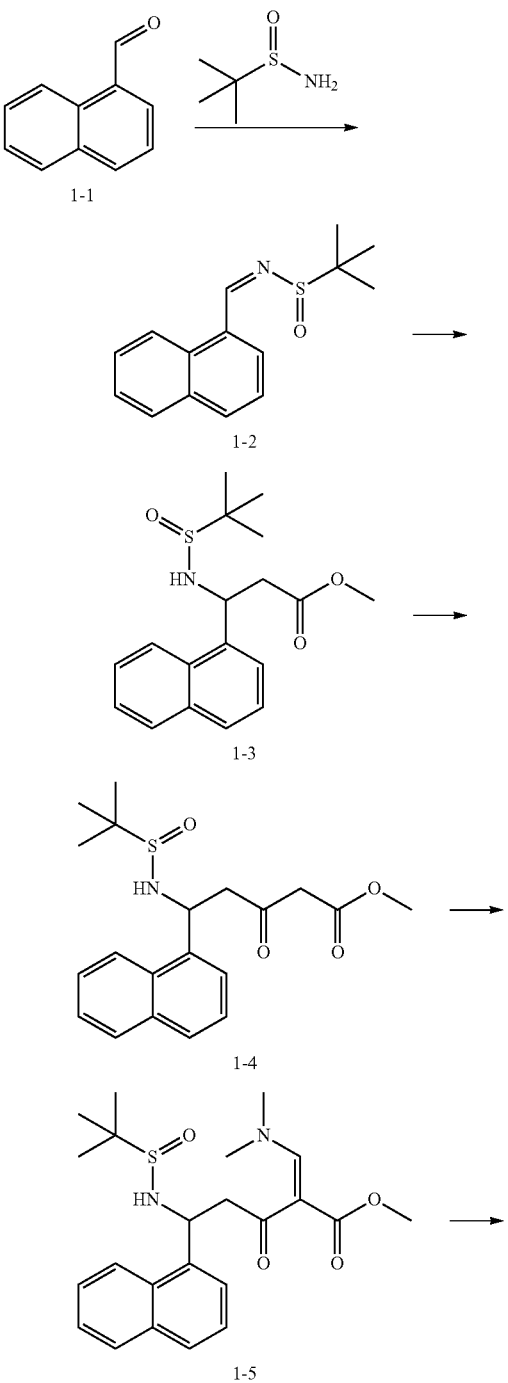

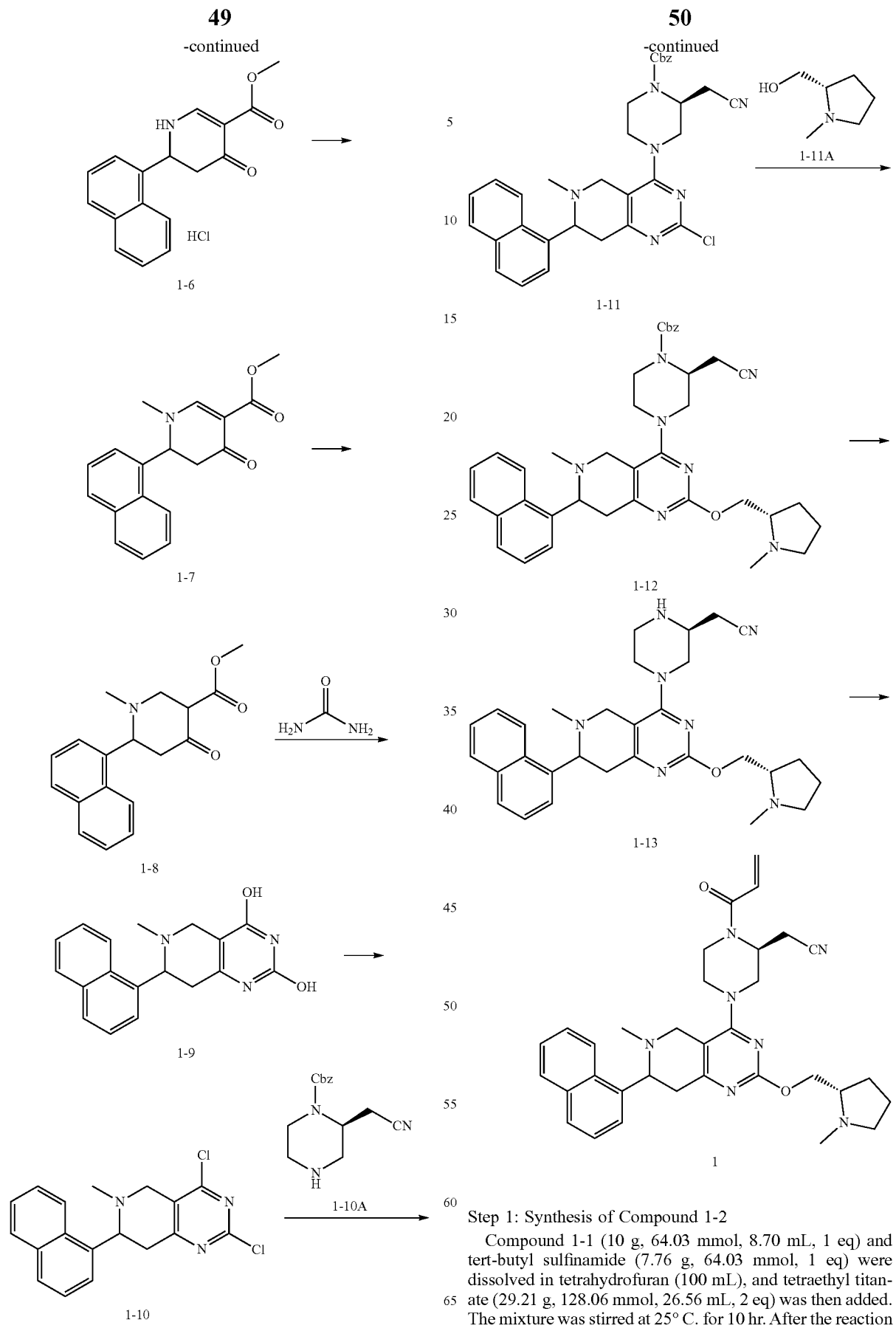
Step 1: Synthesis of Compound 1-2
Compound 1-1 (10 g, 64.03 mmol, 8.70 mL, 1 eq) and tert-butyl sulfinamide (7.76 g, 64.03 mmol, 1 eq) were dissolved in tetrahydrofuran (100 mL), and tetraethyl titanate (29.21 g, 128.06 mmol, 26.56 mL, 2 eq) was then added. The mixture was stirred at 25° C. for 10 hr. After the reaction was completed, 10 g of ice was added under an ice-water bath and a large amount of solid was precipitated. Then tetrahydrofuran (100 mL) was added, and the mixture was filtered. The filtrate was collected and concentrated to give compound 1-2, which was directly used in the next reaction step. $^1$H NMR (400 MHz, CDCl$_3$) δ=9.17 (s, 1H), 9.05 (d, J=8.5 Hz, 1H), 8.05 (dd, J=7.9, 10.8 Hz, 2H), 7.94 (d, J=8.1 Hz, 1H), 7.72-7.63 (m, 1H), 7.59 (t, J=7.6 Hz, 2H), 1.34 (s, 9H); LCMS m/z=260.1 [M+1]$^+$.

Step 2: Synthesis of Compound 1-3

Methyl acetate (4.28 g, 57.83 mmol, 4.60 mL, 1.5 eq) was dissolved in tetrahydrofuran (100 mL) and the mixture was cooled down to −78° C. under nitrogen. Lithium hexamethyldisilazide (1 M, 59.76 mL, 1.55 eq) was added slowly dropwise to the reaction solution. After stirring at −78° C. for 1 hr, compound 1-2 (10 g, 38.56 mmol, 1 eq) was added slowly dropwise to the reaction solution and the mixture was stirred at this temperature for another 1 hr. After the reaction was completed, the reaction solution was poured into saturated aqueous ammonium chloride solution (80 mL) and extracted with ethyl acetate (50 mL×3). The organic phases were combined, washed with saturated brine, dried over anhydrous sodium sulfate, and filtered. The filtrate was collected and concentrated. The crude product was purified by column chromatography (petroleum ether/ethyl acetate=50/1-1/1) to give compound 1-3. $^1$H NMR (400 MHz, CDCl$_3$) δ=8.17 (d, J=8.4 Hz, 1H), 7.89 (d, J=8.0 Hz, 1H), 7.82 (d, J=8.0 Hz, 1H), 7.57 (t, J=6.8 Hz, 2H), 7.54-7.52 (m, 1H), 7.52-7.44 (m, 2H), 4.78 (d, J=2.4 Hz, 1H), 3.69 (s, 3H), 3.09 (d, J=6.4 Hz, 2H), 1.25-1.22 (s, 9H); LCMS m/z=334.1 [M+1]$^+$.

Step 3: Synthesis of Compound 1-4

Compound methyl acetate (5.55 g, 74.98 mmol, 5.96 mL, 5 eq) was dissolved in tetrahydrofuran (50 mL) and the mixture was cooled down to −78° C. under nitrogen. Sodium hexamethyldisilazide (1 M, 74.98 mL, 5 eq) was added to the reaction solution. After stirring at −78° C. for 1 hr, compound 1-3 (5 g, 15.00 mmol, 1 eq) was added slowly dropwise to the reaction solution and the mixture was stirred at this temperature for another 1 hr. After the reaction was completed, the reaction solution was poured into saturated aqueous ammonium chloride solution (50 mL) and extracted with ethyl acetate (50 mL×3). The organic phases were combined, washed with saturated brine (50 mL), dried over anhydrous sodium sulfate, and filtered. The filtrate was collected and concentrated to give compound 1-4, which was directly used in the next reaction step. LCMS m/z=376.1 [M+1]$^+$.

Step 4: Synthesis of Compound 1-5

Compound 1-4 (5 g, 13.32 mmol, 11.92 mL, 1 eq) was dissolved in toluene (50 mL) and N,N-dimethylformamide dimethyl acetal (15.87 g, 133.16 mmol, 17.69 mL, 10 eq) was added and the mixture was stirred to react at 19° C. for 10 hr. After the reaction was completed, the reaction solution was poured into saturated aqueous ammonium chloride solution (80 mL) and extracted with ethyl acetate (50 mL×3). The organic phases were combined, washed with saturated brine (50 mL), dried over anhydrous sodium sulfate, and filtered. The filtrate was collected and concentrated. The crude product was purified by column chromatography (dichloromethane/methanol=100/1-10/1) to give compound 1-5. LCMS m/z=431.1 [M+1]$^+$.

Step 5: Synthesis of Compound 1-6:

Compound 1-5 (2.4 g, 5.57 mmol, 1 eq) was dissolved in hydrochloride/dioxane (4 M, 60.00 mL) and the mixture was stirred at 18° C. for 10 hr. After the reaction was completed, the reaction solution was directly concentrated to give the hydrochloride salt of compound 1-6, which was directly used in the next reaction step. LCMS m/z=282.1 [M+1]$^+$.

Step 6: Synthesis of Compound 1-7

Compound 1-6 hydrochloride (2 g, 6.29 mmol, 1 eq) was dissolved in N,N-dimethylformamide (20 mL), and then potassium carbonate (6.15 g, 18.88 mmol, 3 eq) and iodomethane (1.79 g, 12.59 mmol, 783.65 μL, 2 eq) were added sequentially and stirred at 18° C. for 10 h. After the reaction was completed, the reaction solution was poured into water (30 mL) and extracted with ethyl acetate (30 mL×2). The combined organic phase was washed with saturated brine (50 mL), dried over anhydrous sodium sulfate, and filtered. The filtrate was concentrated to give a crude product. The crude product was purified by column chromatography (dichloromethane/methanol=50/1-10/1) to give compound 1-7. $^1$H NMR (400 MHz, CDCl$_3$) δ=8.47 (s, 1H), 7.96-7.88 (m, 2H), 7.85 (d, J=8.4 Hz, 1H), 7.62-7.51 (m, 2H), 7.48-7.41 (m, 1H), 7.35 (d, J=7.0 Hz, 1H), 5.52-5.39 (m, 1H), 3.83 (s, 3H), 3.19 (s, 3H), 3.23-3.14 (m, 1H), 2.98-2.87 (m, 1H).

Step 7: Synthesis of Compound 1-8

Compound 1-7 (20 mg, 67.72 μmol, 1 eq) was dissolved in ethanol (0.2 mL) and 1,4-dioxane (1 mL). Nickel chloride hexahydrate (19.32 mg, 81.26 μmol, 1.2 eq) was then added. After cooling down to 5-10° C., sodium borohydride (1.28 mg, 33.86 μmol, 0.5 eq) was added and the mixture was reacted at 10° C. for 0.5 h. After the reaction was completed, the mixture was poured into saturated aqueous ammonium chloride solution (5 mL) and extracted with ethyl acetate (10 mL×2). The combined organic phase was washed with saturated brine (5 mL), dried over anhydrous sodium sulfate, and filtered. The filtrate was concentrated to give a crude product. The crude product was purified by thin-layer chromatography preparative plate (developer: petroleum ether/ethyl acetate=3/1) to give compound 1-8. $^1$H NMR (400 MHz, CDCl$_3$) δ=11.99-11.85 (m, 1H), 8.67-8.49 (m, 1H), 7.92-7.85 (m, 1H), 7.85-7.77 (m, 1H), 7.57-7.41 (m, 4H), 3.82 (s, 3H), 3.56-3.51 (m, 1H), 3.16-2.95 (m, 2H), 2.68-2.47 (m, 1H), 2.15 (s, 3H).

Step 8: Synthesis of Compound 1-9

Compound 1-8 (240 mg, 807.14 μmol, 1 eq) and urea (242.36 mg, 4.04 mmol, 216.40 μL, 5 eq) were dissolved in ethanol (5 mL) and sodium methoxide (130.80 mg, 2.42 mmol, 3 eq) was added. After reacting at 85° C. for 10 hr, the reaction solution was slowly poured into water and then ethyl acetate (5 mL) was added. Solids were precipitated. The mixture was filtered, and the solid was collected to give compound 1-9. LCMS m/z=308.1 [M+1]$^+$.

Step 9: Synthesis of Compound 1-10

Compound 1-9 (400 mg, 1.30 mmol, 1 eq) was dissolved in phosphorus oxychloride (132.00 g, 860.89 mmol, 80 mL). The mixture was heated to 105° C. to react for 10 h and then concentrated under reduced pressure to remove the excess phosphorus oxychloride. The residue was dissolved in ethyl acetate (50 mL) and the solution was then added to saturated aqueous sodium bicarbonate solution (20 mL). The aqueous phase was extracted with ethyl acetate (50 mL×3). The combined organic phase was washed with saturated brine (50 mL), dried over anhydrous sodium sulfate, and filtered. The filtrate was concentrated to give a crude product. The crude product was purified by thin layer chromatography column (eluent: petroleum ether/ethyl acetate=20/1-0/1) to give compound 1-10. LCMS m/z=344.0 [M+1]$^+$.

Step 10: Synthesis of Compound 1-11

Compound 1-10 (250 mg, 726.24 μmol, 1 eq) and intermediate 1-10A hydrochloride (279.24 mg, 944.12 μmol, 1.3 eq) were dissolved in isopropanol (2 mL), and N,N-diisopropylethylamine (375.44 mg, 2.90 mmol, 505.98 μL, 4 eq) was added. After reacting at 110° C. for 12 hr, the reaction solution was concentrated directly. The residue was purified by column chromatography (eluent: petroleum ether/ethyl acetate=10/1-1/1) to give compound 1-11. $^1$H NMR (400 MHz, CDCl$_3$) δ=8.60-8.48 (m, 1H), 7.93-7.87 (m, 1H), 7.86-7.80 (m, 1H), 7.58-7.34 (m, 9H), 5.21 (m, 2H), 4.77-4.61 (m, 1H), 4.06 (m, 2H), 3.97-3.75 (m, 2H), 3.62-3.40 (m, 3H), 3.30-3.00 (m, 4H), 2.78-2.64 (m, 1H), 2.26 (s, 1.5H), 2.21 (s, 1.5H); LCMS m/z=567.3 [M+1]$^+$.

Step 11: Synthesis of Compound 1-12

Compound 1-11 (100 mg, 176.34 μmol, 1 eq) and 1-11A (60.93 mg, 529.03 μmol, 62.81 μL, 3 eq) were dissolved in 1,4-dioxane (1.5 mL), and cesium carbonate (172.37 mg, 529.03 μmol, 3 eq), 2-dicyclohexylphosphino-2',6'-diisopropoxy-1,1'-biphenyl (16.46 mg, 35.27 μmol, 0.2 eq) and tris(dibenzylideneacetone)dipalladium (32.30 mg, 35.27 μmol, 0.2 eq) were added. The mixture was reacted at 90° C. under nitrogen for 24 hr. After the reaction was completed, the reaction mixture was concentrated directly. The residue was purified by column chromatography (eluent: dichloromethane/methanol=100/1-10/1) to give compound 1-12. LCMS m/z=646.4 [M+1]$^+$.

Step 12: Synthesis of Compound 1-13

Compound 1-12 (50 mg, 77.42 μmol, 1 eq) was dissolved in tetrahydrofuran (50 mL) and Pd/C (77.4 mg, 10% purity) was added. The reaction system was replaced three times with H$_2$. The mixture was stirred to react at 15 psi, 20° C. for 10 h. After the reaction was completed, the mixture was filtered to give a tetrahydrofuran solution of compound 1-13 (70 mL), which was used directly in the next step. LCMS m/z=512.3 [M+1]$^+$.

Step 13: Synthesis of Compound 1

To the tetrahydrofuran solution of compound 1-13 (70 mL) obtained in the previous step was added N,N-diisopropylethylamine (17.18 mg, 132.90 μmol, 23.15 μL, 2 eq). The mixture was then cooled down to −20 to −30° C., and acryloyl chloride (6.01 mg, 66.45 μmol, 5.42 μL, 1 eq) was added. After 30 min of reaction at this temperature, the reaction solution was poured into water (10 mL), and then extracted with ethyl acetate (10 mL). The organic phase was dried with anhydrous sodium sulfate, and filtered. The filtrate was concentrated to give a crude product. The crude product was purified by a high-performance liquid chromatography column (column: Phenomenex Luna 80*30 mm*3 μm; mobile phase: [10 mM NH$_4$HCO$_3$ aqueous solution-acetonitrile]; acetonitrile %: 30%-60%, 7 min) to give compound 1, which was consisted of two diastereomers as identified by SFC (Chiralcel OD-3 column, P1 Rt=1.93 min, P2 Rt=2.08 min, P1:P2=50.6:49.4). $^1$H NMR (400 MHz, CDCl$_3$) δ=8.66-8.53 (m, 1H), 7.93-7.87 (m, 1H), 7.82 (d, J=8.0 Hz, 1H), 7.56-7.41 (m, 4H), 6.70-6.50 (m, 1H), 6.47-6.34 (m, 1H), 5.84 (d, J=7.2 Hz, 1H), 4.38 (m, 1H), 4.27-4.09 (m, 2H), 4.05-3.78 (m, 4H), 3.60-3.35 (m, 3H), 3.23-3.01 (m, 4H), 2.84-2.60 (m, 3H), 2.50-2.41 (m, 3H), 2.30-2.21 (m, 4H), 2.10-1.98 (m, 1H), 1.90-1.66 (m, 4H). LCMS m/z=566.4 [M+1]$^+$.

Examples 2 and 3

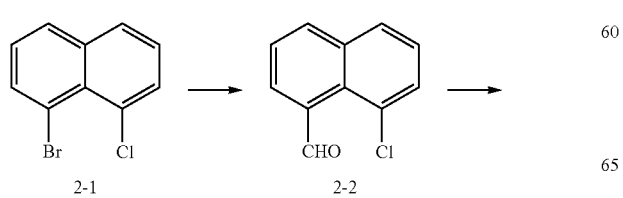

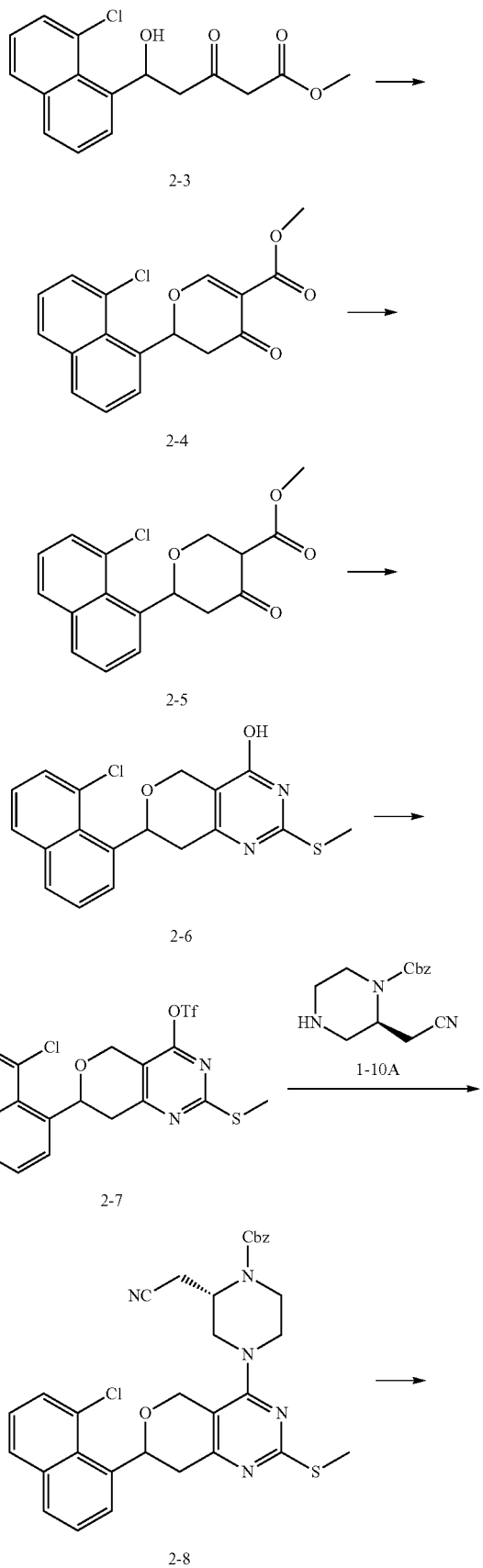

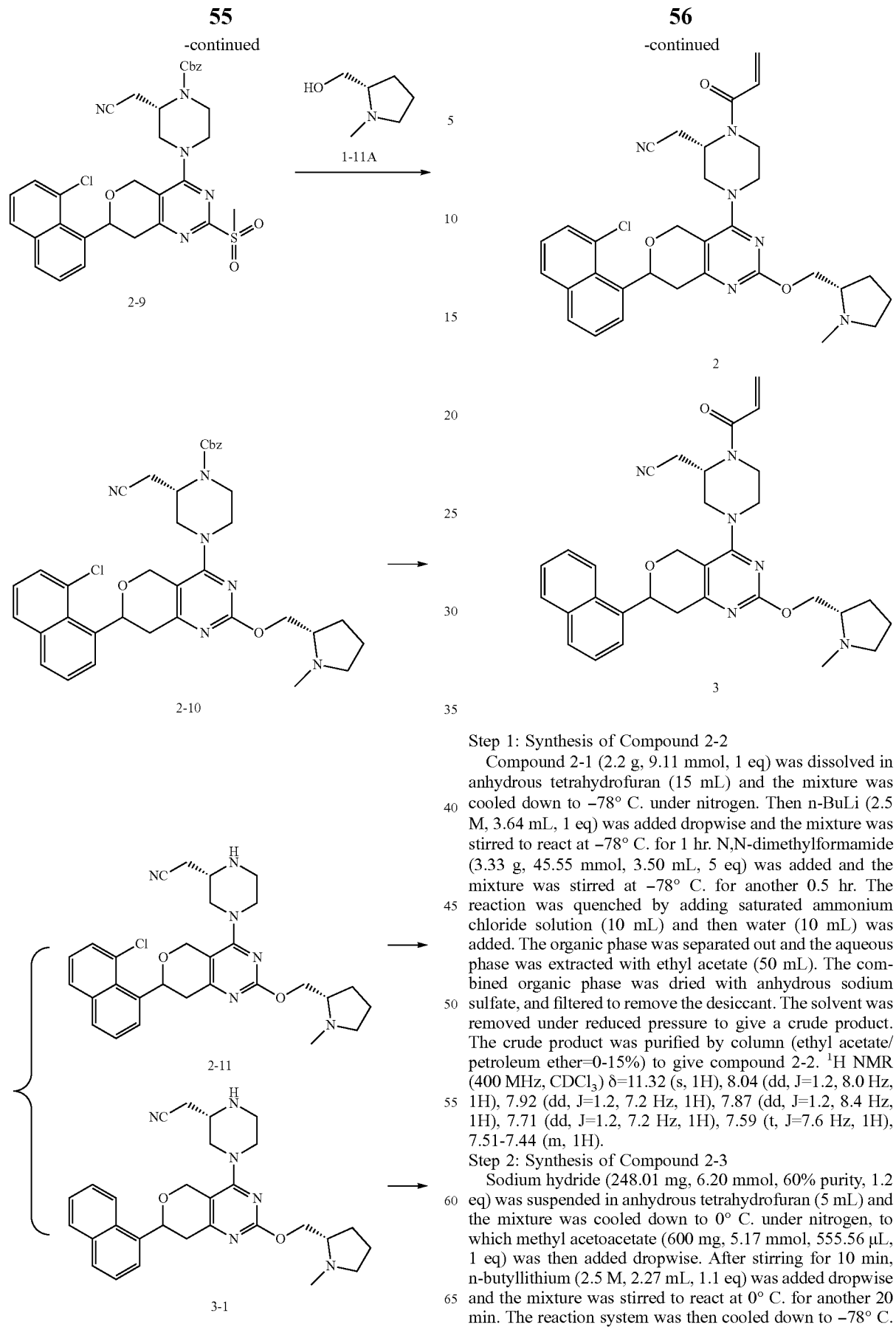

Step 1: Synthesis of Compound 2-2

Compound 2-1 (2.2 g, 9.11 mmol, 1 eq) was dissolved in anhydrous tetrahydrofuran (15 mL) and the mixture was cooled down to −78° C. under nitrogen. Then n-BuLi (2.5 M, 3.64 mL, 1 eq) was added dropwise and the mixture was stirred to react at −78° C. for 1 hr. N,N-dimethylformamide (3.33 g, 45.55 mmol, 3.50 mL, 5 eq) was added and the mixture was stirred at −78° C. for another 0.5 hr. The reaction was quenched by adding saturated ammonium chloride solution (10 mL) and then water (10 mL) was added. The organic phase was separated out and the aqueous phase was extracted with ethyl acetate (50 mL). The combined organic phase was dried with anhydrous sodium sulfate, and filtered to remove the desiccant. The solvent was removed under reduced pressure to give a crude product. The crude product was purified by column (ethyl acetate/petroleum ether=0-15%) to give compound 2-2. $^1$H NMR (400 MHz, CDCl$_3$) δ=11.32 (s, 1H), 8.04 (dd, J=1.2, 8.0 Hz, 1H), 7.92 (dd, J=1.2, 7.2 Hz, 1H), 7.87 (dd, J=1.2, 8.4 Hz, 1H), 7.71 (dd, J=1.2, 7.2 Hz, 1H), 7.59 (t, J=7.6 Hz, 1H), 7.51-7.44 (m, 1H).

Step 2: Synthesis of Compound 2-3

Sodium hydride (248.01 mg, 6.20 mmol, 60% purity, 1.2 eq) was suspended in anhydrous tetrahydrofuran (5 mL) and the mixture was cooled down to 0° C. under nitrogen, to which methyl acetoacetate (600 mg, 5.17 mmol, 555.56 μL, 1 eq) was then added dropwise. After stirring for 10 min, n-butyllithium (2.5 M, 2.27 mL, 1.1 eq) was added dropwise and the mixture was stirred to react at 0° C. for another 20 min. The reaction system was then cooled down to −78° C. in a dry ice acetone bath and a solution of compound 2-2

(1.08 g, 5.68 mmol, 1.1 eq) in tetrahydrofuran (6 mL) was added dropwise. The reaction mixture was stirred for 30 min, then allowed to warm slowly to room temperature and stirred for 30 min. The reaction was quenched by adding water (30 mL) and the aqueous phase was extracted with ethyl acetate (50 mL×2). The combined organic phase was dried with sodium sulfate, and filtered to remove the desiccant. The solvent was removed from the filtrate under reduced pressure to give a crude product. The crude product was purified by column (ethyl acetate/petroleum ether=0-20%) to give compound 2-3. $^1$H NMR (400 MHz, CDCl$_3$) δ=8.07 (d, J=7.6 Hz, 1H), 7.81 (d, J=8.0 Hz, 2H), 7.63-7.49 (m, 2H), 7.35 (t, J=8.0 Hz, 1H), 6.92 (br d, J=9.6 Hz, 1H), 3.75 (s, 3H), 3.55 (s, 2H), 3.37 (dd, J=1.6, 18.1 Hz, 1H), 3.24 (d, J=1.2 Hz, 1H), 2.86-2.77 (m, 1H).

Step 3: Synthesis of Compound 2-4

Compound 2-3 (520 mg, 1.70 mmol, 1 eq) was dissolved in dichloromethane (5 mL) and then N,N-dimethylformamide dimethylacetal (202.01 mg, 1.70 mmol, 225.20 μL, 1 eq) was added. The resulting reaction solution was stirred to react at 25° C. for 1 hr, and then Boron trifluoride etherate complex (240.60 mg, 1.70 mmol, 209.22 μL, 1 eq) was added and the reaction solution was stirred to react at 25° C. for 18 hr. The reaction solution was concentrated under vacuum and the residue was adjusted to pH of 3-4 with 2M hydrochloric acid. The mixture was then extracted with ethyl acetate (30 mL×3). The combined organic phase was concentrated under vacuum to give a crude product. The crude product was purified by column (ethyl acetate/petroleum ether=0-35%) to give compound 2-4. $^1$H NMR (400 MHz, CDCl$_3$) δ=8.56 (d, J=0.8 Hz, 1H), 7.91 (t, J=8.0 Hz, 2H), 7.85 (dd, J=1.2, 8.4 Hz, 1H), 7.65 (dd, J=1.6, 7.6 Hz, 1H), 7.59 (t, J=8.0 Hz, 1H), 7.44-7.35 (m, 2H), 3.87 (s, 3H), 3.27-3.17 (m, 1H), 2.92-2.82 (m, 1H). LCMS m/z=317.0 [M+H]$^+$.

Step 4: Synthesis of Compound 2-5

Compound 2-4 (780 mg, 2.46 mmol, 1 eq) was dissolved in tetrahydrofuran (3 mL) and the mixture was cooled down to −78° C. under nitrogen. Then lithium tri-sec-butylborohydride (1 M, 2.46 mL, 1 eq) was added dropwise and the mixture was stirred to react at −78° C. for 1 hr. The reaction was quenched with saturated ammonium chloride (5 mL) and then extracted with ethyl acetate (50 mL×3). The organic phases were combined and concentrated under vacuum to give a crude product. The crude product was purified by column (ethyl acetate/petroleum ether=0-15%) to give compound 2-5. $^1$H NMR (400 MHz, CDCl$_3$) δ=11.81 (s, 1H), 7.99 (d, J=7.2 Hz, 1H), 7.85-7.80 (m, 2H), 7.63-7.53 (m, 2H), 7.36 (t, J=7.6 Hz, 1H), 6.30 (dd, J=2.8, 10.4 Hz, 1H), 4.68-4.62 (m, 1H), 4.56-4.47 (m, 1H), 3.82 (s, 3H), 3.07-2.98 (m, 1H), 2.57-2.46 (m, 1H).

Step 5: Synthesis of Compound 2-6

Compound 2-5 (497 mg, 1.56 mmol, 1 eq) was dissolved in methanol (2 mL), then 2-methylthiourea sulfate (528.27 mg, 2.81 mmol, 1.8 eq) and sodium methoxide (421.14 mg, 7.80 mmol, 5 eq) were added. The resulting reaction solution was stirred at 25° C. under nitrogen for 18 hr. The methanol was removed under reduced pressure and water (1 mL) was added to the residue. The mixture was adjusted to pH of 5-6 with 2 M hydrochloric acid, and a large amount of white solid was precipitated. The solid was collected by filtration and dried under vacuum to give compound 2-6. The crude product was used directly in the next reaction step. LCMS m/z=359.1 [M+H]$^+$.

Step 6: Synthesis of Compound 2-7

Compound 2-6 (440.00 mg, 1.23 mmol, 1 eq) and N,N-diisopropylethylamine (316.95 mg, 2.45 mmol, 427.15 μL, 2 eq) were added to anhydrous dichloromethane (5 mL) and the mixture was cooled down to 0° C. Triflic anhydride (449.74 mg, 1.59 mmol, 263.00 μL, 1.3 eq) was added. After the addition was completed, the mixture was stirred to react at 0° C. for 60 min. The reaction solution was concentrated under vacuum to give a crude product, which was purified by column (ethyl acetate/petroleum ether=0-6%) to give compound 2-7. $^1$H NMR (400 MHz, CDCl$_3$) δ=7.99 (d, J=7.2 Hz, 1H), 7.90-7.82 (m, 2H), 7.66-7.54 (m, 2H), 7.44-7.33 (m, 1H), 6.46 (dd, J=2.4, 10.4 Hz, 1H), 5.12-5.04 (m, 1H), 4.97-4.89 (m, 1H), 3.63 (dd, J=2.0, 18.0 Hz, 1H), 3.05-2.90 (m, 1H), 2.57 (s, 3H). LCMS m/z=491.0 [M+H]$^+$.

Step 7: Synthesis of Compound 2-8

Compound 2-7 (121 mg, 246.48 μmol, 1 eq) and N,N-diisopropylethylamine (95.57 mg, 739.45 μmol, 128.80 μL, 3 eq) were added to N,N-dimethylformamide (1.5 mL), followed by compound 1-10A hydrochloride (70.31 mg, 237.71 μmol, 1.1 eq). The gas in the reaction solution was replaced with nitrogen and the reaction solution was stirred in an oil bath at 100° C. to react for 1 hr. The reaction solution was concentrated under vacuum to give a crude product, which was purified by column (ethyl acetate/petroleum ether=0-30%) to give compound 2-8. LCMS m/z=600.2 [M+H]$^+$.

Step 8: Synthesis of Compound 2-9

Compound 2-8 (125 mg, 208.29 μmol, 1 eq) was dissolved in dichloromethane (1 mL), then m-chloroperoxybenzoic acid (84.57 mg, 416.58 μmol, 85% purity, 2 eq) was added, and the resulting reaction solution was stirred to react at 20° C. for 8 hr. The reaction solution was filtered to remove insoluble matter and the filtrate was concentrated under vacuum to give a crude product, which was purified by column (ethyl acetate/petroleum ether=0-60%) to give compound 2-9. LCMS m/z=632.3 [M+H]$^+$.

Step 9: Synthesis of Compound 2-10

Compound 2-9 (101 mg, 159.78 μmol, 1 eq) and 1-11A (55.21 mg, 479.34 μmol, 56.91 μL, 3 eq) were dissolved in toluene (0.8 mL). The resulting solution was cooled down to −5° C., then t-BuONa (30.71 mg, 319.56 μmol, 2 eq) was added, and the resulting reaction solution was stirred to react at −5 to 0° C. for 1 hr. The reaction solution was diluted with 3 mL of ethyl acetate and washed with water (1 mL) and saturated brine (1 mL). The organic phase was concentrated under vacuum to give a crude product, which was purified by column (methanol/dichloromethane=0-8%) to give compound 2-10. LCMS m/z=667.3 [M+H]$^+$.

Step 10: Synthesis of a Mixture of Compounds 2-11 and 3-1

Compound 2-10 (101 mg, 151.38 μmol, 1 eq) was dissolved in dichloromethane (1 mL), then palladium acetate (6.80 mg, 30.28 μmol, 0.2 eq) and triethylsilane (88.01 mg, 756.90 μmol, 120.90 μL, 5 eq) were added, and the resulting reaction solution was stirred to react at room temperature for 1 hr. The reaction solution was concentrated under vacuum to give a mixture of compounds 2-11 and 3-1, which was used directly in the next reaction step without purification. Compound 2-11: LCMS m/z=555.3 [M+Na]$^+$; Compound 3-1: LCMS m/z=521.3 [M+Na]$^+$.

Step 11: Synthesis of Compounds 2 and 3

A mixture of compounds 2-11 and 3-1 was dissolved in dichloromethane (1 mL) and then triethylamine (45.95 mg, 454.14 μmol, 63.21 μL, 3 eq) was added. The reaction solution was cooled down to 0° C., then acryloyl chloride (20.55 mg, 227.07 μmol, 18.52 μL, 1.5 eq) was added and the mixture was stirred to react for 30 min. The reaction solution was concentrated under vacuum to give a crude product, which was separated by preparative high-performance liquid chromatography (separation conditions: column: Welch Xtimate C18 150*30 mm*5 μm; mobile phase: [water (0.225% formic acid)-acetonitrile]; acetonitrile %: 15%-55%, 8 min) to give compounds 2 and 3. Compounds 2 and 3 were a pair of diastereoisomers, respectively. Compound 2: LCMS m/z=587.3 [M+H]+; Compound 3: LCMS m/z=553.3 [M+H]+.
Example 4
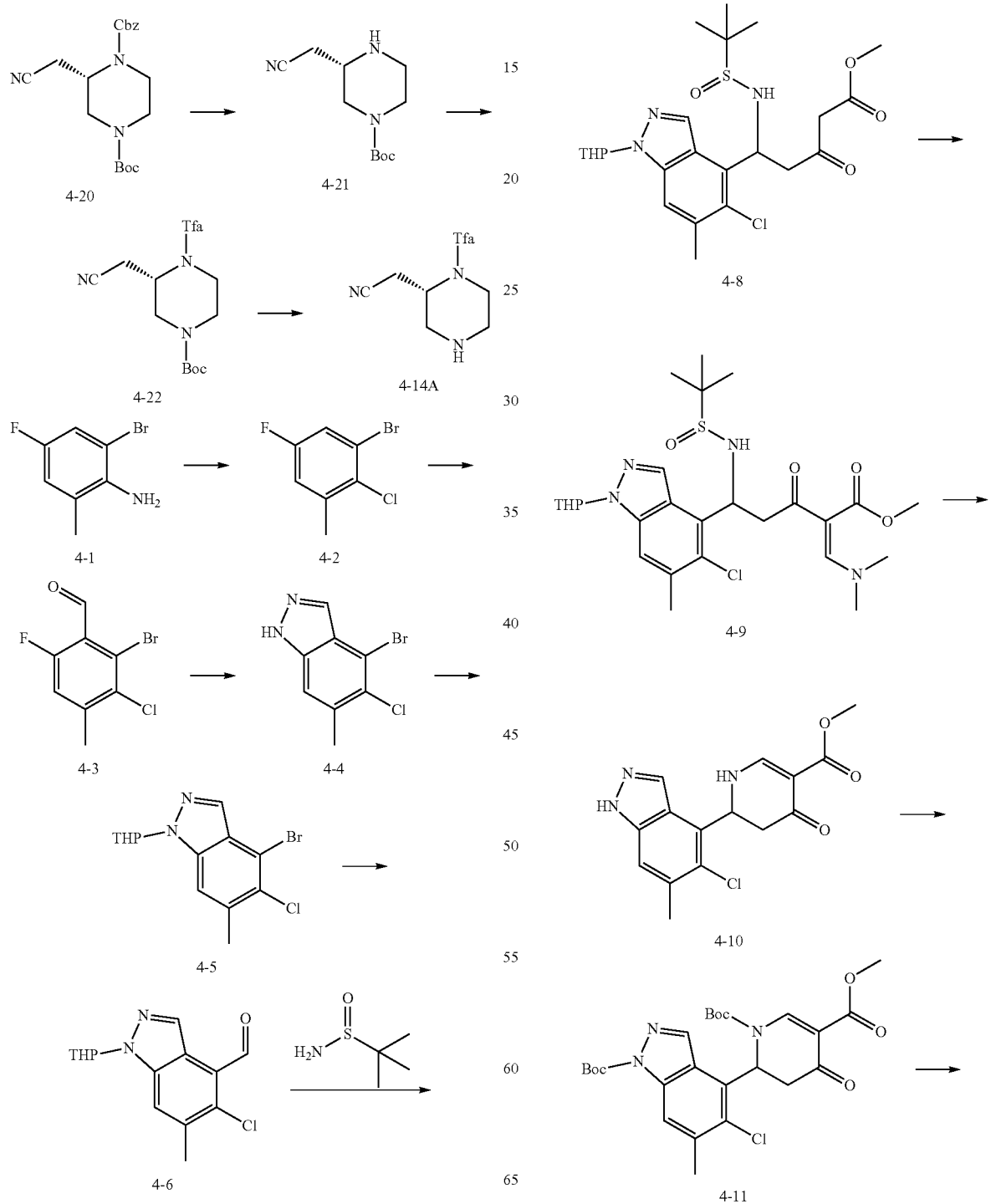

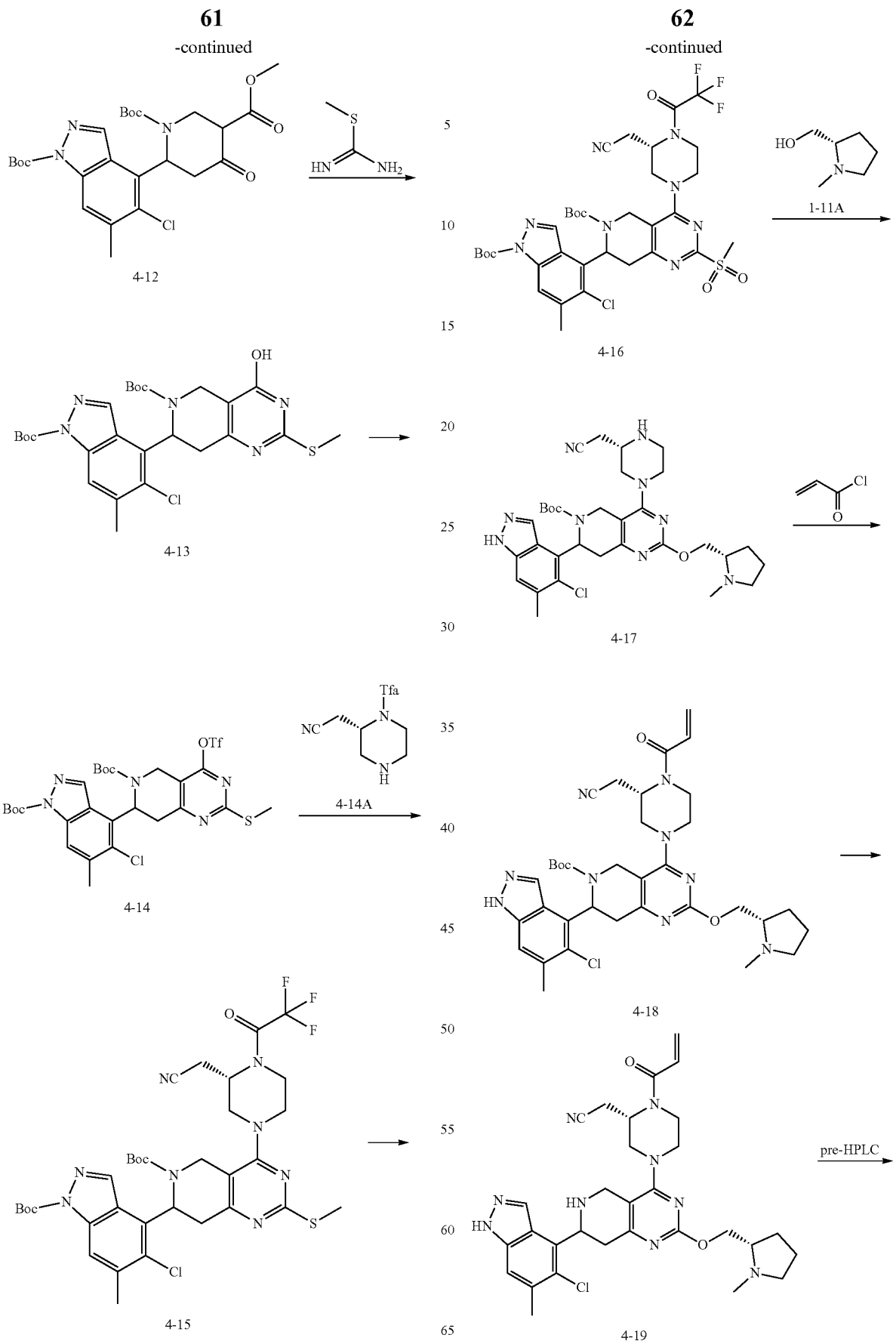

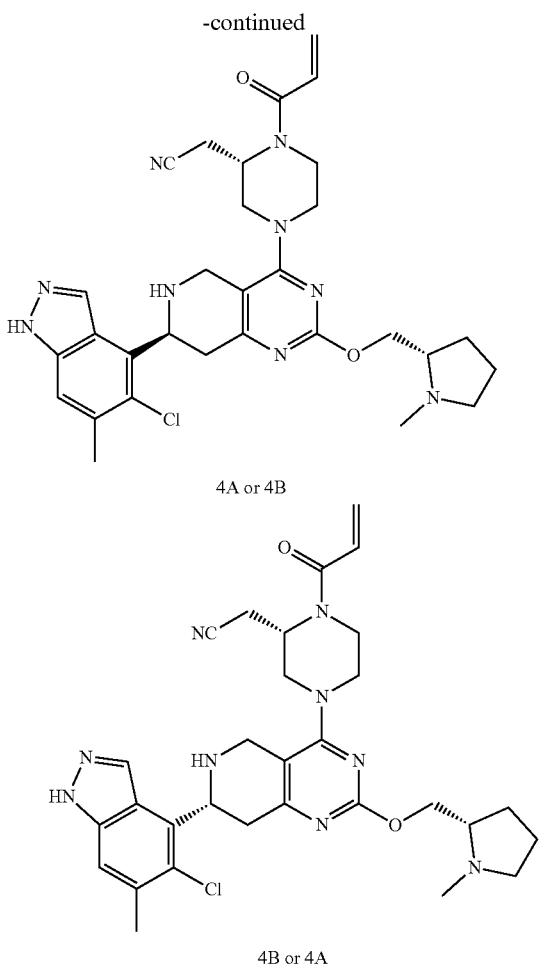

4A or 4B 4B or 4A

Synthesis of Intermediate 4-14A

Step 1: Synthesis of Compound 4-21

Compound 4-20 (3 g, 8.35 mmol, 1 eq) was dissolved in tetrahydrofuran (30 mL), and wet palladium on carbon (1.2 g, 10% mass) was added. The atmosphere was replaced three times with hydrogen (562.02 μg, 278.23 μmol, 1 eq) and the mixture was reacted at room temperature of 25° C., 15 Psi for 2 hr. The reaction solution was filtered, and the mother liquor was collected and concentrated to give the compound 4-21. LCMS m/z=170.1[M-55+H]$^+$.

Step 2: Synthesis of Compound 4-22

Compound 4-21 (0.2 g, 887.76 μmol, 1 eq) was dissolved in tetrahydrofuran (5 mL), and triethylamine (269.50 mg, 2.66 mmol, 370.70 μL, 3 eq) was added. The mixture was cooled down to 0° C. under nitrogen and trifluoroacetic anhydride (205.10 mg, 976.53 μmol, 135.83 μL, 1.1 eq) was added. The mixture was reacted at 0° C. for 0.5 hr. The mixture was poured into saturated aqueous ammonium chloride solution (10 mL), and ethyl acetate (5 mL*2) was added. The mixture was washed with saturated brine (5 mL) and purified by column chromatography (petroleum ether/ethyl acetate=10/1-1/1, TLC: petroleum ether/ethyl acetate=3/1) to give the compound 4-22. $^1$H NMR (400 MHz, CDCl$_3$) δ=4.86 (s, 1H), 4.51-4.06 (m, 2H), 3.88 (d, J=14.0 Hz, 1H), 3.52-3.33 (m, 1H), 3.24 (dd, J=4.0, 14.2 Hz, 1H), 3.12-2.92 (m, 1H), 2.91-2.73 (m, 1H), 2.67 (s, 1H), 1.50 (s, 9H); LCMS: MS m/z=222.0 [M-100+H]$^+$.

Step 3: Synthesis of Compound 4-14A

Compound 4-22 (150 mg, 466.86 μmol, 1 eq) was dissolved in hydrochloride/dioxane (5 M, 8 mL, 85.68 eq). The mixture was reacted at 18° C. under nitrogen for 1 hr and then directly rotary-evaporated to dryness to give the hydrochloride salt of compound 4-14A. LCMS: MS m/z=222.0 [M+H]$^+$ Synthesis of Example 4

Step 1: Synthesis of Compound 4-2

After mixing water (210 mL) and hydrochloric acid (210 mL, 36-38% mass content), compound 4-1 (36.00 g, 176.44 mmol, 1 eq) was added. The mixture was heated to 65° C., reacted for 1 hr, and then cooled down to 0 to 5° C. A solution of sodium nitrite (14.61 g, 211.72 mmol, 1.2 eq) in water (70 mL) was added dropwise, and the mixture was stirred for 15 min. Cuprous chloride (26.20 g, 264.65 mmol, 6.33 mL, 1.5 eq) was dissolved in hydrochloric acid (350 mL, 36-38% mass content) and the solution was cooled down to 0 to 5° C. The above solution was added dropwise to the reaction solution, and the mixture was reacted for another 6 hr. 750 mL of dichloromethane was added to the reaction system, and the mixture was stirred for 20 min. The layers were separated. The organic phase was washed once with 350 mL of saturated brine, dried with 30.00 g of anhydrous sodium sulfate, and filtered. The filtrate was rotary-evaporated under reduced pressure at 45° C. to give compound 4-2. $^1$H NMR (400 MHz, CDCl$_3$) δ=7.24-7.21 (m, 1H), 6.94 (dd, J=2.8, 8.8 Hz, 1H), 2.43 (s, 3H).

Step 2: Synthesis of Compound 4-3

Tetrahydrofuran (395 mL) and compound 4-2 (39.50 g, 176.76 mmol, 1 eq) were added to a pre-prepared clean reaction flask, and stirred. The mixture was cooled down to −70 to −65° C. Lithium diisopropylamide (2 M, 106.05 mL, 1.2 eq) was added dropwise and the mixture was reacted for another 1 hr. Then N,N-dimethylformamide (18.76 g, 256.70 mmol, 19.75 mL, 1.45 eq) was added and the mixture was reacted for another 1 hr. 500 mL of saturated ammonium chloride solution was added to the reaction system, and then the layers were separated. The organic phase was washed once with 300 mL of saturated brine, then dried with 20 g of anhydrous sodium sulfate, and filtered. The filtrate was rotary-evaporated under reduced pressure at 45° C. to give compound 4-3. $^1$H NMR (400 MHz, CDCl$_3$) δ=10.28 (s, 1H), 7.08 (d, J=10.8 Hz, 1H), 2.51 (s, 3H); LCMS m/z=245.0[M+H]$^+$, 247.0[M+3H]$^+$.

Step 3: Synthesis of Compound 4-4

Dimethyl sulfoxide (300 mL) and compound 4-3 (20.00 g, 79.53 mmol, 1 eq) were added to a pre-prepared clean reaction flask and stirred. Then hydrazine hydrate (48.75 g, 954.35 mmol, 47.33 mL, 98% mass content, 12 eq) was added, and the mixture was heated to 130° C. and reacted for 3 hr. The reaction solution was combined with a small-scale reaction solution, and then the mixture was poured into 700 mL of water. The mixture was filtered, and the filter cake was washed with water (100 mL×3 times). The obtained filter cake was dissolved in 300 mL of ethyl acetate and the layers were separated. The organic phase was dried with 50.00 g of anhydrous sodium sulfate and filtered. The filtrate was rotary-evaporated under reduced pressure at 45° C. to give compound 4-4. $^1$H NMR (400 MHz, CDCl$_3$) δ=10.38 (brs, 1H), 8.03 (s, 1H), 7.33 (s, 1H), 2.57 (s, 3H); LCMS m/z=245.1[M+H]$^+$, 247.1[M+3H]$^+$.

Step 4: Synthesis of Compound 4-5

Dichloromethane (200 mL) and compound 4-4 (20.00 g, 81.47 mmol, 1 eq) were added to a pre-prepared clean reaction flask and stirred. Then pyridinium p-toluenesulfonate (2.05 g, 8.15 mmol, 0.1 eq) and 2-methylhydroxy- 3,4-dihydropyran (20.56 g, 244.40 mmol., 3 eq) were added sequentially. The mixture was reacted at 20° C. for 12 hr. After 200 mL of water was added to the reaction system, the layers of the reaction solution were directly separated. The organic phase was dried with 20.00 g of anhydrous sodium sulfate, and filtered. The filtrate was rotary-evaporated under reduced pressure at 45° C. to give a crude compound. The crude product was purified by column chromatography (petroleum ether/ethyl acetate=100/0-70/30, TLC: petroleum ether/ethyl acetate=5/1) to give compound 4-5. $^1$H NMR (400 MHz, CDCl$_3$) δ=7.95 (s, 1H), 7.44 (s, 1H), 5.67 (dd, J=2.8, 8.8 Hz, 1H), 4.02-3.98 (m, 1H), 3.79-3.71 (m, 1H), 2.57 (s, 3H), 2.54-2.46 (m, 1H), 2.18-2.05 (m, 2H), 1.80-1.66 (m, 3H); LCMS m/z=329.0[M+H]$^+$, 331.0[M+3H]$^+$.

Step 5: Synthesis of Compound 4-6

Tetrahydrofuran (160 mL) and compound 4-5 (16 g, 48.54 mmol, 1 eq) were added to a pre-prepared clean reaction flask and stirred. After the mixture was cooled down to −70 to −65° C., n-butyllithium (2.5 M, 21.36 mL, 1.1 eq) was slowly added dropwise and the mixture was reacted for another 1 hr. Then N,N-dimethylformamide (35.48 g, 485.41 mmol, 37.35 mL, 10 eq) was added and the mixture was reacted for another 0.5 hr. After adding 250 mL of saturated ammonium chloride solution, the layers were separated. The organic phase was washed once with 150 mL of saturated brine, dried with anhydrous sodium sulfate, and filtered. The filtrate was rotary-evaporated under reduced pressure at 45° C. to give an oily substance. The oily substance was mixed with 7 mL of ethyl acetate. The mixture was slurried for 20 min, and then filtered. The filter cake was rotary-evaporated under reduced pressure at 45° C. to give compound 4-6. $^1$H NMR (400 MHz, CDCl$_3$) δ=10.72 (s, 1H), 8.63 (s, 1H), 7.74 (s, 1H), 5.70 (dd, J=2.8, 8.8 Hz, 1H), 3.98-3.94 (m, 1H), 3.75-3.68 (m, 1H), 2.55 (s, 3H), 2.53-2.45 (m, 1H), 2.16-2.05 (m, 2H), 1.83-1.61 (m, 3H); LCMS m/z=279.1[M+H]$^+$.

Step 6: Synthesis of Compound 4-7

Tetrahydrofuran (54 mL) and compound 4-6 (5.4 g, 19.37 mmol, 1 eq) were added to a pre-prepared clean reaction flask and stirred. Then tert-butyl sulfinamide (2.58 g, 21.31 mmol, 232.15 μL, 1.1 eq) and tetraisopropyl titanate (8.84 g, 38.75 mmol, 8.04 mL, 2 eq) were added, and the mixture was reacted at 20° C. for 12 hr. After adding 50 mL of saturated ammonium chloride solution to the reaction system, the layers were separated. The organic phase was dried with 3.00 g of anhydrous sodium sulfate, and then filtered. The filtrate was rotary-evaporated under reduced pressure at 45° C. The crude product was purified by column chromatography (petroleum ether/ethyl acetate=100/0 to 50/50, TLC: petroleum ether/ethyl acetate=10/1) to give compound 4-7. LCMS m/z=382.2[M+H]$^+$.

Step 7: Synthesis of Compound 4-8

Tetrahydrofuran (35 mL) and sodium hydride (829.50 mg, 20.74 mmol, 60% mass content, 1.2 eq) were added to a pre-prepared clean reaction flask, and stirred. Then the mixture was cooled down to 0 to 5° C. and methyl acetoacetate (2.41 g, 20.74 mmol, 2.23 mL, 1.2 eq) was added dropwise. The mixture was reacted for 20 min. Then n-butyllithium (2.5 M, 7.60 mL, 1.1 eq) was added dropwise and the mixture was reacted for another 20 min. After the mixture was cooled down to −70 to −65° C., a solution of compound 4-7 (6.60 g, 17.28 mmol, 1 eq) in tetrahydrofuran (35 mL) was added dropwise and the mixture was reacted for another 20 min. The mixture was slowly warmed to room temperature of 20° C. and reacted for another 0.5 hr. The reaction solution was poured into 100 mL of saturated ammonium chloride solution. After combining with the 1 g batch, the layers were separated. The organic phase was dried with 3.00 g of anhydrous sodium sulfate and filtered. The filtrate was rotary-evaporated under reduced pressure at 45° C. The crude product was purified by column chromatography (petroleum ether/ethyl acetate=100/0-20/80, TLC: PE/EtOAc=0:1) to give compound 4-8. $^1$H NMR (400 MHz, CDCl$_3$) δ=8.20 (s, 1H), 7.44 (d, J=5.6 Hz, 1H), 5.72-5.64 (m, 2H), 4.04-3.99 (m, 1H), 3.77-3.69 (m, 4H), 3.57-3.46 (m, 2H), 3.15-3.08 (m, 1H), 2.59-2.52 (m, 4H), 2.16-2.05 (m, 2H), 1.83-1.65 (m, 4H), 1.20-1.18 (m, 9H); LCMS m/z=498.2[M+H]$^+$.

Step 8: Synthesis of Compound 4-9

Toluene (66 mL) and compound 4-8 (6.60 g, 13.25 mmol, 1 eq) were added to a pre-prepared clean reaction flask and stirred. Then N,N-dimethylformamide dimethyl acetal (4.74 g, 39.76 mmol, 5.28 mL, 3 eq) was added, and the mixture was reacted at room temperature of 20° C. for 12 hr. 60 mL of water and 60 mL of ethyl acetate were added to the reaction system and the mixture was stirred for 5 min. The layers were separated. The organic phase was washed once with 60 mL of saturated brine, dried with 5.00 g of anhydrous sodium sulfate and filtered. The filtrate was rotary-evaporated under reduced pressure at 50° C. to give compound 4-9, which was directly used in the next step.

Step 9: Synthesis of Compound 4-10

Compound 4-9 (50 mg, 90.40 μmol, 1 eq) was dissolved in hydrochloride/ethyl acetate (3 mL). The mixture was stirred at 18° C. for 20 min. The reaction solution was concentrated directly to give a crude product as a hydrochloride salt of compound 4-10. LCMS m/z=320.0 [M+H]$^+$ Step 10: Synthesis of Compound 4-11

Compound 4-10 (5.00 g, 14.04 mmol, 1 eq, HCl) was dissolved in dichloromethane (50 mL), and triethylamine (5.97 g, 58.96 mmol, 8.21 mL, 4.2 eq), tert-butyl dicarbonate (12.25 g, 56.15 mmol, 12.90 mL, 4 eq), and 4-dimethylaminopyridine (1.71 g, 14.04 mmol, 1 eq) were added. The reaction mixture was stirred at 18° C. for 10 hr. The reaction mixture was combined with the 0.5 g batch for treatment. The mixture was quenched with saturated aqueous ammonium chloride solution (100 mL), and extracted with dichloromethane (30 mL*2 times). The combined organic phase was dried over anhydrous sodium sulfate and concentrated to give a crude product. The crude product was purified by column chromatography (petroleum ether/ethyl acetate=50/1-0/1, TLC: petroleum ether/ethyl acetate=1/1) to give compound 4-11. $^1$H NMR (400 MHz, CDCl$_3$) δ=9.02 (s, 1H), 8.12 (s, 1H), 7.89 (s, 1H), 6.16 (dd, J=5.2, 8.8 Hz, 1H), 3.77 (s, 3H), 3.10 (dd, J=8.4, 16.0 Hz, 1H), 2.82 (m, 1H), 2.48 (s, 3H), 1.63 (s, 9H), 1.18 (s, 9H). LCMS m/z=520.1[M+H]$^+$.

Step 11: Synthesis of Compound 4-12

Compound 4-11 (3.00 g, 5.77 mmol, 1 eq) was dissolved in tetrahydrofuran (30 mL), and the solution was cooled down to −78° C. Lithium tri-sec-butylborohydride (1 M, 5.77 mL, 1 eq) was added dropwise to the reaction solution under nitrogen and the mixture was stirred for 0.5 hr. The reaction mixture was quenched with saturated aqueous ammonium chloride solution (30 mL) and extracted with ethyl acetate (20 mL×2 times). The organic phases were combined, dried with anhydrous sodium sulfate, and concentrated to give a crude product of compound 4-12. LCMS m/z=522.2[M+H]$^+$, 466.1[M-56+H]$^+$.

Step 12: Synthesis of Compound 4-13

Compound 4-12 (2.30 g, 4.41 mmol, 1 eq) and 2-methyl-2-thioseudourea disulfate (1.66 g, 8.81 mmol, 2 eq, H$_2$SO$_4$) were dissolved in methanol (430 mL), and sodium methoxide (476.05 mg, 8.81 mmol, 2 eq) was added. The mixture was stirred at 18° C. for 1.5 hr. Then sodium methoxide (357.04 mg, 6.61 mmol, 1.5 eq) was added to the reaction solution, and the mixture was stirred at 18° C. for 10 hr. The mixture was rotary-evaporated to dryness and water (50 mL) was added. The mixture was adjusted to pH of 2-3 with 1 M dilute hydrochloric acid and white solids were precipitated. The solid was collected by filtration. The crude product was purified by column chromatography (petroleum ether/ethyl acetate=10/1-0/1, TLC: petroleum ether/ethyl acetate=1/1) to give compound 4-13. LCMS m/z=562.1[M+H]$^+$.

Step 13: Synthesis of Compound 4-14

Compound 4-13 (0.328 g, 583.55 µmol, 1 eq) and N,N-diisopropylethylamine (377.09 mg, 2.92 mmol, 508.21 µL, 5 eq) were dissolved in dichloromethane (10 mL) and triflic anhydride (246.96 mg, 875.32 µmol, 144.42 µL. 1.5 eq) was added at 0° C. The mixture was stirred at 0° C. for 1 hr. The mixture was combined with the 0.56 g batch for treatment. The mixture was poured into saturated aqueous ammonium chloride solution (50 mL), and extracted with ethyl acetate (20 mL×3 times). The organic phase was washed with saturated brine, dried over anhydrous sodium sulfate, and filtered. The filtrate was concentrated to give a crude product. The crude product was purified by column chromatography (petroleum ether/ethyl acetate=20/1-5/1, TLC: petroleum ether/ethyl acetate=5/1) to give compound 4-14. $^1$H NMR (400 MHz, CDCl3) δ=8.21-8.11 (m, 1H), 8.00-7.90 (m, 1H), 5.86-5.69 (m, 1H), 5.25-5.09 (m, 1H), 4.68-4.46 (m, 1H), 3.57-3.42 (m, 1H), 3.27-3.08 (m, 1H), 2.66-2.41 (m, 6H), 1.79-1.67 (m, 9H), 1.21-1.07 (m, 9H); LCMS m/z=637.9[M-56+H]$^+$, 639.8[M-56+3H]$^+$.

Step 14: Synthesis of Compound 4-15

Compound 4-14 (630 mg, 907.60 µmol, 1 eq) and compound 4-14A (420.90 mg, 1.63 mmol, 1.8 eq, HCl) were dissolved in N,N-dimethylformamide (15 mL), and N,N-diisopropylethylamine (469.19 mg, 3.63 mmol, 632.33 µL, 4 eq) was added. The mixture was stirred at 20° C. for 2 hr. The mixture was poured into water (30 mL), and extracted with ethyl acetate (20 mL×3). The organic phase was washed with saturated brine (10 mL), dried over anhydrous sodium sulfate, and filtered. The filtrate was concentrated to give a crude product, which was purified by column chromatography (petroleum ether/ethyl acetate=50/1-1/1, TLC: petroleum ether/ethyl acetate=0/1) to give compound 4-15. $^1$H NMR (400 MHz, CDCl3) δ=8.18-8.05 (m, 1H), 8.04-7.93 (m, 1H), 5.75-5.45 (m, 1H), 5.06-4.89 (m, 1H), 4.66-4.35 (m, 1H), 4.19-3.84 (m, 3H), 3.82-3.45 (m, 1H), 3.43-3.12 (m, 2H), 3.06-2.75 (m, 6H), 2.61-2.38 (m, 5H), 1.79-1.60 (m, 9H), 1.14-0.85 (s, 9H); LCMS m/z=765.0[M+H]$^+$.

Step 15: Synthesis of Compound 4-16

Compound 4-15 (400.00 mg, 522.71 µmol, 1 eq) was dissolved in dichloromethane (8 mL), and m-chloroperoxybenzoic acid (200.00 mg, 985.11 µmol, 85% mass content, 1.88 eq) was added. The mixture was stirred at 20° C. for 2 hr. The mixture was combined with the 200 mg batch for treatment. The reaction solution was washed with aqueous sodium sulfite (20 mL, 10%), dried over anhydrous sodium sulfate, and filtered. The filtrate was concentrated to give a crude product. The crude product was purified by column chromatography (SiO$_2$ 100 mesh, petroleum ether/ethyl acetate=50/1-1/1, TLC: petroleum ether/ethyl acetate=2/1) to give compound 4-16. LCMS m/z=697.1[M-100+H]$^+$.

Step 16: Synthesis of Compound 4-17

Compound 1-11A (57.79 mg, 501.73 µmol, 59.57 µL, 4 eq) was dissolved in toluene (1 mL), and sodium tert-butoxide (42.19 mg, 439.01 µmol, 3.5 eq) was added at 0° C. The mixture was stirred for 15 min. Then a solution of compound 4-16 (100.00 mg, 125.43 µmol, 1 eq) in 0.1 mL toluene was added slowly to the reaction solution, and the mixture was reacted at 0° C. for 30 min. The reaction mixture was quenched with water (5 mL) and extracted with ethyl acetate (5 mL×2). The organic phases were combined to give compound 4-17. LCMS m/z=636.1[M+H]$^+$.

Step 17: Synthesis of Compound 4-18

Compound 4-17 (79.80 mg, 125.44 µmol, 1 eq) was dissolved in dichloromethane (2 mL), and N,N-diisopropylethylamine (81.06 mg, 627.18 µmol, 109.24 µL, 5 eq) was added at 18° C. The mixture was cooled down to −78° C. Acryloyl chloride (4.54 mg, 50.17 µmol, 4.09 µL, 0.4 eq) was added slowly to the reaction solution and the mixture was reacted at −78° C. for 0.5 hr. 8.00 mg of additional acryloyl chloride was added, and the mixture was reacted for another 1 hr. The reaction mixture was quenched with saturated aqueous ammonium chloride (5 mL) and extracted with dichloromethane (5 mL*2). The organic phases were combined. The crude product was added to potassium carbonate (1.7 M, 1 mL)/methanol (1 mL) and the mixture was stirred at 18° C. for 1 hr. The product was determined (time=0.943) to give compound 4-18. LCMS m/z=690.3 [M+H]$^+$.

Step 18: Synthesis of Compounds 4A and 4B

Compound 4-18 (100 mg, 144.88 µmol, 1 eq) was dissolved in dichloromethane (2 mL) and trifluoroacetic acid (3.08 g, 27.01 mmol, 2.00 mL, 186.45 eq), and the mixture was reacted at 18° C. for 1 hr. The mixture was concentrated to give compound 4-19. The compound 4-19 was purified by a high-performance liquid chromatography column (Column: Phenomenex luna C18 100*40 mm*5 µm; mobile phase: [H$_2$O (0.1% TFA)-acetonitrile]; acetonitrile %: 5%-30%, 8 min). To the sample was added 0.2 mL of 0.05 mol/L dilute hydrochloric acid. The mixture was concentrated under vacuum to give compound 4A hydrochloride (time-to-peak: 2.417 min, LCMS m/z=590.1 [M+H]+, 295.9 [M/2+H]$^+$) and compound 4B hydrochloride (time-to-peak: 2.388 min, LCMS m/z=590.1 [M+H]+, 295.9[M/2+H]$^+$).

Example 5

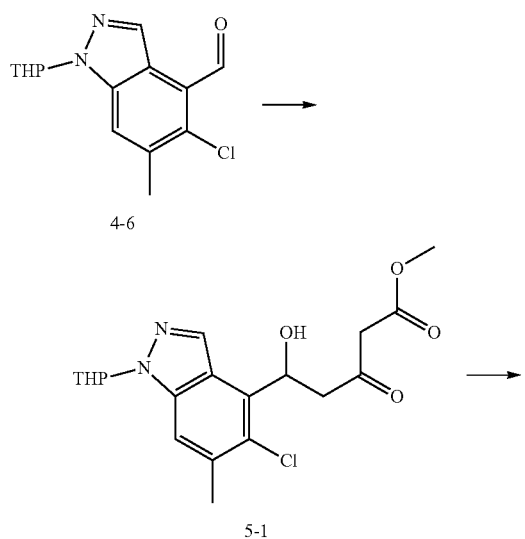

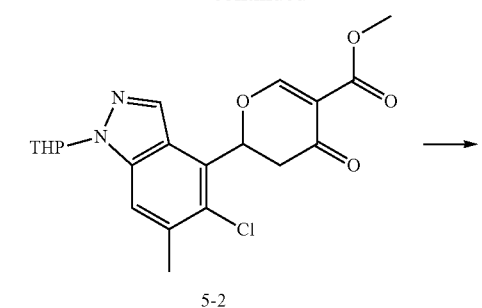
5-2
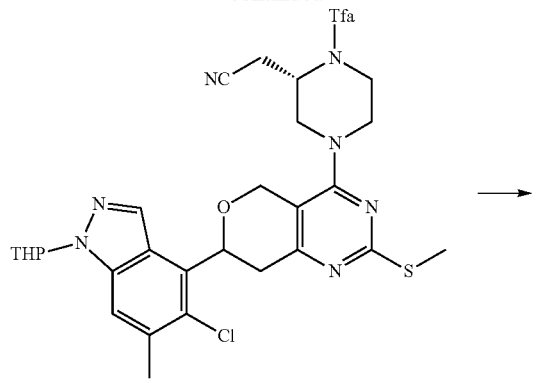
5-7
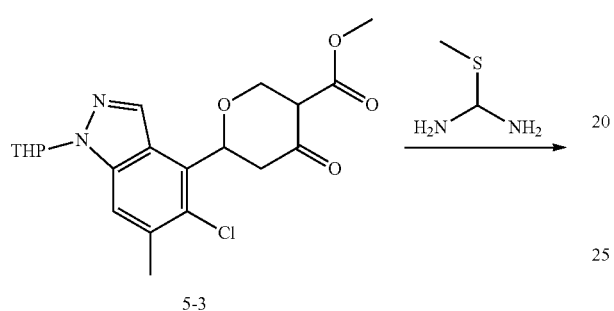
5-3
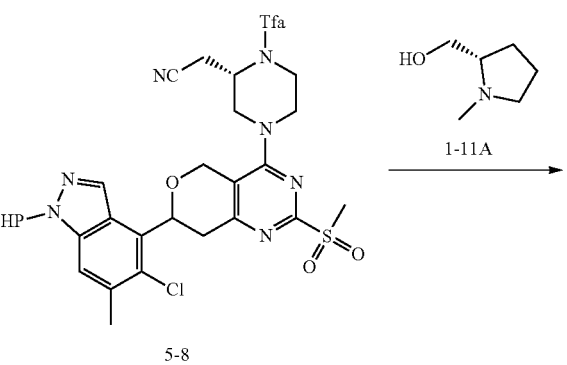
5-8
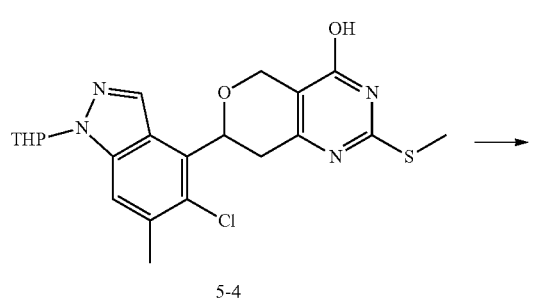
5-4
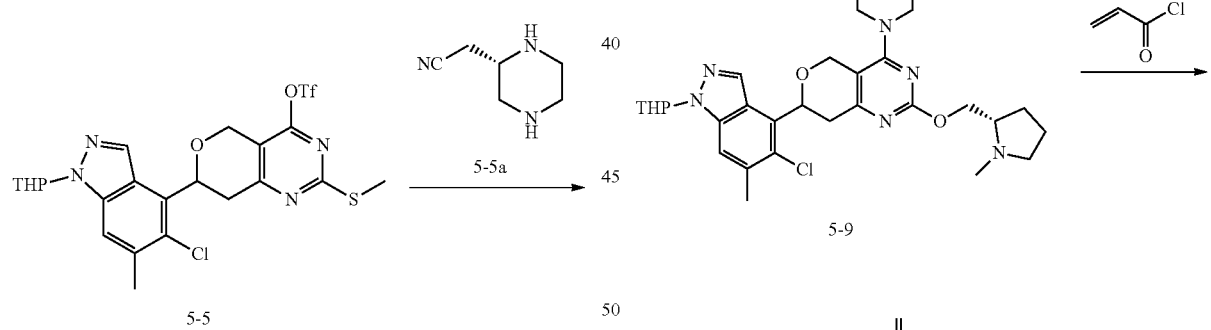
5-5 5-9
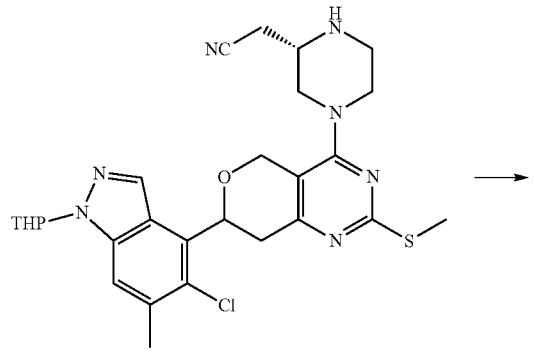
5-6
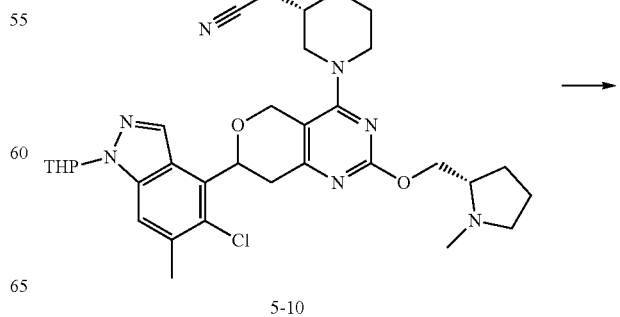
5-10

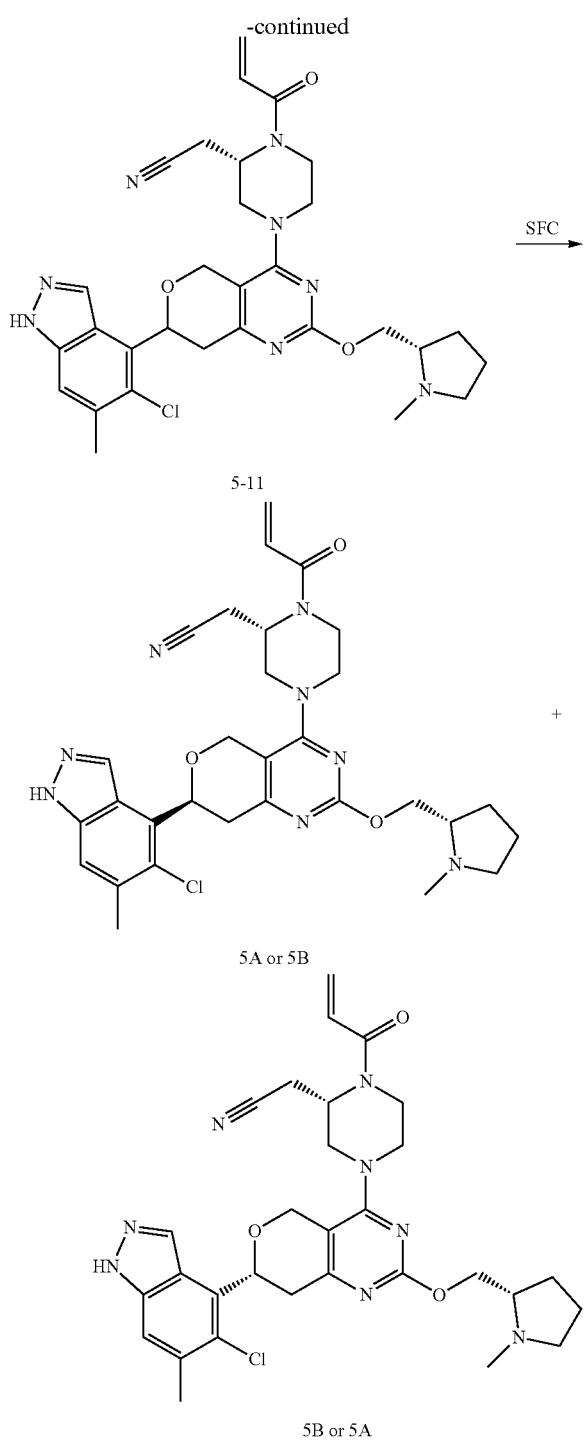

5-11

5A or 5B 5B or 5A

Step 1: Synthesis of Compound 5-1

Tetrahydrofuran (27 mL) and sodium hydride (789.28 mg, 19.73 mmol, 60% mass content, 2 eq) were added to a pre-prepared clean reaction flask, and stirred. Then the mixture was cooled down to 0 to 5° C. and methyl acetoacetate (2.29 g, 19.73 mmol, 2.12 mL, 2 eq) was added dropwise. The mixture was reacted for 30 min. Then n-butyllithium (2.5 M, 7.50 mL, 1.9 eq) was added dropwise, and the mixture was reacted for another 30 min. The mixture was then cooled down to −70 to −65° C. A solution of compound 4-6 (2.75 g, 9.87 mmol, 1 eq) in tetrahydrofuran (27 mL) was added dropwise, and the mixture was reacted for another 0.5 hr. The reaction solution was quenched by pouring into 50 mL of saturated ammonium chloride solution. The organic phase was dried with 1.50 g of anhydrous sodium sulfate and filtered. The filtrate was rotary-evaporated under reduced pressure at 45° C. The crude product was purified by column chromatography (petroleum ether/ethyl acetate=100/0-70/30, TLC: petroleum ether/ethyl acetate=1/1) to give compound 5-1. $^1$H NMR (400 MHz, CDCl$_3$) δ=8.40 (d, J=2.8 Hz, 1H), 7.41 (d, J=11.6 Hz, 1H), 5.95-5.91 (m, 1H), 5.69-5.64 (m, 1H), 4.04-3.98 (m, 1H), 3.78-3.70 (m, 4H), 3.56 (d, J=0.8 Hz, 2H), 3.37 (d, J=3.2, 8.4 Hz, 1H), 3.08-2.99 (m, 2H), 2.61-2.54 (m, 1H), 2.50 (s, 3H), 2.18-2.04 (m, 2H), 1.81-1.70 (m, 2H). LCMS: MS m/z=395.0[M+H]$^+$.

Step 2: Synthesis of Compound 5-2

Dichloromethane (25 mL) and compound 5-1 (1.6 g, 4.05 mmol, 1 eq) were added to a pre-prepared clean reaction flask and stirred. Then N,N-dimethylformamide dimethyl acetal (724.30 mg, 6.08 mmol, 807.47 μL, 1.5 eq) was added and the mixture was reacted at room temperature of 20° C. for 12 hr. Then the mixture was cooled down to 0 to 5° C. Boron trifluoride etherate (575.13 mg, 4.05 mmol, 500.11 μL, 1 eq) was added. The mixture was reacted at room temperature of 20° C. for another 1 hr. The reaction solution was rotary-evaporated under reduced pressure at 30° C. to give compound 5-2, which was used directly in the next step.

Step 3: Synthesis of Compound 5-3

Tetrahydrofuran (58 mL) and compound 5-2 (3.9 g, 8.40 mmol, 87.233% mass content, 1 eq) were added to a pre-prepared clean reaction flask and stirred. The mixture was cooled down to −70 to −65° C. and lithium tri-sec-butylborohydride (1 M, 9.24 mL, 1.1 eq) was added dropwise. The mixture was reacted for 0.5 h. The reaction solution was poured into 50 mL of saturated ammonium chloride solution. The organic phase was dried with 2.00 g of anhydrous sodium sulfate and filtered. The filtrate was rotary-evaporated under reduced pressure at 45° C. The crude product was purified by column chromatography (petroleum ether/ethyl acetate=100/0-70/30, TLC: petroleum ether/ethyl acetate=5/1) to give compound 5-3. LCMS: MS m/z=407.0 [M+H]$^+$ Step 4: Synthesis of Compound 5-4

Methanol (4 mL), compound 5-3 (0.65 g, 1.60 mmol, 1 eq), and methyl isothiourea sulfate (1.22 g, 6.39 mmol, 4 eq, H$_2$SO$_4$) were added to a pre-prepared reaction flask and stirred. Then sodium methoxide (172.61 mg, 3.20 mmol, 2 eq) was added and the mixture was reacted at room temperature of 25° C. for 1 hr. After additional sodium methoxide (172.62 mg, 3.20 mmol, 2 eq) was added, the mixture was reacted for another 15 hr. The reaction solution was rotary-evaporated under reduced pressure at 45° C. 10 mL of water was added to the obtained white solid, and the mixture was extracted with 10 mL of ethyl acetate. The layers were separated. The organic phase was washed once with 10 mL of saturated brine, dried with 0.50 g of anhydrous sodium sulfate, and filtered. The filtrate was rotary-evaporated under reduced pressure at 45° C. The crude product was purified by column chromatography (petroleum ether/ethyl acetate=100/0-40/60, TLC: petroleum ether/ethyl acetate=1/1) to give compound 5-4. LCMS: MS m/z=447.0[M+H]$^+$.

Step 5: Synthesis of Compound 5-5

Dichloromethane (20 mL) and compound 5-4 (610 mg, 1.36 mmol, 1 eq) were added to a pre-prepared clean reaction flask and stirred. After the mixture was cooled down to 0 to 5° C., N,N-diisopropylethylamine (617.36 mg, 4.78 mmol, 832.02 μL, 3.5 eq) and triflic anhydride (770.13 mg, 2.73 mmol, 450.37 μL, 2 eq) were added sequentially. The mixture was reacted for 0.5 hr. The reaction solution was poured into 20 mL of saturated ammonium chloride solution, and then the layers were separated. The organic phase was washed once with 10 mL of saturated brine, dried with anhydrous sodium sulfate, and filtered. The filtrate was rotary-evaporated under reduced pressure at 45° C. The crude product was purified by column chromatography (petroleum ether/ethyl acetate=100/0-70/30, TLC: petroleum ether/ethyl acetate=5/1) to give compound 5-5. 1H NMR (400 MHz, CDCl$_3$) δ=8.26 (d, J=5.2 Hz, 1H), 7.48 (d, J=14.4 Hz, 1H), 5.73-5.67 (m, 1H), 5.53-5.49 (m, 1H), 5.15 (dd, J=3.2, 15.6 Hz, 1H), 4.88 (d, J=15.6 Hz, 1H), 4.06-3.99 (m, 1H), 3.80-3.72 (m, 1H), 3.30-3.25 (m, 1H), 3.12-3.04 (m, 1H), 2.61-2.49 (m, 7H), 2.19-2.07 (m, 2H), 1.83-1.68 (m, 3H).

Step 6: Synthesis of Compound 5-6

N,N-dimethylformamide (5 mL) and compound 5-5 (0.33 g, 569.94 μmol, 1 eq) were added to a pre-prepared clean reaction flask and stirred. Then N,N-diisopropylethylamine (368.29 mg, 2.85 mmol, 496.35 μL, 5 eq) and compound 5-5a (143 mg., 1.14 mmol, 2.00 eq, 2HCl) was added sequentially. The mixture was heated to 100° C. and reacted for 1 hr. The reaction solution was poured into 20 mL of saturated ammonium chloride solution and the mixture was then added to 10 mL of ethyl acetate. The layers were separated. The organic phase was dried with anhydrous sodium sulfate, and filtered. The filtrate was rotary-evaporated under reduced pressure at 45° C. The crude product was purified by column chromatography (dichloromethane/methanol=100/0-85/15, TLC: dichloromethane/methanol=15/1) to give compound 5-6. $^1$H NMR (400 MHz, CDCl$_3$) δ=8.22 (d, J=4.4 Hz, 1H), 7.45 (d, J=8.8 Hz, 1H), 5.71-5.66 (m, 1H), 5.57-5.53 (m, 1H), 4.89-4.80 (m, 2H), 4.05-3.86 (m, 2H), 3.77-3.32 (m, 1H), 3.60-3.57 (m, 1H), 3.39-3.38 (m, 1H), 3.31-3.26 (m, 1H), 3.23-3.17 (m, 1H), 3.12-3.09 (m, 1H), 3.02-2.96 (m, 3H), 2.93-2.83 (m, 2H), 2.57-2.56 (m, 1H), 2.54-2.52 (m, 7H), 2.16-2.04 (m, 2H), 1.79-1.71 (m, 3H). LCMS: MS m/z=554.0[M+H]$^+$.

Step 7: Synthesis of Compound 5-7

Compound 5-6 (190 mg, 342.90 μmol, 1 eq) was dissolved in tetrahydrofuran (2 mL), and stirred. Then the mixture was cooled down to 0 to 5° C., and trifluoroacetic anhydride (108.03 mg, 514.34 μmol, 71.54 μL, 1.5 eq) and triethylamine (121.44 mg, 1.20 mmol, 167.04 μL, 3.5 eq) were added. The mixture was reacted for 0.5 h. The reaction solution was poured into 10 mL of saturated ammonium chloride solution, and then extracted with 10 mL dichloromethane. The organic phase was washed once with saturated brine, dried with anhydrous sodium sulfate, and filtered. The filtrate was rotary-evaporated under reduced pressure at 45° C. to give compound 5-7. LCMS: MS m/z=650.2[M+H]$^+$.

Step 8: Synthesis of Compound 5-8

Dichloromethane (5 mL) and compound 5-7 (0.2 g, 290.04 μmol, 94.281% mass content, 1 eq) were added to a pre-prepared clean reaction flask and stirred. Then m-chloroperoxybenzoic acid (143.96 mg, 667.37 μmol, 80% mass content, 2.30 eq) was added and the mixture was reacted at room temperature of 25° C. for 0.5 h. The reaction solution was poured into 20 mL of sodium thiosulfate solution (10%), and the mixture was extracted with 15 mL of dichloromethane. The organic phase was dried with anhydrous sodium sulfate, and filtered. The filtrate was rotary-evaporated under reduced pressure at 45° C. The crude product was purified by column chromatography (dichloromethane/methanol=100/0-85/15, TLC: dichloromethane/methanol=15/1) to give compound 5-8. LCMS: MS m/z=682.0[M+H]$^+$ Step 9: Synthesis of Compound 5-9

Toluene (5 mL) and compound 1-11A (148.59 mg, 1.29 mmol, 153.18 μL, 4 eq) were added to a pre-prepared clean reaction flask and stirred. Then the mixture was cooled down to 0 to 5° C. and sodium tert-butoxide (123.98 mg, 1.29 mmol, 4 eq) was added. The mixture was reacted for 15 min. A solution of compound 5-8 (0.22 g, 322.53 μmol, 1 eq) in 0.2 mL of toluene was quickly added, and the mixture was reacted for 0.5 hr. The reaction solution was poured into 10 mL of saturated ammonium chloride solution, and the mixture was extracted with 10 mL of dichloromethane. The organic phase was washed once with 10 mL of saturated brine, dried with 0.50 g of anhydrous sodium sulfate, and filtered. The filtrate was rotary-evaporated under reduced pressure at 45° C. to give compound 5-9. LCMS: MS m/z=621.4 [M+H]$^+$ Step 10: Synthesis of Compound 5-10

Dichloromethane (5 mL) and compound 5-9 (98.26 mg, 125.80 μmol, 79.529% mass content, 1 eq) were added to a pre-prepared reaction flask and stirred. The mixture was then cooled down to −60° C. and N,N-diisopropylethylamine (162.59 mg, 1.26 mmol, 219.12 μL, 10 eq) was added. A solution of acryloyl chloride (17.08 mg, 188.70 μmol, 15.39 μL, 1.5 eq) in 0.3 mL of dichloromethane was added dropwise, and the mixture was reacted for 10 min. The reaction solution was poured into 5 mL of saturated ammonium chloride solution and the layers were separated. The organic phase was washed once with 5 mL of saturated brine, dried with anhydrous sodium sulfate, and filtered. The filtrate was rotary-evaporated under reduced pressure at 35° C. to give compound 5-10, which was used directly in the next step. LCMS: MS m/z=675.1 [M+H]$^+$ Step 11: Synthesis of Compounds 5A and 5B Dichloromethane/trifluoroacetic acid (4 mL, 5/3) and compound 5-10 (0.1 g, 148.10 μmol, 1 eq) were added to a reaction flask and the mixture was reacted at room temperature of 25° C. for 0.5 h. The reaction solution was slowly added dropwise to 15 mL of saturated sodium bicarbonate solution, and then the mixture was extracted with 10 mL of dichloromethane. The organic phase was washed once with 10 mL of saturated brine, dried with anhydrous sodium sulfate, and filtered. The filtrate was rotary-evaporated under reduced pressure at 30° C. The crude product was purified by a high-performance liquid chromatography column (Column: Phenomenex Gemini-NX 150*30 mm*5 μm; mobile phase: [H$_2$O(0.1% TFA)-acetonitrile]; acetonitrile %: 20%-50%, 9 min) to give compound 5-11. Compound 5-11 was resolved by SFC (DAICEL CHIRALPAK AS (250 mm*30 mm, 10 μm); mobile phase: [0.1% NH$_3$H$_2$O EtOH]; ethanol: 50%-50%, 15 min).

5A was obtained (time-to-peak in chiral column: 1.516). SFC resolution method (column: Chiralpak AD-3, 50×4.6 mm, I.D., 3 μm; Mobile phase: A (CO2) and B (isopropanol, containing 0.05% diethanolamine); Gradient: B %=5-50%, 3 min; Flow rate: 3.4 mL/min; Wavelength: 220 nm; Pressure: 1800 psi. Optical purity: 91.04%. $^1$H NMR (400 MHz, CDCl$_3$) δ=8.26 (s, 1H), 7.37 (s, 1H), 6.62-6.56 (m, 1H), 6.42-6.38 (m, 1H), 5.84 (d, J=11.6 Hz, 1H), 5.58 (dd, J=4.0, 11.2 Hz, 1H), 4.94 (s, 2H), 4.55-4.43 (m, 1H), 4.27-4.18 (m, 1H), 4.02-3.87 (m, 1H), 3.76-3.73 (m, 1H), 3.23-3.18 (m, 4H), 3.07-2.98 (m, 2H), 2.87-2.74 (m, 3H), 2.56-2.53 (m, 6H), 2.13-2.07 (m, 1H), 1.82-1.76 (m, 3H), 1.37-1.29 (m, 3H). LCMS: MS m/z=591.2[M+H]$^+$.

5B was obtained (time-to-peak in chiral column: 1.800). SFC resolution method (column: Chiralpak AD-3, 50×4.6 mm, I.D., 3 μm; Mobile phase: A (CO2) and B (isopropanol, containing 0.05% diethanolamine); Gradient: B %=5-50%, 3 min; Flow rate: 3.4 mL/min; Wavelength: 220 nm; Pressure: 1800 psi. Optical purity: 99.74%. $^1$H NMR (400 MHz, CDCl$_3$) δ=8.31 (s, 1H), 7.36 (s, 1H), 6.63-6.53 (m, 1H), 6.42-6.37 (m, 1H), 5.83 (d, J=11.6 Hz, 1H), 5.59 (dd, J=4.0, 11.2 Hz, 1H), 4.98-4.88 (m, 2H), 4.55-4.80 (m, 1H), 4.24-4.19 (m, 1H), 4.01-3.97 (m, 1H), 3.93-3.85 (m, 1H), 3.74-3.69 (m, 1H), 3.56-3.52 (m, 1H), 3.28-3.05 (m, 3H), 3.03-2.95 (m, 1H), 2.83-2.69 (m, 3H), 2.58-2.53 (m, 6H), 2.43-2.33 (m, 1H), 2.12-2.06 (m, 1H), 1.91-1.86 (m, 1H), 1.81-1.79 (m, 2H), 1.45-1.30 (m, 2H). LCMS: MS m/z=591.2 [M+H]$^+$.
Example 6
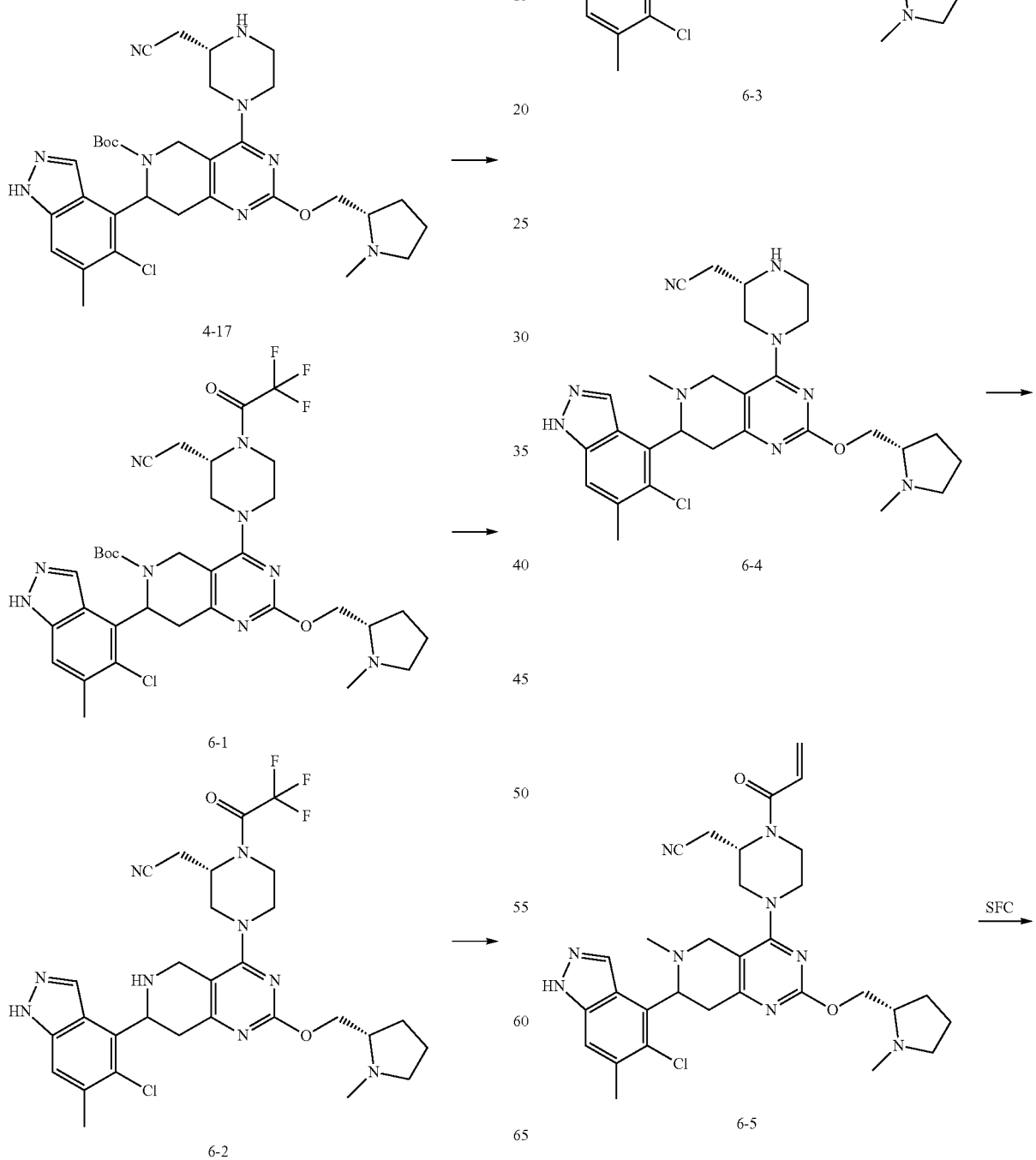

-continued

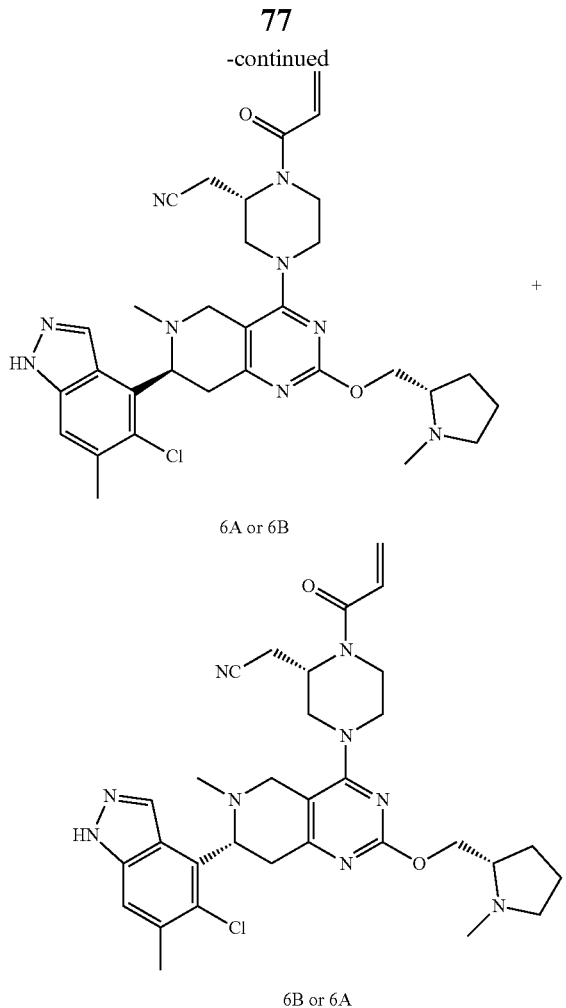

6A or 6B 6B or 6A

Step 1: Synthesis of Compound 6-1

Compound 4-17 (190 mg, 298.65 μmol, 1 eq) and N,N-diisopropylethylamine (192.99 mg, 1.49 mmol, 260.10 μL, 5 eq) were dissolved in dichloromethane (5 mL), and trifluoroacetic anhydride (94.09 mg, 447.98 μmol, 62.31 μL, 1.5 eq) was added at 0° C. The mixture was reacted at 0° C. for 0.5 hr. The reaction mixture was quenched with saturated aqueous ammonium chloride (5 mL), and extracted with dichloromethane (5 mL*2). The organic phases were combined, dried over anhydrous sodium sulfate, and filtered. The filtrate was concentrated to give compound 6-1. LCMS: MS m/z=732.3[M+H]$^+$ Step 2: Synthesis of Compound 6-2

Compound 6-1 (200 mg, 273.15 μmol, 1 eq) was dissolved in dichloromethane (4 mL), and trifluoroacetic acid (3.08 g, 27.01 mmol, 2 mL, 98.89 eq) was added at 0° C. The mixture was reacted at 18° C. for 0.5 hr. The mixture was directly rotary-evaporated to dryness to give a crude product, which was purified by a high-performance liquid chromatography column (Phenomenex Gemini-NX 150*30 mm*5 μm; mobile phase: [H$_2$O(0.1% TFA)-acetonitrile]; acetonitrile %: 30%-60%, 9 min) to give compound 6-2. LCMS: MS m/z=632.3[M+H]$^+$ Step 3: Synthesis of Compound 6-3

Compound 6-2 (110 mg, 174.03 μmol, 1 eq) and paraformaldehyde (88.91 mg, 1.74 mmol, 10 eq) were dissolved in 1,2-dichloroethane (1 mL) and methanol (1 mL). Glacial acetic acid (1.05 mg, 17.40 μmol, 9.95e-1 μL, 0.1 eq) was added and the mixture was stirred for 30 min. Sodium cyanoborohydride (21.87 mg, 348.06 μmol, 2 eq) was added and the mixture was stirred at 25° C. for 10 hr. The mixture was poured into saturated aqueous ammonium chloride (10 mL), and dichloromethane (5 mL×3) was added. The organic phase was dried over anhydrous sodium sulfate, filtered and concentrated to give compound 6-3. LCMS: MS m/z=646.1 [M+H]$^+$, 647.7 [M+2H]$^+$ Step 4: Synthesis of Compound 6-4

Compound 6-3 (90 mg, 139.30 μmol, 1 eq) was dissolved in methanol (3 mL), and potassium carbonate (1.7 M, 2.70 mL, 32.95 eq) was added. The mixture was reacted at 18° C. for 1 hr. The reaction mixture was quenched with saturated aqueous ammonium chloride (5 mL), and extracted with ethyl acetate (5 mL×2). The organic phases were combined, washed with saturated brine, dried over anhydrous sodium sulfate, and filtered. The filtrate was concentrated to give compound 6-4. LCMS: MS m/z=550.2[M+H]$^+$, 551.8[M+2H]$^+$.

Step 5: Synthesis of Compounds 6A and 6B

Compound 6-4 (76 mg, 138.16 μmol, 1 eq) was dissolved in dichloromethane (20 mL), and N,N-diisopropylethylamine (267.83 mg, 2.07 mmol, 360.96 μL, 15 eq) was added. Acryloyl chloride (12.50 mg, 138.16 μmol, 11.27 μL, 1 eq) was added at −60° C. The mixture was reacted at −60° C. for 0.5 hr. The mixture was quenched with saturated aqueous ammonium chloride (5 mL), and extracted with ethyl acetate (5 mL×2). The organic phases were combined and concentrated to give compound 6-5, which was purified by a high-performance liquid chromatography column (Column: Phenomenex Gemini-NX C18 75*30 mm*3 μm; mobile phase: [H$_2$O(0.04% NH$_3$H$_2$O+10 mM NH$_4$HCO$_3$)-ACN]; acetonitrile %: 25%-55%, 6 min) to give compound 6-5, which was isolated by SFC (column: Phenomenex Gemini-NX C18 75*30 mm*3 μm; mobile phase: [H$_2$O(0.04% NH$_3$H$_2$O+10 mM NH$_4$HCO$_3$)-ACN]; acetonitrile %: 25%-55%, 6 min) to give compound 6A ((time-to-peak in chiral column=1.435 min), SFC analysis method (column: Chiralpak AD-3, 50×4.6 mm, I.D., 3 μm; Mobile phase: A (CO2) and B (isopropanol, containing 0.05% diethanolamine); Gradient: B %=5-50%, 3 min; Flow rate: 3.4 mL/min; Wavelength: 220 nm; Pressure: 1800 psi. Optical purity: 87.38%. LCMS: MS m/z=604.1[M+H]+) and compound 6B ((time-to-peak in chiral column=1.643), SFC analysis method (column: Chiralpak AD-3, 50×4.6 mm, I.D., 3 μm; Mobile phase: A (CO2) and B (isopropanol, containing 0.05% diethanolamine); Gradient: B %=5-50%, 3 min; Flow rate: 3.4 mL/min; Wavelength: 220 nm; Pressure: 1800 psi. Optical purity: 100%. LCMS: MS m/z=604.1 [M+H]+).

Example 7

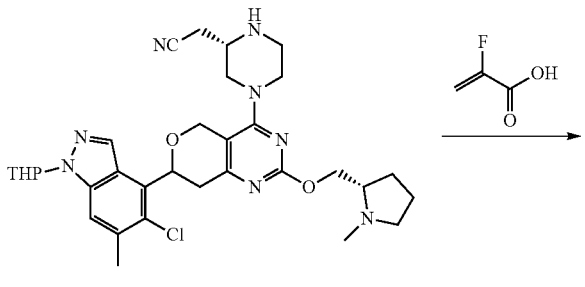

5-9

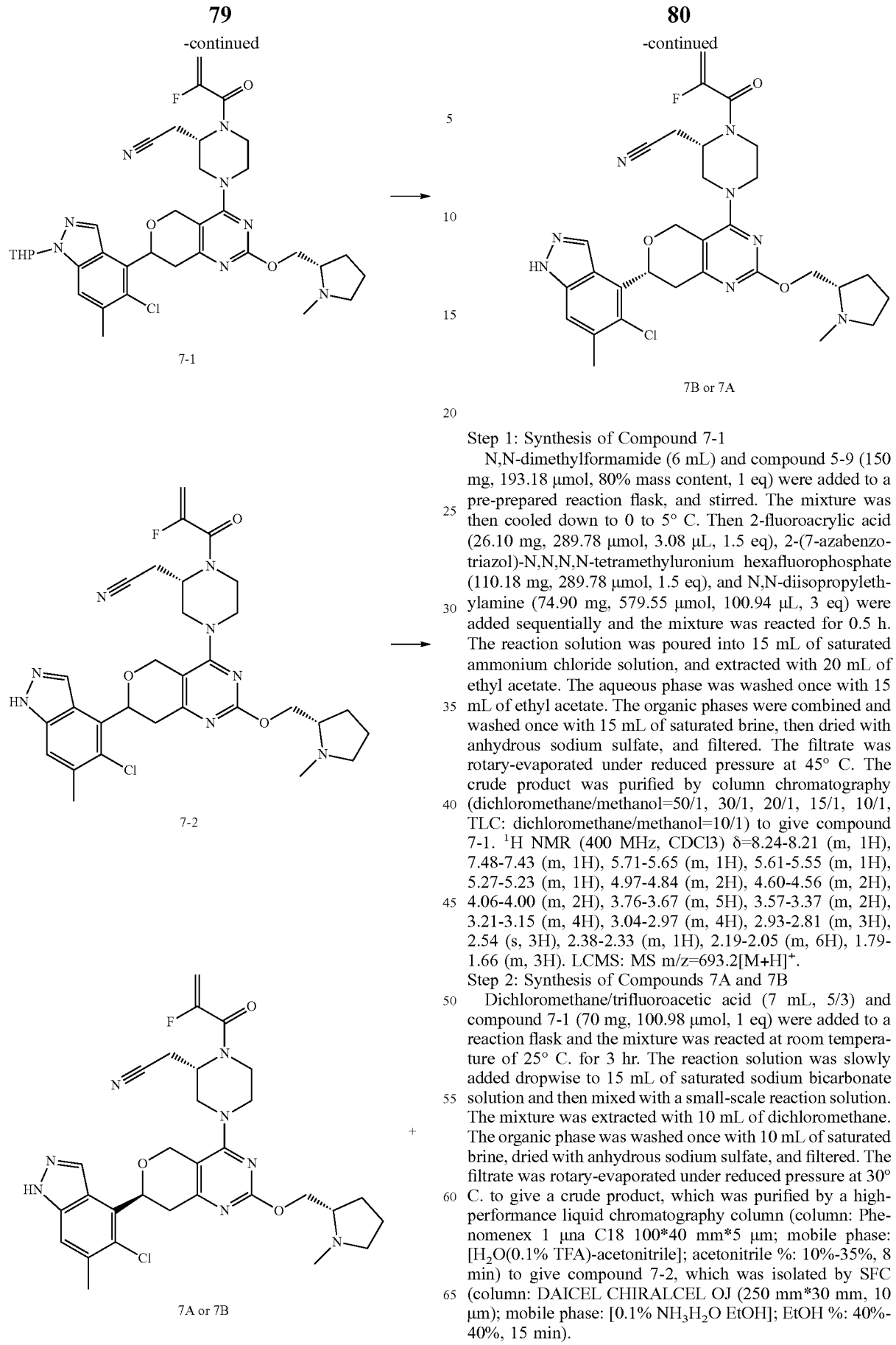

Step 1: Synthesis of Compound 7-1

N,N-dimethylformamide (6 mL) and compound 5-9 (150 mg, 193.18 μmol, 80% mass content, 1 eq) were added to a pre-prepared reaction flask, and stirred. The mixture was then cooled down to 0 to 5° C. Then 2-fluoroacrylic acid (26.10 mg, 289.78 μmol, 3.08 μL, 1.5 eq), 2-(7-azabenzotriazol)-N,N,N,N-tetramethyluronium hexafluorophosphate (110.18 mg, 289.78 μmol, 1.5 eq), and N,N-diisopropylethylamine (74.90 mg, 579.55 μmol, 100.94 μL, 3 eq) were added sequentially and the mixture was reacted for 0.5 h. The reaction solution was poured into 15 mL of saturated ammonium chloride solution, and extracted with 20 mL of ethyl acetate. The aqueous phase was washed once with 15 mL of ethyl acetate. The organic phases were combined and washed once with 15 mL of saturated brine, then dried with anhydrous sodium sulfate, and filtered. The filtrate was rotary-evaporated under reduced pressure at 45° C. The crude product was purified by column chromatography (dichloromethane/methanol=50/1, 30/1, 20/1, 15/1, 10/1, TLC: dichloromethane/methanol=10/1) to give compound 7-1. $^1$H NMR (400 MHz, CDCl3) δ=8.24-8.21 (m, 1H), 7.48-7.43 (m, 1H), 5.71-5.65 (m, 1H), 5.61-5.55 (m, 1H), 5.27-5.23 (m, 1H), 4.97-4.84 (m, 2H), 4.60-4.56 (m, 2H), 4.06-4.00 (m, 2H), 3.76-3.67 (m, 5H), 3.57-3.37 (m, 2H), 3.21-3.15 (m, 4H), 3.04-2.97 (m, 4H), 2.93-2.81 (m, 3H), 2.54 (s, 3H), 2.38-2.33 (m, 1H), 2.19-2.05 (m, 6H), 1.79-1.66 (m, 3H). LCMS: MS m/z=693.2[M+H]$^+$.

Step 2: Synthesis of Compounds 7A and 7B

Dichloromethane/trifluoroacetic acid (7 mL, 5/3) and compound 7-1 (70 mg, 100.98 μmol, 1 eq) were added to a reaction flask and the mixture was reacted at room temperature of 25° C. for 3 hr. The reaction solution was slowly added dropwise to 15 mL of saturated sodium bicarbonate solution and then mixed with a small-scale reaction solution. The mixture was extracted with 10 mL of dichloromethane. The organic phase was washed once with 10 mL of saturated brine, dried with anhydrous sodium sulfate, and filtered. The filtrate was rotary-evaporated under reduced pressure at 30° C. to give a crude product, which was purified by a high-performance liquid chromatography column (column: Phenomenex 1 μna C18 100*40 mm*5 μm; mobile phase: [H$_2$O(0.1% TFA)-acetonitrile]; acetonitrile %: 10%-35%, 8 min) to give compound 7-2, which was isolated by SFC (column: DAICEL CHIRALCEL OJ (250 mm*30 mm, 10 μm); mobile phase: [0.1% NH$_3$H$_2$O EtOH]; EtOH %: 40%-40%, 15 min).

Compound 7A was obtained (time-to-peak in chiral column: 1.263 min). SFC resolution method (column: Chiralcel OJ-3, 50×4.6 mm I.D., 3 μm; Mobile phase: A (CO2) and B (ethanol, containing 0.05% diisopropylamine); Gradient: B %=5-50%, 3 min; Flow rate: 3.4 mL/min; Wavelength: 220 nm; Pressure: 1800 psi. Optical purity: 91.94%. $^1$HNMR (400 MHz, CDCl$_3$) δ=8.29 (s, 1H), 7.35 (s, 1H), 5.61-5.57 (m, 1H), 5.48-5.32 (m, 1H), 5.28-5.24 (m, 1H), 4.95-4.86 (m, 3H), 4.44-4.43 (m, 1H), 4.20-4.16 (m, 2H), 3.97-3.93 (m, 1H), 3.80-3.78 (m, 1H), 3.50-3.48 (m, 1H), 3.27-3.22 (m, 1H), 3.14-2.95 (m, 4H), 2.81-2.71 (m, 3H), 2.52-2.50 (m, 7H), 2.34-2.28 (m, 1H), 2.08-2.02 (m, 1H), 1.91-1.84 (m, 2H). LCMS: MS m/z=609.2[M+H]$^+$.

Compound 7B was obtained (time-to-peak in chiral column: 1.393 min). SFC resolution method (column: Chiralcel OJ-3, 50×4.6 mm I.D., 3 μm; Mobile phase: A (CO2) and B (ethanol, containing 0.05% diisopropylamine); Gradient: B %=5-50%, 3 min; Flow rate: 3.4 mL/min; Wavelength: 220 nm; Pressure: 1800 psi. Optical purity: 82.48%. $^1$HNMR (400 MHz, CDCl3) δ=8.26 (s, 1H), 7.35 (s, 1H), 5.59-5.55 (m, 1H), 5.48-5.36 (m, 1H), 5.29-5.24 (m, 1H), 4.93 (s, 2H), 4.42-4.40 (m, 1H), 4.24-4.20 (m, 2H), 3.73-3.70 (m, 1H), 3.24-2.98 (m, 8H), 2.90-2.71 (m, 3H), 2.53-2.48 (m, 7H), 2.33-2.31 (m, 1H), 2.09-2.04 (m, 1H), 1.89-1.85 (m, 2H). LCMS: MS m/z=609.1 [M+H]$^+$.

Example 8

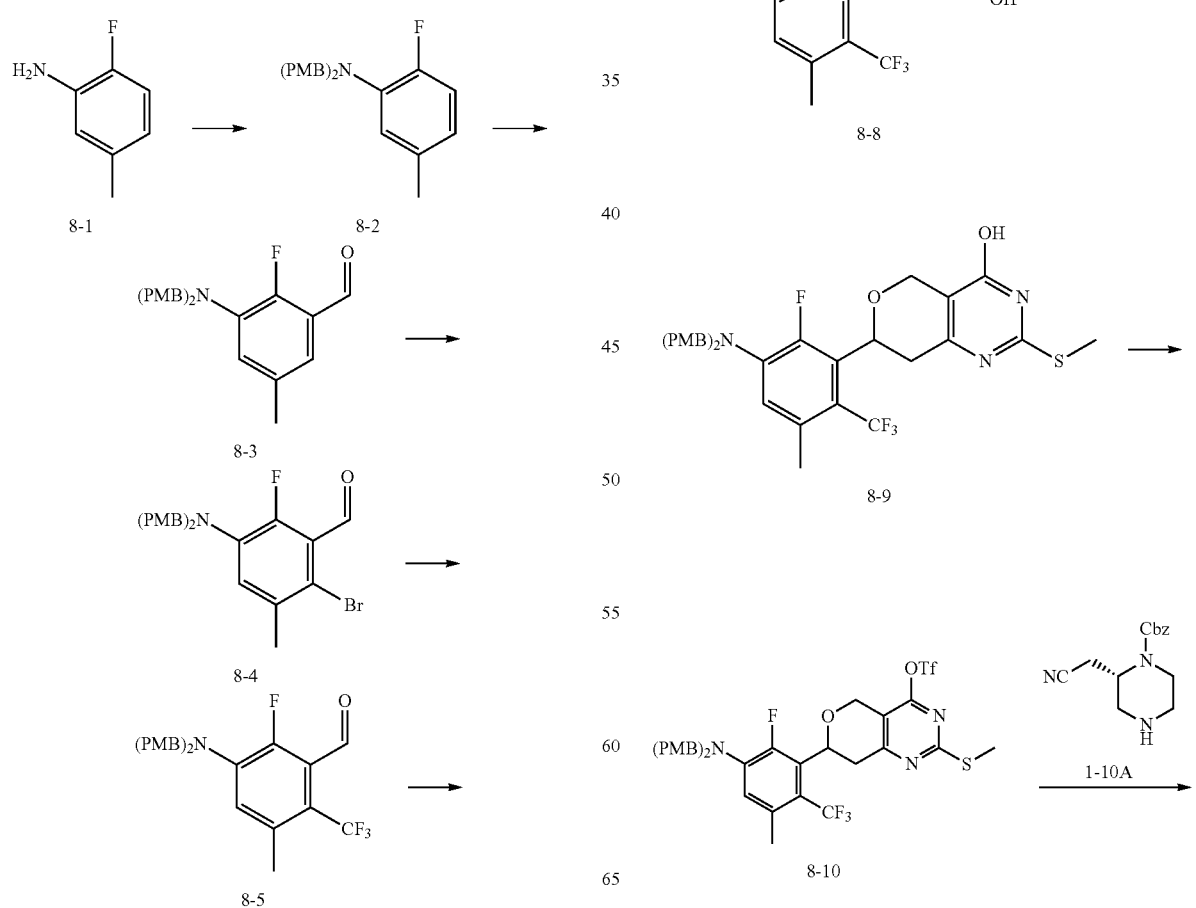

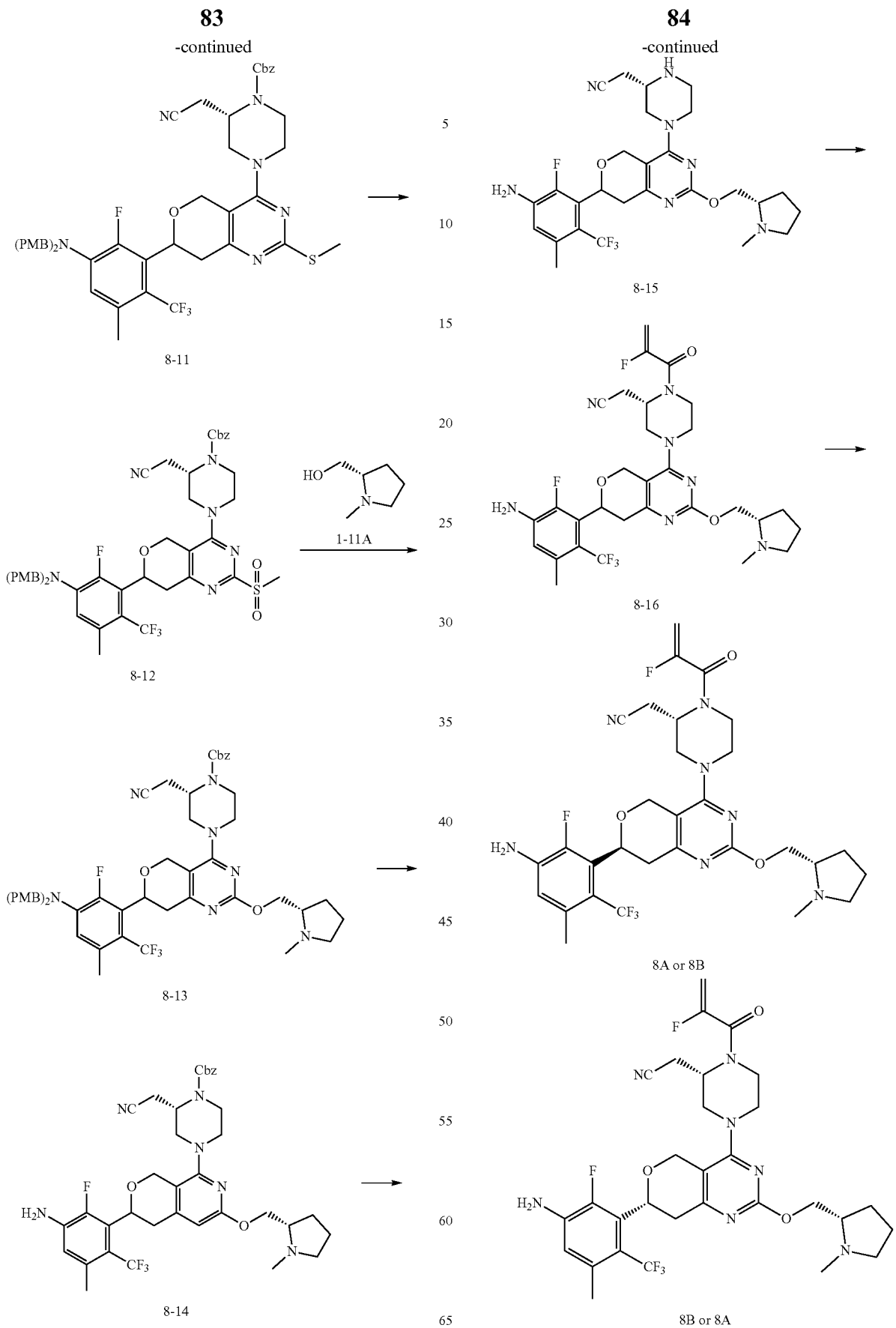

Step 1: Synthesis of Compound 8-2

In a dry 2 L three-necked flask (in anhydrous and oxygen-free environment), sodium hydride (39.12 g, 978.08 mmol, 60% mass content, 2.4 eq) was added to N,N-dimethylformamide (510 mL) and the reaction system became non-homogeneous and gray. The mixture was cooled down to 0° C., and a solution of compound 8-1 (51 g, 407.53 mmol, 1 eq) in N,N-dimethylformamide (200 mL) was added dropwise under nitrogen. The mixture was reacted at 0° C. for 0.5 hr. p-Methoxybenzyl chloride (140.41 g, 896.57 mmol, 122.10 mL, 2.2 eq) was added and the reaction system was slowly warmed up to 20° C. The reaction system became earthy red and reacted under nitrogen for 7.5 hr. The reaction solution was slowly added to 200 mL of saturated ammonium chloride, and extracted with methyl tert-butyl ether (200 mL×2). The organic phases were combined, washed with 200 mL of saturated brine, dried with anhydrous sodium sulfate, and filtered. The filtrate was then concentrated to give a crude product. The crude product was separated by chromatography purification system COMBI-FLASH (gradient elution: petroleum ether:ethyl acetate=10:0-10:1, petroleum ether:ethyl acetate=10:1) to give compound 8-2. $^1$H NMR (400 MHz, CDCl3) δ=7.23-7.18 (m, 4H), 6.91-6.87 (m, 1H), 6.82-6.76 (m, 4H), 6.65-6.59 (m, 2H), 4.20 (s, 4H), 3.79 (s, 6H), 2.19 (s, 3H). LCMS: MS m/z=366.1 [M+H]$^+$.

Step 2: Synthesis of Compound 8-3

2,2,6,6-tetramethylpiperidine (31.31 g, 221.65 mmol, 37.63 mL, 3 eq) was added to anhydrous tetrahydrofuran (300 mL), and the mixture was cooled down to −5° C. n-Butyllithium (2.5 M, 94.57 mL, 3.2 eq) was added dropwise, and the mixture was reacted at −5 to 0° C. for 15 min. The mixture was cooled down to −60° C., and a solution of compound 8-2 (27 g, 73.88 mmol, 1 eq) in tetrahydrofuran (60 mL) was added. The mixture was reacted at −60° C. for 0.5 h. N,N-dimethylformamide (108.00 g, 1.48 mol, 113.69 mL, 20 eq) was added rapidly and the mixture was reacted at −60° C. for 10 min. 400 mL of saturated ammonium chloride was added to the reaction solution and the mixture was extracted with 200 mL×2 of methyl tert-butyl ether. The organic phases were combined, washed with 200 mL of saturated brine, dried with anhydrous sodium sulfate, and filtered. The filtrate was concentrated to give a crude product, which was slurried with 70 mL of a solvent mixture of petroleum ether and methyl tert-butyl ether (petroleum ether:methyl tert-butyl ether=5:1) for 0.5 hr, and then filtered. The filter cake was rotary-evaporated to dryness, and the filtrate was stirred and purified by column (petroleum ether:ethyl acetate=100:0-10:1) to give compound 8-3. $^1$H NMR (400 MHz, CDCl$_3$) δ=10.43-10.35 (m, 1H), 7.21-7.18 (m, 5H), 6.92-6.81 (m, 5H), 4.25 (s, 4H), 3.80 (s, 6H), 2.23 (s, 3H). LCMS: MS m/z=394.2[M+H]$^+$.

Step 3: Synthesis of Compound 8-4

Compound 8-3 (17.8 g, 45.24 mmol, 1 eq) was added to N,N-dimethylformamide (170 mL). Bromosuccinimide (8.05 g, 45.24 mmol, 1 eq) was added and the mixture was reacted at 20° C. for 20 min. The reaction solution was added to 300 mL of water, and extracted with 150 mL×2 of methyl tert-butyl ether. The organic phases were combined, washed with 100 mL×2 of saturated brine, dried with anhydrous sodium sulfate, and filtered. The filtrate was concentrated. The crude product was slurried with a solvent mixture of ethyl acetate and methyl tert-butyl ether (ethyl acetate:methyl tert-butyl ether=1:1) for 0.5 hr, and then filtered. The filter cake was rotary-evaporated to dryness to give compound 8-4. $^1$H NMR (400 MHz, CDCl$_3$) δ=10.39 (s, 1H), 7.17 (d, J=8.8 Hz, 4H), 6.89 (d, J=8.8 Hz, 1H), 6.85-6.82 (m, 4H), 4.22 (s, 4H), 3.79 (s, 6H), 2.28 (s, 3H). LCMS: MS m/z=472.1[M+H]$^+$, 474.1[M+3H]$^+$.

Step 4: Synthesis of Compound 8-5

Compound 8-4 (19.3 g, 40.86 mmol, 1 eq) was added to N,N-dimethylformamide (190 mL). Cuprous iodide (15.56 g, 81.72 mmol, 2 eq) and methyl fluorosulfonyldifluoroacetate (39.25 g, 204.30 mmol, 25.99 mL, 5 eq) were added, and the mixture was reacted at 100° C. under nitrogen for 1 hr. The reaction solution was filtered through a pad of diatomaceous earth. The filtrate was added to 300 mL of water, and extracted with 150 mL×2 of methyl tert-butyl ether. The organic phases were combined, washed with saturated brine (200 mL×2), dried with anhydrous sodium sulfate, and filtered. The filtrate was concentrated. The crude product was purified by column (petroleum ether:ethyl acetate=100:0-10:1, petroleum ether:ethyl acetate=5:1) to give compound 8-5. $^1$H NMR (400 MHz, CDCl$_3$) δ=10.37 (q, J=4.0 Hz, 1H), 7.18-7.11 (m, 4H), 6.89-6.82 (m, 4H), 6.73 (d, J=8.8 Hz, 1H), 4.36 (s, 4H), 3.81 (s, 6H), 2.37-2.29 (m, 3H). LCMS: MS m/z=484.0[M+Na]$^+$.

Step 5: Synthesis of Compound 8-6

Anhydrous tetrahydrofuran (50 mL) and sodium hydride (1.17 g, 29.26 mmol, 60% mass content, 3 eq) were added to a dry three-necked flask. The mixture was cooled down to 0° C. Methyl acetoacetate (3.40 g, 29.26 mmol, 3.15 mL, 3 eq) was added dropwise under nitrogen and the mixture was reacted at 0° C. under nitrogen for 0.5 hr. n-Butyllithium (2.5 M, 11.70 mL, 3 eq) was added dropwise, and the mixture was reacted at 0° C. for 0.5 hr. The mixture was cooled down to −60° C. A solution of compound 8-5 (4.5 g, 9.75 mmol, 1 eq) in tetrahydrofuran (20 mL) was added dropwise, and the mixture was reacted at −60° C. for 0.5 hr. 100 mL of saturated ammonium chloride solution was added to the reaction solution, and the mixture was extracted with 30 mL of ethyl acetate. The organic phase was washed with 80 mL of saturated brine, dried with anhydrous sodium sulfate, and filtered. The filtrate was concentrated to give a crude product, which was combined and purified by column (petroleum ether:ethyl acetate=100:0-3:1, petroleum ether:ethyl acetate=3:1) to give compound 8-6 as a yellow oil. $^1$H NMR (400 MHz, CDCl3) δ=7.18-7.15 (m, 4H), 6.90-6.78 (m, 4H), 6.61 (d, J=8.8 Hz, 1H), 5.72-5.57 (m, 1H), 4.31 (m, 4H), 3.81 (s, 6H), 3.76 (s, 3H), 3.56 (s, 2H), 3.50-3.38 (m, 1H), 2.98-2.93 (m, 1H), 2.38-2.26 (m, 3H). LCMS: MS m/z=578.1[M+H]$^+$.

Step 6: Synthesis of Compound 8-7

Compound 8-6 (3 g, 5.19 mmol, 1 eq) was added to anhydrous dichloromethane (30 mL), and N,N-dimethylformamide dimethyl acetal (742.74 mg, 6.23 mmol, 828.02 μL, 1.2 eq) was added. The mixture was reacted at 20° C. for 16 hr. Boron trifluoride etherate (884.66 mg, 6.23 mmol, 769.27 μL, 1.2 eq) was added, and the mixture was reacted at 20° C. for 1 hr. The reaction solution was added to 20 mL of saturated sodium bicarbonate solution. The layers were separated, and the aqueous phase was extracted with 20 mL of dichloromethane. The organic phases were combined, dried with anhydrous sodium sulfate, and filtered. The filtrate was concentrated. The crude product was purified by column (petroleum ether:ethyl acetate=100:0-3:1, petroleum ether:ethyl acetate=3:1) to give compound 8-7. $^1$H NMR (400 MHz, CDCl$_3$) δ=8.43 (d, J=0.8 Hz, 1H), 7.21-7.10 (m, 4H), 6.91-6.81 (m, 4H), 6.70 (d, J=8.8 Hz, 1H), 5.93 (dd, J=3.2, 14.8 Hz, 1H), 4.35 (s, 4H), 3.8 (s, 3H), 3.81 (s, 6H), 3.38-3.29 (m, 1H), 2.68 (dd, J=3.6, 16.8 Hz, 1H), 2.39-2.24 (m, 3H). LCMS: MS m/z=588.2[M+H]$^+$.

Step 7: Synthesis of Compound 8-8

Compound 8-7 (2.1 g, 3.57 mmol, 1 eq) was added to anhydrous tetrahydrofuran (21 mL). The mixture was cooled down to −60° C., and lithium tri-sec-butylborohydride (1 M, 4.29 mL, 1.2 eq) was added under nitrogen. The mixture was reacted at −60° C. for 0.5 hr. The reaction solution was added to 30 mL of saturated ammonium chloride. The layers were separated after extraction. The organic phase was washed with 20 mL of saturated brine, dried with anhydrous sodium sulfate, and filtered. The filtrate was concentrated to give a crude product, which was purified by column (petroleum ether:ethyl acetate=100:0-3:1, petroleum ether:ethyl acetate=3:1) to give compound 8-8. $^1$H NMR (400 MHz, CDCl3) δ=7.167-7.14 (m, 4H), 6.87-6.83 (m, 4H), 6.63 (d, J=8.8 Hz, 1H), 5.05-5.00 (m, 1H), 4.61-4.58 (m, 1H), 4.42-4.24 (m, 5H), 3.85-3.73 (m, 10H), 3.13-3.05 (m, 1H), 2.47-2.38 (m, 1H), 2.35-2.31 (m, 3H). LCMS: MS m/z=600.1 [M+H]$^+$, Step 8: Synthesis of Compound 8-9

Compound 8-8 (1.27 g, 2.15 mmol, 1 eq) was added to ethanol (15 mL) and water (3 mL), and sodium bicarbonate (3.62 g, 43.08 mmol, 1.68 mL, 20 eq) and methyl isothiourea sulfate (4.05 g, 21.54 mmol, 10 eq) were added. The mixture was reacted at 50° C. for 4 hr. The reaction solution was added to 40 mL of water, and extracted with 20 mL×2 of ethyl acetate. The organic phases were combined, washed with 20 mL×2 of saturated brine, dried with anhydrous sodium sulfate, and filtered. The filtrate was concentrated. The crude product was purified by column (petroleum ether:ethyl acetate=100:0-1:1, petroleum ether:ethyl acetate=1:1) to give compound 8-9. $^1$H NMR (400 MHz, CDCl3) δ=7.22-7.14 (m, 4H), 6.91-6.82 (m, 4H), 6.65 (dd, J=8.4 Hz 1H), 5.12-5.08 (m, 1H), 4.97-4.91 (m, 1H), 4.67-4.57 (m, 1H), 4.45-4.22 (m, 4H), 3.88-3.74 (m, 6H), 3.43-3.35 (m, 1H), 2.77-2.72 (m, 1H), 2.59 (m, 3H), 2.40-2.31 (m, 3H). LCMS: MS m/z=630.2[M+H]$^+$.

Step 9: Synthesis of Compound 8-10

Compound 8-9 (0.57 g, 905.25 μmol, 1 eq) was added to anhydrous dichloromethane (6 mL), and N,N-diisopropylethylamine (409.48 mg, 3.17 mmol, 551.86 μL, 3.5 eq) and triflic anhydride (510.81 mg, 1.81 mmol, 298.72 μL, 2 eq) were added at 0° C. The mixture was reacted at 0 to 5° C. for 5 hr. The reaction solution was added to 20 mL of saturated ammonium chloride, and extracted with 10 mL of dichloromethane. The organic phase was dried with anhydrous sodium sulfate, and filtered. The filtrate was concentrated. The crude product was purified by column (petroleum ether:ethyl acetate=100:0-5:1, petroleum ether:ethyl acetate=3:1) to give compound 8-10. $^1$H NMR (400 MHz, CDCl3) δ=7.21-7.11 (m, 4H), 6.90-6.80 (m, 4H), 6.66 (d, J=8.4 Hz, 1H), 5.19-5.15 (m, 1H), 5.04-4.93 (m, 1H), 4.77-4.72 (m, 1H), 4.41-4.19 (m, 4H), 3.80 (s, 6H), 3.62-3.54 (m, 1H), 3.11-2.97 (m, 1H), 2.56 (s, 3H), 2.42-2.31 (m, 3H). LCMS: MS m/z=762.2[M+H]$^+$.

Step 10: Synthesis of Compound 8-11

Compound 8-10 (0.45 g, 590.76 μmol, 1 eq) was added to N,N-dimethylformamide (5 mL), and N,N-diisopropylethylamine (229.05 mg, 1.77 mmol, 308.69 μL, 3 eq) and compound 1-10A (306.37 mg, 1.18 mmol, 2 eq, HCl) were added sequentially. The mixture was reacted at 50° C. for 2 hr. The reaction solution was poured into 20 mL of water, and filtered. The filter cake was dissolved in 20 mL of methyl tert-butyl ether, and washed with 20 mL of saturated brine. The organic phase was dried with anhydrous sodium sulfate, and filtered. The filtrate was concentrated to give compound 8-11. $^1$H NMR (400 MHz, CDCl3) δ=7.44-7.32 (m, 5H), 7.16-7.13 (m, 4H), 6.85-6.82 (m, 4H), 6.63 (d, J=7.6 Hz, 1H), 5.21-5.15 (m, 2H), 4.80-4.66 (m, 3H), 4.39-4.22 (m, 4H), 3.93-3.88 (m, 1H), 3.80 (s, 6H), 3.71-3.55 (m, 1H), 3.52-3.29 (m, 2H), 3.25-3.08 (m, 3H), 3.06-2.96 (m, 2H), 2.91-2.77 (m, 1H), 2.71-2.68 (m, 1H), 2.52 (s, 3H), 2.35-2.30 (m, 3H). LCMS: MS m/z=871.4[M+H]$^+$.

Step 11: Synthesis of Compound 8-12

Compound 8-11 (580.00 mg, 665.94 μmol, 1 eq) was added to anhydrous dichloromethane (6 mL), and m-chloroperoxybenzoic acid (359.13 mg, 1.66 mmol, 80% mass content, 2.5 eq) was added. The mixture was reacted at 25° C. for 0.5 hr. The reaction solution was poured into 20 mL of sodium thiosulfate solution (10%), and extracted with 10 mL of dichloromethane. The organic phase was dried with anhydrous sodium sulfate, and filtered. The filtrate was rotary-evaporated under reduced pressure at 45° C. The crude product was purified by column (petroleum ether:ethyl acetate=100:0-1:1, petroleum ether:ethyl acetate=1:1) to give compound 8-12. $^1$H NMR (400 MHz, CDCl3) δ=7.40-7.37 (m, 5H), 7.17-7.12 (m, 4H), 6.86-6.82 (m, 4H), 6.67-6.64 (d, J=8.4 Hz, 1H), 5.19 (s, 2H), 4.86-4.79 (m, 2H), 4.71-4.63 (m, 1H), 4.35-4.24 (m, 4H), 3.82-3.81 (m, 1H), 3.80 (s, 6H), 3.64-3.50 (m, 2H), 3.46-3.33 (m, 2H), 3.30-3.27 (m, 4H), 3.25-3.11 (m, 3H), 2.71-2.65 (m, 1H), 2.52-2.45 (m, 1H), 2.38-2.30 (m, 3H). LCMS: MS m/z=903.3 [M+H]$^+$.

Step 12: Synthesis of Compound 8-13

Compound 1-11A (117.35 mg, 1.02 mmol, 120.98 μL, 4 eq) was added to dioxane (5 mL). The mixture was cooled down to 0-5° C. Sodium tert-butoxide (97.91 mg, 1.02 mmol, 4 eq) was added and the mixture was reacted for 10 min. A solution of compound 8-12 (230.00 mg, 254.72 μmol, 1 eq) in toluene (1 mL) was added and the mixture was reacted for 0.5 hr. The reaction solution was added to 20 mL of saturated ammonium chloride, and extracted with 10 mL×2 of ethyl acetate. The organic phases were combined, washed with 20 mL of saturated brine, dried with anhydrous sodium sulfate, and filtered. The filtrate was concentrated. The crude product was purified by column (petroleum ether:ethyl acetate=1:1-0:1, dichloromethane:methanol=100:0-10:1, dichloromethane:methanol=10:1) to give compound 8-13. LCMS: MS m/z=938.2[M+H]$^+$.

Step 13: Synthesis of Compound 8-14

Compound 8-13 (0.15 g, 159.91 μmol, 1 eq) was added to anhydrous dichloromethane (5 mL), and trifluoroacetic acid (0.5 mL) was added. The mixture was reacted at 25° C. for 2.5 hr. The reaction solution was added to 10 mL of saturated sodium bicarbonate solution, and extracted with 5 mL×2 of dichloromethane. The organic phases were combined, dried with anhydrous sodium sulfate, and filtered. The filtrate was concentrated to give compound 8-14. LCMS: MS m/z=698.2[M+H]$^+$.

Step 14: Synthesis of Compound 8-15

Compound 8-14 (0.17 g, 243.65 μmol, 1 eq) was added to anhydrous methanol (2 mL) and anhydrous tetrahydrofuran (2 mL). Palladium on carbon (0.15 g, 10% mass content) was added and the mixture was reacted at 25° C. under hydrogen (15 psi) for 0.5 hr. The reaction solution was directly filtered to recover the catalyst and the filtrate was concentrated to give compound 8-15 as a yellow solid. LCMS: MS m/z=564.2[M+H]$^+$.

Step 15: Synthesis of Compounds 8A and 8B

Compound 8-15 (60 mg, 106.46 μmol, 1 eq), 2-fluoroacrylic acid (11.50 mg, 127.75 μmol, 1.2 eq) and 2-(7-azabenzotriazol)-N,N,N',N'-tetramethyluronium hexafluorophosphate (60.72 mg, 159.69 μmol, 1.5 eq) were added to N,N-dimethylformamide (1 mL). N,N-diisopropylethylamine (41.28 mg, 319.38 μmol, 55.63 μL, 3 eq) was added, and the mixture was reacted at 25° C. for 0.5 hr. The reaction solution was added to 10 mL of saturated ammonium chloride, and extracted with 5 mL×2 of ethyl acetate. The organic phases were combined, washed with 5 mL×2 of saturated brine, dried over anhydrous sodium sulfate and filtered. The filtrate was concentrated to give compound 8-16, which was purified by a high-performance liquid chromatography column (column: Phenomenex Gemini-NX 150*30 mm*5 μm; mobile phase: [H$_2$O(0.1% TFA)-ACN]; acetonitrile %: 20%-50%, 9 min). The fractions were concentrated under vacuum. 5 mL of deionized water and 0.5 mL of acetonitrile were added, and then 2 drops of 1M hydrochloric acid solution were added. The mixture was concentrated under vacuum to give compound 8A hydrochloride ((time-to-peak: 1.379 min). SFC resolution method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi. Optical purity: 80.82%. LCMS: MS m/z=636.4[M+H]$^+$) and compound 8B hydrochloride ((time-to-peak: 1.789 min). SFC resolution method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi. Optical purity: 75.56%). $^1$H NMR (400 MHz, CDCl$_3$) δ=6.59 (d, J=8.4 Hz, 1H), 5.50-5.33 (m, 1H), 5.29-5.16 (m, 2H), 4.82-4.69 (m, 2H), 4.39 (dd, J=5.2, 10.8 Hz, 1H), 4.16 (dd, J=6.8, 10.4 Hz, 1H), 4.04 (s, 2H), 3.94 (d, J=14.0 Hz, 1H), 3.68 (d, J=11.6 Hz, 1H), 3.50-3.32 (m, 2H), 3.10 (br t, J=7.2 Hz, 1H), 3.05-2.94 (m, 2H), 2.79 (br d, J=7.2 Hz, 2H), 2.71-2.62 (m, 1H), 2.48 (s, 3H), 2.39 (q, J=4.0 Hz, 3H), 2.32-2.22 (m, 1H), 2.11-1.99 (m, 1H), 1.93-1.66 (m, 6H). LCMS: MS m/z=636.4[M+H]$^+$.

Example 9

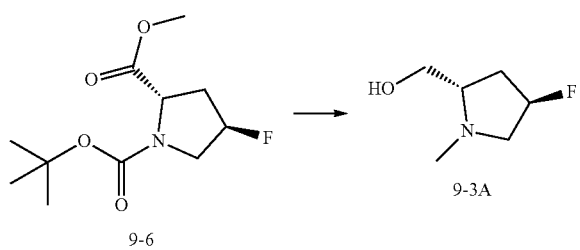

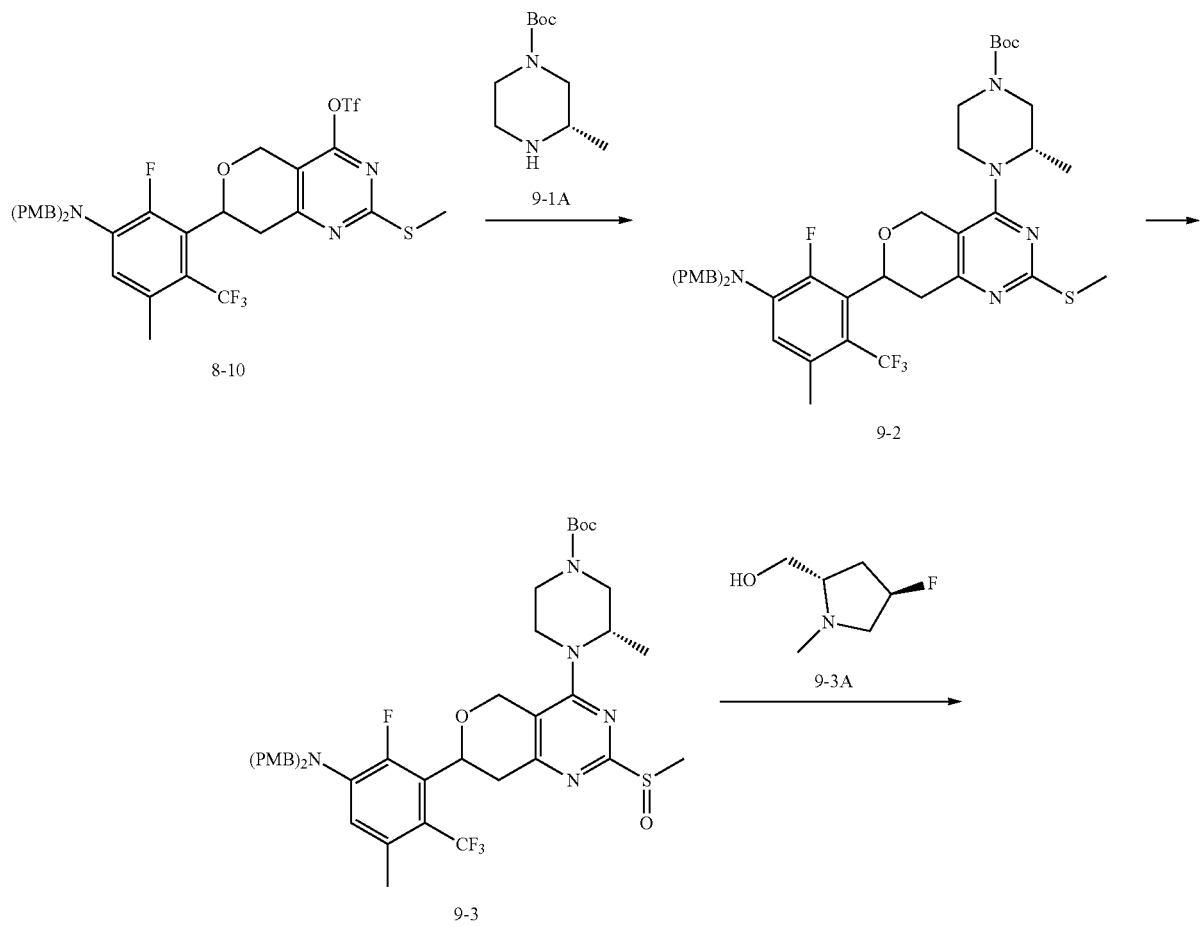

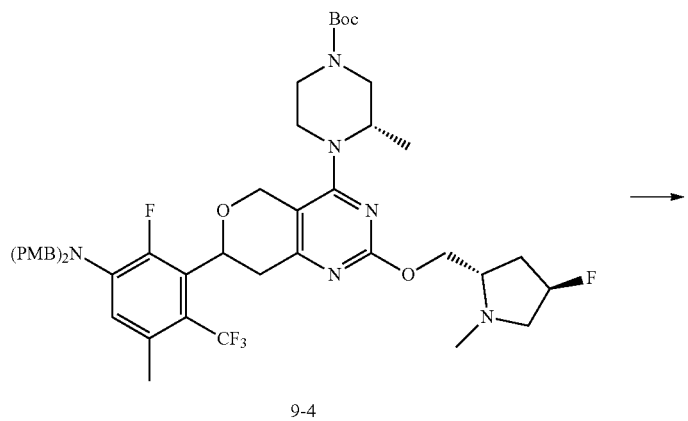

9-4

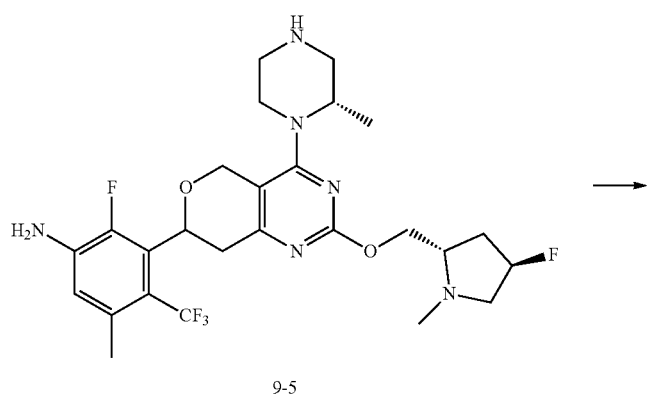

9-5

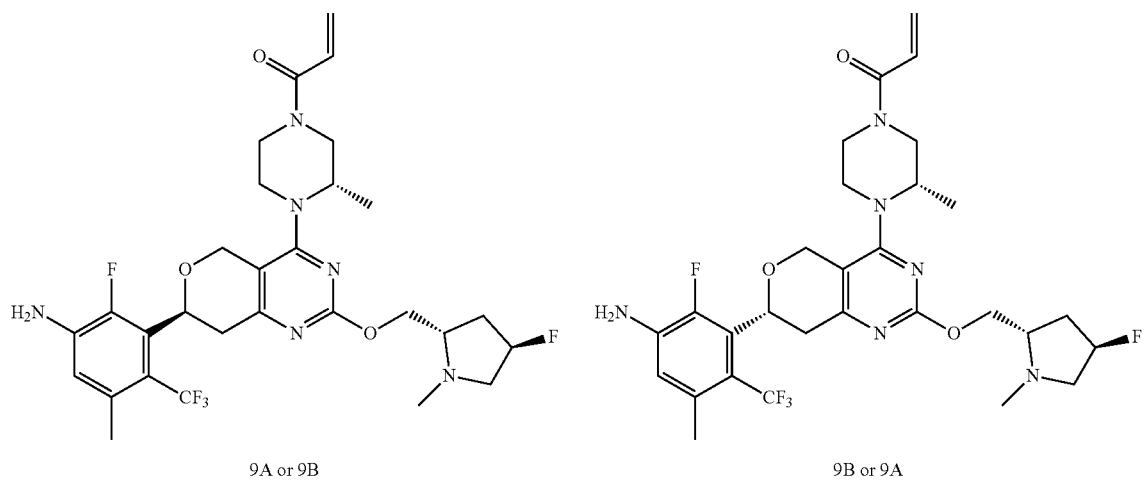

9A or 9B            9B or 9A

Step 1: Synthesis of Compound 9-3A

Anhydrous tetrahydrofuran (30 mL) was added to a dry reaction flask, and then compound 9-6 (1.5 g, 6.07 mmol, 1 eq) was added. The reaction system was cooled down to 10° C. Lithium aluminum hydride (690.66 mg, 18.20 mmol, 3 eq) was added in batches, and the reaction system was reacted at 15° C. for 16 h. Sodium sulfate decahydrate (4 g) was added to the reaction solution and the mixture was stirred for 1 h. The mixture was filtered. The filter cake was added to tetrahydrofuran (20 mL×2) and the mixture was stirred for 0.5 hr. The mixtures were separately filtered. The filtrates were combined, and concentrated under reduced pressure to give compound 9-3A, which was used directly in the next step without purification. $^1$H NMR (400 MHz, CDCl$_3$) δ ppm 5.25-4.98 (m, 1H) 3.75-3.65 (m, 1H) 3.61-3.43 (m, 2H) 2.83-2.74 (m, 1H) 2.71-2.56 (m, 1H) 2.39 (s, 3H) 2.14-2.03 (m, 2H). LCMS m/z=134.2 [M+H]$^+$.

Step 2: Synthesis of Compound 9-2

N,N-dimethylformamide (6 mL) was added to a dry reaction flask, followed by compound 8-10 (0.55 g, 722.04 μmol, 1 eq), N,N-diisopropylethylamine (279.95 mg, 2.17 mmol, 377.29 uL, 3 eq) and compound 9-1A (289.22 mg, 1.44 mmol, 2 eq). The reaction system was reacted at 50° C. under nitrogen for 50 min. Additional compound 9-1A (50 mg) was added, and the mixture was reacted for another 0.5 h. TLC (petroleum ether:ethyl acetate=3:1) showed that the raw material disappeared and new spots appeared. After the reaction system was cooled down to room temperature (15° C.), the reaction solution was added to saturated ammonium chloride solution (30 mL), and extracted with methyl tert-butyl ether (10 mL×2). The organic phases were combined, washed with saturated brine (20 mL×2), dried with anhydrous sodium sulfate, and filtered. The filtrate was concentrated under reduced pressure to give compound 9-2, which was used directly in the next step without purification. LCMS m/z=812.4[M+H]$^+$ Step 3: Synthesis of Compound 9-3

Dichloromethane (10 mL) was added to a dry reaction flask, and then compound 9-2 (0.65 g, 800.57 μmol, 1 eq) and m-chloroperoxybenzoic acid (207.23 mg, 960.68 μmol, 80% purity, 1.2 eq) were added. The reaction system was reacted at 15° C. for 0.5 hr. The reaction solution was poured into water (20 mL). Sodium thiosulfate solution (20 mL, 10%) was added and the mixture showed negative by starch-KI paper. The mixture was then extracted with dichloromethane (20 mL). The organic phase was dried with anhydrous sodium sulfate and filtered. The filtrate was concentrated under reduced pressure at 40° C. to give a crude product, which was purified by column (petroleum ether:ethyl acetate=3:1 to 0:1) according to TLC (petroleum ether:ethyl acetate=0:1, RF=0.53) to give compound 9-3. $^1$H NMR (400 MHz, CDCl$_3$) δ ppm 7.16 (d, J=7.60 Hz, 4H) 6.84 (d, J=8.40 Hz, 4H) 6.66 (s, 1H) 5.26 (d, J=10.42 Hz, 1H), 4.85-4.68 (m, 2H) 4.39-4.20 (m, 4H) 4.09-3.90 (m, 2H) 3.89-3.67 (m, 7H) 3.66-3.42 (m, 2H) 3.40-3.16 (m, 2H) 3.14-2.75 (m, 4H) 2.34 (d, J=4.00 Hz, 3H) 1.49 (s, 9H) 1.43-1.37 (m, 2H) 1.19 (m, 2H), LCMS m/z=828.2[M+H]$^+$ Step 4: Synthesis of Compound 9-4

Toluene (6 mL) was added to a dry reaction flask, and then compound 9-3A (289.51 mg, 2.17 mmol, 28.68 μL, 4 eq) was added. The reaction system was cooled down to 0° C. Sodium tert-butoxide (208.93 mg, 2.17 mmol, 4 eq) was added and the reaction system was reacted at 0 to 5° C. for 10 min. A solution of compound 9-3 (0.45 g, 543.53 μmol, 1 eq) in toluene (2 mL) was added and the reaction system was reacted at 0 to 5° C. for 0.5 hours. The reaction solution was washed with saturated ammonium chloride (20 mL×2), followed by saturated brine (20 mL), dried with anhydrous sodium sulfate, and filtered. The filtrate was concentrated under reduced pressure to give compound 9-4, which was used directly in the next step without purification. $^1$H NMR (400 MHz, CDCl$_3$) δ ppm 7.15 (d, J=7.60 Hz, 4H) 6.84 (d, J=8.40 Hz, 4H) 6.62 (d, J=7.20 Hz, 1H) 5.29-5.04 (m, 3H) 4.29 (d, J=14.80 Hz, 4H) 3.80 (s, 6H) 3.44-3.34 (m, 2H) 3.30-3.21 (m, 1H) 3.06-2.79 (m, 2H) 2.68-2.52 (m, 5H) 2.47 (s, 3H) 2.42-2.27 (m, 5H) 2.25-2.08 (m, 5H) 1.49 (s, 9H) 1.38 (d, J=6.40 Hz, 2H) 1.14 (d, J=6.80 Hz, 1H). LCMS m/z=897.3 [M+H]$^+$ Step 5: Synthesis of Compound 9-5

Dichloromethane (15 mL) was added to a dry reaction flask, and then compound 9-4 (0.6 g, 668.91 μmol, 1 eq) and trifluoroacetic acid (3 mL) were added. The reaction system was reacted at 15° C. for 2.5 h. Additional trifluoroacetic acid (0.5 mL) was added, and the mixture was reacted for another 1 h. Additional trifluoroacetic acid (0.5 mL) was added, and the mixture was reacted for another 1 h. The reaction solution was slowly added to saturated sodium bicarbonate solution (80 mL), and extracted with dichloromethane (30 mL×2). The organic phases were combined, dried with anhydrous sodium sulfate, and filtered. The filtrate was concentrated under reduced pressure to give a crude product, which was purified by column (dichloromethane:methanol=100:0-1:1) according to TLC (dichloromethane:methanol=5:1) to give compound 9-5. $^1$H NMR (400 MHz, CDCl$_3$) δ ppm 6.59 (d, J=8.40 Hz, 1H) 5.29-5.07 (m, 2H) 4.75-4.67 (m, 1H) 4.52-4.38 (m, 1H) 4.32-4.16 (m, 1H) 4.08-3.87 (m, 3H) 3.66-3.26 (m, 4H) 3.25-2.8 (m, 6H) 2.72-2.59 (m, 1H) 2.54 (d, J=2.00 Hz, 3H) 2.44-2.26 (m, 3H) 2.11-1.86 (m, 1H) 1.52 (d, J=6.80 Hz, 1H) 1.26 (d, J=6.80 Hz, 2H). LCMS m/z=557.3[M+H]$^+$.

Step 6: Synthesis of Compounds 9A and 9B

Dichloromethane (5 mL) was added to a dry reaction flask, followed by acrylic acid (21.75 mg, 301.85 μmol, 20.72 μL, 1.2 eq) and N,N-diisopropylethylamine (97.53 mg, 754.62 μmol, 131.44 μL, 3 eq). The reaction system was cooled down to −60° C. and 0-(7-azabenzotriazol-1-yl)-N,N,N,N-tetramethyluronium hexafluorophosphate (114.77 mg, 301.85 μmol, 1.2 eq) was added. The reaction system was reacted at −60° C. for 10 min. Compound 9-5 (0.14 g, 251.54 μmol, 1 eq) was added, and the mixture was reacted for another 1 hour. The reaction solution was diluted with dichloromethane (10 mL), washed with saturated ammonium chloride solution (10 mL×2), dried with anhydrous sodium sulfate, and filtered. The filtrate was concentrated under reduced pressure. The product was purified by a high-performance liquid chromatography column {(column: Phenomenex luna C18 80*40 mm*3 μm; mobile phase: [H$_2$O(0.04% HCl)-ACN]; acetonitrile %: 20%-32%, 7 min]}, lyophilized, and then subjected to chiral separation according to SFC {(column: DAICEL CHIRALCEL OD (250 mm*30 mm, 10 μm); mobile phase: [0.1%$_0$NH$_3$H$_2$O MEOH]; MeOH %: 60%-60%, 9 min)} to give compound 9A ((time-to-peak in chiral column: 1.594 min), SFC analysis method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi. Optical purity: 100%). $^1$H NMR (400 MHz, CDCl$_3$) δ ppm 6.71-6.49 (m, 2H) 6.42-6.28 (m, 1H) 5.77 (d, J=10.80 Hz, 1H) 5.50 to 5.04 (m, 3H) 4.71 (s, 3H) 4.49-4.22 (m, 2H) 4.03 (s, 3H) 3.78 (d, J=9.20 Hz, 1H) 3.64 (s, 1H) 3.51-3.17 (m, 4H) 3.14-3.00 (m, 4H) 2.64-2.48 (m, 1H) 2.40 (d, J=4.00 Hz, 4H) 1.16 (d, J=10.40 Hz, 3H). LCMS m/z=611.3 [M+H]$^+$) and compound 9B ((time-to-peak in chiral column: 1.903 min), SFC analysis method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi. Optical purity: 100%). $^1$H NMR (400 MHz, CDCl$_3$) δ ppm 6.69-6.54 (m, 2H) 6.42-6.30 (m, 1H) 5.77 (d, J=10.80 Hz, 1H) 5.47-5.01 (m, 3H) 4.71 (s, 3H) 4.49-4.23 (m, 2H) 4.03 (s, 3H) 3.94-3.72 (m, 1H) 3.64 (s, 1H) 3.53-3.22 (m, 4H) 3.14-3.01 (m, 4H) 2.62-2.49 (m, 1H) 2.40 (d, J=4.00 Hz, 4H) 1.16 (d, J=10.40 Hz, 3H). LCMS m/z=611.3 [M+H]$^+$).

Example 10
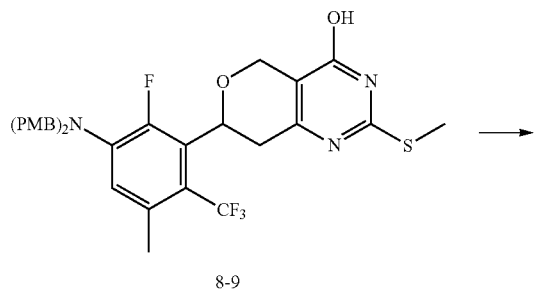
8-9
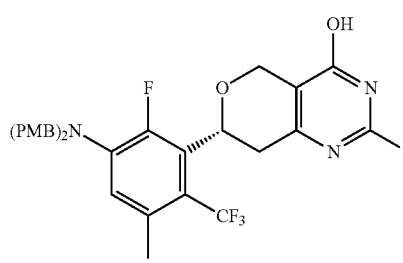
10-1A or 10-1B
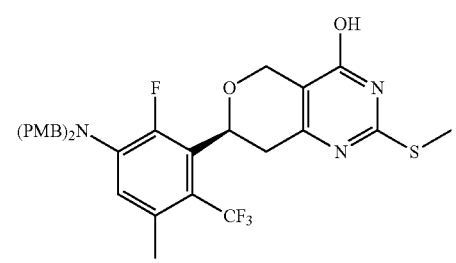
10-1B or 10-1A
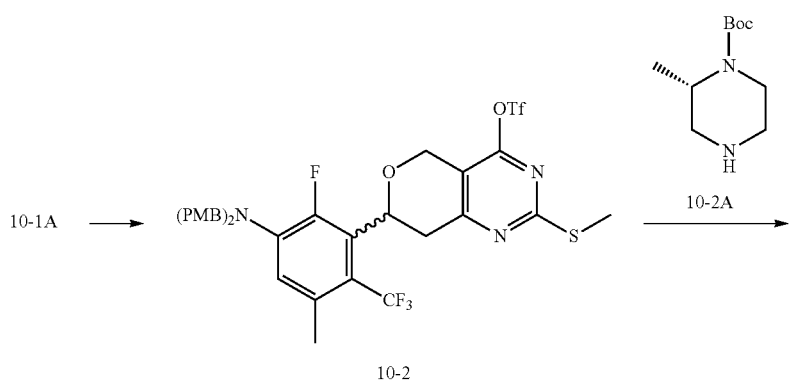
10-1A → 10-2 → 10-2A →
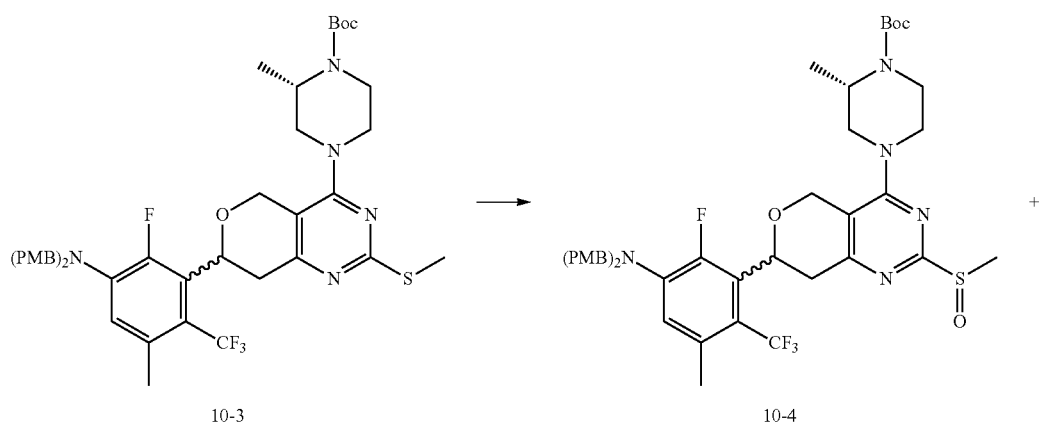
10-3     10-4

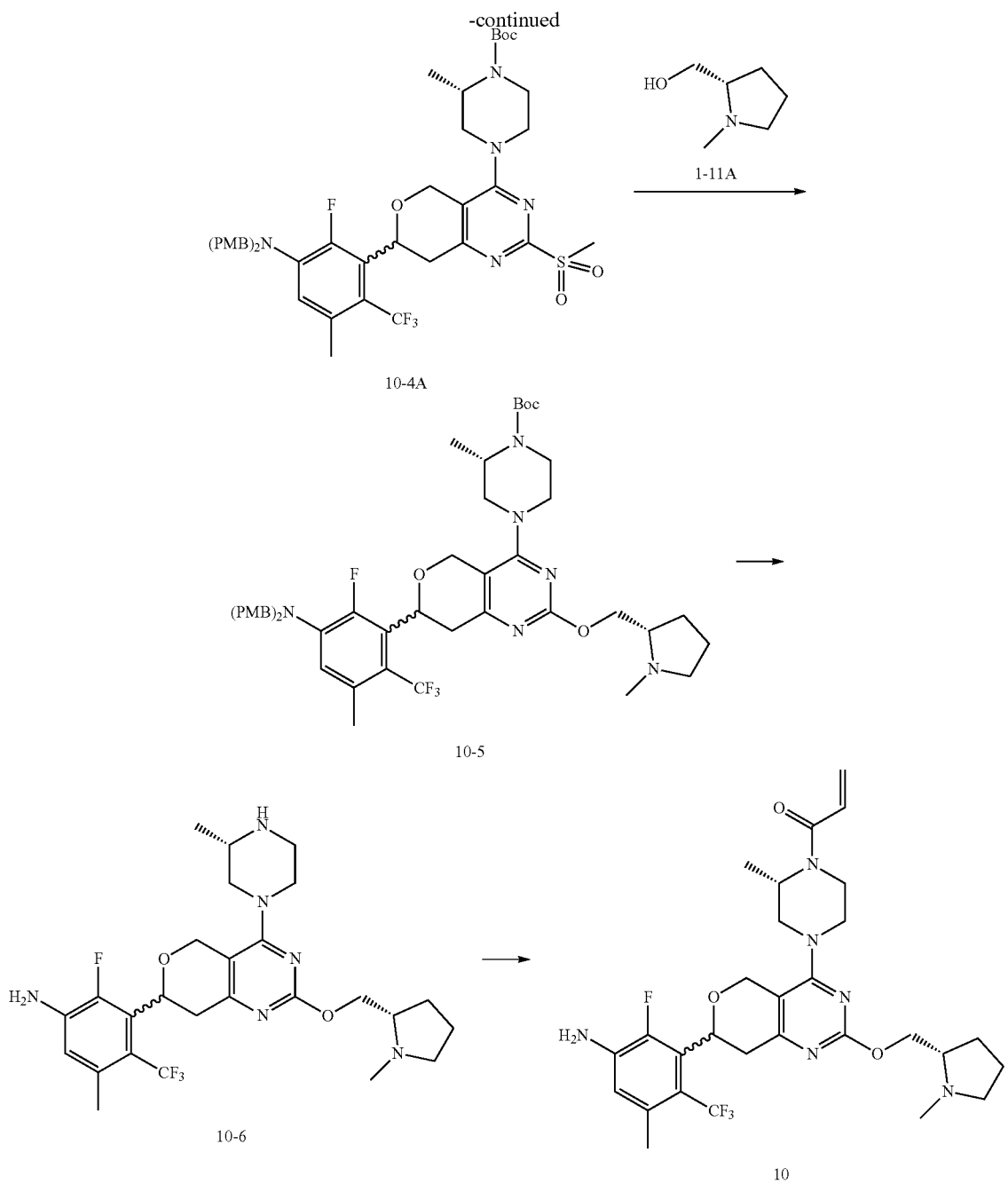

Step 1: Synthesis of Compounds 10-1A and 10-1B

Compound 8-9 (9 g, 15.27 mmol, 1 eq) was dissolved in ethanol (100 mL) and water (20 mL), and then 2-methyl-2-thioisourea sulfate (42.49 g, 152.65 mmol, 10 eq) and sodium bicarbonate (25.65 g, 305.31 mmol, 11.87 mL, 20 eq) were added. The reaction solution was stirred at 30° C. for 4 hr. 100 mL of saturated ammonium chloride solution was added to the reaction solution. The mixture was extracted with ethyl acetate (100 mL×2), washed with 80 mL of saturated brine, dried with anhydrous sodium sulfate, and filtered. The filtrate was concentrated to give a crude product, which was purified by column (petroleum ether: ethyl acetate=10%-20%-30%) according to TLC (petroleum ether:ethyl acetate=0:1), and then resolved by SFC (Column: DAICEL CHIRALPAK AD (250 mm*50 mm, 10 μm); mobile phase: [0.1% NH$_3$.H$_2$O EtOH]; EtOH %: 45%-45%, 6.3 min) to give compound 10-1A (time-to-peak: 1.665) and Compound 10-1B (time-to-peak: 2.446).

Step 2: Synthesis of Compound 10-2

Compound 10-1A (2 g, 3.18 mmol, 1 eq) was dissolved in dichloromethane (20 mL), and N,N-diisopropylethylamine (1.23 g, 9.53 mmol, 1.66 mL, 3 eq) was added. The reaction system was cooled down to 0 to 10° C., and triflic anhydride (1.34 g, 4.76 mmol, 786.11 μL, 1.5 eq) was slowly added. The reaction system was reacted at this temperature for 15 min. Saturated aqueous ammonium chloride solution (15 mL) was poured into the reaction system and the layers were separated. The aqueous phase was extracted with dichloromethane (15 mL×2). The organic phases were combined, dried over anhydrous sodium sulfate, and filtered. The filtrate was concentrated to give a crude product. The crude product was purified by column chromatography (PE/EtOAc=100/1-0/1) according to TLC (PE/EtOAc=10/1) to give compound 10-2. LCMS m/z=762.2[M+H]$^+$.

Step 3: Synthesis of Compound 10-3

N,N-dimethylformamide (2 mL) was added to a dry reaction flask, followed by compound 10-2 (0.16 g, 210.05 μmol, 1 eq), N,N-diisopropylethylamine (81.44 mg, 630.15 μmol, 109.76 μL, 3 eq) and compound 10-2A (50.48 mg, 252.06 μmol, 1.2 eq). The reaction system was reacted at 50° C. under nitrogen for 1 hour. TLC (petroleum ether:ethyl acetate=3:1) showed that the raw material disappeared and new spots appeared. Methyl tert-butyl ether (10 mL) was added to the reaction solution. The mixture was washed with saturated ammonium chloride solution (20 mL×2) followed by saturated brine (10 mL), dried with anhydrous sodium sulfate, and filtered. The filtrate was concentrated under reduced pressure to give compound 10-3, which was used directly in the next step without purification. $^1$H NMR (400 MHz, CDCl$_3$) δ ppm 7.12 (d, J=8.80 Hz, 4H) 6.81 (d, J=8.80 Hz, 4H) 6.60 (d, J=8.80 Hz, 1H) 5.19 (d, J=8.00 Hz, 1H) 4.72 (s, 2H) 4.37-4.22 (m, 4H) 3.88 (d, J=13.2 Hz, 1H) 3.77 (s, 6H) 3.71-3.56 (dd, J=12.80, 13.20 Hz, 2H) 3.40 (dd, J=12.40, 12.40 Hz, 1H) 3.31 (m, 2H) 3.20 (s, 1H) 3.03-2.91 (m, 2H) 2.50 (s, 3H) 2.35-2.25 (m, 3H) 1.46 (s, 9H) 1.13 (d, J=6.80 Hz, 3H).

Step 4: Synthesis of Compound 10-4

Dichloromethane (5 mL) was added to a dry reaction flask and compound 10-3 (0.21 g, 258.64 μmol, 1 eq) and m-chloroperoxybenzoic acid (66.95 mg, 310.37 μmol, 80% purity, 1.2 eq) were added. The reaction system was reacted at 15° C. for 0.5 h. To the reaction solution was added sodium thiosulfate solution (15 mL, 10%). The mixture showed negative by starch-KI paper. The mixture was then extracted with dichloromethane (15 mL), dried with anhydrous sodium sulfate, and filtered. The filtrate was concentrated under reduced pressure to give a crude product, which was purified by column (petroleum ether:ethyl acetate=10:1 to 0:1) according to TLC (petroleum ether:ethyl acetate=0:1) to give compounds 10-4 and 10-4A. $^1$H NMR (400 MHz, CDCl$_3$) δ ppm 7.20 (s, 4H), 6.84 (d, J=8.80 Hz, 4H), 6.79-6.62 (s, 1H), 5.24 (d, J=10.80 Hz, 1H), 4.87-4.74 (m, 2H), 4.36 (s, 4H), 3.99-3.83 (m, 3H), 3.83-3.71 (m, 7H), 3.62-3.43 (m, 2H), 3.40-3.27 (m, 3H), 3.22-3.06 (m, 2H), 2.92 (d, J=5.20 Hz, 1H), 2.34 (s, 3H), 1.49 (s, 9H), 1.16 (d, J=6.80 Hz, 3H). LCMS m/z=828.2M+H]$^+$.

Step 5: Synthesis of Compound 10-5

Toluene (1 mL) was added to a dry reaction flask and compound 1-11A (38.95 mg, 338.19 μmol, 4 eq) was added. The reaction system was cooled down to 0° C. Sodium tert-butoxide (32.50 mg, 338.19 μmol, 4 eq) was added and the mixture was reacted for 10 min. A mixture of compound 10-4 (0.07 g, 84.55 μmol, 1 eq) and 10-4A (71.35 mg, 84.55 μmol, 1 eq) in toluene (1 mL) was added and the mixture was reacted for 0.5 h. To the reaction solution was added 10 mL of ethyl acetate and then the mixture was washed with 10 mL of saturated ammonium chloride solution and saturated brine, respectively. The organic phase was dried with anhydrous sodium sulfate, and filtered. The filtrate was concentrated under reduced pressure to give compound 10-5, which was used directly in the next step without purification. LCMS m/z=879.3 [M+H]$^+$.

Step 6: Synthesis of Compound 10-6

Dichloromethane (5 mL) was added to a dry reaction flask, and compound 10-5 (0.16 g, 182.03 μmol, 1 eq) and trifluoroacetic acid (1.25 mL) were added. The reaction system was stirred at 18° C. for 1.5 hours. Additional trifluoroacetic acid (0.25 mL) was added and the mixture was reacted for another 1.5 h. Water (5 mL) was added to the reaction solution. The aqueous phase was collected, adjusted to pH of 8 with saturated sodium bicarbonate solution, and extracted with dichloromethane (20 mL×2). The organic phases were combined, dried with anhydrous sodium sulfate, and filtered. The filtrate was concentrated under reduced pressure to give compound 10-6, which was used directly in the next step without purification. LCMS m/z=539.2[M+H]$^+$.

Step 7: Synthesis of Compound 10

Dichloromethane (5 mL) was added to a dry reaction flask, followed by acrylic acid (5.54 mg, 76.87 μmol, 5.28 μL, 2 eq), compound 10-6 (23 mg, 38.43 μmol, 90% purity, 1 eq) and N,N-diisopropylethylamine (14.90 mg, 115.30 μmol, 20.08 μL, 3 eq). The reaction system was cooled down to −60° C. and O-(7-azabenzotriazol-1-yl)-N,N,N,N-tetramethyluronium hexafluorophosphate (17.54 mg, 46.12 μmol, 1.2 eq) was added. The mixture was then stirred for 0.5 hr. The reaction mixture was combined with the batch of compound 10-6 (19.49 mg) for treatment. Water (5 ml) was added to the reaction solution, and the layers were separated. The organic phase was concentrated under reduced pressure and separated on a high-performance liquid chromatography column {column: Phenomenex luna C18 80*40 mm*3 μm; [H$_2$O(0.04% HCl)-ACN]; acetonitrile %: 20%-40%, 7 min} to give compound 10. LCMS m/z=593.4[M+H]$^+$.

Example 11

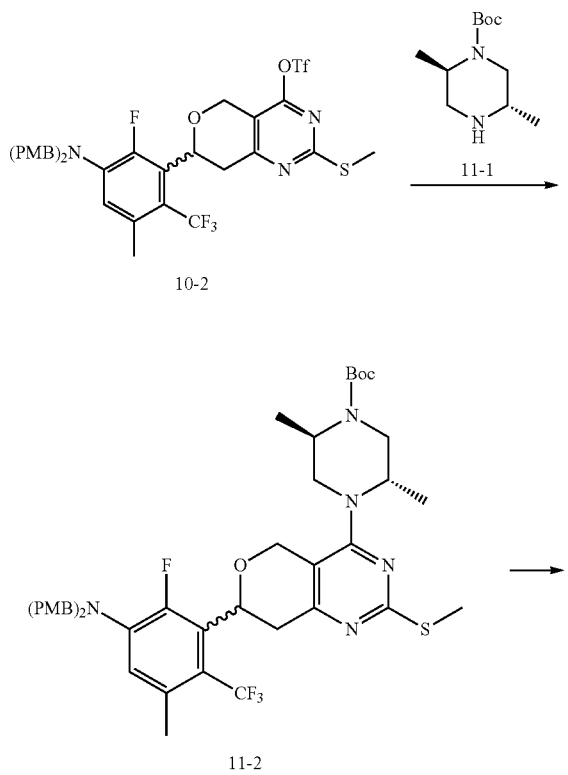

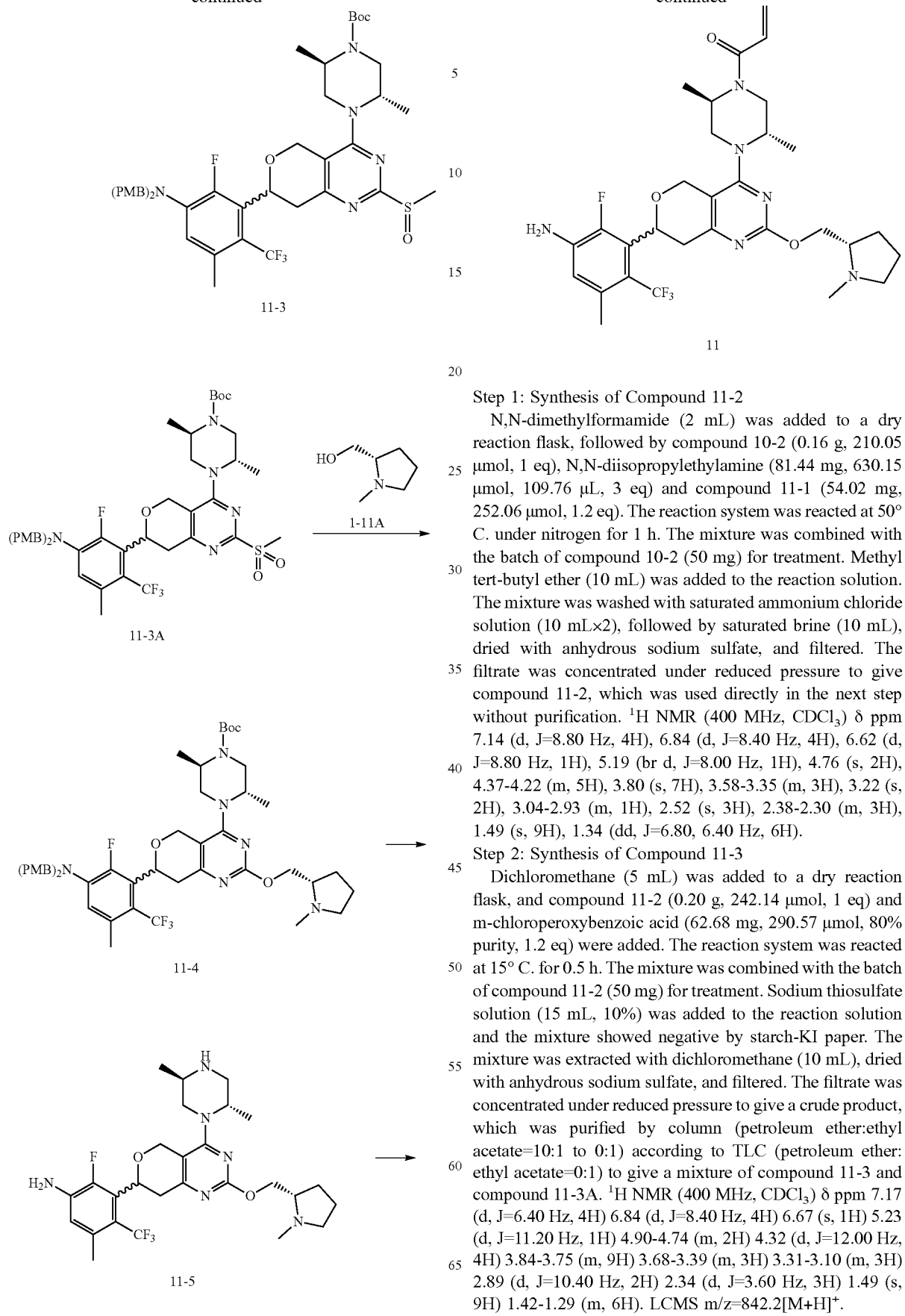

Step 1: Synthesis of Compound 11-2

N,N-dimethylformamide (2 mL) was added to a dry reaction flask, followed by compound 10-2 (0.16 g, 210.05 μmol, 1 eq), N,N-diisopropylethylamine (81.44 mg, 630.15 μmol, 109.76 μL, 3 eq) and compound 11-1 (54.02 mg, 252.06 μmol, 1.2 eq). The reaction system was reacted at 50° C. under nitrogen for 1 h. The mixture was combined with the batch of compound 10-2 (50 mg) for treatment. Methyl tert-butyl ether (10 mL) was added to the reaction solution. The mixture was washed with saturated ammonium chloride solution (10 mL×2), followed by saturated brine (10 mL), dried with anhydrous sodium sulfate, and filtered. The filtrate was concentrated under reduced pressure to give compound 11-2, which was used directly in the next step without purification. $^1$H NMR (400 MHz, CDCl$_3$) δ ppm 7.14 (d, J=8.80 Hz, 4H), 6.84 (d, J=8.40 Hz, 4H), 6.62 (d, J=8.80 Hz, 1H), 5.19 (br d, J=8.00 Hz, 1H), 4.76 (s, 2H), 4.37-4.22 (m, 5H), 3.80 (s, 7H), 3.58-3.35 (m, 3H), 3.22 (s, 2H), 3.04-2.93 (m, 1H), 2.52 (s, 3H), 2.38-2.30 (m, 3H), 1.49 (s, 9H), 1.34 (dd, J=6.80, 6.40 Hz, 6H).

Step 2: Synthesis of Compound 11-3

Dichloromethane (5 mL) was added to a dry reaction flask, and compound 11-2 (0.20 g, 242.14 μmol, 1 eq) and m-chloroperoxybenzoic acid (62.68 mg, 290.57 μmol, 80% purity, 1.2 eq) were added. The reaction system was reacted at 15° C. for 0.5 h. The mixture was combined with the batch of compound 11-2 (50 mg) for treatment. Sodium thiosulfate solution (15 mL, 10%) was added to the reaction solution and the mixture showed negative by starch-KI paper. The mixture was extracted with dichloromethane (10 mL), dried with anhydrous sodium sulfate, and filtered. The filtrate was concentrated under reduced pressure to give a crude product, which was purified by column (petroleum ether:ethyl acetate=10:1 to 0:1) according to TLC (petroleum ether:ethyl acetate=0:1) to give a mixture of compound 11-3 and compound 11-3A. $^1$H NMR (400 MHz, CDCl$_3$) δ ppm 7.17 (d, J=6.40 Hz, 4H) 6.84 (d, J=8.40 Hz, 4H) 6.67 (s, 1H) 5.23 (d, J=11.20 Hz, 1H) 4.90-4.74 (m, 2H) 4.32 (d, J=12.00 Hz, 4H) 3.84-3.75 (m, 9H) 3.68-3.39 (m, 3H) 3.31-3.10 (m, 3H) 2.89 (d, J=10.40 Hz, 2H) 2.34 (d, J=3.60 Hz, 3H) 1.49 (s, 9H) 1.42-1.29 (m, 6H). LCMS m/z=842.2[M+H]$^+$.

Step 3: Synthesis of Compound 11-4

Toluene (1 mL) was added to a dry reaction flask and compound 1-11A (46.51 mg, 403.82 μmol, 4 eq) was added. The reaction system was cooled down to 0° C. Sodium tert-butoxide (38.81 mg, 403.82 μmol, 4 eq) was added and the mixture was reacted for 10 min. A mixture of compound 11-3 (0.085 g, 100.96 μmol, 1 eq) and compound 11-3A (86.62 mg, 100.96 μmol, 1 eq) in toluene (1 mL) was added and the reaction system was stirred for 0.5 h. The mixture was combined with the batch of compound 11-3 (10 mg) for treatment. To the reaction solution was added 10 mL of ethyl acetate, and then the mixture was washed with 10 mL of saturated ammonium chloride solution and saturated brine, respectively, dried with anhydrous sodium sulfate, and filtered. The filtrate was concentrated under reduced pressure to give compound 11-4, which was used directly in the next step without purification. LCMS m/z=893.4[M+H]$^+$.

Step 4: Synthesis of Compound 11-5

Dichloromethane (5 mL) was added to a dry reaction flask, and compound 11-4 (0.13 g, 145.57 μmol, 1 eq) and trifluoroacetic acid (1.25 mL) were added. The reaction system was reacted at 18° C. for 1.5 h. Additional trifluoroacetic acid (0.25 mL) was added and the mixture was reacted for another 1.5 h. The mixture was combined with the batch of 11-4 (15 mg) for treatment. Water (5 mL) was added to the reaction solution. The aqueous phase was collected, adjusted to pH of 8 with saturated sodium bicarbonate solution, and extracted with dichloromethane (20 mL×2). The organic phases were combined, dried with anhydrous sodium sulfate and filtered. The filtrate was concentrated under reduced pressure to give compound 11-5, which was used directly in the next step without purification. LCMS m/z=553.2[M+H]$^+$.

Step 5: Synthesis of Compound 11

Dichloromethane (5 mL) was added to a dry reaction flask, and acrylic acid (14.08 mg, 195.44 μmol, 13.41 μL, 2 eq), compound 11-5 (60.00 mg, 97.72 μmol, 90% purity, 1 eq) and N,N-diisopropylethylamine (37.89 mg, 293.16 μmol, 51.06 μL, 3 eq) were then added. The reaction system was cooled down to −60° C. O-(7-azabenzotriazol-1-yl)-N,N,N,N-tetramethyluronium hexafluorophosphate (44.59 mg, 117.26 μmol, 1.2 eq) was added. The mixture was then stirred for 0.5 h. The reaction mixture was combined with the batch of compound 11-5 (20 mg) for treatment. Water (5 ml) was added to the reaction solution. The layers were separated. The organic phase was concentrated under reduced pressure and purified by a high-performance liquid chromatography column {column: Phenomenex luna C18 80*40 mm*3 μm; mobile phase: [H$_2$O(0.04% HCl)-ACN]; acetonitrile %: 15%-40%, 7 min} to give compound 11. $^1$H NMR (400 MHz, CD$_3$OD) δ=6.92-6.75 (m, 1H), 6.74-6.70 (m, 1H), 6.33-6.24 (m, 1H), 5.88-5.77 (m, 1H), 5.28-5.18 (m, 1H), 4.82-4.63 (m, 2H), 4.56-4.43 (m, 1H), 4.42-4.23 (m, 1H), 4.01-3.81 (m, 2H), 3.79-3.59 (m, 2H), 3.57-3.41 (m, 1H), 3.32-3.20 (m, 5H), 3.17-3.02 (m, 3H), 2.84 (m, 2H), 2.51-2.35 (m, 3H), 2.31-1.99 (m, 3H), 1.49-1.29 (m, 6H). LCMS m/z=607.5[M+H]$^+$.

Example 12

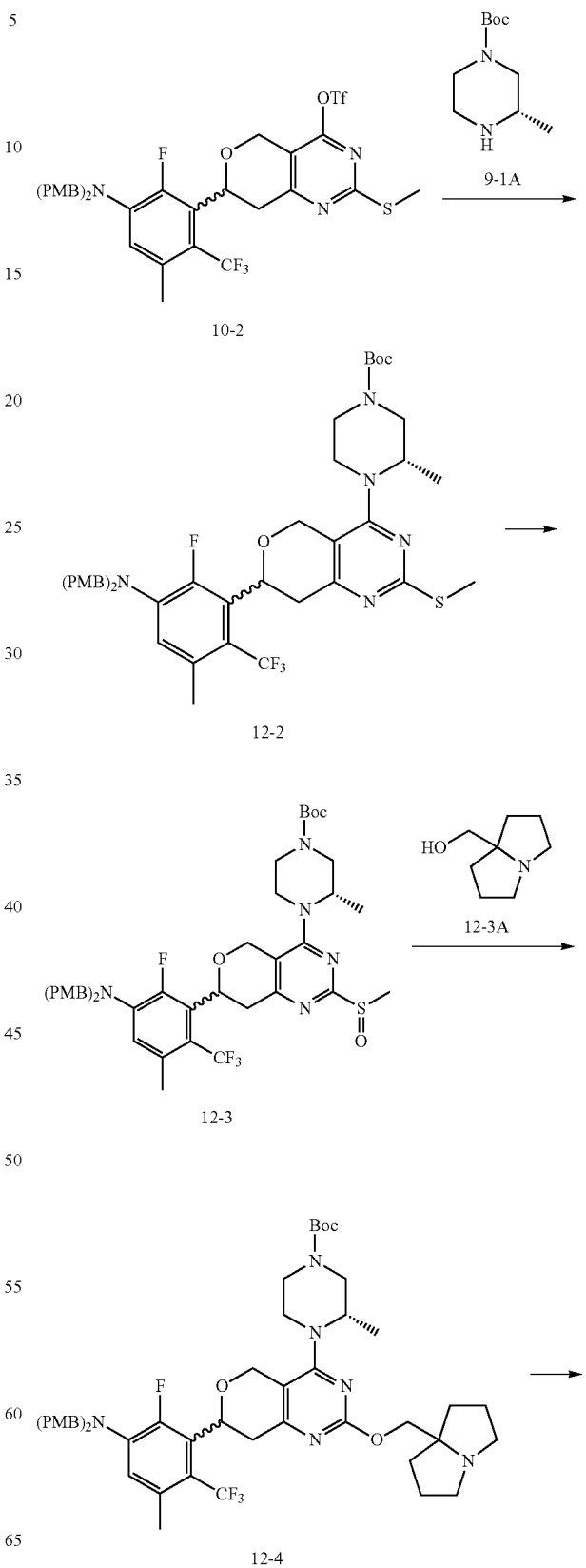

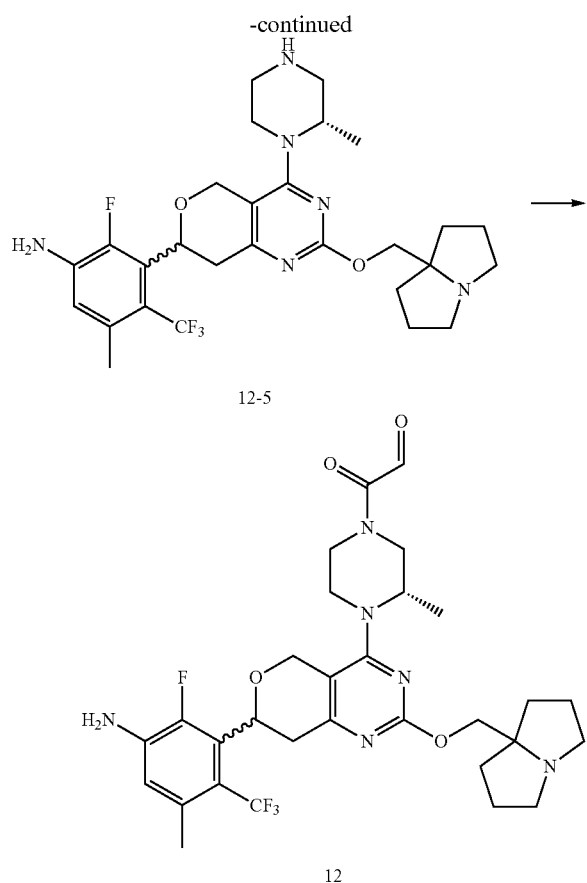

Step 1: Synthesis of Compound 12-2

N,N-dimethylformamide (2 mL) was added to a dry reaction flask, followed by compound 10-2 (0.2 g, 262.56 μmol, 1 eq), N,N-diisopropylethylamine (101.80 mg, 787.69 μmol, 137.20 μL, 3 eq) and compound 9-1A (63.10 mg, 315.07 μmol, 1.2 eq). The reaction system was reacted at 50° C. under nitrogen for 30 min. Additional compound 9-1A (30 mg, 0.6 eq) was added and the mixture was reacted for another 30 min. To the reaction solution was added saturated ammonium chloride solution (10 mL), and the mixture was extracted with methyl tert-butyl ether (5 mL). The organic phase solution was washed successively with saturated ammonium chloride solution (10 mL) and saturated brine (10 mL), dried with anhydrous sodium sulfate, and filtered. The filtrate was concentrated under reduced pressure to give compound 12-2, which was used directly in the next step without purification. $^1$H NMR (400 MHz, CDCl$_3$) δ ppm 7.14 (d, J=8.80 Hz, 4H) 6.84 (d, J=8.40 Hz, 4H) 6.62 (d, J=8.80 Hz, 1H) 5.21 (d, J=7.20 Hz, 1H) 4.78-4.63 (m, 2H) 4.38-4.15 (m, 4H) 4.00-3.82 (m, 2H) 3.80 (s, 6H) 3.73-3.60 (m, 1H) 3.48-3.33 (m, 1H) 3.22 (s, 2H) 3.16-2.80 (m, 3H) 2.51 (s, 3H) 2.38-2.30 (m, 3H) 1.49 (s, 9H) 1.38 (d, J=6.80 Hz, 3H). LCMS m/z=812.3 [M+H]$^+$.

Step 2: Synthesis of Compound 12-3

Dichloromethane (5 mL) was added to a dry reaction flask, followed by compound 12-2 (0.18 g, 221.70 μmol, 1 eq) and m-chloroperoxybenzoic acid (57.39 mg, 266.03 μmol, 80% purity, 1.2 eq). The reaction system was reacted at 15° C. for 0.5 h. The mixture was combined with the batch of compound 12-2 (30 mg) for treatment. Sodium thiosulfate solution (10 mL, 10%) was added to the reaction solution, and the mixture showed negative by starch-KI paper. The mixture was extracted with dichloromethane (3 mL), dried with anhydrous sodium sulfate, and filtered. The filtrate was concentrated under reduced pressure to give a crude product, which was purified by column (petroleum ether:ethyl acetate=10:1 to 0:1) according to TLC (petroleum ether: ethyl acetate=0:1) to give compound 12-3. $^1$H NMR (400 MHz, CDCl$_3$) δ ppm 7.17 (br s, 4H) 6.84 (br d, J=8.40 Hz, 4H) 6.67 (br s, 1H) 5.25 (br d, J=9.60 Hz, 1H) 4.89-4.64 (m, 2H) 4.32 (br d, J=10.40 Hz, 4H) 4.09-3.86 (m, 3H) 3.84-3.68 (m, 7H) 3.64-3.51 (m, 1H) 3.37-2.97 (m, 4H) 2.95-2.81 (m, 3H) 2.34 (br d, J=3.60 Hz, 3H) 1.49 (s, 9H) 1.41 (br s, 3H). LCMS m/z=828.2[M+H]$^+$.

Step 3: Synthesis of Compound 12-4

Toluene (1 mL) was added to a dry reaction flask, then compound 12-3A (66.52 mg, 471.06 μmol, 3 eq) was added. The reaction system was cooled down to 0° C., then tert-butanol sodium (45.27 mg, 471.06 μmol, 3 eq) was added. The mixture was stirred for 10 min, and then a solution of compound 12-3 (0.13 g, 157.02 μmol, 1 eq) in toluene (0.5 mL) was added. The mixture was stirred for 0.5 h. The mixture was combined with the batch of compound 12-3 (20 mg) for treatment. 10 mL of ethyl acetate was added to the reaction solution. The mixture was then washed with 10 mL of saturated ammonium chloride solution and saturated brine, respectively, dried with anhydrous sodium sulfate, and filtered. The filtrate was concentrated under reduced pressure to give compound 12-4, which was used directly in the next step without purification. LCMS m/z=905.3 [M+H]$^+$.

Step 4: Synthesis of Compound 12-5

Dichloromethane (6 mL) was added to a dry reaction flask, and then compound 12-4 (0.18 g, 198.89 μmol, 1 eq) and trifluoroacetic acid (1.5 mL) were added. The reaction system was stirred at 18° C. for 3.5 hours. Water (5 mL) was added to the reaction solution. The aqueous phase was collected, adjusted to pH of 8 with saturated sodium bicarbonate solution, and extracted with dichloromethane (20 mL×2). The organic phases were combined, dried with anhydrous sodium sulfate and filtered. The filtrate was concentrated under reduced pressure to give compound 12-5, which was used directly in the next step without purification. LCMS m/z=565.2[M+H]$^+$.

Step 5: Synthesis of Compound 12

Dichloromethane (5 mL) was added to a dry reaction flask and stirred. Acrylic acid (11.49 mg, 159.40 μmol, 10.94 μL, 2 eq), compound 12-5 (50 mg, 79.70 μmol, 90% purity, 1 eq) and N,N-diisopropylethylamine (30.90 mg, 239.10 μmol, 41.65 μL, 3 eq) were added. The reaction system was cooled down to −60° C. and O-(7-azabenzotriazol-1-yl)-N,N,N,N-tetramethyluronium hexafluorophosphate (36.37 mg, 95.64 μmol, 1.2 eq) was added. The mixture was then stirred for 0.5 h. The reaction mixture was combined with the batch of compound 12-5 (20 mg) for treatment. To the reaction solution was added water (5 ml). The layers were separated. The organic phase was dried with anhydrous sodium sulfate and filtered. The filtrate was concentrated under reduced pressure to give a crude product, which was purified by a high-performance liquid chromatography column {column: Phenomenex luna C18 80*40 mm*3 μm; mobile phase: [H$_2$O(0.04% HCl)-ACN]; acetonitrile %: 15%-40%, 7 min} to give compound 12 (time-to-peak: 1.509). SFC analysis method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 m/min; Wavelength: 220 nm; Pressure: 1800 psi. Optical purity: 99.4%. $^1$H NMR (400 MHz, CD$_3$OD) δ=6.89-6.71 (m, 1H), 6.71-6.65 (d, J=8.8 Hz, 1H), 6.32-6.19 (m, 1H), 5.84-5.75 (m, 1H), 5.26-5.15 (m, 1H), 4.68-4.60 (m, 1H), 4.52 (s, 2H), 4.50-4.45 (m, 1H), 4.39-4.32 (m, 1H), 4.27-4.16 (m, 1H), 4.15-3.89 (m, 2H), 3.76-3.61 (m, 2H), 3.60-3.32 (m, 2H), 3.28-3.13 (m, 3H), 3.09-3.00 (m, 1H), 2.96-2.85 (m, 1H), 2.38-2.32 (m, 3H), 2.32-2.24 (m, 2H), 2.24-2.12 (m, 4H), 2.12-2.03 (m, 2H), 1.42-1.31 (m, 3H). LCMS m/z=619.3[M+H]$^+$.

Example 13

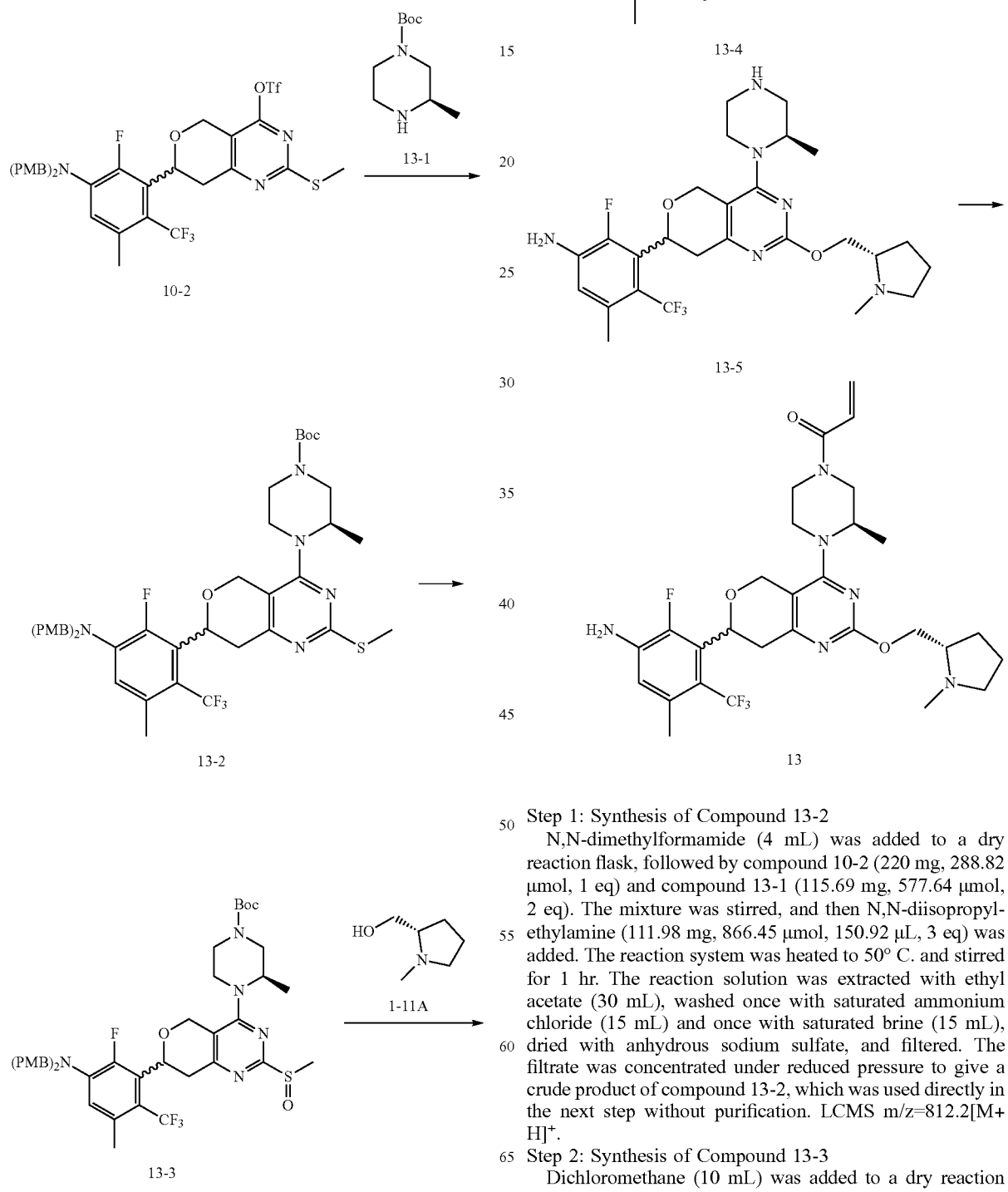

Step 1: Synthesis of Compound 13-2

N,N-dimethylformamide (4 mL) was added to a dry reaction flask, followed by compound 10-2 (220 mg, 288.82 μmol, 1 eq) and compound 13-1 (115.69 mg, 577.64 μmol, 2 eq). The mixture was stirred, and then N,N-diisopropylethylamine (111.98 mg, 866.45 μmol, 150.92 μL, 3 eq) was added. The reaction system was heated to 50° C. and stirred for 1 hr. The reaction solution was extracted with ethyl acetate (30 mL), washed once with saturated ammonium chloride (15 mL) and once with saturated brine (15 mL), dried with anhydrous sodium sulfate, and filtered. The filtrate was concentrated under reduced pressure to give a crude product of compound 13-2, which was used directly in the next step without purification. LCMS m/z=812.2[M+H]$^+$.

Step 2: Synthesis of Compound 13-3

Dichloromethane (10 mL) was added to a dry reaction flask and compound 13-2 (200.00 mg, 246.33 μmol, 1 eq)

was added. The mixture was stirred, and m-chloroperoxybenzoic acid (60.01 mg, 295.59 µmol, 85% purity, 1.2 eq) was added. The reaction system was stirred at 25° C. for 1 h. The reaction solution was diluted with dichloromethane (20 mL), then washed once with 5% sodium thiosulfate (10 mL) and once with saturated brine (10 mL), dried with anhydrous sodium sulfate and filtered. The filtrate was concentrated under reduced pressure to give a crude product, which was purified by column (petroleum ether:ethyl acetate=90:10 to 50:50) according to TLC (petroleum ether: ethyl acetate=1:1) to give compound 13-3. LCMS m/z=828.3[M+H]$^+$.

Step 3: Synthesis of Compound 13-4

Toluene (5 mL) was added to a dry reaction flask, and then compound 1-11A (112.68 mg, 978.35 µmol, 4.5 eq) was added. The mixture was stirred. Then sodium tert-butoxide (94.02 mg, 978.35 µmol, 4.5 eq) was added and the reaction system was cooled down to 0° C. and stirred for 10 min. Compound 13-3 (180 mg, 217.41 µmol, 1 eq) was then added and the reaction system was stirred at 0° C. for 1 hour. The reaction mixture was combined with the batch of compound 13-3 (60 mg) for treatment. The reaction solution was extracted with ethyl acetate (30 mL). The organic phase solution was washed once with saturated ammonium chloride solution (10 mL) and once with saturated brine (10 mL), dried with anhydrous sodium sulfate and filtered. The filtrate was concentrated under reduced pressure to give a crude product of compound 13-4, which was used directly in the next step without purification. LCMS m/z=879.3 [M+H]$^+$.

Step 4: Synthesis of Compound 13-5

Dichloromethane (5 mL) was added to a dry reaction flask, and then compound 13-4 (260 mg, 295.79 µmol, 1 eq) was added. The mixture was stirred. Potassium acetate (2.82 g, 24.70 mmol, 1.83 mL, 83.50 eq) was added and the reaction system was stirred at 20° C. for 2 hr. Water (30 mL) was added to the reaction solution and the layers were separated. The aqueous phase was adjusted to pH of 9 with saturated sodium bicarbonate, and then extracted with ethyl acetate (15 mL×2). The organic phases were combined, washed with saturated brine (10 mL), dried with anhydrous sodium sulfate and filtered. The filtrate was concentrated under reduced pressure to give a crude product of compound 13-5, which was directly used in the next step without purification. LCMS m/z=539.2[M+H]$^+$.

Step 5: Synthesis of Compound 13

Dichloromethane (5 mL) was added to a dry reaction flask, followed by acrylic acid (10.84 mg, 150.40 µmol, 10.32 µL, 1 eq), compound 13-5 (90 mg, 150.40 µmol, 90% purity, 1 eq) and N,N-diisopropylethylamine (58.31 mg, 451.19 µmol, 78.59 µL, 3 eq). The mixture was stirred. The reaction system was cooled down to −60° C., and O-(7-azabenzotriazol-1-yl)-N,N,N,N-tetramethyluronium hexafluorophosphate (68.62 mg, 180.47 µmol, 1.2 eq) was added. The mixture was stirred for 0.5 h. The reaction mixture was combined with the batch of compound 13-5 (30 mg) for treatment. Water (5 mL) was added to the reaction solution, and the layers were separated. The organic phase solution was directly concentrated under reduced pressure to give a crude product, which was purified by a high-performance liquid chromatography column {column: Welch Xtimate C18 100*25 mm*3 µm; mobile phase: [H$_2$O(0.05% HCl)-ACN]; acetonitrile %: 15%-45%, 8 min} to give compound 13 (time-to-peak: 1.683). SFC analysis method (column: Chiralcel OD-3, 50×4.6 mm I.D., 3 µm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi, Optical purity: 95.48%). $^1$H NMR (400 MHz, CD$_3$OD) δ=6.87-6.73 (m, 1H), 6.68 (d, J=8.4 Hz, 1H), 6.25 (dd, J=3.8, 16.6 Hz, 1H), 5.78 (d, J=11.6 Hz, 1H), 5.20 (dd, J=4.0, 11.2 Hz, 1H), 4.83-4.75 (m, 2H), 4.74-4.61 (m, 2H), 4.60-4.45 (m, 2H), 4.32 (d, J=13.0 Hz, 1H), 4.17-3.92 (m, 1H), 3.90-3.80 (m, 1H), 3.71-3.57 (m, 2H), 3.55-3.42 (m, 1H), 3.39-3.32 (m, 1H), 3.27-3.18 (m, 2H), 3.04 (s, 3H), 2.99-2.85 (m, 2H), 2.41-2.30 (m, 4H), 2.22-1.95 (m, 3H), 1.11 (d, J=6.6 Hz, 3H), LCMS m/z=593.3[M+H]$^+$.

Example 14

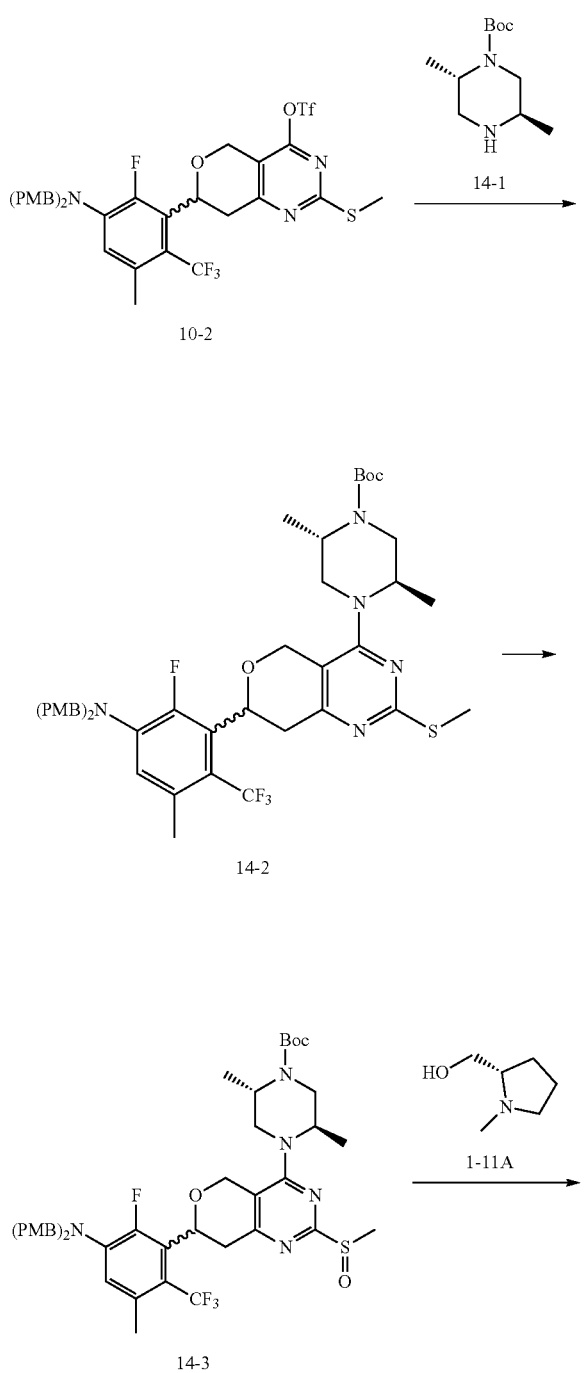

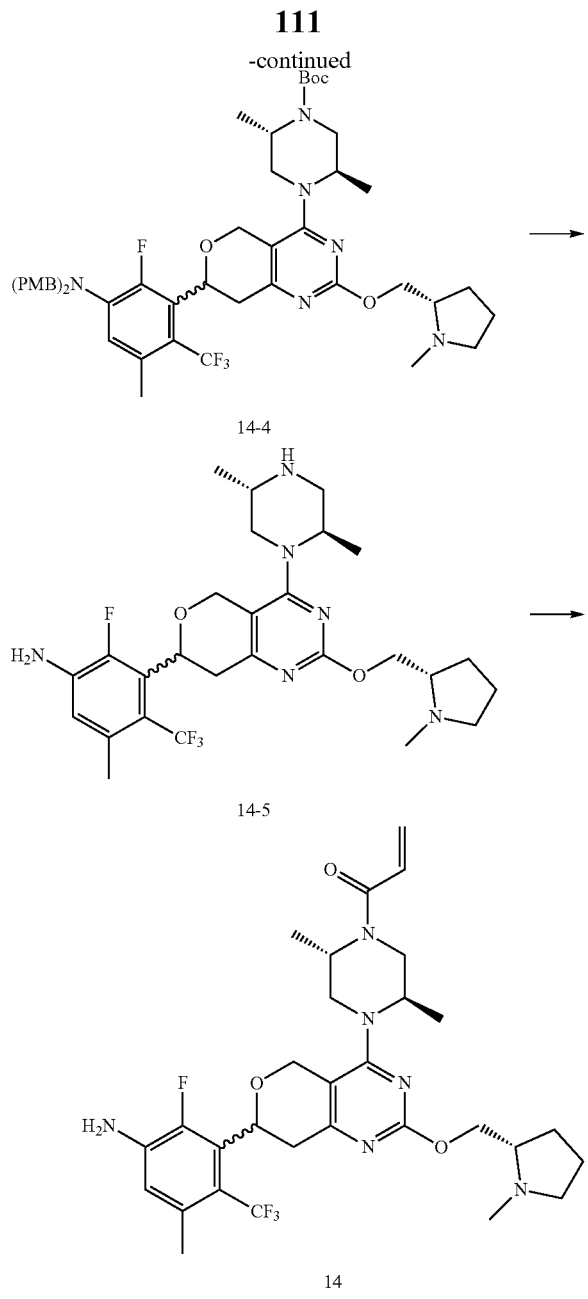

Step 1: Synthesis of Compound 14-2

N,N-dimethylformamide (4 mL) was added to a dry reaction flask, followed by compound 10-2 (220 mg, 288.82 µmol, 1 eq), compound 14-1 (123.79 mg, 577.64 µmol, 2 eq) and N,N-diisopropylethylamine (111.98 mg, 866.45 µmol, 150.92 µL, 3 eq). The mixture was stirred. The reaction system was stirred at 50° C. for 1 hr. The reaction solution was extracted with ethyl acetate (30 mL). The organic phase solution was collected, washed once with saturated ammonium chloride solution (15 mL) and once with saturated brine (15 mL), dried with anhydrous sodium sulfate and filtered. Then the filtrate was concentrated under reduced pressure to give a crude product of compound 14-2, which was used directly in the next step without purification. LCMS m/z=826.3 [M+H]$^+$.

Step 2: Synthesis of Compound 14-3

Dichloromethane (10 mL) was added to a dry reaction flask, followed by compound 14-2 (350.18 mg, 423.97 µmol, 1 eq), and the mixture was stirred. m-Chloroperoxybenzoic acid (109.75 mg, 508.77 µmol, 80% purity, 1.2 eq) was added and the reaction system was stirred at 25° C. for 1 h. A more polar main spot was detected. The reaction solution was diluted with dichloromethane (10 mL), then washed once with 5% sodium thiosulfate (10 mL) and once with saturated brine (10 mL), dried with anhydrous sodium sulfate, and filtered. The filtrate was concentrated under reduced pressure to give a crude product. The crude product was purified by column (petroleum ether:ethyl acetate=90:10 to 50:50) according to TLC (petroleum ether:ethyl acetate=0:1) to give compound 14-3. LCMS m/z=842.3[M+H]$^+$.

Step 3: Synthesis of Compound 14-4

Toluene (5 mL) was added to a dry reaction flask, and then compound 1-11A (98.73 mg, 857.24 µmol, 4.5 eq) was added and stirred. Then sodium tert-butoxide (82.38 mg, 857.24 µmol, 4.5 eq) was added, and the reaction system was cooled down to 0° C. and stirred for 10 min. A solution of compound 14-3 (160.39 mg, 190.50 µmol, 1 eq) in toluene (2 mL) was added, and the reaction system was stirred at 0 C for 1 h. The reaction mixture was combined with the batch of compound 14-3 (50 mg) for treatment. The reaction solution was extracted with ethyl acetate (30 mL). The organic phase solution was collected, washed once with saturated ammonium chloride solution (10 mL) and once with saturated brine (10 mL), dried with anhydrous sodium sulfate, and filtered. The filtrate was concentrated under reduced pressure to give a crude product of compound 14-4, which was used directly in the next step without purification. LCMS m/z=893.4[M+H]$^+$.

Step 4: Synthesis of Compound 14-5

Dichloromethane (5 mL) was added to a dry reaction flask and then compound 14-4 (260 mg, 291.15 µmol, 1 eq) was added. The mixture was stirred. Trifluoroacetic acid (2.77 g, 24.31 mmol, 1.8 mL, 83.50 eq) was added and the reaction system was stirred at 20° C. for 2 hr. The reaction solution was diluted with dichloromethane (20 mL), and then water (20 mL) was added. The layers were separated. The aqueous phase was adjusted to pH of 8 with saturated sodium bicarbonate, and then extracted with ethyl acetate (20 mL×2). The organic phases were combined, washed with saturated brine (10 mL), dried with anhydrous sodium sulfate, and filtered. The filtrate was concentrated under reduced pressure to give a crude product of compound 14-5, which was directly used in the next step without purification. LCMS m/z=553.2[M+H]$^+$.

Step 5: Synthesis of Compound 14

Dichloromethane (5 mL) was added to a dry reaction flask, followed by acrylic acid (10.56 mg, 146.58 µmol, 10.06 µL, 1 eq), compound 14-5 (90 mg, 146.58 µmol, 90% purity, 1 eq) and N,N-diisopropylethylamine (56.83 mg, 439.73 µmol, 76.59 µL, 3 eq). The mixture was stirred and the reaction system was cooled down to −60° C. O-(7-azabenzotriazol-1-yl)-N,N,N,N-tetramethyluronium hexafluorophosphate (66.88 mg, 175.89 µmol, 1.2 eq) was added. The mixture was then stirred for 0.5 h. The reaction was quenched by adding water (5 mL) and the layers were separated. The organic phase was dried with anhydrous sodium sulfate and filtered. The filtrate was concentrated under reduced pressure to give a crude product. The crude product was purified by a high-performance liquid chromatography column {column: Welch Xtimate C18 100*25 mm*3 µm; mobile phase: [H$_2$O(0.05% HCl)-ACN]; acetonitrile %: 15%-45%, 8 min} to give compound 14. $^1$H NMR (400 MHz, CDCl$_3$) 6.69-6.62 (m, 1H), 6.62-6.48 (m, 1H), 6.47-6.34 (m, 1H), 5.91-5.76 (m, 1H), 5.34 (s, 1H), 5.25-

5.14 (m, 1H), 5.10-4.99 (m, 1H), 4.86-4.64 (m, 2H), 4.62-4.30 (m, 2H), 4.21-4.11 (m, 1H), 4.06-3.93 (m, 2H), 3.90-3.73 (m, 2H), 3.71-3.59 (m, 1H), 3.57-3.49 (m, 3H), 3.47-3.33 (m, 1H), 3.28-3.15 (m, 2H), 3.09-2.92 (m, 1H), 2.50-2.35 (m, 4H), 2.26-2.09 (m, 2H), 1.43-1.32 (m, 4H), 1.31-1.25 (m, 2H), LCMS m/z=607.4[M+H]⁺.

Example 15

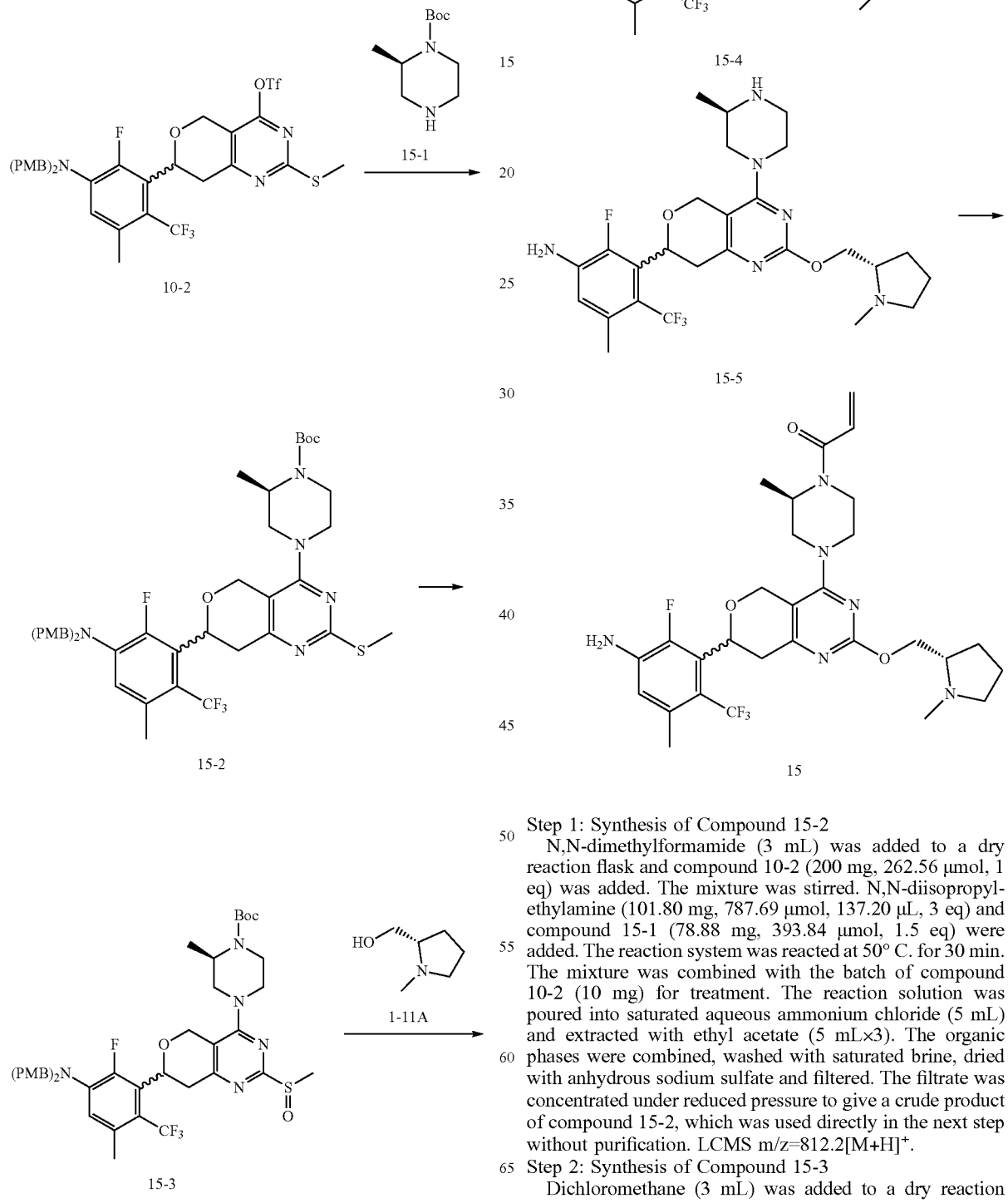

Step 1: Synthesis of Compound 15-2

N,N-dimethylformamide (3 mL) was added to a dry reaction flask and compound 10-2 (200 mg, 262.56 μmol, 1 eq) was added. The mixture was stirred. N,N-diisopropyl-ethylamine (101.80 mg, 787.69 μmol, 137.20 μL, 3 eq) and compound 15-1 (78.88 mg, 393.84 μmol, 1.5 eq) were added. The reaction system was reacted at 50° C. for 30 min. The mixture was combined with the batch of compound 10-2 (10 mg) for treatment. The reaction solution was poured into saturated aqueous ammonium chloride (5 mL) and extracted with ethyl acetate (5 mL×3). The organic phases were combined, washed with saturated brine, dried with anhydrous sodium sulfate and filtered. The filtrate was concentrated under reduced pressure to give a crude product of compound 15-2, which was used directly in the next step without purification. LCMS m/z=812.2[M+H]⁺.

Step 2: Synthesis of Compound 15-3

Dichloromethane (3 mL) was added to a dry reaction flask, and then compound 15-2 (0.24 g, 295.59 μmol, 1 eq)

was added. The mixture was stirred. m-Chloroperoxybenzoic acid (66.95 mg, 310.37 μmol, 80% purity 1.05 eq) was added and the reaction system was reacted at 25° C. for 30 min. The reaction solution was quenched with aqueous sodium sulfite (5 mL 5%). The layers were separated. The aqueous phase was extracted with dichloromethane (5 mL×2). The organic phases were combined, dried with anhydrous sodium sulfate, and filtered. The filtrate was concentrated under reduced pressure to give a crude product. The aqueous phase was detected with starch-potassium iodide test paper, and showed non-oxidative. The aqueous phase was discarded. The crude product was purified by column chromatography (petroleum ether:ethyl acetate=50:1 to 0:1) according to TLC (petroleum ether: ethyl acetate=1:1, product Rf=0.51) to give compound 15-3. $^1$H NMR (400 MHz, CDCl$_3$) δ=7.17-7.06 (m, 4H), 6.83-6.72 (m, 4H), 6.71-6.60 (m, 1H), 5.24-5.10 (m, 1H), 4.87-4.64 (m, 2H), 4.44-4.17 (m, 4H), 3.98-3.81 (m, 2H), 3.78-3.69 (m, 6H), 3.67-3.43 (m, 2H), 3.20-2.97 (m, 4H), 2.88-2.78 (m, 3H), 2.32-2.20 (m, 3H), 1.47-1.37 (m, 9H), 1.32-1.23 (m, 3H). LCMS m/z=828.3 M+H]$^+$.

Step 3: Synthesis of Compound 15-4

Toluene (1 mL) was added to a dry reaction flask, and compound 15-3 (180 mg, 217.41 μmol, 1 eq) was added. The mixture was stirred. The reaction system was cooled down to 0-5° C., and sodium tert-butoxide (2.68 mg, 652.23 μmol, 3 eq) was added. The mixture was stirred for 10 min. A solution of compound 1-11A (75.12 mg, 652.23 μmol, 77.44 μL, 3 eq) in toluene (0.3 mL) was added to the above reaction solution and the reaction system was reacted at 0 to 5° C. for 30 min. The reaction solution was poured into saturated aqueous ammonium chloride (5 mL) and extracted with ethyl acetate (5 mL×3). The organic phases were combined, washed with saturated brine (5 mL), dried with anhydrous sodium sulfate, and filtered. The filtrate was concentrated under reduced pressure to give a crude product of compound 15-4, which was used directly in the next step without purification. LCMS m/z=879.4[M+H]$^+$.

Step 4: Synthesis of Compound 15-5

Dichloromethane (4 mL) was added to a dry reaction flask, and compound 15-4 (160 mg, 182.03 μmol, 1 eq) was added. The mixture was stirred. The reaction system was cooled down to 0-5° C. Trifluoroacetic acid (1.23 g, 10.81 mmol, 800.00 μL, 59.36 eq) was added, and the mixture was stirred for 4 hours. The reaction solution was added to saturated aqueous sodium bicarbonate (10 mL). The layers were separated. The mixture was extracted with dichloromethane (5 mL×2). The organic phases were combined, dried with anhydrous sodium sulfate, and filtered. The filtrate was concentrated under reduced pressure to give a crude product of compound 15-5, which was used directly in the next step without purification. LCMS m/z=539.2[M+H]$^+$.

Step 5: Synthesis of Compound 15

Dichloromethane (10 mL) was added to a dry reaction flask, and then compound 15-5 (0.06 g, 111.40 μmol, 1 eq) and acrylic acid (16.06 mg, 222.81 μmol, 15.29 μL, 2 eq) were added. The mixture was stirred. Then N,N-diisopropylethylamine (28.80 mg, 222.81 μmol, 38.81 μL, 2 eq) was added, and the reaction system was cooled down to −60° C. O-(7-azabenzotriazol-1-yl)-N,N,N,N-tetramethyluronium hexafluorophosphate (63.54 mg, 167.11 μmol, 1.5 eq) was added and the reaction system was reacted at −60° C. for 0.5 h. The mixture was combined with the batch of compound 15-5 (20 mg) for treatment. Dichloromethane (5 mL) was added to the reaction solution. The reaction solution was washed with saturated ammonium chloride solution (5 mL×2), dried with anhydrous sodium sulfate, and filtered. The filtrate was concentrated under reduced pressure to give a crude product. The crude product was purified by a high-performance liquid chromatography column {column: Phenomenex Luna C18 200*40 mm*10 μm; mobile phase: [H$_2$O(0.04% HCl)-ACN]; acetonitrile %: 1%-50%, 8 min}. One drop of ammonia water was added to the fraction solution, and the solution showed alkaline. The solution was concentrated to remove the organic solvent and lyophilized to give compound 15. $^1$H NMR (400 MHz, CD$_3$OD) δ=7.24-7.07 (m, 2H), 6.80 (dd, J=10.8, 16.8 Hz, 1H), 6.71 (d, J=8.6 Hz, 1H), 6.24 (d, J=16.8 Hz, 1H), 5.79 (d, J=11.7 Hz, 1H), 5.24-5.16 (m, 1H), 4.76 (d, J=13.8 Hz, 3H), 4.57 (dd, J=7.2, 12.5 Hz, 2H), 4.07-3.86 (m, 3H), 3.73 (s, 1H), 3.17 (d, J=11.4 Hz, 3H), 3.07 (s, 3H), 2.90 (d, J=14.8 Hz, 1H), 2.46-2.34 (m, 4H), 2.33-2.30 (m, 1H), 2.26-1.95 (m, 3H), 1.41 (s, 3H). LCMS m/z=593.2[M+H]$^+$.

Example 16

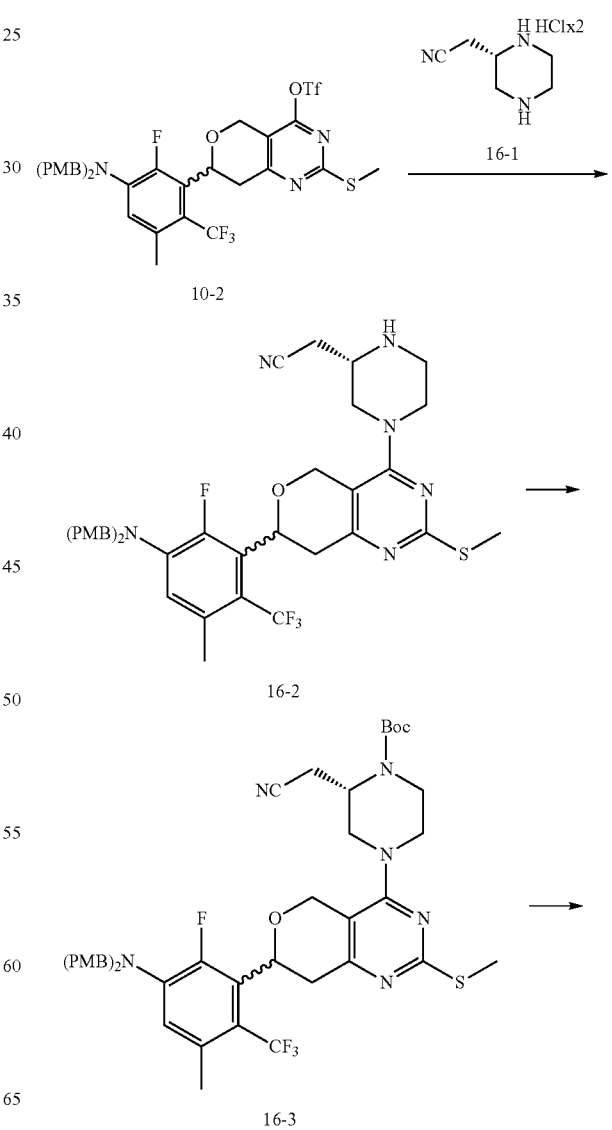

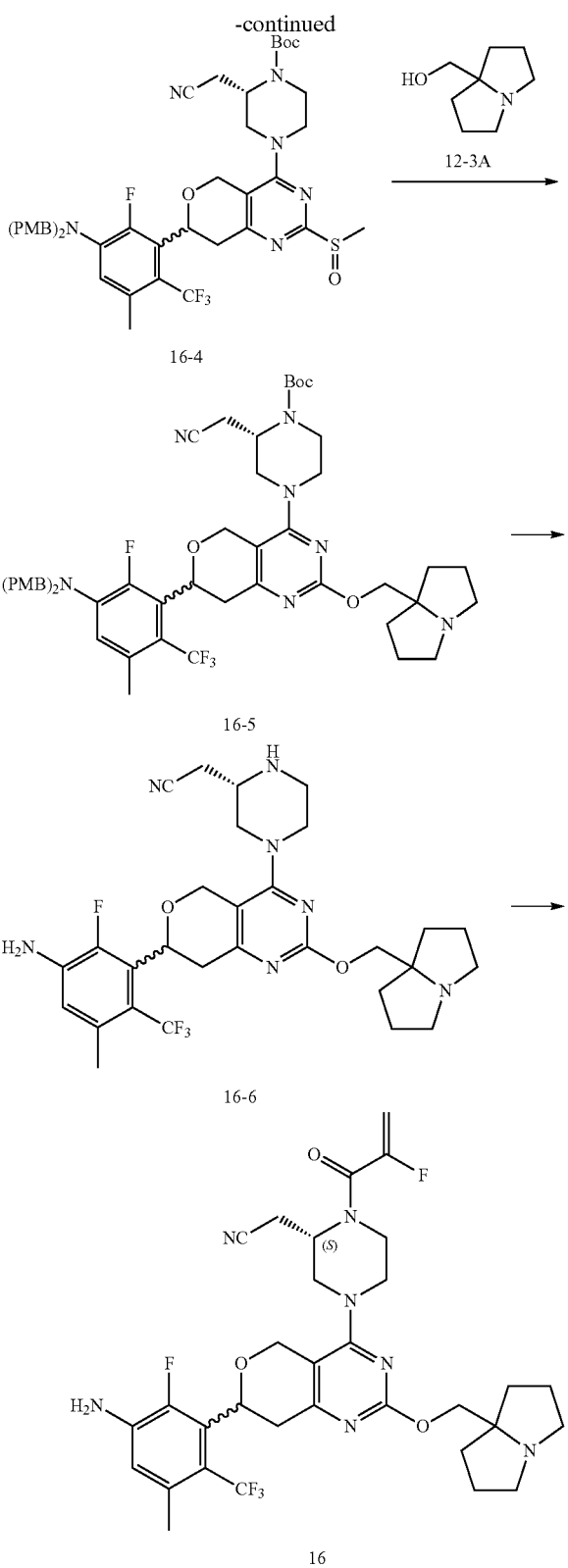

Step 1: Synthesis of Compound 16-2

N,N-dimethylformamide (3 mL) was added to a dry reaction flask, and compound 10-2 (200 mg, 262.56 μmol, 1 eq) was added. The mixture was stirred. N,N-diisopropylethylamine (101.80 mg, 787.69 μmol, 137.20 μL, 3 eq) and compound 16-1 (78.02 mg, 393.84 μmol, 1.5 eq, 2HCl) were added, and the reaction system was reacted at 50° C. for 30 min. The mixtures were combined for treatment. The reaction solution was poured into saturated aqueous ammonium chloride (15 mL) and extracted with ethyl acetate (10 mL×3). The organic phases were combined, washed with saturated brine (20 mL), dried with anhydrous sodium sulfate, and filtered. The filtrate was concentrated under reduced pressure to give a crude product of compound 16-2, which was used directly in the next step without purification. LCMS m/z=737.2 [M+H]$^+$.

Step 2: Synthesis of Compound 16-3

N,N-dimethylformamide (3 mL) was added to a dry reaction flask, and compound 16-2 (230 mg, 312.15 μmol, 1 eq) was added. The mixture was stirred. N,N-diisopropylethylamine (121.03 mg, 936.46 μmol, 163.11 μL, 3 eq) and di-tert-butyl dicarbonate (74.94 mg, 343.37 μmol, 78.88 μL, 1.1 eq) were added, and the reaction system was reacted at 20° C. for 10 h. The reaction solution was poured into saturated aqueous ammonium chloride (15 mL) and extracted with ethyl acetate (10 mL×2). The organic phases were combined, washed with saturated brine (5 mL), dried with anhydrous sodium sulfate, and filtered. The filtrate was concentrated under reduced pressure to give a crude product. The crude product was purified by column chromatography (petroleum ether:ethyl acetate=100:1-0:1) according to TLC (petroleum ether:ethyl acetate=3:1) to give compound 16-3. $^1$H NMR (400 MHz, CDCl$_3$) δ=7.16 (d, J=8.4 Hz, 4H), 6.85 (d, J=8.6 Hz, 4H), 6.64 (d, J=8.0 Hz, 1H), 5.22 (d, J=7.2 Hz, 1H), 4.90-4.68 (m, 2H), 4.61 (s, 1H), 4.41-4.21 (m, 4H), 4.04 (s, 1H), 3.80 (s, 6H), 3.71 (s, 1H), 3.50 (d, J=11.0 Hz, 2H), 3.30 (s, 1H), 3.24-3.02 (m, 2H), 2.90 (d, J=2.0 Hz, 1H), 2.78-2.58 (m, 2H), 2.55 (s, 3H), 2.34 (d, J=4.0 Hz, 3H), 1.51 (s, 9H). LCMS m/z=837.2[M+H]$^+$.

Step 3: Synthesis of Compound 16-4

Dichloromethane (0.3 mL) was added to a dry reaction flask, and compound 16-3 (230 mg, 274.81 μmol, 1 eq) was added. The mixture was stirred. m-Chloroperoxybenzoic acid (61.37 mg, 302.29 μmol, 85% purity, 1.1 eq) was added, and the reaction system was reacted at 20° C. for 1 hour. The reaction solution was poured into 5% aqueous sodium sulfite solution (5 mL) and the layers were separated. The aqueous phase was extracted with dichloromethane (5 mL×2). The organic phases were combined, dried with anhydrous sodium sulfate, and filtered. The filtrate was concentrated under reduced pressure to give a crude product. The aqueous phase was tested with starch-potassium iodide test paper, and showed non-oxidative. The aqueous phase was discarded. The crude product was purified by column chromatography (petroleum ether:ethyl acetate=100:1-0:1) according to TLC (petroleum ether:ethyl acetate=1:1) to give compound 16-4. LCMS m/z=853.2[M+H]$^+$.

Step 4: Synthesis of Compound 16-5

Toluene (2 mL) was added to a dry reaction flask, and compound 16-4 (158 mg, 185.24 μmol, 1 eq) was added. The mixture was stirred. The reaction system was cooled down to 0° C. Sodium tert-butoxide (35.60 mg, 370.49 μmol, 2 eq) was added. The mixture was stirred for 15 min, and compound 12-3A (65.40 mg, 463.11 μmol, 2.5 eq) was added. The reaction system was reacted at 0° C. for 30 min. The reaction solution was poured into saturated aqueous ammonium chloride (5 mL) and extracted with ethyl acetate (5 mL×3). The organic phases were combined, washed with saturated brine (3 mL), dried with anhydrous sodium sulfate, and filtered. The filtrate was concentrated under reduced pressure to give a crude product of compound 16-5, which was used directly in the next step without purification. LCMS m/z=930.4 [M+H]⁺.

Step 5: Synthesis of Compound 16-6

Dichloromethane (5 mL) was added to a dry reaction flask, and compound 16-5 (0.18 g, 193.54 μmol, 1 eq) was added. The mixture was stirred. Then trifluoroacetic acid (1 mL) was added and the reaction system was reacted at 18° C. for 3 hours. Water (10 mL) was added to the reaction solution, and the mixture was extracted. The layers were separated. The aqueous phase was collected, adjusted to pH of 8 with saturated sodium bicarbonate solution, and extracted with dichloromethane (20 mL×2). The organic phases were combined, dried with anhydrous sodium sulfate, and filtered. The filtrate was concentrated under reduced pressure to give a crude product of compound 16-6, which was used directly in the next step without purification. LCMS m/z=590.2[M+H]⁺

Step 6: Synthesis of Compound 16

Compound 16-6 (62.77 mg, 106.46 μmol, 1 eq), 2-fluoroacrylic acid (19.17 mg, 212.92 μmol, 2 eq), and N,N-diisopropylethylamine (41.28 mg, 319.38 μmol, 55.63 μL, 3 eq) were dissolved in DCM (5 mL), and the mixture was cooled down to −60° C. O-(7-azabenzotriazol-1-yl)-N,N,N,N-tetramethyluronium hexafluorophosphate (48.58 mg, 127.75 μmol, 1.2 eq) was added. The mixture was stirred for 0.5 hr. The reaction solution was combined with the batch of compound 16-6 (20.92 mg) for treatment. 5 mL of water was added to the reaction solution. The layers were separated. The organic phase was concentrated, and purified by a high-performance liquid chromatography column {column: Phenomenex luna C18 80*40 mm*3 μm; mobile phase: [H₂O(0.04% HCl)-ACN]; acetonitrile %: 20%-40%, 7 min} to give compound 16. ¹H NMR (400 MHz, CD₃OD) δ=6.73 (d, J=8.6 Hz, 1H), 5.45-5.21 (m, 3H), 4.87-4.80 (m, 2H), 4.57 (s, 2H), 4.19 (br d, J=13.7 Hz, 1H), 3.98 (br d, J=13.1 Hz, 1H), 3.75-3.66 (m, 2H), 3.56-3.49 (m, 1H), 3.37 (s, 3H), 3.32-3.27 (m, 2H), 3.26-3.11 (m, 1H), 3.06-2.87 (m, 1H), 3.06-2.87 (m, 1H), 3.06-2.87 (m, 1H), 2.44-2.03 (m, 12H). LCMS m/z=662.4[M+H]⁺.

Example 17

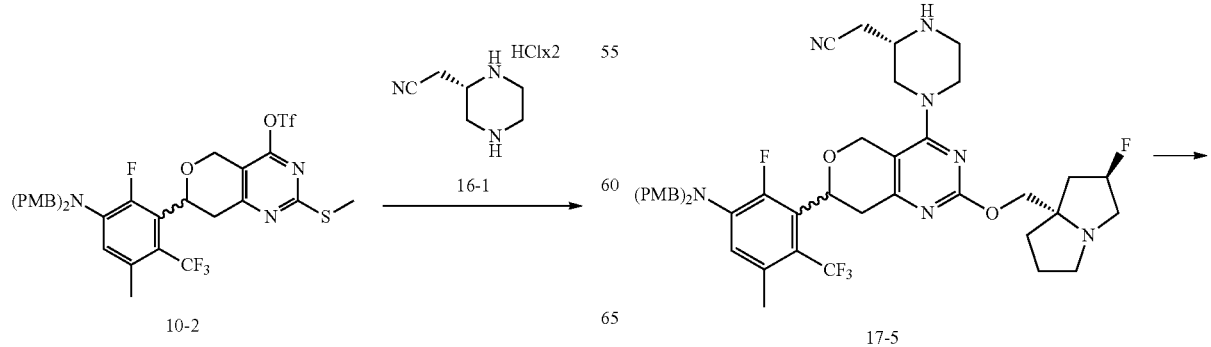

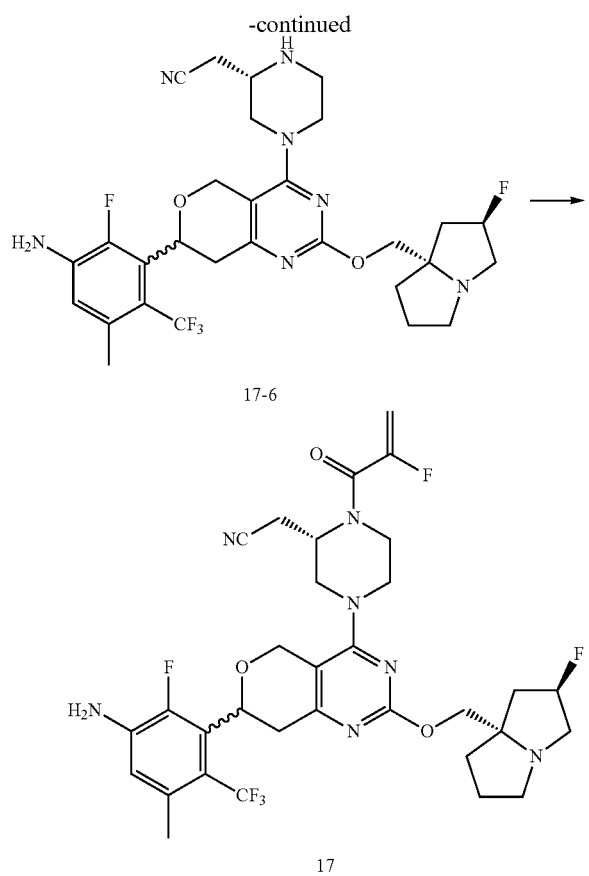

Step 1: Synthesis of Compound 17-2

N,N-dimethylformamide (30 mL) was added to a dry reaction flask, and then compound 10-2 (2.8 g, 3.68 mmol, 1 eq) was added. The mixture was stirred. N,N-diisopropylethylamine (1.43 g, 11.03 mmol, 1.92 mL, 3 eq) and compound 16-1 (873.80 mg, 4.41 mmol, 1.2 eq, 2HCl) were added, and the reaction system was reacted at 50° C. under nitrogen for 1 h. The mixture was combined with the batch of compound 10-2 (0.2 g) for treatment. Methyl tert-butyl ether (30 mL) was added to the reaction solution, and the mixture was washed twice with saturated ammonium chloride solution (30 mL×2) and twice with saturated brine (30 mL×2), dried with anhydrous sodium sulfate, and filtered. The filtrate was concentrated under reduced pressure to give a crude product of compound 17-2, which was used directly in the next step without purification. $^1$H NMR (400 MHz, CDCl$_3$) δ ppm 7.15 (d, J=8.80 Hz, 4H), 6.84 (d, J=8.40 Hz, 4H), 6.63 (d, J=8.40 Hz, 1H), 5.22 (dd, J=11.20, 4.00 Hz, 1H), 4.71 (s, 2H), 4.36-4.20 (m, 4H), 4.06 (d, J=12.80 Hz, 1H), 3.80 (s, 6H), 3.61-3.50 (m, 2H), 3.43 (dd, J=18.80, 11.60 Hz, 2H), 3.27-3.15 (m, 2H), 3.12-2.98 (m, 2H), 2.85-2.66 (m, 2H), 2.53 (s, 3H), 2.38-2.31 (m, 3H), LCMS m/z=737.2[M+H]$^+$.

Step 2: Synthesis of Compound 17-3

Dichloromethane (25 mL) was added to a dry reaction flask and compound 17-2 (2.3 g, 3.12 mmol, 1 eq) was added. The mixture was stirred. The reaction system was cooled down to 0° C. Triethylamine (789.67 mg, 7.80 mmol, 1.09 mL, 2.5 eq) and trifluoroacetic anhydride (983.42 mg, 4.68 mmol, 651.27 μL, 1.5 eq) were added, and the reaction system was reacted at 0 to 5° C. for 0.5 hr. The mixture was combined with the batch of compound 17-2 (0.3 g) for treatment. The reaction solution was washed with a saturated ammonium chloride solution (20 mL×2), dried with anhydrous sodium sulfate, and filtered. The filtrate was concentrated under reduced pressure to give a crude product of compound 17-3, which was used directly in the next step without purification. $^1$H NMR (400 MHz, CDCl$_3$) δ ppm 7.15 (d, J=8.40 Hz, 4H), 6.84 (d, J=8.40 Hz, 4H), 6.65 (br d, J=8.40 Hz, 1H), 5.29-5.20 (m, 1H), 4.77 (s, 2H), 4.38-4.24 (m, 4H), 4.05-3.88 (m, 2H), 3.80 (s, 6H), 3.78-3.60 (m, 2H), 3.59-3.37 (m, 2H), 3.14-2.99 (m, 2H), 2.98-2.93 (m, 1H), 2.91-2.86 (m, 1H), 2.78 (t, J=6.80 Hz, 1H), 2.53 (s, 3H), 2.39-2.30 (m, 3H), LCMS m/z=833.1 [M+H]$^+$.

Step 3: Synthesis of Compound 17-4

Dichloromethane (30 mL) was added to a dry reaction flask, and compound 17-3 (2.6 g, 3.12 mmol, 1 eq) was added. The mixture was stirred. m-Chloroperoxybenzoic acid (697.20 mg, 3.43 mmol, 85% purity, 1.1 eq) was added, and the reaction system was reacted at 18° C. for 0.5 h. The reaction system was combined with the batch of compound 17-3 (0.2 g) for treatment. Sodium thiosulfate solution (20 mL 10%) was added to the reaction solution, and the mixture showed negative by starch-KI paper. The mixture was extracted with dichloromethane (20 mL×2), dried with anhydrous sodium sulfate, and filtered. The filtrate was concentrated under reduced pressure to give a crude product, which was purified by column (petroleum ether:ethyl acetate=10:1-0:1) according to TLC (petroleum ether:ethyl acetate=0:1) to give compound 17-4. $^1$H NMR (400 MHz, CDCl$_3$) δ ppm 7.15 (d, J=8.40 Hz, 4H), 6.84 (d, J=8.40 Hz, 4H), 6.66 (d, J=8.40 Hz, 1H), 5.27 (d, J=9.20 Hz, 1H), 4.93-4.982 (m, 2H), 4.38-4.24 (m, 4H), 4.10-3.99 (m, 2H), 3.98-3.88 (m, 1H), 3.87-3.68 (m, 8H), 3.67-3.54 (m, 1H), 3.54-2.98 (m, 3H), 2.93-2.79 (m, 4H), 2.78-2.65 (m, 1H), 2.35 (d, J=3.60 Hz, 3H), LCMS m/z=849.1 [M+H]$^+$.

Step 4: Synthesis of Compound 17-5

Toluene (1 mL) was added to a dry reaction flask, and compound 17-4A (78.77 mg, 494.80 μmol, 3 eq) was added. The mixture was stirred. the reaction system was cooled down to 0° C., and sodium tert-butoxide (47.55 mg, 494.80 μmol, 3 eq) was added. The mixture was stirred for 10 min, and then a solution of compound 17-4 (0.14 g, 164.93 μmol, 1 eq) in toluene (0.5 mL) was added. The mixture was reacted for another 0.5 h. The reaction system was combined with the batch of compound 17-4 (20 mg) for treatment. The reaction solution was diluted with ethyl acetate (5 mL), washed sequentially with saturated ammonium chloride (10 mL×2) and saturated brine (10 mL), dried with anhydrous sodium sulfate, and filtered. The filtrate was concentrated under reduced pressure to give a crude product of compound 17-5, which was used directly in the next step without purification. LCMS m/z=848.3[M+H]$^+$.

Step 5: Synthesis of Compound 17-6

Dichloromethane (12 mL) was added to a dry reaction flask, and then compound 17-5 (160.00 mg, 188.70 μmol, 1 eq) was added. The mixture was stirred. Then trifluoroacetic acid (2 mL) was added, and the reaction system was reacted at 18° C. for 2 h. The reaction system was combined with the batch of compound 17-5 (20 mg) for treatment. Water (10 mL) was added to the reaction solution. The layers were separated after extraction. The aqueous phase was adjusted to pH of 8 with saturated sodium bicarbonate solution, and extracted with dichloromethane (10 mL×2). The organic phases were combined, dried with anhydrous sodium sulfate, and filtered. The filtrate was concentrated under reduced pressure to give a crude product of compound 17-6, which was used directly in the next step without purification. LCMS m/z=608.3 [M+H]$^+$.

Step 6: Synthesis of Compound 17

Dichloromethane (5 mL) was added to a dry reaction flask, and then compound 17-6 (50 mg, 82.29 μmol, 1 eq), 2-fluoroacrylic acid (14.82 mg, 164.58 μmol, 2 eq), and N,N-diisopropylethylamine (31.90 mg, 246.87 μmol, 43.00 μL, 3 eq) were added. The mixture was stirred. The reaction system was cooled down to −60° C. and O-(7-azabenzotriazol-1-yl)-N,N,N,N-tetramethyluronium hexafluorophosphate (37.55 mg, 98.75 μmol, 1.2 eq) was added. The mixture was then stirred for 0.5 h. The mixtures were combined for treatment. The reaction mixture was quenched by adding water (5 mL) to the reaction solution and the layers were separated. The organic phase was dried with anhydrous sodium sulfate and filtered. The filtrate was concentrated under reduced pressure to give a crude product, which was purified by a high-performance liquid chromatography column {column: Welch Xtimate C18 100*25 mm*3 μm; mobile phase: [H$_2$O(0.05% HCl)-ACN]; acetonitrile %: 20%-50%, 8 min} to give compound 17. SFC analysis method (column: Chiralcel OD-3, 50×4.6 mm I.D., 3 μm; Mobile phase: A (CO2) and B (methanol, containing 0.05% diisopropylamine); Gradient: B %=5-50%, 3 min; Flow rate: 3.4 mL/min; Wavelength: 220 nm; Pressure: 1800 psi, Optical purity: 99.21%, time-to-peak: 1.840). $^1$H NMR (400 MHz, CD$_3$OD) δ=6.80-6.68 (m, 1H), 5.73-5.51 (m, 1H), 5.46-5.19 (m, 3H), 5.05-4.90 (m, 3H), 4.74-4.58 (m, 2H), 4.37-4.26 (m, 1H), 4.20-4.06 (m, 2H), 4.05-3.84 (m, 3H), 3.79-3.59 (m, 2H), 3.54-3.43 (m, 1H), 3.42-3.35 (m, 1H), 3.31-3.24 (m, 1H), 3.13-2.89 (m, 3H), 2.82-2.52 (m, 2H), 2.50-2.42 (m, 1H), 2.41-2.30 (m, 5H), 2.29-2.18 (m, 1H).

Example 18

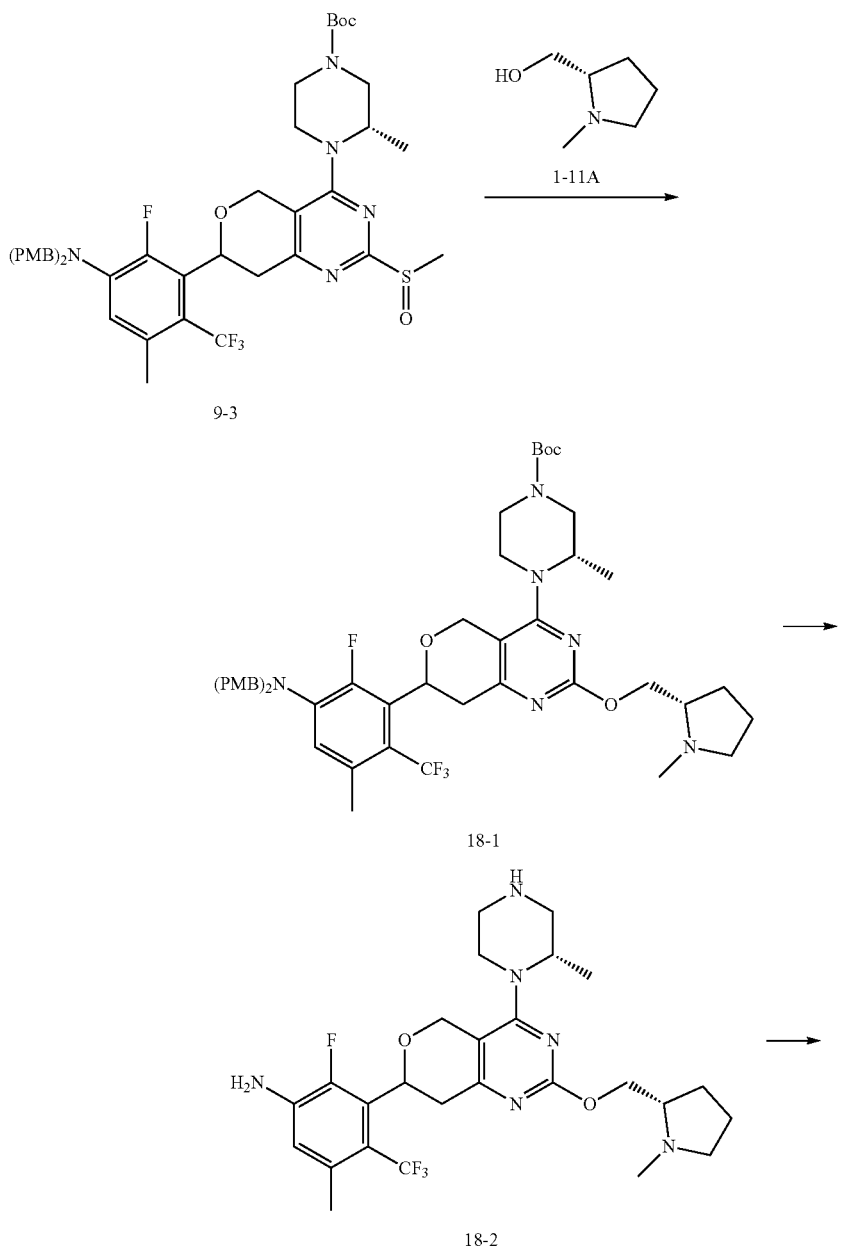

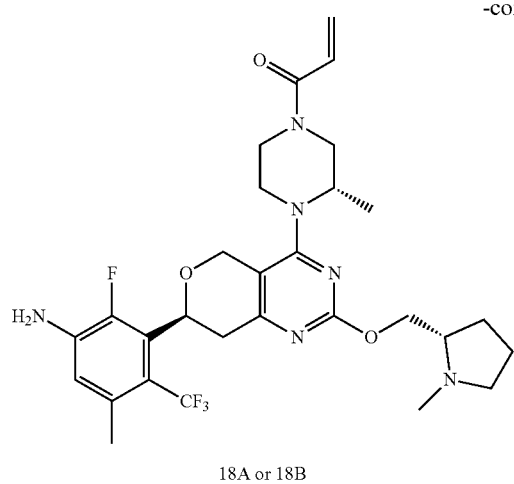

18A or 18B

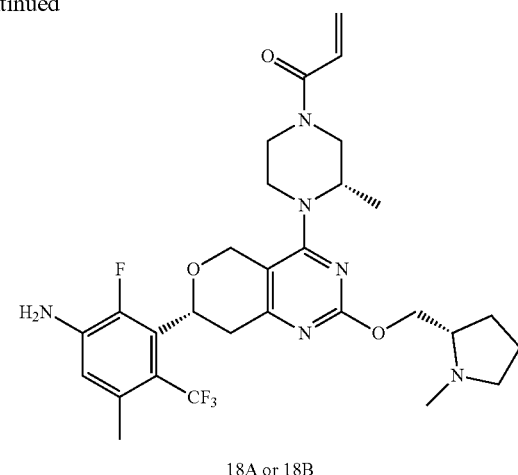

18A or 18B

Step 1: Synthesis of Compound 18-1

1-11A (194.75 mg, 1.69 mmol, 200.78 μL, 4 eq) was added to anhydrous toluene (16 mL). The mixture was cooled down to 0° C., and sodium tert-butoxide (162.50 mg, 1.69 mmol, 4 eq) was added. The mixture was reacted at 0 to 5° C. for 10 min. A solution of compound 9-3 (0.35 g, 422.74 μmol, 1 eq) in toluene (5 mL) was added, and the mixture was reacted at 0 to 5° C. for 0.5 h. The mixture was combined with the batch of compound 9-3 (50 mg) for treatment. The reaction solution was washed with 20 mL×2 of saturated ammonium chloride and 20 mL of saturated brine, dried with anhydrous sodium sulfate, and filtered. The filtrate was concentrated to give compound 18-1. MS m/z=879.2[M+H]$^+$.

Step 2: Synthesis of Compound 18-2

Compound 18-1 (0.4 g, 455.07 μmol, 1 eq) was added to anhydrous dichloromethane (12 mL), and trifluoroacetic acid (2.4 mL) was added. The mixture was reacted at 25° C. for 1.5 h. The mixture was combined with the batch of compound 18-1 (50 mg) for treatment. Saturated sodium bicarbonate was slowly added to the reaction solution until pH was 7-8. The mixture was extracted with 20 mL of dichloromethane, dried with anhydrous sodium sulfate, and filtered. The filtrate was then concentrated to dryness by rotary evaporation to give compound 18-2. LCMS m/z=539.1 [M+H]$^+$ Step 3: Synthesis of Compounds 18A and 18B Compound 18-2 (36.80 mg, 510.60 μmol, 35.04 μL, 1.1 eq), acrylic acid (36.80 mg, 510.60 μmol, 35.04 μL, 1.1 eq) and N,N-diisopropylethylamine (179.97 mg, 1.39 mmol, 242.55 μL, 3 eq) were added to anhydrous dichloromethane (5 mL). The mixture was cooled down to −60° C., and O-(7-azabenzotriazol-1-yl)-N,N,N,N-tetramethyluronium hexafluorophosphate (176.50 mg, 464.18 μmol, 1 eq) was added. The mixture was reacted at −60° C. for 30 min. The reaction solution was diluted with 10 mL of dichloromethane, washed with 10 mL×2 of saturated ammonium chloride, dried with anhydrous sodium sulfate, and filtered. The filtrate was then concentrated. The residue was purified by a high-performance liquid chromatography column (column: Phenomenex luna C18 100*40 mm*5 μm; mobile phase: [H$_2$O(0.1% TFA)-ACN]; acetonitrile %: 10%-40%, 8 min), lyophilized, and then subjected to chiral separation according to SFC (column: DAICEL CHIRALCEL OD(250 mm*30 mm, 10 μm); mobile phase: [0.1%$_0$NH$_3$H$_2$O ETOH]; ethanol %: 50%-50%, 15 min) to give compound 18A ((chiral time-to-peak: 1.479). SFC resolution method (column: Chiralcel OD-3, 50×4.6 mm I.D., 3 μm; Mobile phase: A (CO$_2$) and B (methanol, containing 0.05% diisopropylamine); Gradient: B %=5-50%, 3 min; Flow rate: 3.4 mL/min; Wavelength: 220 nm; Pressure: 1800 psi, Optical purity 100%). MS m/z=593.3[M+H]$^+$, $^1$H NMR (400 MHz, CDCl$_3$) δ=6.66-6.50 (m, 2H), 6.36 (d, J=16.8 Hz, 1H), 5.76 (d, J=10.0 Hz, 1H), 5.20 (d, J=7.6 Hz, 1H), 4.58-4.53 (m, 1H), 4.45-4.20 (m, 2H), 4.01 (s, 3H), 3.85-3.23 (m, 6H), 3.04-2.86 (m, 2H), 2.67 (s, 2H), 2.47-2.33 (m, 3H), 2.22-1.53 (m, 8H), 1.23-1.04 (m, 3H)) and compound 18B ((chiral time-to-peak: 1.642), SFC resolution method (column: Chiralcel OD-3, 50×4.6 mm I.D., 3 μm; Mobile phase: A (CO$_2$) and B (methanol, containing 0.05% diisopropylamine); Gradient: B %=5-50%, 3 min; Flow rate: 3.4 mL/min; Wavelength: 220 nm; Pressure: 1800 psi, Optical purity 97.8%). LCMS m/z=593.3[M+H]$^+$. $^1$H NMR (400 MHz, CDCl$_3$) δ=6.72-6.48 (m, 2H), 6.35 (dd, J=1.6, 16.8 Hz, 1H), 5.76 (d, J=10.4 Hz, 1H), 5.20 (d, J=7.6 Hz, 1H), 4.83-4.57 (m, 3H), 4.18-3.99 (m, 3H), 3.94-3.51 (m, 2H), 3.50-3.20 (m, 2H), 3.11-2.75 (m, 6H), 2.43-2.35 (m, 3H), 2.35-1.80 (m, 8H), 1.38 (d, J=6.4 Hz, 3H)).

Example 19

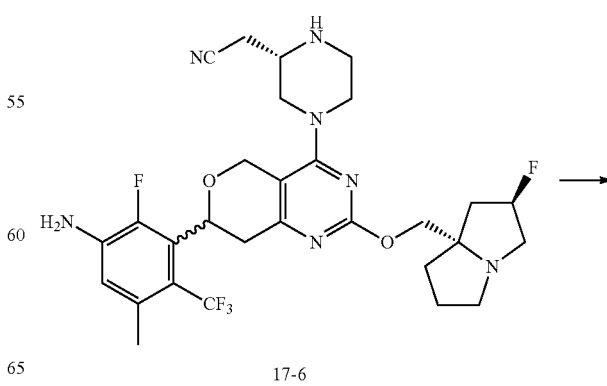

17-6

-continued

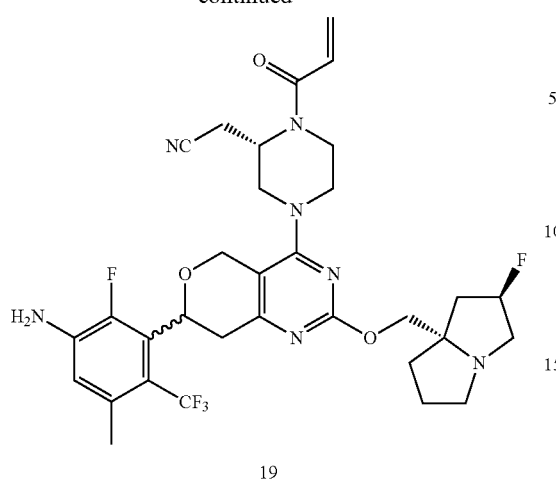

19

Step 1: Synthesis of Compound 19

Dichloromethane (5 mL) was added to a dry reaction flask, and then compound 17-6 (25 mg, 42.40 μmol, 1 eq), acrylic acid (6.11 mg, 84.80 μmol, 5.82 μL, 2 eq) and N,N-diisopropylethylamine (16.44 mg, 127.20 μmol, 22.16 μL, 3 eq) were added. The mixture was stirred. The reaction system was cooled down to 0° C., and O-(7-azabenzotriazol-1-yl)-N,N,N,N-tetramethyluronium hexafluorophosphate (19.35 mg, 50.88 μmol, 1.2 eq) was added. The mixture was stirred at 20° C. for 3 hr. The reaction was quenched by adding water (5 mL) to the reaction solution and the layers were separated. The organic phase was dried with anhydrous sodium sulfate and filtered. The filtrate was concentrated under reduced pressure to give a crude product, which was purified by a high-performance liquid chromatography column {column: Phenomenex luna C18 80*40 mm*3 μm; mobile phase: [H$_2$O(0.04% HCl)-ACN]; B %: 18%-34%, 7 min} to give compound 19. LCMS m/z=622.2[M+H]$^+$.

Example 20

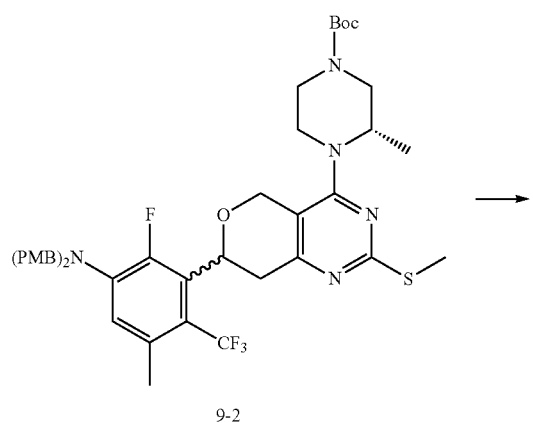

9-2

-continued

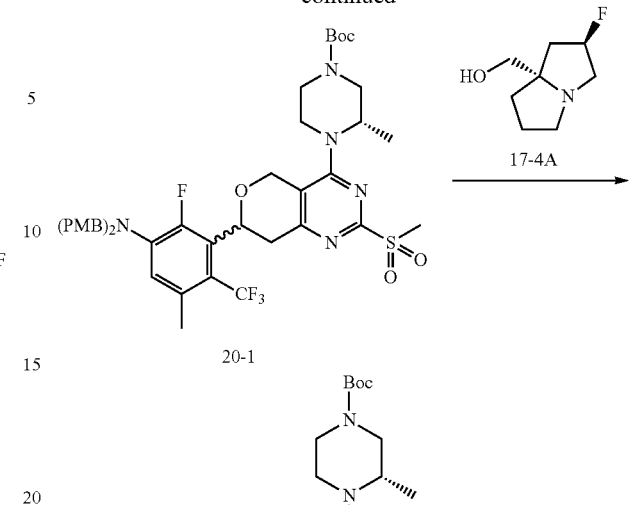

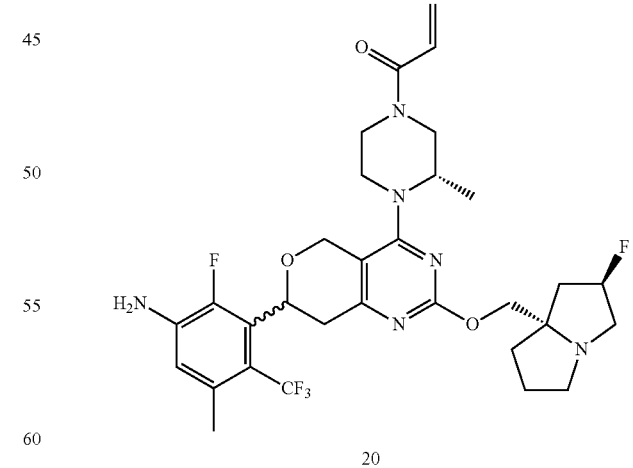

Step 1: Preparation of Intermediate 20-1

Compound 9-2 (90 mg, 110.85 μmol) was dissolved in dichloromethane (2 mL) and m-chloroperoxybenzoic acid (45.01 mg, 221.70 μmol, 85% content) was added. The reaction solution was stirred at 20° C. for another 3 h. The organic solvent was removed under reduced pressure, and the resulting crude product was purified by preparative thin layer chromatography plate (developer: dichloromethane:methanol=20:1) to give compound 20-1. MS m/z=844.4 [M+H]$^+$.

Step 2: Preparation of Intermediate 20-2

Compound 17-4A (12.26 mg, 77.02 µmol) was dissolved in anhydrous tetrahydrofuran (2 mL) at 20° C. Sodium tert-butoxide (7.40 mg, 77.02 µmol) was added and the reaction solution was stirred for another 30 min. A solution of compound 20-1 (50 mg, 59.25 µmol) in tetrahydrofuran (0.5 mL) was added and the reaction solution was stirred at this temperature for 0.5 h. The organic solvent was removed under reduced pressure and the resulting crude product was purified by preparative thin layer chromatography plate (developer: dichloromethane:methanol=10:1) to give compound 20-2. MS m/z=923.6 [M+H]$^+$.

Step 3: Preparation of Compound 20-3

Compound 20-2 (45 mg, 48.75 µmol) was dissolved in anhydrous dichloromethane (2 mL), and trifluoroacetic acid (1.5 mL) was added. The reaction solution was stirred at 20° C. for another 2 h. The solvent was removed under reduced pressure, and the resulting crude product was dissolved in 20 mL of dichloromethane. 3 g of solid sodium bicarbonate was added, and the mixture was stirred at room temperature for another 1 h. The mixture was filtered, and the organic solvent was removed under reduced pressure to give a crude product of 20-3, which was used directly in the next reaction step without further purification.

Step 4: Preparation of Compound 20

Compound 20-3 (20 mg, 34.33 µmol) was dissolved in anhydrous dichloromethane (2 mL) at 20° C. Diisopropylethylamine (13.31 mg, 102.99 µmol, 17.94 µL) and acryloyl chloride (4.66 mg, 51.49 µmol, 4.20 µL) were added, and the reaction solution was stirred at this temperature for another 16 hr. The organic solvent was removed under reduced pressure and the crude product was purified by high-performance liquid chromatography (column: Welch Xtimate C18 100*40 mm*3 µm; mobile phase: [water (0.075% trifluoroacetic acid)-acetonitrile]; acetonitrile: 22%-52%, 8 min) to give the trifluoroacetate salt of compound 20. MS m/z=637.4 [M+H]$^+$.

Biological Assay Data:

Assay Example 1: Assay of Inhibitory Effect of Compounds on the Proliferation of KRAS$^{G12C}$-Mutated MIA-PA-CA-2 Cells 1.1 Purpose of the Assay Compounds were assayed for IC$_{50}$ of inhibition of proliferation of KRAS$^{G12C}$-mutated MIA-PA-CA-2 cells.

1.2 Reagent

The main reagent used in this assay included CellTiter-Glo (Promega, Cat. No. G7573).

1.3 Instrument

The main instrument used in this assay was PerkinElmer EnVision multi-function microplate reader.

1.4 Method of the Assay

1) Adherent cells were digested with trypsin to form a cell suspension, and the cell suspension was counted for later use.
2) An appropriate amount of cells was added into a centrifuge tube, and a cell culture medium was added to make up the required volume; then the cells were plated to a 96-well plate at a final density of 2000 cells/well, 100 µL of culture medium.
3) After incubating for 24 hr, the compound was formulated to 10 mM with DMSO, and serially diluted 3-fold with DPBS (Dulbecco's Phosphate Buffered Saline) to 9 points; 10 µL was added to each well in duplicate. 10 µL of DPBS per well was added to the assay control wells (Con).
4) On the same day, 50 µL of CellTiter Glo was added to another cell culture plate without compounds, and the fluorescence value was read by EnVision. The value was marked as Day 0 value.
5) After 72 h incubation of cells treated with compounds, the plate was removed, and 50 µL of CellTiter Glo was added to the cell plate. The fluorescence value was read by EnVision.
6) Data analysis: The inhibition rate of cells in each well was calculated according to the following equation:

$$\text{Inhibition rate \%} = \left(1 - \frac{FCpd}{FCon - FDay0}\right) * 100\%$$

$F_{Day0}$ was the reading value of the original cell number assay well without compound treatment;

$F_{con}$ was the fluorescence reading value of the Con group after 72 hr of incubation.

$F_{Cpd}$ was the fluorescence reading value of each compound well after 72 hr of incubation.

7) Log(agonist) vs. response—Variable slope nonlinear fit analysis on the inhibition rate data (inhibition rate %) of compounds was performed to give IC$_{50}$ values of compounds by GraphPad Prism software using the following equation:

$$Y = \text{Bottom} + (\text{Top} - \text{Bottom})/(1 + 10^{\wedge}((\text{Log IC}_{50} - X) * \text{Hill-Slope}))$$

1.5 Results of the Assay

TABLE 1

Assay results of compounds of the present disclosure on the inhibition of proliferation of KRAS$^{G12C}$-mutated MIA-PA-CA-2 cells

| Compound No. | IC$_{50}$ (nM) |
|---|---|
| 1 | 5.21 |
| 8B hydrochloride | 2.7 |
| 9B | 6.98 |
| 12 | 1.30 |
| 16 | 2.22 |
| 17 | 0.44 |
| 18B | 3.29 |

The assay results showed that the compounds of the present disclosure have good inhibitory activity on cell proliferation of KRAS$^{G12C}$-mutated MIA-PA-CA-2 cell line.

Assay Example 2: H358 Cell Assay 2.1 Purpose of the Assay

Compounds were assayed for IC$_{50}$ of inhibition of proliferation of KRAS$^{G12C}$-mutated H358 cells.

2.2 Reagent

The main reagents used in this assay included RPMI-1640 medium, penicillin/streptomycin antibiotics purchased from Vicente, fetal bovine serum purchased from Biosera, Cell-Titer-Glo (cell viability chemiluminescence detection reagent) reagent purchased from Promega, and NCI-H358 cell line purchased from the Cell Bank of the Chinese Academy of Sciences.

2.3 Instrument

The main instrument used in this assay was a Nivo multi-label analyzer (PerkinElmer).

2.4 Method of the Assay:
1) NCI-H358 cells were inoculated in a white 96-well plate, and each well contained 80 µL of cell suspension and 4000 NCI-H358 cells. The cell plate was incubated in a carbon dioxide incubator overnight.
2) The compounds to be assayed were serially diluted 5-fold with a multi-channel pipette to obtain nine concentrations, i.e., from 2 mM to 5.12 nM. The assay was carried out in duplicate. 78 µL of medium was added to the intermediate plate, and then 2 µL of the serially diluted compound was transferred to each well of the intermediate plate according to the corresponding position. After mixing well, 20 µL per well was transferred to the cell plate. The concentrations of compounds transferred to the cell plate ranged from 10 µM to 0.0256 nM. The cell plate was incubated in a carbon dioxide incubator for 5 days. Another cell plate was prepared, and the signal value of the cell plate was read on the day of compound addition as the maximum value (Max value in the equation below) to participate in data analysis. 25 µL of cell viability chemiluminescence detection reagent was added to each well of the cell plate, and the plate was incubated at room temperature for 10 minutes to stabilize the luminescence signal. A multi-label analyzer was used for reading the plate.
3) 25 µL of cell viability chemiluminescence detection reagent was added to each well of the cell plate, and the plate was incubated at room temperature for 10 minutes to stabilize the luminescence signal. A multi-label analyzer was used for reading the plate.

Data Analysis:

The equation (Sample−Min)/(Max−Min)*100% was used to convert the raw data into inhibition rate, and the $IC_{50}$ value can be obtained by curve fitting with four parameters ("log(inhibitor) vs. response—Variable slope" mode in GraphPad Prism). The inhibitory activity of compounds of the present disclosure on NCI-H358 cell proliferation was provided in Table 2.

TABLE 2

Assay results of compounds of the present disclosure for inhibition of proliferation of $KRAS^{G12C}$-mutated H358 cells

| Compound | NCI-H358 $IC_{50}$ (nM) |
|---|---|
| 1 | 68.2 |
| 2 | 19.0 |
| 4B hydrochloride | 27.0 |
| 5B | 12.9 |
| 6A | <4.6 |
| 8B hydrochloride | <4.6 |
| 9B | 5.5 |
| 10 | 70 |
| 11 | 6.7 |
| 12 | 2.5 |
| 13 | 32.6 |
| 15 | 9.2 |
| 16 | 1.7 |
| 17 | 0.6 |
| 18B | 4.7 |

Conclusion: Some compounds of the present disclosure exhibit good inhibitory activity on the proliferation of NCI-H358 cells.

Assay Example 3: Metabolic Stability of Hepatocytes

Purpose of the assay: Metabolic stabilities of assay compounds in hepatocytes of CD-1 mice, SD rats, beagle dogs, cynomolgus monkeys, and human were assayed, respectively.

Procedure of the assay: Several 96-well sample precipitation plates were prepared and named T0, T15, T30, T60, T90, T120, T0-MC, T120-MC and blank substrates, respectively. The recovery medium and incubation medium were taken out in advance and placed in a 37° C. water bath for pre-heating. Cryopreserved hepatocytes were removed from the liquid nitrogen tank and immediately immersed in a 37° C. water bath (approximately 90 seconds). After the cryopreserved hepatocytes had thawed and loosened, they were poured into a centrifuge tube containing 40 mL of recovery medium, and the tube was gently inverted to allow the cells to be resuspended in the recovery medium. The cells were centrifuged at 100×g at room temperature for 5 min, and the supernatant was removed. The hepatocytes were resuspended in an appropriate volume of incubation medium, and the cell viability was calculated by Trypan Blue staining method. 198 µL of hepatocyte suspension ($0.51 \times 10^6$ cells/mL) was added to the preheated incubation plate. For the culture medium control group, 198 µL of hepatocyte-free incubation medium was added to T0-MC and T120-MC incubation plate. All incubation plates were pre-incubated in a 37° C. incubator for 10 minutes. Then 2 µL of working solutions of the assay sample and the control compound were added, respectively, and the mixture was mixed well. The incubation plate was immediately put into the shaker in the incubator, and the reaction was initiated while starting the timer. For each time point of each compound, 2 duplicate samples were prepared. The incubation conditions were 37° C., saturated humidity, and 5% $CO_2$. In the assay system, the final concentration of the assay sample was 1 µM, the final concentration of the control sample was 3 µM, the final concentration of hepatocytes was $0.5 \times 10^6$ cells/mL, and the final concentration of the total organic solvent was 0.96%, of which the final concentration of DMSO was 0.1%. At the end of the incubation for the corresponding time point, the incubation plate was taken out, and 25 µL of a mixture of compound and control compound with cells was added to the sample plate containing 125 µL of stop solution (200 ng/mL tolbutamide and labetalol in acetonitrile). For the Blank sample plate, 25 µL of hepatocyte-free incubation medium was added directly. After sealing, all sample plates were shaken on a shaker at 600 rpm for 10 minutes, and then centrifuged at 3220×g for 20 minutes. Supernatants of the assay sample and the control sample were diluted with ultrapure water at a ratio of 1:3. All samples were mixed well and analyzed by LC/MS/MS.

The assay results are shown in Table 3.

TABLE 3

Metabolic stability of the assay compounds in hepatocytes of CD-1 mice, SD rats, beagle dogs, cynomolgus monkeys, and human

| Compound | Species | $T_{1/2}$ (min) | $CL_{int(hep)}$ (µL/min/$10^6$) | $CL_{int(liver)}$ (mL/min/kg) |
|---|---|---|---|---|
| 8B | CD-1 mice | 18.2 | 76.3 | 906.0 |
| | SD rats | 185.2 | 7.5 | 35.0 |
| | Cynomolgus monkeys | 136.1 | 10.2 | 36.7 |
| | Beagle dogs | >216.8 | <6.4 | <44 |
| | Human | 199.5 | 6.9 | 19.3 |
| 17 | CD-1 mice | 9.5 | 146.3 | 1738.1 |
| | SD rats | 20.6 | 67.4 | 315.2 |
| | Cynomolgus monkeys | 27.0 | 51.3 | 184.7 |
| | Beagle dogs | 182.2 | 7.6 | 52.3 |
| | Human | 99.5 | 13.9 | 38.7 |

Conclusion: Metabolic assay in hepatocytes of various species showed that the compounds of the present disclosure have good metabolic stability.

Assay Example 4: In Vitro Stability Assay in Liver Microsomes

Purpose of the assay: Metabolic stabilities of the assay compounds in liver microsomes of CD-1 mice, SD rats, beagle dogs, cynomolgus monkeys, and human were assayed, respectively.

Procedure of the assay: Two 96-well incubation plates were prepared and named T60 incubation plate and NCF60 incubation plate, respectively. 445 µL of microsomal working solutions (liver microsomal protein concentration of 0.56 mg/mL) were added to the T60 incubation plate and the NCF60 incubation plate, respectively, and then the above incubation plates were pre-incubated in a 37° C. water bath for about 10 minutes.

After the pre-incubation, 5 µL of working solutions of the assay sample or the control compound were added to the T60 incubation plate and the NCF60 incubation plate, respectively, and the mixture was mixed well. 50 µL of potassium phosphate buffer was added to each well of the NCF60 incubation plate to initiate the reaction. 180 µL of stop solution (200 ng/mL tolbutamide and 200 ng/mL labetalol in acetonitrile) and 6 uL of NADPH regeneration system working solution were added to the T0 stop plate, and 54 µL of sample was transferred from T60 incubation plate to T0 stop plate (generation of T0 sample). The reaction was initiated by adding 44 µL of NADPH regeneration system working solution to each well of the T60 incubation plate. Only 54 µL of microsome working solution, 6 uL of NADPH regeneration system working solution and 180 µL of stop solution were added to the Blank plate. Therefore, in samples of the assay compound or the control compound, the final reaction concentration of compound, testosterone, diclofenac and propafenone was 1 µM, the concentration of liver microsomes was 0.5 mg/mL, and the final reaction concentrations of DMSO and acetonitrile in the reaction system were 0.01% (v/v) and 0.99% (v/v), respectively.

After an appropriate time (e.g., 5, 15, 30, 45 and 60 minutes) of incubation, 180 µL of stop solutions (200 ng/mL tolbutamide and 200 ng/mL labetalol in acetonitrile) were added to the sample wells of each stop plate, respectively. 60 µL of sample was removed from the T60 incubation plate to stop the reaction. All sample plates were shaken well and then centrifuged at 3220×g for 20 minutes. Then 80 µL of supernatant was taken out from each well, and diluted in 240 µL of pure water for liquid chromatography-tandem mass spectrometry analysis. All samples were injected and analyzed by liquid chromatography-tandem mass spectrometry.

TABLE 4

Metabolic stability of the assay compounds in liver microsomes of CD-1 mice, SD rats, beagle dogs, cynomolgus monkeys, and human

| Compound | Species | $T_{1/2}$ (min) | $CL_{int(hep)}$ (µL/min/10$^6$) | $CL_{int(liver)}$ (mL/min/kg) |
|---|---|---|---|---|
| 8B | CD-1 mice | 12.6 | 110.1 | 436.1 |
|  | SD rats | >145 | <9.6 | <17.3 |
|  | Cynomolgus monkeys | 23.3 | 59.5 | 80.3 |
|  | Beagle dogs | >145 | <9.6 | <13.8 |
|  | Human | 60.3 | 23.0 | 20.7 |
| 17 | CD-1 mice | 4.9 | 284.6 | 1126.8 |
|  | SD rats | 23.0 | 60.2 | 108.3 |
|  | Cynomolgus monkeys | 6.2 | 224.6 | 303.2 |
|  | Beagle dogs | >145 | <9.6 | <13.8 |
|  | Human | 20.4 | 67.9 | 61.1 |

Conclusion: The assay of the metabolic stability in liver microsomes showed that the compounds of the present disclosure have good metabolic stability.

Assay Example 5: Stability Assay in Plasma

Purpose of the assay: Stabilities of the assay compounds in plasma of CD-1 mice and human were assayed, respectively.

Procedure of the assay: Cryopreserved plasma was thawed for 10-20 min. After the plasma was completely thawed, it was placed in a centrifuge and centrifuged at 3220×g for 5 min to remove any suspended matter and sediment in the plasma. 96-well incubation plates were prepared and named T0, T10, T30, T60, T120, respectively. 98 µL of blank plasmas of mouse, rat, canine, monkey and human were added to the corresponding incubation plates, then 2 µL of working solutions of the compound or the control compound were added to the corresponding plates in duplicate. All samples were incubated in a 37° C. water bath. The final incubation concentrations of the compound and the control compounds bisacodyl, enalapril maleate, procaine and probanthine were 2 µM, and the final organic phase content was 2.0%. At the end of incubation for each time point, the corresponding incubation plate was removed and 400 µL of a solution of 200 ng/mL of tolbutamide and labetalol in acetonitrile was added to each corresponding sample well to precipitate the protein. All sample plates were sealed and shaken well, and then centrifuged at 3220×g for 20 minutes. 50 µL of supernatant was taken out and diluted in 100 µL of ultrapure water. All samples were mixed well and then analyzed by LC/MS/MS.

TABLE 5

Stability of the assay compounds in plasma of CD-1 mice and human

| Compound | Species | Detection of assay compound content within 120 min |
|---|---|---|
| 8B | CD-1 mice | 110% |
|  | Human | 114% |
| 17 | CD-1 mice | 94% |
|  | Human | 93% |

Conclusion: The compounds of the present disclosure have good stability in plasma of human and mouse.

Assay Example 6: Stability Assay in Whole Blood

Purpose of the assay: Stabilities of the assay compounds in whole blood of CD-1 mice, SD rats, Beagle dogs and cynomolgus monkeys were assayed, respectively.

Procedure of the assay: On the day of the assay or the day before the assay, fresh whole blood from CD-1 mice, SD rats, beagle dogs, and cynomolgus monkeys was collected using anticoagulant EDTA-K2. Prior to the start of the assay, the whole blood was mixed with PBS in 1:1 (v: v) and the mixture was preheated in a 37° C. water bath for 10-20 minutes. 96-well incubation plates were prepared and named T0, T30, T60, T240, respectively. In the corresponding incubation plates, including T0, T30, T60 and T240 incubation plates, 2 µL of working solutions of the compound or the control compound were mixed with 98 µL of blank whole blood of mice, rats, canines, monkeys and human in duplicate. All samples were incubated in a 37° C. water bath. The final incubation concentration of the compound was 5 µM and the final incubation concentration of the control compound was 2 µM. At the end of incubation for each time point, the corresponding incubation plate was removed and 100 µL of ultrapure water was immediately added to the corresponding sample wells, and mixed well. 800 μL of a solution of 200 ng/mL tolbutamide and labetalol in acetonitrile was added to precipitate the protein. The sample plates were sealed and shaken well, and then centrifuged at 3220×g for 20 min. 150 μL of supernatant was taken out and analyzed by LC/MS/MS.

TABLE 6

Stability of the assay compounds in the whole blood of CD-1 mice, SD rats, beagle dogs, and cynomolgus monkeys

| Compound | Species | Detection of assay compound content within 120 min |
|---|---|---|
| 8B | CD-1 mice | 100% |
|  | SD rats | 104% |
|  | Cynomolgus monkeys | 58% |
|  | Beagle dogs | 96% |
| 17 | CD-1 mice | 117% |
|  | SD rats | 115% |
|  | Cynomolgus monkeys | 77% |
|  | Beagle dogs | 102% |

Conclusion: The stability assay in the whole blood of various species showed that the compounds of the present disclosure have good stability in whole blood.

Assay Example 7: Assay of Protein Binding Rate

Purpose of the assay: Protein binding rate of the assay compounds in plasma of CD-1 mice, SD rats, beagle dogs, cynomolgus monkeys and human was determined by equilibrium dialysis.

TABLE 7

Protein binding rate of the assay compounds in CD-1 mice, SD rats, beagle dogs, cynomolgus monkeys, and human

| Compound | Species | Protein unbound rate |
|---|---|---|
| 8B | CD-1 mice | 12.0 |
|  | SD rats | 9.8 |
|  | Cynomolgus monkeys | 23.9 |
|  | Beagle dogs | 6.0 |
|  | Human | 10.6 |
| 17 | CD-1 mice | 1.5 |
|  | SD rats | 4.8 |
|  | Cynomolgus monkeys | 7.8 |
|  | Beagle dogs | 3.3 |
|  | Human | 4.8 |

Conclusion: Assay on plasma binding rates of various species showed that the compounds of the present disclosure have higher protein unbound rate in plasma.

Assay Example 8: Assay on Pharmacokinetics In Vivo

1) Assay on the Pharmacokinetics of the Assay Compounds by Oral Administration and Intravenous Injection in SD Rats The assay compound was mixed with 5% dimethyl sulfoxide/95% (10% hydroxypropyl-β-cyclodextrin) solution. The mixture was vortexed and sonicated to prepare a 1 mg/mL clear solution, which was filtered through a microporous membrane for later use. Male SD rats aged 7 to 10 weeks were selected, and administered candidate compound solutions intravenously or orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 8:

TABLE 8

Pharmacokinetic results of the assay compounds

| Route of administration | Pharmacokinetic parameters | Compound 8B | Compound 17 |
|---|---|---|---|
|  | Plasma protein unbound rate PPB (Unbound %) | 9.8 | 4.8 |
| Intravenous injection administration | Dose (mg/kg) | 2.0 | 2.0 |
|  | Half-life period, $T_{1/2}$ (h) | 2.8 | 1.9 |
|  | Clearance rate, CL (ml/min/kg) | 85.2 | 71.5 |
|  | Apparent volume of distribution, $Vd_{ss}/Vd_{ss, u}$ (L/kg) | 17.9/203 | 10.6/221 |
|  | $AUC_{0-last}/AUC_u$ (nM · h) | 544/53.3 | 653/31.3 |
| Oral administration | Dose (mg/kg) | 9.7 | 9.8 |
|  | Time-to-peak, $T_{max}$ (h) | 1.5 | 1.5 |
|  | Peak concentration, $C_{max}/C_{max, u}$ (nM) | 218/21.3 | 220/10.6 |
|  | $AUC_{0-last}/AUC_u$ (nM · h) | 1211/119 | 995/47.8 |
|  | Bioavailability F (%) | 44.5% | 30.5% |

Note:
$Vd_{ss, u}$ is the apparent volume of distribution under unbound plasma protein ($Vd_{ss, u} = Vd_{ss}$/PPB(Unbound %)); $C_{max, u}$ and $AUC_{0-last, u}$ are the corresponding values under unbound plasma protein ($C_{max, u} = C_{max}$ × PPB(Unbound %); $AUC_{0-last, u} = AUC_{0-last}$ × PPB(Unbound %))
Conclusion: PK assay showed that the compounds of the present disclosure have higher unbound plasma exposure and good oral bioavailability in rats.

Procedure of the assay: Plasma samples with a compound concentration of 2 μM were prepared using plasma of the above five species, placed in a 96-well equilibrium dialysis device, and dialyzed with phosphate buffer solution at 37±1° C. for 4 hours. Warfarin was used as the control compound in this assay. The concentrations of the assay compounds in plasma and dialysis buffer were determined by LC-MS/MS method.

2) Assay on the Pharmacokinetics of the Assay Compounds by Oral Administration and Intravenous Injection in CD Mice The assay compound was mixed with 5% dimethyl sulfoxide/95% (10% hydroxypropyl-β-cyclodextrin) solution. The mixture was vortexed and sonicated to prepare a 1 mg/mL clear solution, which was filtered through a microporous membrane for later use. Male CD mice aged 7 to 10 weeks were selected, and administered candidate compound solutions intravenously or orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 9:

2. Tumor Measurements and Assay Indicators

Tumor diameter was measured with vernier caliper twice a week. The calculation formula of tumor volume was: $V=0.5a \times b^2$, where a and b represent the long and short diameters of the tumor, respectively.

TABLE 9

Pharmacokinetic results of the assay compounds

| Route of administration | Pharmacokinetic parameters | Compound 8B | Compound 17 |
|---|---|---|---|
| | Plasma protein unbound rate PPB (Unbound %) | 1.54 | 12.0 |
| Intravenous injection administration | Dose (mg/kg) | 2.39 | 2.0 |
| | Half-life period, $T_{1/2}$ (h) | 1.0 | 1.7 |
| | Clearance rate, CL (ml/min/kg) | 37.3 | 40.6 |
| | Apparent volume of distribution, $Vd_{ss}/Vd_{ss, u}$ (L/kg) | 2.6/168.8 | 3.9/32.3 |
| | $AUC_{0-last}/AUC_u$ (nM · h) | 1311/20.2 | 1297/155.6 |
| Oral administration | Dose (mg/kg) | 14.7 | 10.3 |
| | Time-to-peak, $T_{max}$ (h) | 0.25 | 1.0 |
| | Peak concentration, $C_{max}/C_{max, u}$ (nM) | 1460/22.5 | 431/51.7 |
| | $AUC_{0-last}/AUC_u$ (nM · h) | 2403/37.0 | 1422/170.6 |
| | Bioavailability F (%) | 24.4% | 21.9% |

Note:
$Vd_{ss, u}$ is the apparent volume of distribution under unbound plasma protein ($Vd_{ss, u} = Vd_{ss}$/PPB(Unbound %)); $C_{max, u}$, and $AUC_{0-last, u}$, are the corresponding values under unbound plasma protein ($C_{max, u} = C_{max}$ × PPB(Unbound %); $AUC_{0-last, u} = AUC_{0-last}$ × PPB(Unbound %))
Conclusion: PK assay showed that the compounds of the present disclosure have higher unbound plasma exposure and good oral bioavailability in mice.

Assay Example 9: Assay on Pharmacodynamics In Vivo

Assay on Pharmacodynamics In Vivo in a Subcutaneously Transplanted Tumor Model of Human Pancreatic Cancer Mia PaCa-2 Cells in Balb/c Nude Mice 1. Cell Culture and Tumor Tissue Preparation Cell culture: Human pancreatic cancer Mia PaCa-2 cells (ATCC-CRL-1420) were cultured in monolayer in vitro in DMEM medium with 10% fetal calf serum and 2.5% horse serum in a 37° C., 5% carbon dioxide incubator. Cells were passaged by routine digestion with trypsin-EDTA twice a week. When the cell saturation reached 80%-90% and the cell number met the requirement, the cells were harvested, counted, and resuspended in an appropriate amount of PBS. Matrigel was added in a ratio of 1:1 to obtain a cell suspension with a cell density of $25 \times 10^6$ cells/mL.

Cell inoculation: 0.2 mL ($5 \times 10^6$ cells/mouse) of Mia PaCa-2 cells (plus Matrigel, 1:1 by volume) were subcutaneously inoculated into the right back of each mouse. When the average tumor volume reached 190 mm³, mice were randomized into groups based on tumor volume and administration was initiated according to the protocol in Table 10.

The anti-tumor efficacy of compounds was evaluated by TGI (%) or relative tumor proliferation rate T/C (%). Relative tumor proliferation rate T/C (%)=TRTV/CRTV×100% (TRTV: RTV in a treatment group; CRTV: RTV in a negative control group). The relative tumor volume (RTV) was calculated according to results of tumor measurement, and the calculation formula was RTV=Vt/V0, where V0 was average tumor volume measured at the time of administration by group (i.e., D0), and Vt was average tumor volume at the time of a certain measurement. For TRTV and CRTV, data on the same day were used.

TGI (%) reflected tumor growth inhibition rate. TGI (%)=[(1−(average tumor volume at the end of administration of a treatment group−average tumor volume at the beginning of administration of the treatment group))/(average tumor volume at the end of treatment of a vehicle control group−average tumor volume at the beginning of treatment of the vehicle control group)]×100%.

3. Results of the Assay

Figure 2:
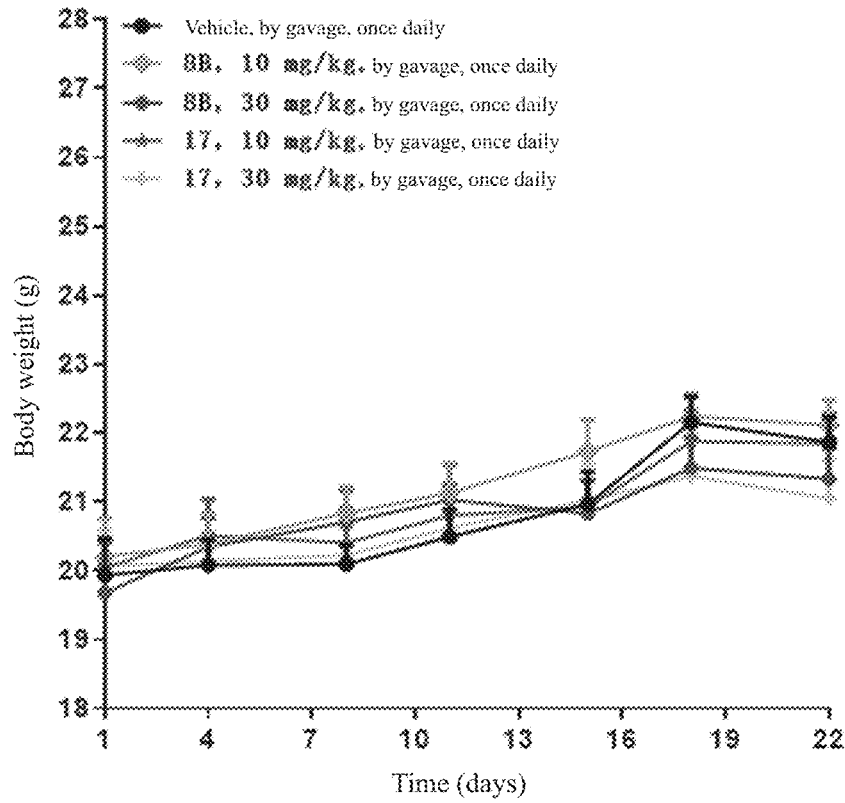
FIG. 2 shows changes in animal body weight over time at different doses.

The assay results are shown in FIGS. 1 and 2.

The results at 22 days of administration are shown in Table 11.

TABLE 10

Assay animal grouping and administration protocol

| Group | Number of animals | Compound | Dosage (mg/kg) | Administration volume (µL/g) | Route of administration | Administration frequency |
|---|---|---|---|---|---|---|
| 1 | 6 | Vehicle | — | 10 | PO | QD x22 |
| 2 | 6 | 8B | 10 | 10 | PO | QD x22 |
| 3 | 6 | 8B | 30 | 10 | PO | QD x22 |
| 4 | 6 | 17 | 10 | 10 | PO | QD x22 |
| 5 | 6 | 17 | 30 | 10 | PO | QD x22 |

Note:
PO indicates oral administration;
QD indicates once daily.

TABLE 11

T/C and TGI on day 22 of administration

| Compound | Dosage | Average tumor volume | T/C | TGI |
|---|---|---|---|---|
| Vehicle | N/A | 2016.29 mm³ | N/A | N/A |
| 8B | 10 mg/kg | 745.84 mm³ | 36.99% | 66.89% |
| 8B | 30 mg/kg | 227.15 mm³ | 11.28% | 94.23% |
| 17 | 10 mg/kg | 249.87 mm³ | 12.39% | 93.06% |
| 17 | 30 mg/kg | 124.14 mm³ | 6.16% | 99.64% |

Conclusion: The compounds of the present disclosure have significant tumor-inhibiting effect. Moreover, the body weight of mice in each dose group is stable, and there is no obvious intolerance.

What is claimed is:

1. A compound represented by formula (III) or a pharmaceutically acceptable salt thereof,

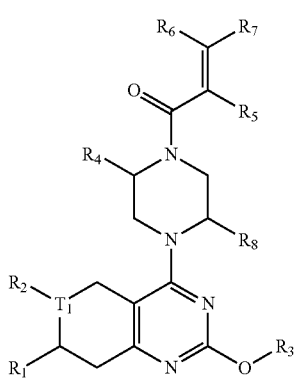

(III)

wherein
T₁ is selected from O and N;
R₁ is selected from $C_{6-10}$ aryl and 5- to 10-membered heteroaryl, wherein the $C_{6-10}$ aryl and 5- to 10-membered heteroaryl are optionally substituted with 1, 2, 3, 4 or 5 $R_a$;
when T₁ is O, R₂ is not present;
when T₁ is N, R₂ is selected from H, $C_{1-3}$ alkyl, —C(=O)—$C_{1-3}$ alkyl and —S(=O)₂—$C_{1-3}$ alkyl, wherein the $C_{1-3}$ alkyl, —C(=O)—$C_{1-3}$ alkyl and —S(=O)₂-$C_{1-3}$ alkyl are optionally substituted with 1, 2 or 3 $R_b$;
R₃ is $C_{1-3}$ alkyl, wherein the $C_{1-3}$ alkyl is optionally substituted with 1, 2 or 3 $R_c$;
R₄ is selected from H and $C_{1-3}$ alkyl, wherein the $C_{1-3}$ alkyl is optionally substituted with 1, 2 or 3 $R_d$;
R₅, R₆ and R₇ are each independently selected from H, F, Cl, Br, I, and $C_{1-3}$ alkyl, wherein the $C_{1-3}$ alkyl is optionally substituted with 1, 2 or 3 F;
R₈ is selected from H and CH₃;
$R_a$ is each independently selected from F, Cl, Br, I, OH, NH₂, CN, $C_{1-3}$ alkyl, $C_{1-3}$ alkoxy, $C_{2-3}$ alkynyl and $C_{2-3}$ alkenyl, wherein the $C_{1-3}$ alkyl, $C_{1-3}$ alkoxy, $C_{2-3}$ alkynyl and $C_{2-3}$ alkenyl are optionally substituted with 1, 2 or 3 F;
$R_b$ is each independently selected from F, Cl, Br, I, OH and NH₂;
$R_c$ is each independently selected from 4- to 8-membered heterocycloalkyl, wherein the 4- to 8-membered heterocycloalkyl is optionally substituted with 1, 2 or 3 R;
$R_d$ is each independently selected from F, Cl, Br, I, OH, NH₂ and CN;
R is each independently selected from H, F, Cl, Br, OH, CN, $C_{1-3}$ alkyl, $C_{1-3}$ alkoxy and —$C_{1-3}$ alkyl-O—C(=O)—$C_{1-3}$ alkylamino;
provided that when R₁ is naphthyl, the naphthyl is optionally substituted with F, Cl, Br, OH, NH₂, CF₃, CH₂CH₃ and —C≡CH, and R₅, R₆ and R₇ are each independently H.

2. The compound according to claim 1, or a pharmaceutically acceptable salt thereof, wherein $R_a$ is each independently selected from F, Cl, Br, I, OH, NH₂, CN, CH₃, CH₂CH₃, OCH₃, OCH₂CH₃, —CH=CH₂, —CH₂—CH=CH₂ and —C≡CH, wherein the CH₃, CH₂CH₃, OCH₃, OCH₂CH₃, —CH=CH₂, —CH₂—CH=CH₂ and —C≡CH are optionally substituted with 1, 2 or 3 F;
alternatively, wherein $R_a$ is each independently selected from F, OH, NH₂, CH₃, CF₃, CH₂CH₃ and —C≡CH.

3. The compound according to claim 1, or a pharmaceutically acceptable salt thereof, wherein R₁ is selected from phenyl, naphthyl, indolyl and indazolyl, wherein the phenyl, naphthyl, indolyl and indazolyl are optionally substituted with 1, 2 or 3 $R_a$.

4. The compound according to claim 3, or a pharmaceutically acceptable salt thereof, wherein R₁ is selected from

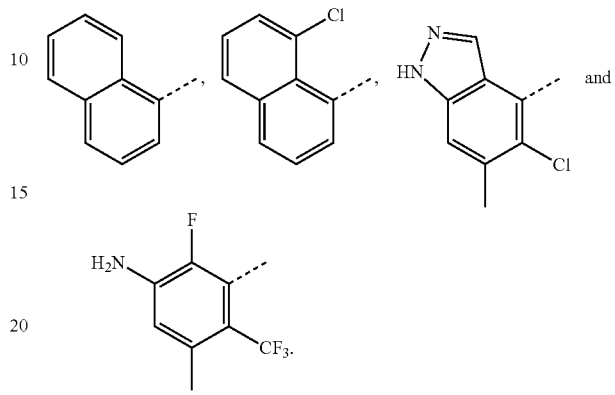

5. The compound according to claim 1, or a pharmaceutically acceptable salt thereof, wherein R₂ is selected from H, CH₃, CH₂CH₃ and CH(CH₃)₂, wherein the CH₃, CH₂CH₃ and CH(CH₃)₂ are optionally substituted with 1, 2 or 3 $R_b$;
alternatively, wherein R₂ is selected from H and CH₃.

6. The compound according to claim 1, or a pharmaceutically acceptable salt thereof, wherein R is each independently selected from H, F, Cl, Br, OH, CN, CH₃, CH₂CH₃, CH₂CF₃, OCH₃, OCF₃ and

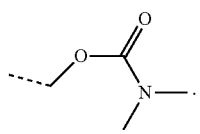

7. The compound according to claim 1, or a pharmaceutically acceptable salt thereof, wherein $R_c$ is selected from tetrahydropyrrolyl and hexahydro-1H-pyrrolizinyl, wherein the tetrahydropyrrolyl and hexahydro-1H-pyrrolizinyl are optionally substituted with 1, 2 or 3 R;
alternatively, wherein $R_c$ is selected from

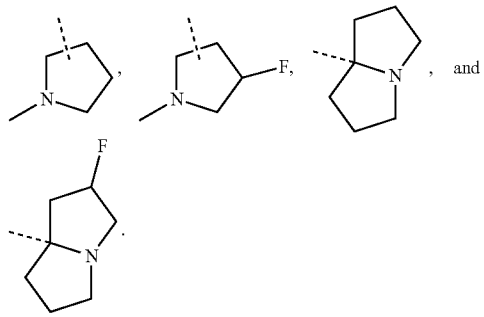

8. The compound according to claim 1, or a pharmaceutically acceptable salt thereof, wherein $R_c$ is selected from

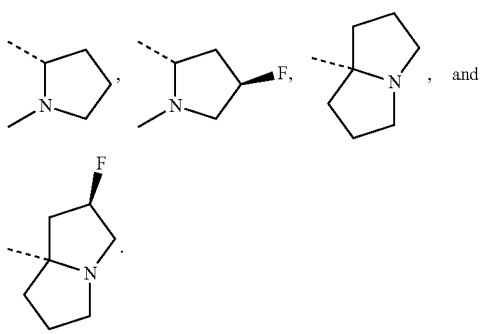

9. The compound according to claim 1, or a pharmaceutically acceptable salt thereof, wherein $R_3$ is $CH_3$, wherein the $CH_3$ is optionally substituted with 1, 2 or 3 $R_c$.

10. The compound according to claim 9, or a pharmaceutically acceptable salt thereof, wherein $R_3$ is selected from

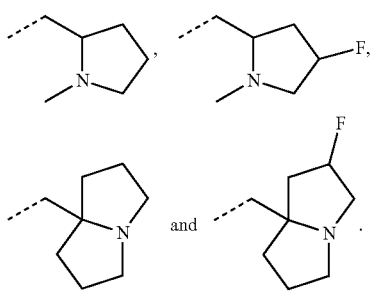

11. The compound according to claim 1, or a pharmaceutically acceptable salt thereof, wherein $R_3$ is selected from

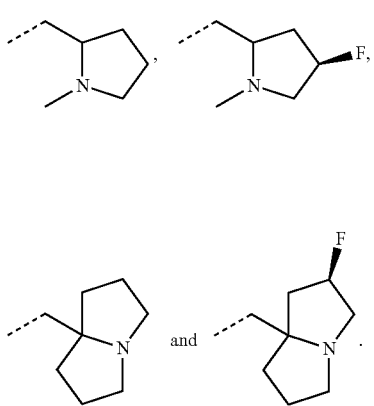

12. The compound according to claim 1, or a pharmaceutically acceptable salt thereof, wherein $R_4$ is selected from H and $CH_3$, wherein the $CH_3$ is optionally substituted with 1, 2 or 3 $R_d$;

alternatively, wherein $R_4$ is selected from H, $CH_3$ and $CH_2CN$.

13. The compound according to claim 1, or a pharmaceutically acceptable salt thereof, wherein the compound is selected from

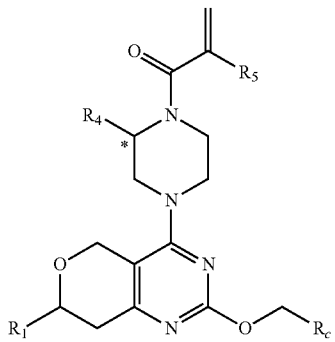

wherein $R_1$ is as defined in claim 1;

$R_4$ is $C_{1-3}$ alkyl, wherein the $C_{1-3}$ alkyl is optionally substituted with 1, 2 or 3 $R_d$;

$R_d$ is each independently selected from F, Cl, Br, I, OH, $NH_2$ and CN;

$R_5$ is as defined in claim 1;

$R_c$ is as defined in claim 1;

the carbon atom with "*" is a chiral carbon atom, which exists in the form of (R) or (S) single enantiomer or is enriched in one enantiomer.

14. The compound according to claim 1, or a pharmaceutically acceptable salt thereof, wherein the compound is selected from

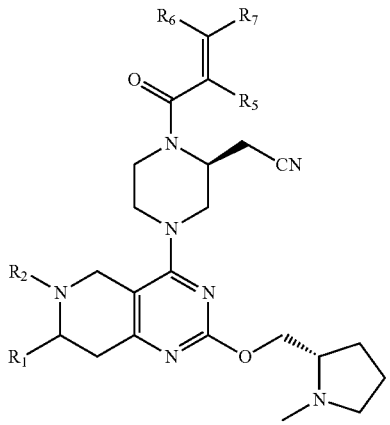

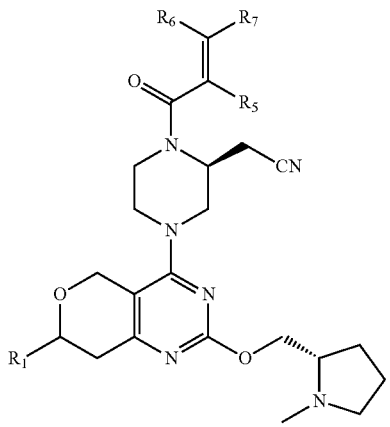

-continued
(IV-1)
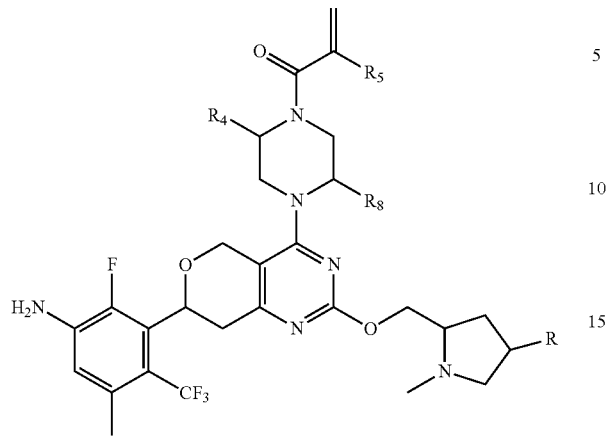
(IV-2)
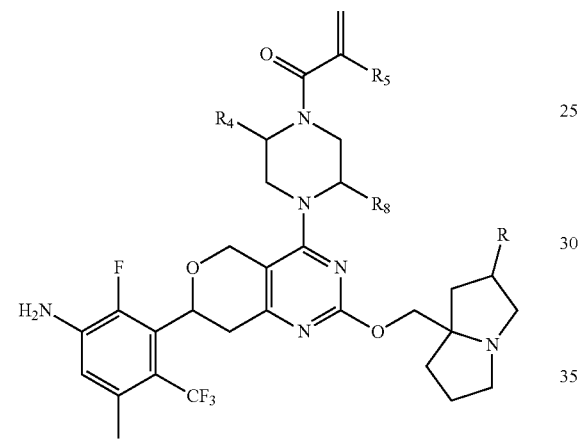
wherein
R₁,
R₂,
R₄,
R₅, R₆, R₇, R₈ and
R are defined in claim 1.
15. A compound represented by the following formula, or a pharmaceutically acceptable salt thereof,
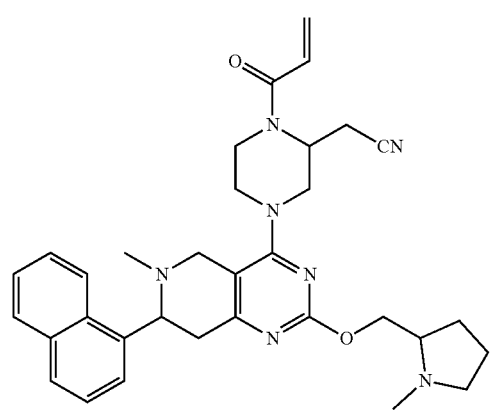
-continued
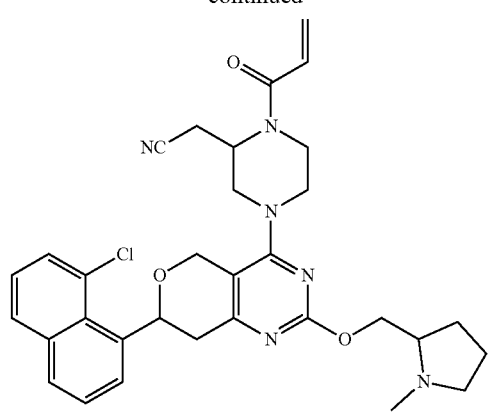
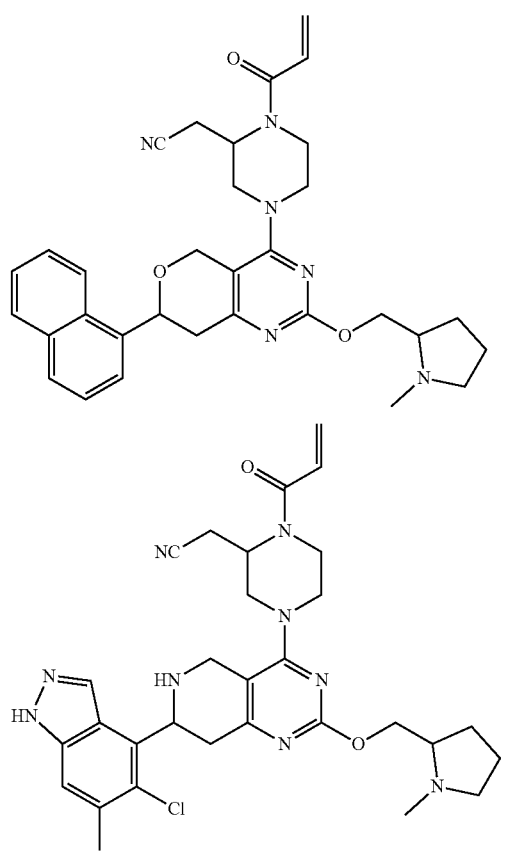
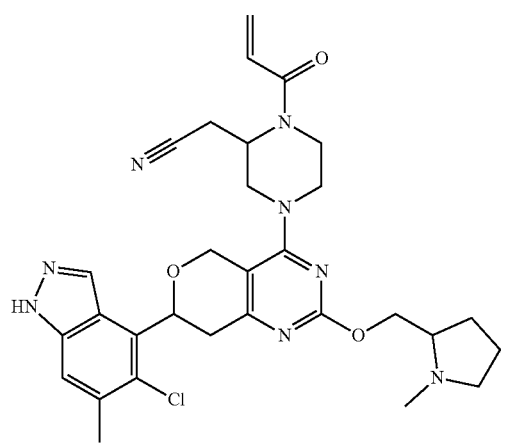

145
-continued
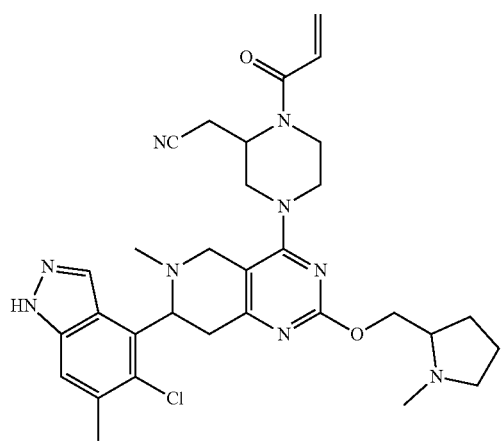
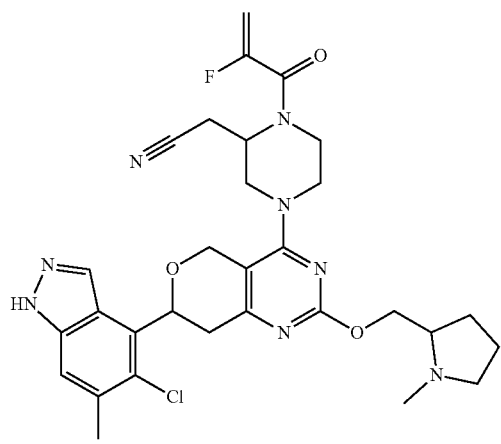
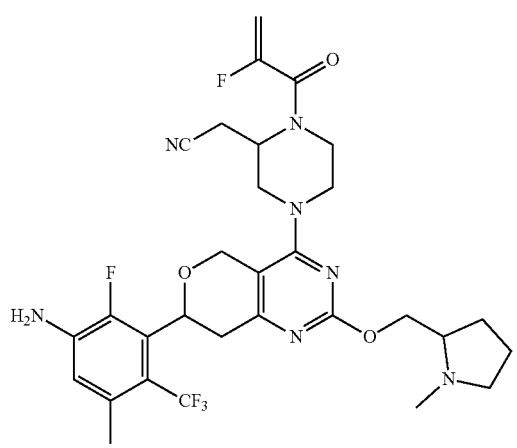
146
-continued
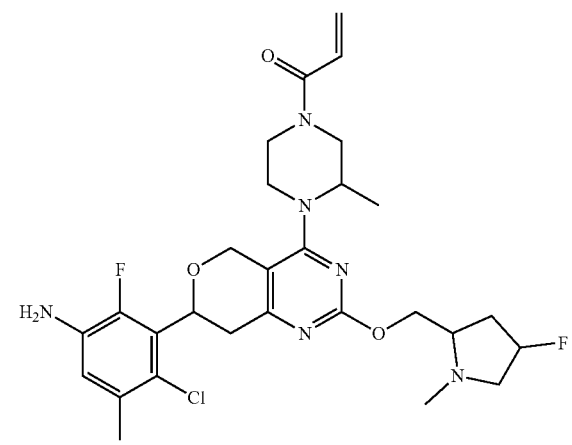
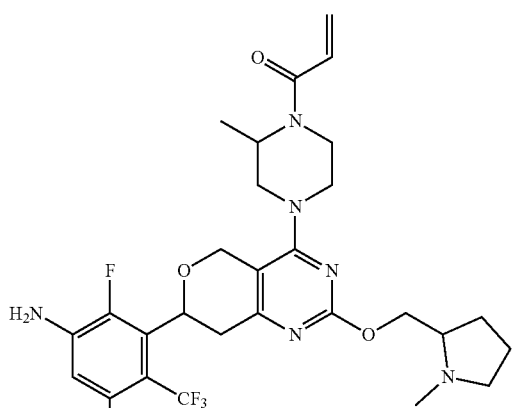
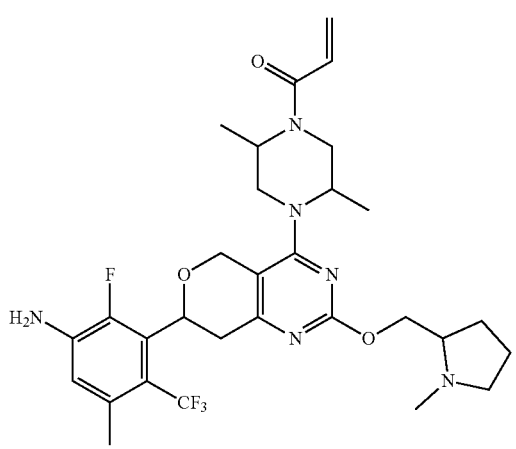

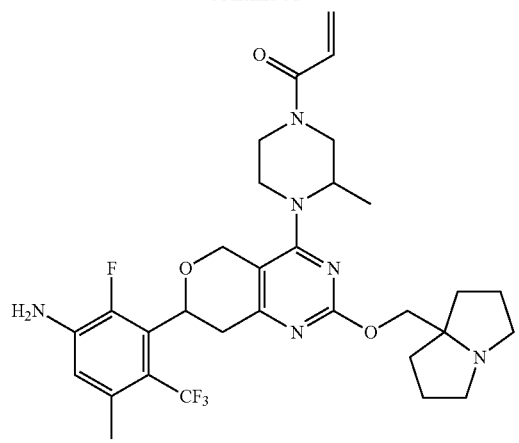
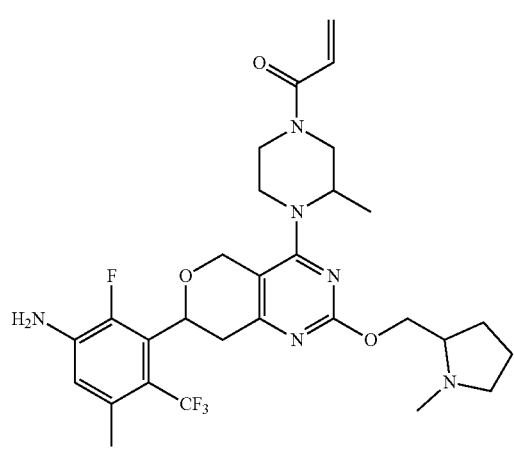
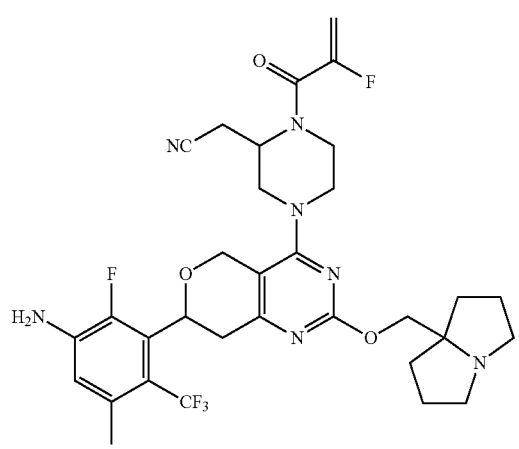
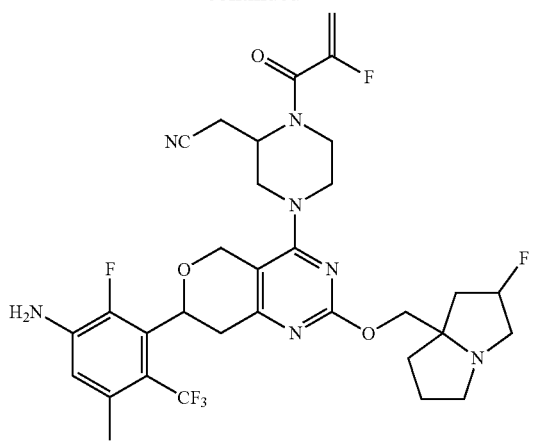
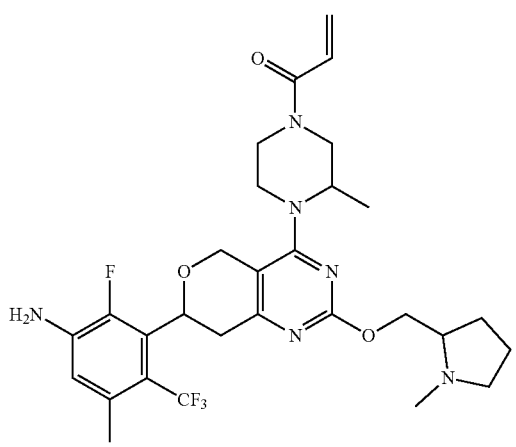
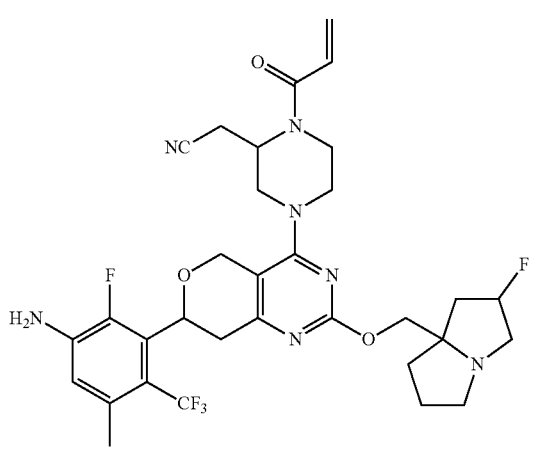

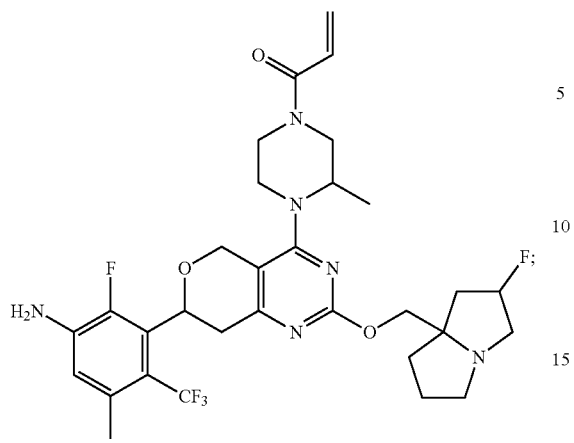
alternatively, wherein the compound is selected from
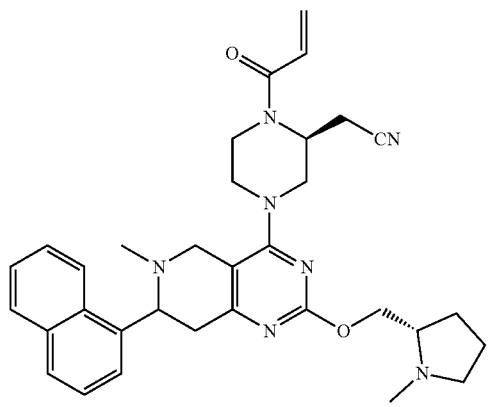
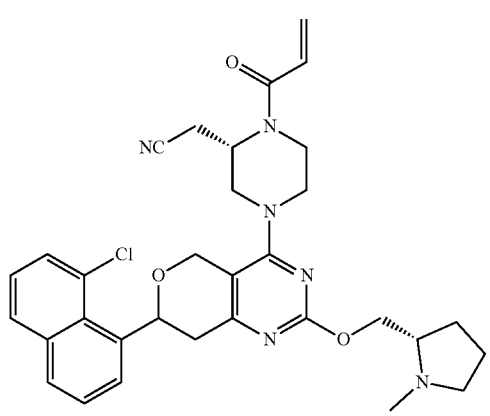
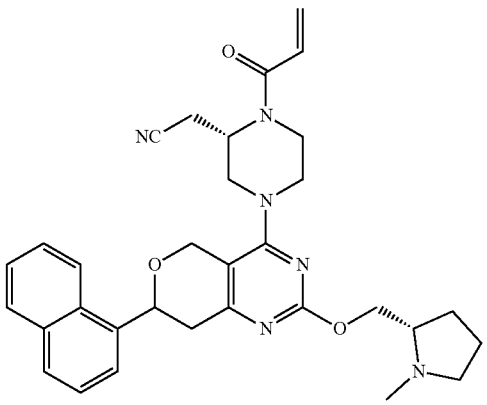
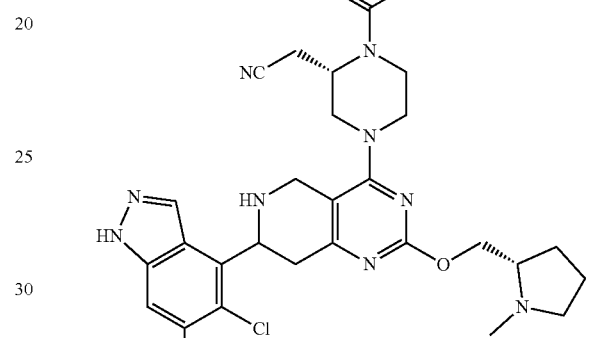
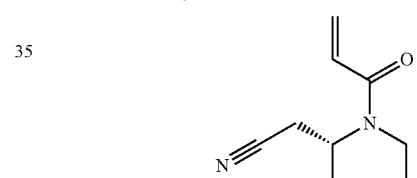
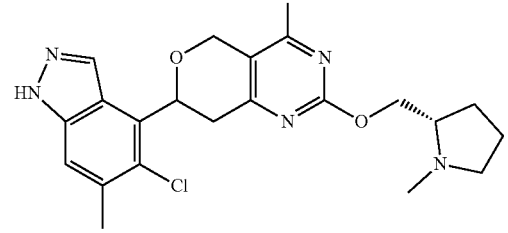
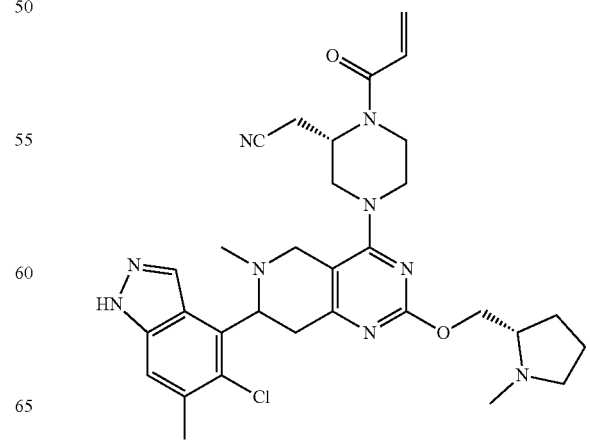

| 151 -continued | 152 -continued |
|---|---|
| 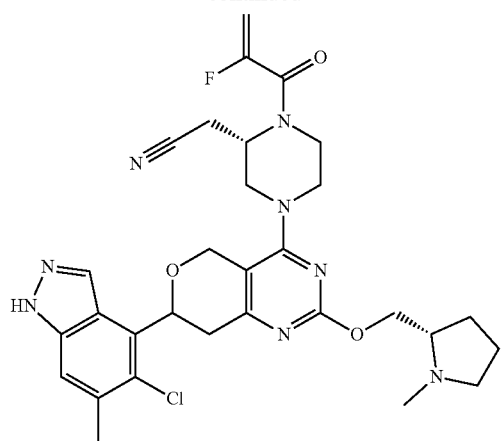 | 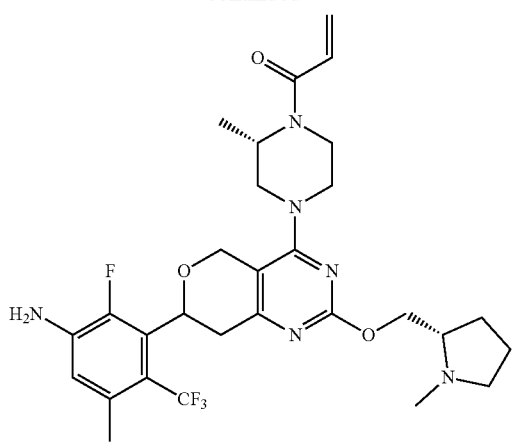 |
| 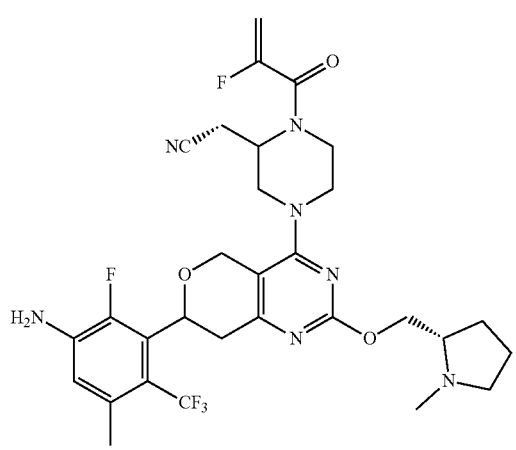 | 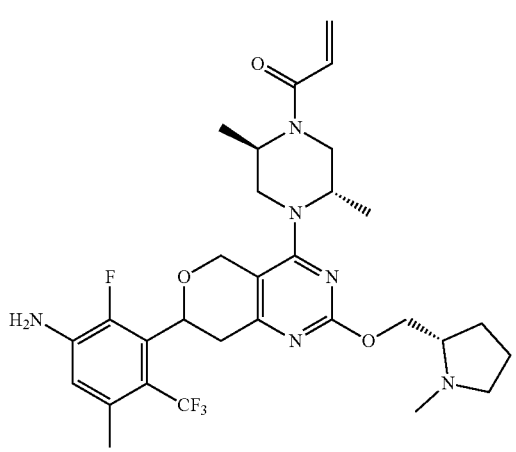 |
| 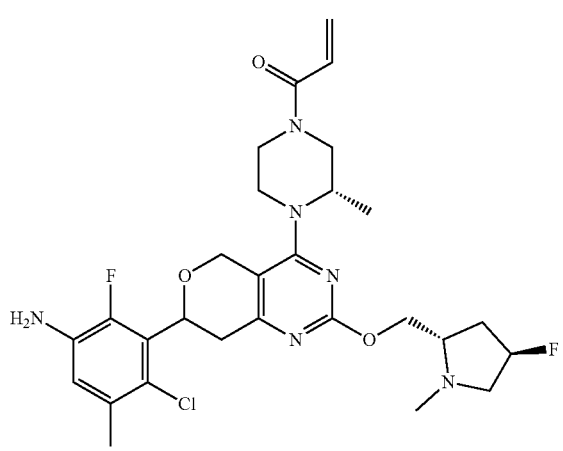 | 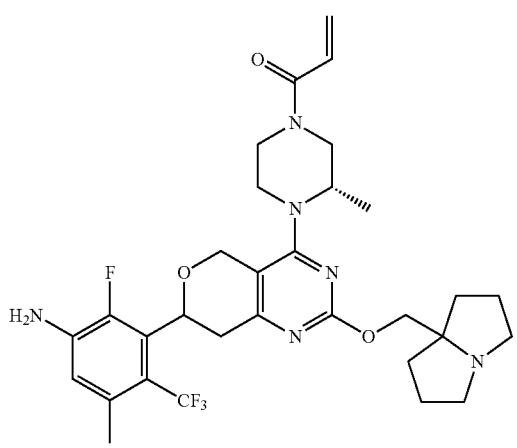 |

153
-continued
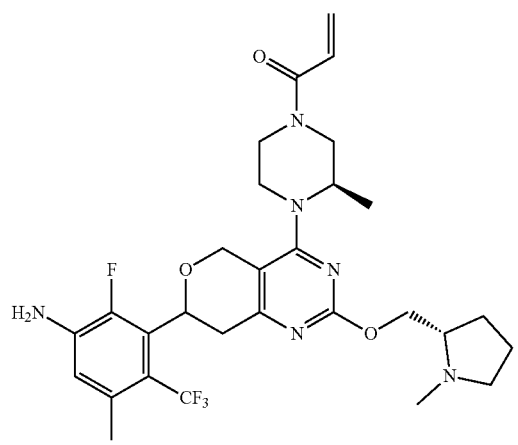
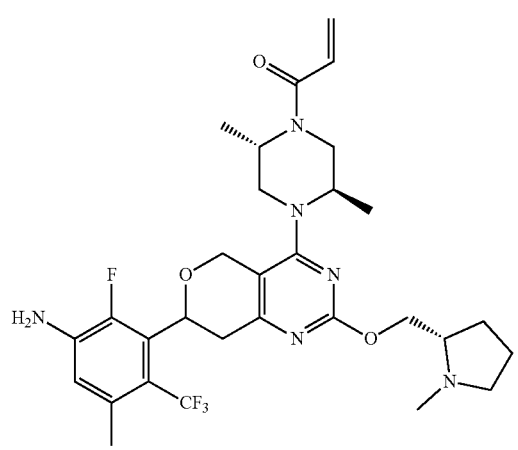
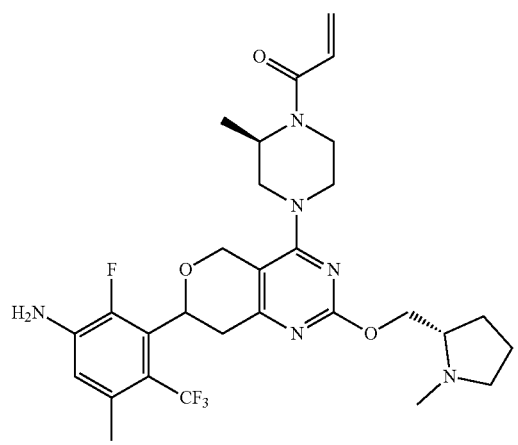
154
-continued
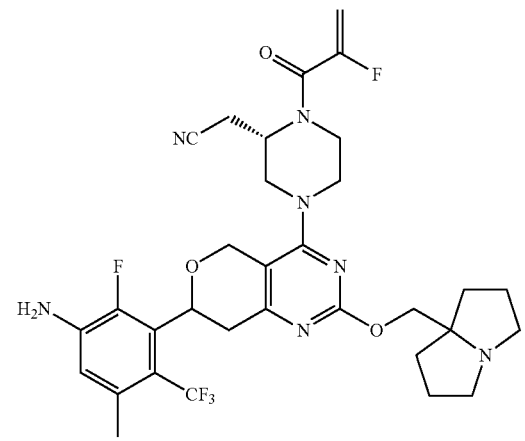
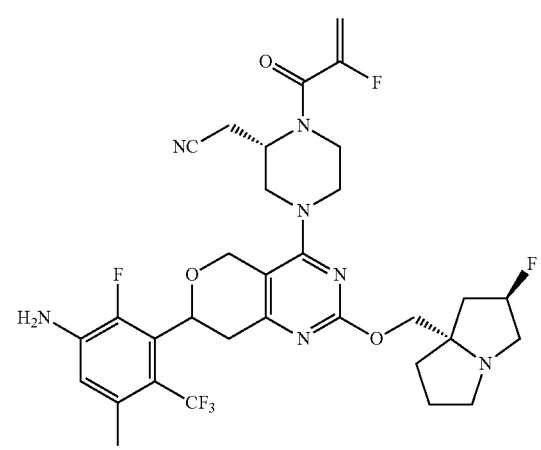
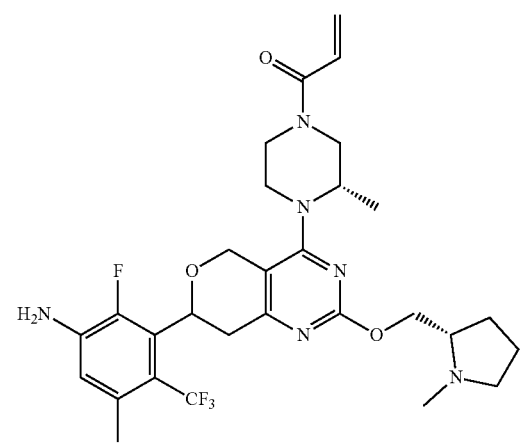

155
-continued
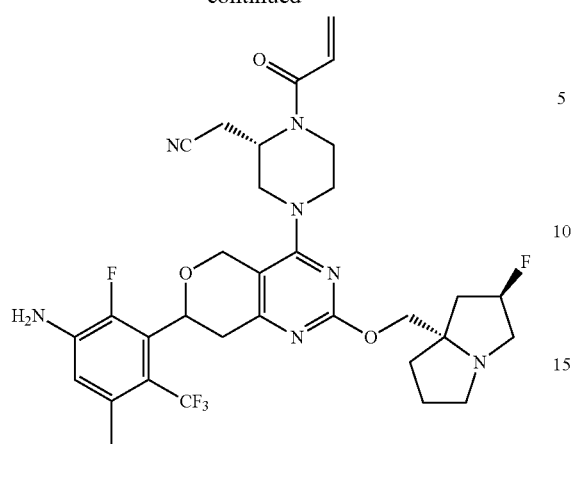
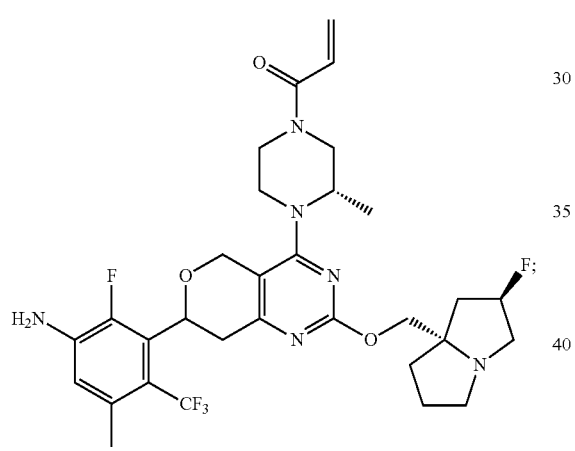
alternatively, wherein the compound is selected from
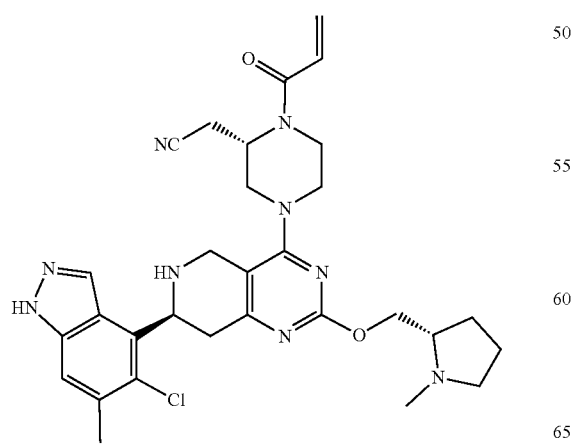
156
-continued
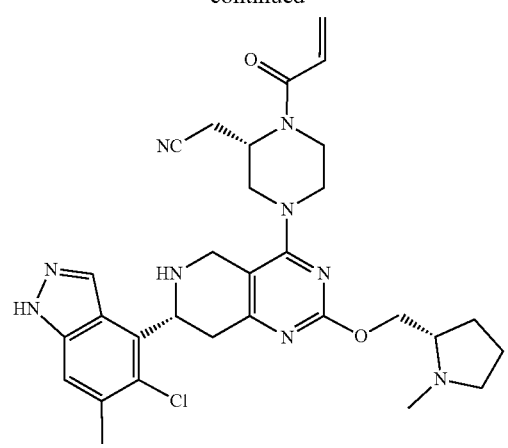
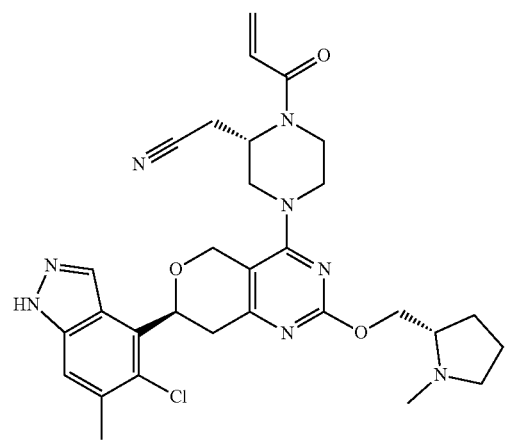
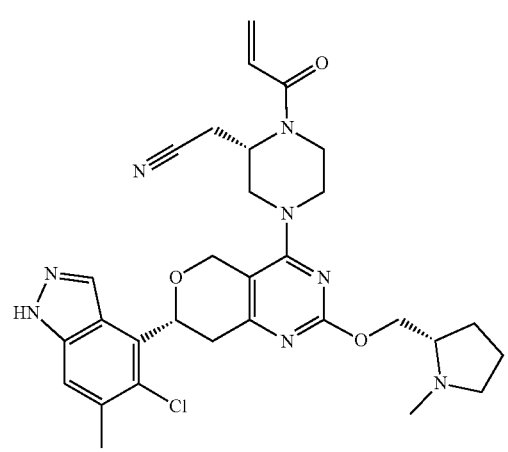

157
-continued
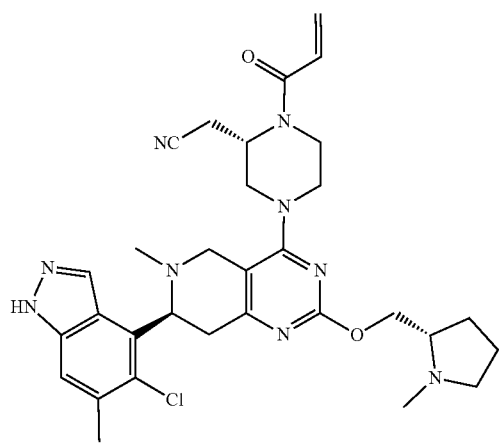
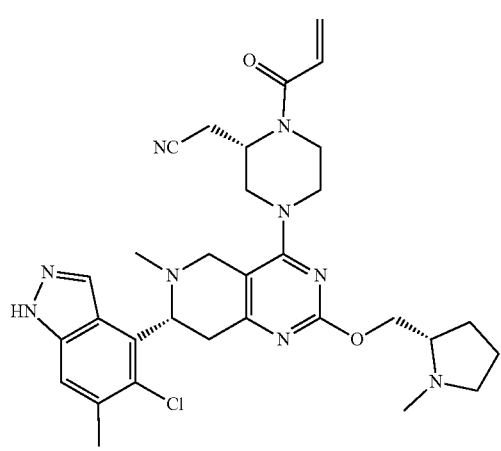
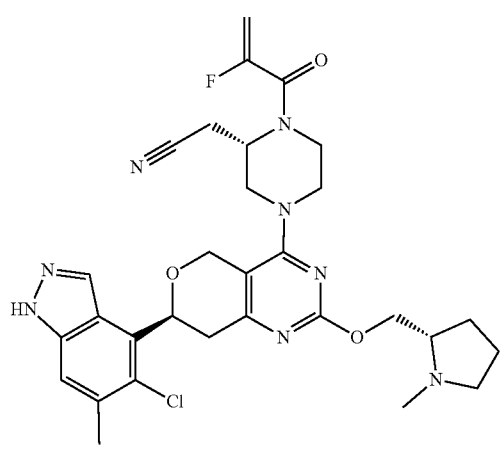
158
-continued
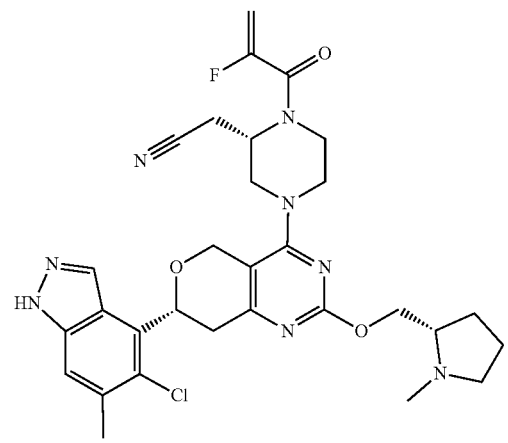
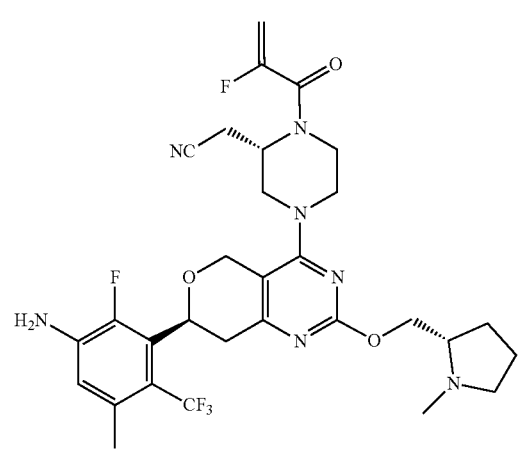
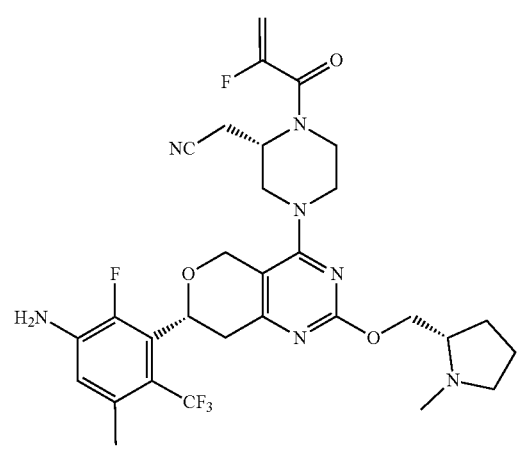

159
-continued
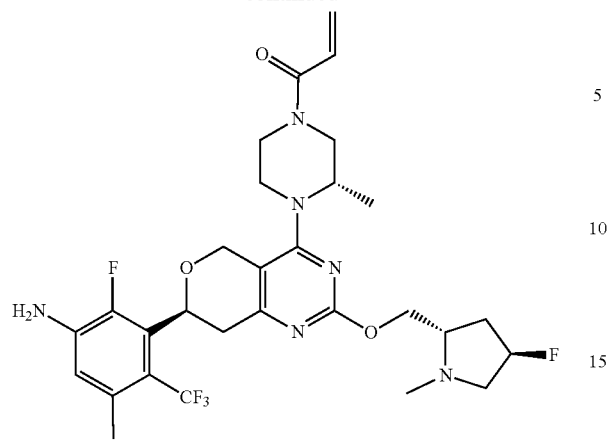
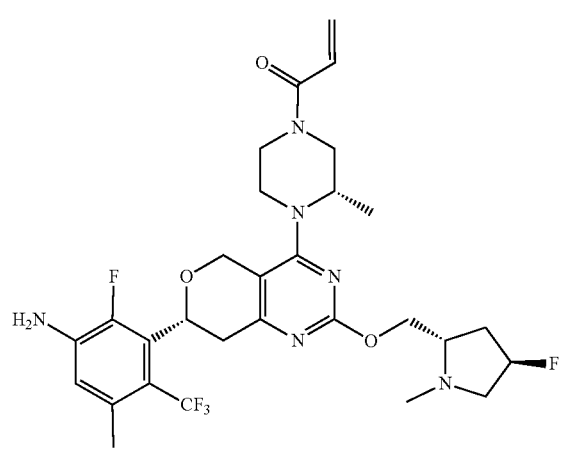
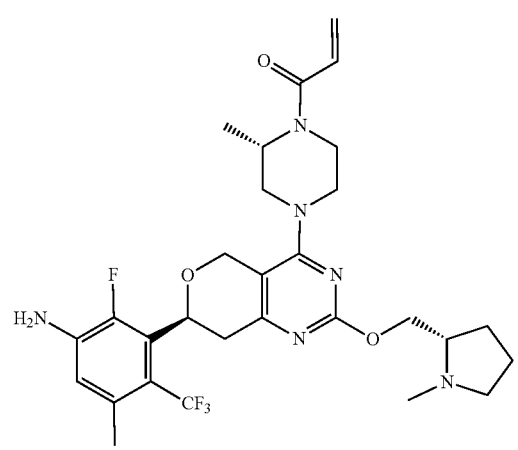
160
-continued
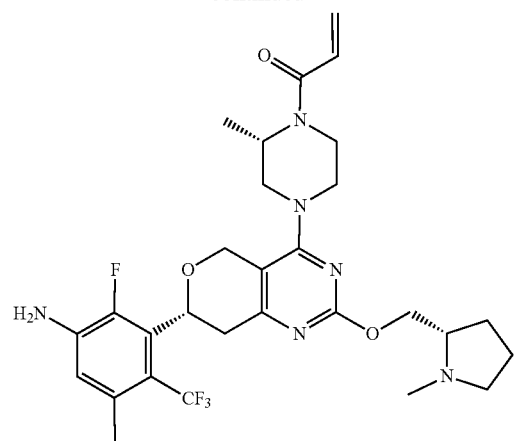
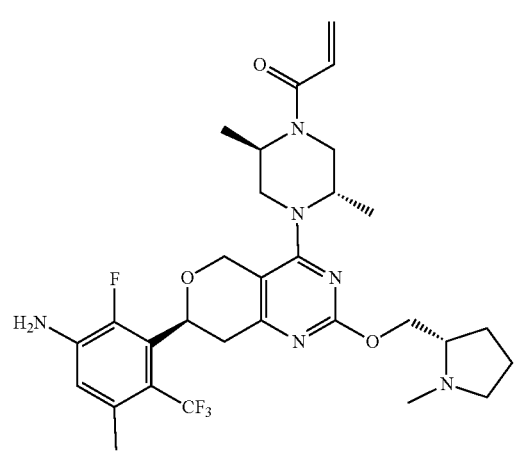
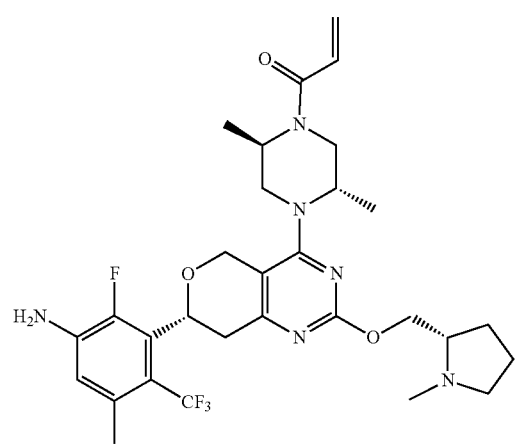

161
-continued
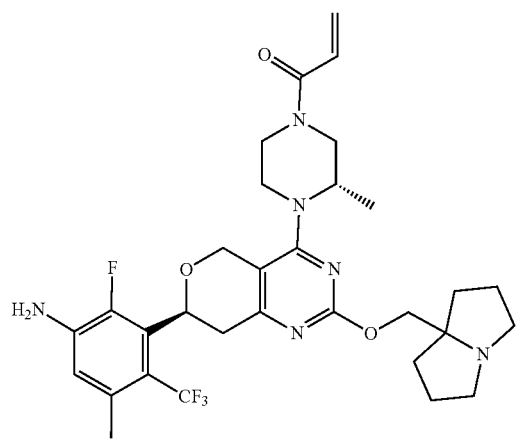
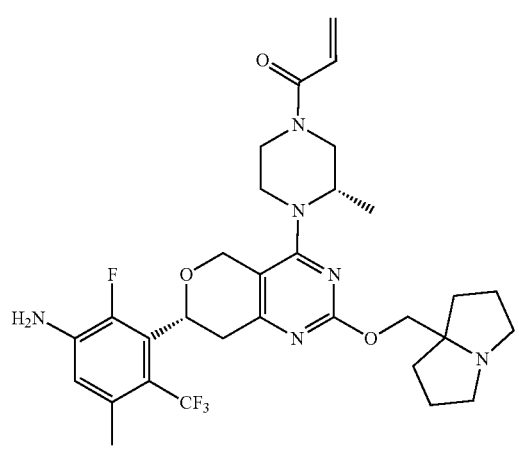
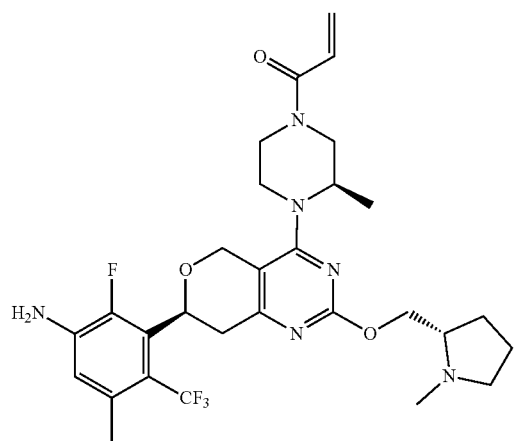
162
-continued
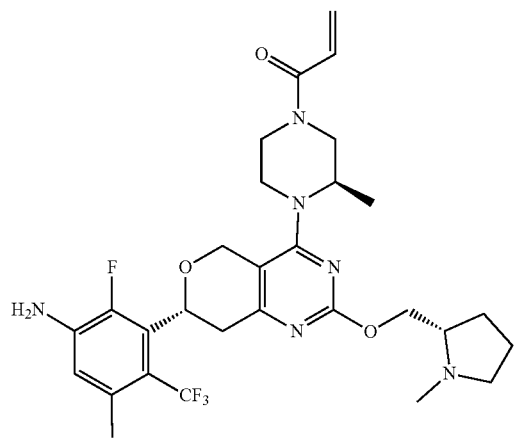
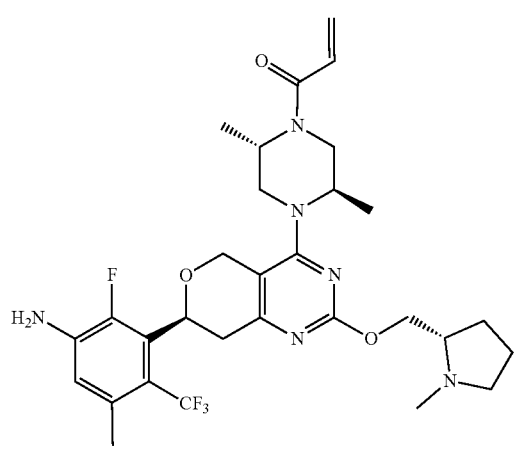
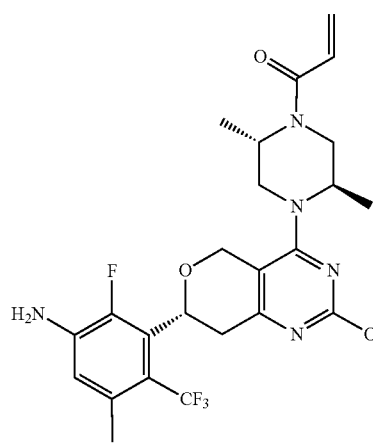

163
-continued
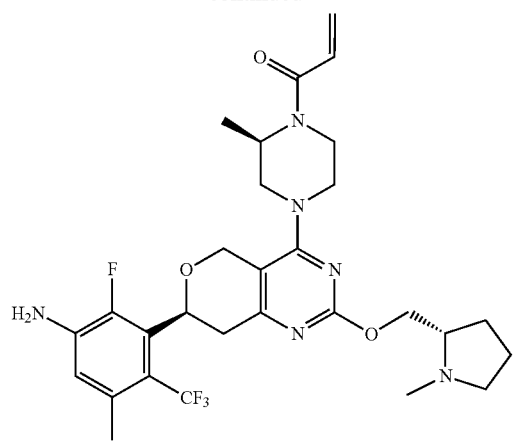
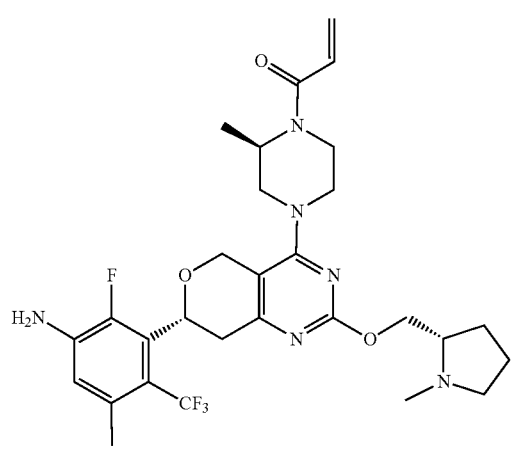
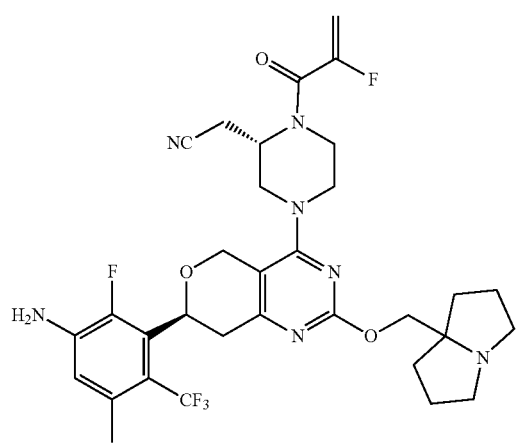
164
-continued
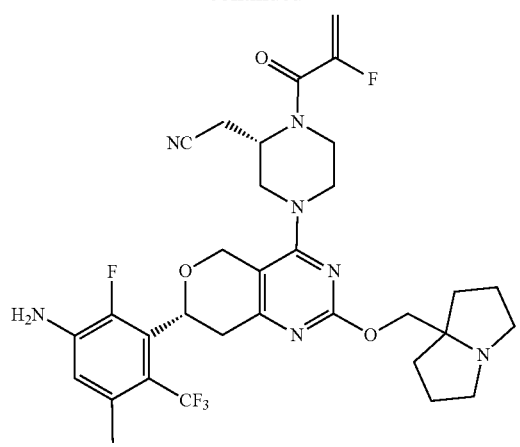
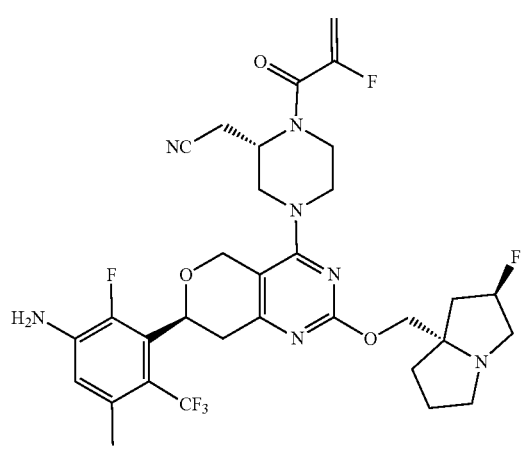
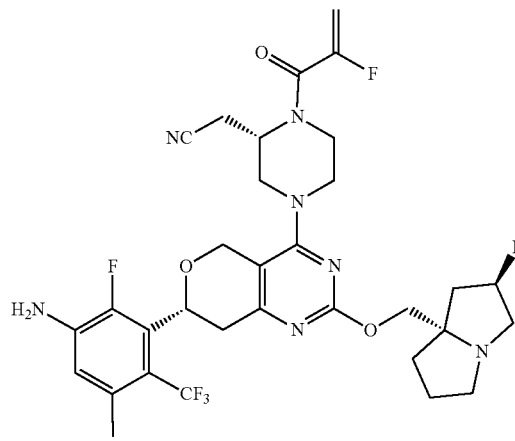

165
-continued
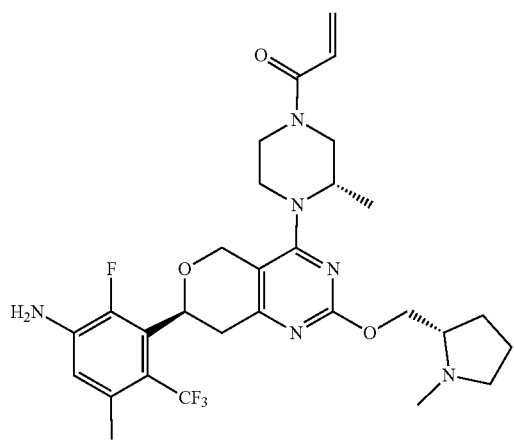
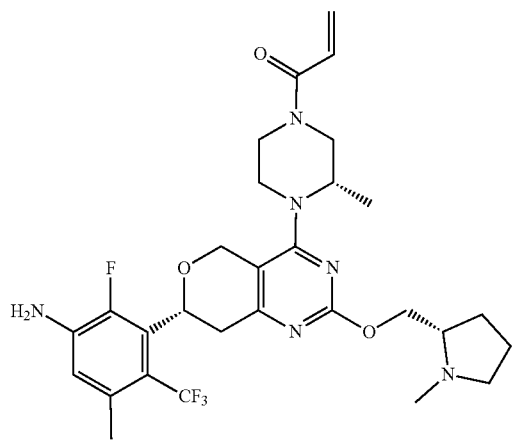
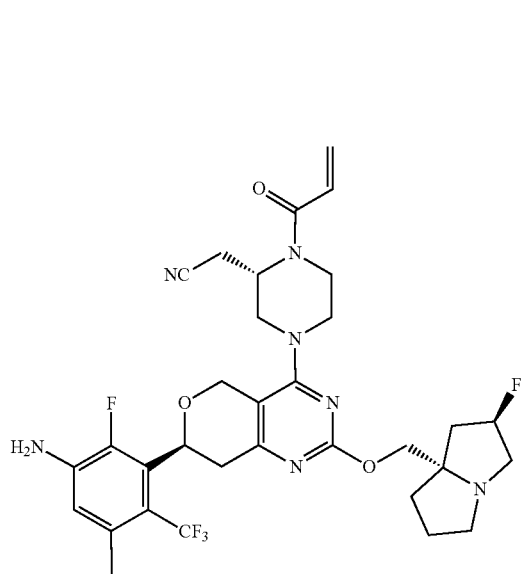
166
-continued
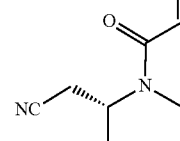
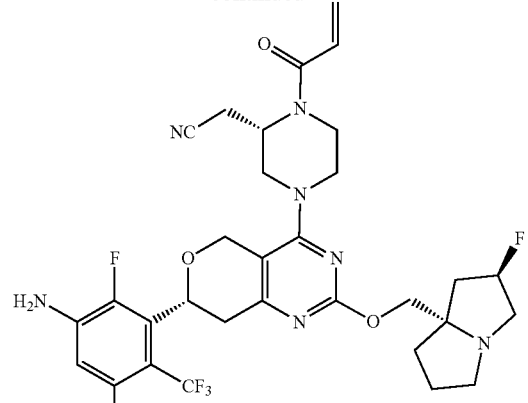
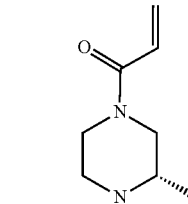
16. A pharmaceutical composition, comprising the compound according to claim 1 or a pharmaceutically acceptable salt thereof.
17. A compound according to claim 1, or a pharmaceutically acceptable salt thereof, wherein the compound is selected from (P-1)

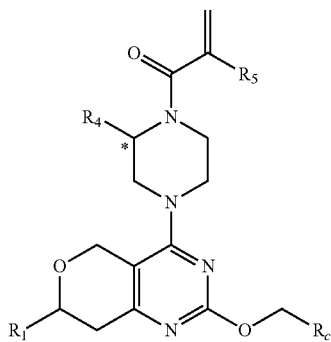

wherein

R₁ is

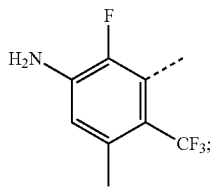

R₄ is CH₂CN, which exists in the form of (S) single enantiomer or is enriched in (S) enantiomer;

R₅ is selected from H, F, Cl, Br, I, and $C_{1-3}$ alkyl, wherein the $C_{1-3}$ alkyl is optionally substituted with 1, 2 or 3 F;

$R_c$ is selected from

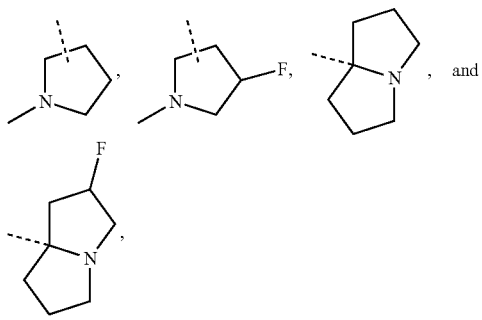

alternatively, is selected from

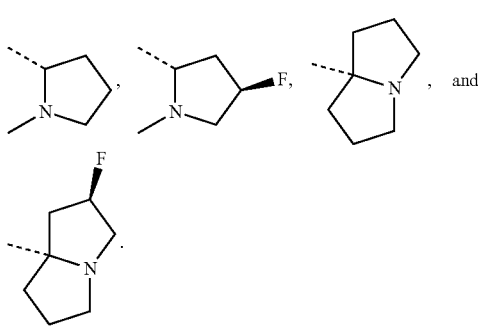

18. A compound according to claim 1, or a pharmaceutically acceptable salt thereof, wherein the compound is selected from (IV-1)

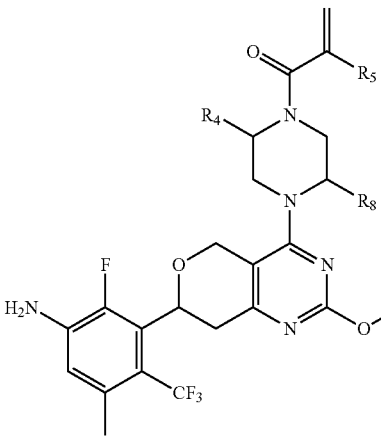

(IV-2)

wherein

R₄ is selected from H, CH₃ and CH₂CN, which exists in the form of (R) single enantiomer or is enriched in (R) enantiomer;

R₈ is selected from H and CH₃, which exists in the form of (S) single enantiomer or is enriched in (S) enantiomer;

R₅ is selected from H, F, Cl, Br, I, and $C_{1-3}$ alkyl, wherein the $C_{1-3}$ alkyl is optionally substituted with 1, 2 or 3 F; and R is selected from H, F, Cl, Br, and $C_{1-3}$ alkyl.

19. A compound according to claim 1, which is:
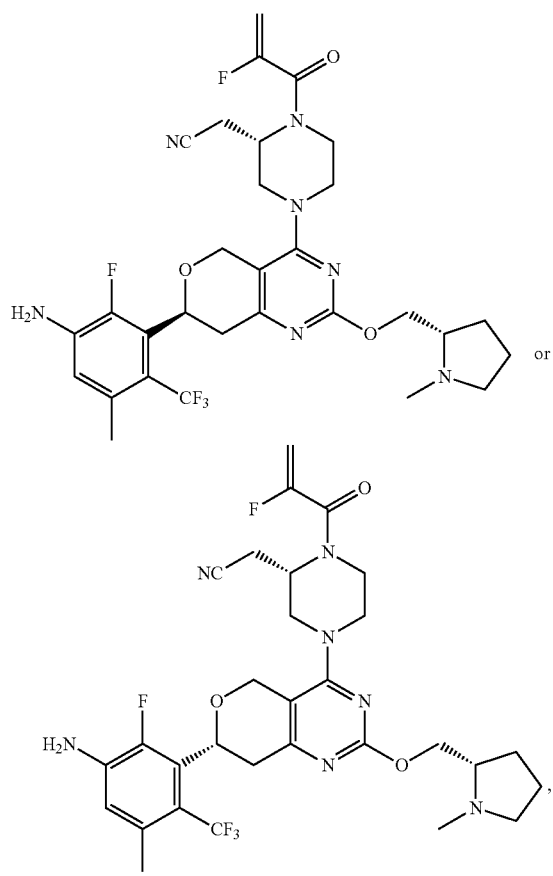
or a pharmaceutically acceptable salt thereof.
20. A compound according to claim 1, which is:
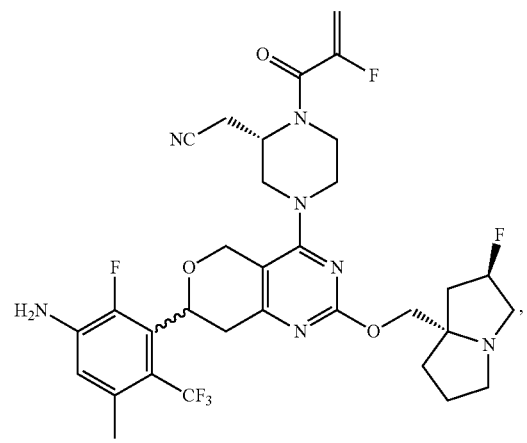 [SMILES: C=C(F)C(=O)N1CCN(c2nc(OC[C@@]34CCCN3C[C@H](F)C4)nc3c2COC(c2c(F)c(N)cc(C)c2C(F)(F)F)C3)C[C@@H]1CC#N]
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 12,162,880 B2 | Page 1 of 1 |
| APPLICATION NO. | : 17/905973 | |
| DATED | : December 10, 2024 | |
| INVENTOR(S) | : Yang Zhang et al. | |

It is certified that error appears in the above-identified patent and that said Letters Patent is hereby corrected as shown below:

In the Claims

At Column 142, Claim number 13, Line number 22:
"$R_a$ is each independently selected from F, Cl, Br, I, OH,"
Should read:
--$R_d$ is each independently selected from F, Cl, Br, I, OH,--

Signed and Sealed this
Twenty-fifth Day of February, 2025

Coke Morgan Stewart
*Acting Director of the United States Patent and Trademark Office*